US009896664B2

(12) United States Patent
Bell et al.

(10) Patent No.: US 9,896,664 B2
(45) Date of Patent: *Feb. 20, 2018

(54) ONCOLYTIC RHABDOVIRUS

(71) Applicants: OTTAWA HOSPITAL RESEARCH INSTITUTE, Ottawa (CA); CHILDREN'S HOSPITAL OF EASTERN ONTARIO RESEARCH INSTITUTE INC., Ottawa (CA)

(72) Inventors: John C. Bell, Ottawa (CA); David F. Stojdl, Ottawa (CA)

(73) Assignee: Turnstone Limited Partnership, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/696,028

(22) Filed: Apr. 24, 2015

(65) Prior Publication Data

US 2015/0275185 A1    Oct. 1, 2015

Related U.S. Application Data

(62) Division of application No. 13/514,837, filed as application No. PCT/IB2010/003396 on Dec. 10, 2010, now Pat. No. 9,045,729.

(60) Provisional application No. 61/285,461, filed on Dec. 10, 2009.

(51) Int. Cl.
| C12N 7/00 | (2006.01) |
| A61K 45/06 | (2006.01) |
| A61K 35/766 | (2015.01) |
| A61K 35/768 | (2015.01) |

(52) U.S. Cl.
CPC .............. *C12N 7/00* (2013.01); *A61K 35/766* (2013.01); *A61K 35/768* (2013.01); *A61K 45/06* (2013.01); *C12N 2760/20021* (2013.01); *C12N 2760/20032* (2013.01); *C12N 2760/20062* (2013.01); *C12N 2760/20071* (2013.01)

(58) Field of Classification Search
None
See application file for complete search history.

(56) References Cited

U.S. PATENT DOCUMENTS

| 4,554,101 A | 11/1985 | Hopp |
| 4,683,195 A | 7/1987 | Mullis et al. |
| 4,683,202 A | 7/1987 | Mullis |
| 4,684,611 A | 8/1987 | Schilperoort et al. |
| 4,800,159 A | 1/1989 | Mullis et al. |
| 4,879,236 A | 11/1989 | Smith et al. |
| 4,883,750 A | 11/1989 | Whiteley et al. |
| 4,946,773 A | 8/1990 | Maniatis et al. |
| 4,952,500 A | 8/1990 | Finnerty et al. |
| 5,220,007 A | 6/1993 | Pederson et al. |
| 5,279,721 A | 1/1994 | Schmid |
| 5,284,760 A | 2/1994 | Feinstone et al. |
| 5,302,523 A | 4/1994 | Coffee et al. |
| 5,322,783 A | 6/1994 | Tomes et al. |
| 5,354,670 A | 10/1994 | Nickoloff et al. |
| 5,366,878 A | 11/1994 | Pederson et al. |
| 5,384,253 A | 1/1995 | Krzyzek et al. |
| 5,389,514 A | 2/1995 | Taylor |
| 5,399,363 A | 3/1995 | Liversidge et al. |
| 5,464,765 A | 11/1995 | Coffee et al. |
| 5,466,468 A | 11/1995 | Schneider et al. |
| 5,538,877 A | 7/1996 | Lundquist et al. |
| 5,538,880 A | 7/1996 | Lundquist et al. |
| 5,543,158 A | 8/1996 | Gref et al. |
| 5,550,318 A | 8/1996 | Adams et al. |
| 5,563,055 A | 10/1996 | Townsend et al. |
| 5,580,859 A | 12/1996 | Felgner et al. |
| 5,585,461 A | 12/1996 | Townsend et al. |
| 5,589,466 A | 12/1996 | Felgner et al. |
| 5,591,616 A | 1/1997 | Hiei et al. |
| 5,610,042 A | 3/1997 | Chang et al. |
| 5,635,377 A | 6/1997 | Pederson et al. |
| 5,641,515 A | 6/1997 | Ramtoola et al. |
| 5,656,610 A | 8/1997 | Shuler et al. |
| 5,702,932 A | 12/1997 | Hoy et al. |
| 5,736,524 A | 4/1998 | Content et al. |
| 5,739,169 A | 4/1998 | Ocain et al. |
| 5,780,448 A | 7/1998 | Davis |
| 5,789,166 A | 8/1998 | Bauer et al. |
| 5,789,215 A | 8/1998 | Berns et al. |
| 5,798,208 A | 8/1998 | Crea |
| 5,801,005 A | 9/1998 | Cheever et al. |
| 5,824,311 A | 10/1998 | Greene et al. |
| 5,830,650 A | 11/1998 | Crea |

(Continued)

FOREIGN PATENT DOCUMENTS

| CA | 2739963 A1 | 4/2010 |
| CN | 1962911 A | 5/2007 |

(Continued)

OTHER PUBLICATIONS

Baker et al., Protein Structure Predication and Structural Genomics, Science (2001) vol. 294, No. 5540, pp. 93-96.*
Attwood, T. The Babel of Bioinformatics, Science (2000) vol. 290, No. 5491, pp. 471-473.*
Brun et al. Identification of genetically modified Maraba virus as an oncolytic rhabdovirus. Mol Ther. Aug. 2010;18(8):1440-9.*
Edbrooke et al., "Identification of cis-Acting Sequences Responsible for Phorbol Ester Induction of Human Serum Amyloid A Gene Expression via a Nuclear Factor kB-Like Transcription Factor", Molecular and Cellular Biology, May 1989, vol. 9, No. 5, pp. 1908-1916.
Edlund et al., "Cell-Specific Expression of the Rat Insulin Gene: Evidence for Role of Two Distinct 5' Flanking Elements", Science, vol. 230, No. 4728, Nov. 22, 1985, pp. 912-916.

(Continued)

*Primary Examiner* — Michelle S Horning
(74) *Attorney, Agent, or Firm* — Borden Ladner Gervais LLP; David Nauman

(57) ABSTRACT

Embodiments of the invention include compositions and methods related to Maraba virus and their use as anti-cancer therapeutics. Such rhabdoviruses possess tumor cell killing properties in vitro and in vivo.

21 Claims, 17 Drawing Sheets

(56) References Cited

U.S. PATENT DOCUMENTS

| | | |
|---|---|---|
| 5,830,880 A | 11/1998 | Sedlacek et al. |
| 5,840,873 A | 11/1998 | Nelson et al. |
| 5,843,640 A | 12/1998 | Patterson et al. |
| 5,843,650 A | 12/1998 | Segev |
| 5,843,651 A | 12/1998 | Stimpson et al. |
| 5,843,663 A | 12/1998 | Stanley et al. |
| 5,846,225 A | 12/1998 | Rosengart et al. |
| 5,846,233 A | 12/1998 | Lilley et al. |
| 5,846,708 A | 12/1998 | Hollis et al. |
| 5,846,709 A | 12/1998 | Segev |
| 5,846,717 A | 12/1998 | Brow et al. |
| 5,846,726 A | 12/1998 | Nadeau et al. |
| 5,846,729 A | 12/1998 | Wu et al. |
| 5,846,783 A | 12/1998 | Wu et al. |
| 5,846,945 A | 12/1998 | McCormick |
| 5,849,481 A | 12/1998 | Urdea et al. |
| 5,849,483 A | 12/1998 | Shuber et al. |
| 5,849,486 A | 12/1998 | Heller et al. |
| 5,849,487 A | 12/1998 | Hase et al. |
| 5,849,497 A | 12/1998 | Steinman |
| 5,849,546 A | 12/1998 | Sousa et al. |
| 5,849,547 A | 12/1998 | Cleuziat et al. |
| 5,851,770 A | 12/1998 | Babon et al. |
| 5,851,772 A | 12/1998 | Mirzabekov et al. |
| 5,853,990 A | 12/1998 | Winger et al. |
| 5,853,992 A | 12/1998 | Glazer et al. |
| 5,853,993 A | 12/1998 | Dellinger et al. |
| 5,856,092 A | 1/1999 | Dale et al. |
| 5,858,652 A | 1/1999 | Laffler et al. |
| 5,861,244 A | 1/1999 | Wang et al. |
| 5,863,732 A | 1/1999 | Richards |
| 5,863,753 A | 1/1999 | Haugland et al. |
| 5,866,331 A | 2/1999 | Singer et al. |
| 5,866,337 A | 2/1999 | Schon |
| 5,866,366 A | 2/1999 | Kallender |
| 5,871,986 A | 2/1999 | Boyce |
| 5,882,864 A | 3/1999 | An et al. |
| 5,900,481 A | 5/1999 | Lough et al. |
| 5,905,024 A | 5/1999 | Mirzabekov et al. |
| 5,910,407 A | 6/1999 | Vogelstein et al. |
| 5,912,124 A | 6/1999 | Kumar |
| 5,912,145 A | 6/1999 | Stanley |
| 5,912,148 A | 6/1999 | Eggerding |
| 5,916,776 A | 6/1999 | Kumar |
| 5,916,779 A | 6/1999 | Pearson et al. |
| 5,919,626 A | 7/1999 | Shi et al. |
| 5,919,630 A | 7/1999 | Nadeau et al. |
| 5,922,574 A | 7/1999 | Minter |
| 5,925,517 A | 7/1999 | Tyagi et al. |
| 5,925,525 A | 7/1999 | Fodor et al. |
| 5,925,565 A | 7/1999 | Berlioz et al. |
| 5,928,862 A | 7/1999 | Morrison |
| 5,928,869 A | 7/1999 | Nadeau et al. |
| 5,928,870 A | 7/1999 | Lapidus et al. |
| 5,928,905 A | 7/1999 | Stemmer et al. |
| 5,928,906 A | 7/1999 | Koster et al. |
| 5,929,227 A | 7/1999 | Glazer et al. |
| 5,932,413 A | 8/1999 | Celebuski |
| 5,932,451 A | 8/1999 | Wang et al. |
| 5,935,791 A | 8/1999 | Nadeau et al. |
| 5,935,819 A | 8/1999 | Eichner et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,965,535 A | 10/1999 | Chaux et al. |
| 5,981,274 A | 11/1999 | Tyrrell et al. |
| 5,994,624 A | 11/1999 | Trolinder et al. |
| 9,045,729 B2 * | 6/2015 | Bell .................. C12N 7/00 |
| 9,707,285 B2 | 7/2017 | Lichty et al. |
| 2004/0170607 A1 | 9/2004 | Bell et al. |
| 2011/0250188 A1 | 10/2011 | Von Laer et al. |
| 2015/0275185 A1 | 10/2015 | Bell et al. |
| 2015/0307559 A1 | 10/2015 | Stojdl et al. |

FOREIGN PATENT DOCUMENTS

| | | |
|---|---|---|
| CN | 102026645 A | 4/2011 |
| EP | 0320308 | 6/1989 |
| EP | 0329822 | 8/1989 |
| GB | 2202328 | 9/1988 |
| JP | 2004-525855 T | 8/2004 |
| JP | 2005509404 A | 4/2005 |
| RU | 2301260 C2 | 6/2007 |
| RU | 2011130511 A | 11/2013 |
| WO | 1987/006270 | 10/1987 |
| WO | 1988/010315 | 12/1988 |
| WO | 1989/006700 | 7/1989 |
| WO | 1989/009284 | 10/1989 |
| WO | 9007641 A1 | 7/1990 |
| WO | 1991/009944 | 7/1991 |
| WO | 9409699 A1 | 5/1994 |
| WO | 1995/006128 | 3/1995 |
| WO | 2001/19380 A2 | 3/2001 |
| WO | 2009/016433 | 2/2009 |
| WO | 2009/036137 A1 | 3/2009 |
| WO | 2010105347 A1 | 9/2010 |
| WO | 2011070440 A2 | 6/2011 |
| WO | 2014127478 A1 | 8/2014 |

OTHER PUBLICATIONS

Endo et al., "Virus-mediated oncolysis induces danger singal and stimulates cytotoxic T-lymphocyte activity via proteasome activator upregulation", Oncogene, 2008, published online Nov. 5, 2007, vol. 27, pp. 2375-2381.

Fechheimer et al., "Transfection of mammalian cells with plasmid DNA by scrape loading and sonication loading", Proc. Natl. Acad. Sci, USA, vol. 84, Dec. 1987, Cell Biology, pp. 8463-8467.

Feng et al., "HIV-1 tat trans-activation requires the loop sequence within tar," Nature, vol. 334, Jul. 14, 1988, pp. 165-167.

Ferran et al., "The Vesicular Stomatitis Virus Matrix Protein Inhibits Transcription from the Human Beta Interferon Promoter", Journal of Virology, Jan. 1997, vol. 71, pp. 371-377.

Firak et al., "Minimal Transcriptional Enhancer of Simian Virus 40 Us a 74-Base-Pair Sequence That Has Interacting Domains", Molecular and Cellular Biology, Nov. 1986, vol. 6, pp. 3667-3676.

Foecking et al, "Powerful and Versatile Enhancer-Promoter Unit for Mammalian Expression Vectors", Gene, vol. 45, 1986, issue 1, pp. 101-105.

Fuerst et al., "Eukaryotic transient-expression system based on recombinant vaccinia virus that synthesizes bacteriophage T7 RNA polymerase", Proc. Natl. Acad. Sco. USA, vol. 83, Nov. 1986, pp. 8122-8126.

Fujita et al., "Interferon-Beta Gene Regulation: Tandemly Repeated Sequences of a Synthetic 6 bp Oligomer Function as a Virus-Inducible Enhancer", Cell., vol. 49, May 8, 1987, pp. 357-369.

Gilles et al., "A Tissue-specific Transcription Enhancer Element is Located in the Major Intron of a Rearranged Immunoglobulin Heavy Chain Gene", Cell, vol. 33, Jul. 1983, pp. 717-728.

Gloss et al., "The upstream regulator region of the human papilloma virus-16 contains an E2 protein-independent enhancer which is specific for cervical carcinoma cells and regulated by glucocorticoid hormones", The EMBO Journal, vol. 6, Dec. 1, 1987, pp. 3735-3743.

Godbout et al., "Fine-Structure Mapping of the Three Mouse alpha-Fetoprotein Gene Enhancers", Molecular and Cellular Biology, Mar. 1988, vol. 8, No. 3, pp. 1169-1178.

Goodbourn et al., "Overlapping positive and negative regulatory domains of the human beta-interferon gene", Proc. Natl. Acad. Sci. USA, vol. 85, Mar. 1988, pp. 1447-1451.

Goodbourn et al., "The Human beta-Interferon Gene Enhancer Is under Negative Control", Cell, vol. 45, May 23, 1986, pp. 601-610.

Gopal, "Gene Transfer Method for Transient Gene Expression, Stable Transformation, and Cotransformation of Suspension Cell Cultures", Molecular and Cellular Biology, May 1985, vol. 5, No. 5, pp. 1188-1190.

(56) References Cited

OTHER PUBLICATIONS

Graham et al., "A New Technique for the Assay of Infectivity of Human Adenovirus 5 DNA", Virology, vol. 52, 1973, accepted for publication Jan. 17, 1973, pp. 456-467.
Greene et al., "HIV-1, HTLV-1 and normal T-cell growth: transcriptional strategies and surprises", Immunology Today, vol. 10, No. 8, Aug. 1989, pp. 272-278.
Gromeier et al., "Intergeneric Poliovirus Recombinants for the Treatment of Malignant Glioma", PNAS, Jun. 6, 2000, vol. 97, No. 12, pp. 6803-6808.
Grosschedl et al., "Cell-Type Specificity of Immunoglobulin Gene Expression is Regulated by at Least Three DNA Sequence Elements", Cell., vol. 41, Jul. 1985, pp. 885-897.
Grote et al., "Live attenuated measles virus induces regression of human lymphoma xenografts in immunodeficient mice", Blood, vol. 97, No. 12, Jun. 15, 2001, pp. 3746-3754.
Hanibuchi et al., "Therapeutic Efficacy of Mouse-Human Chimeric Anti-Ganglioside GM2 Monoclonal Antibody Against Multiple Organ Micrometastases of Human Lung Cancer in NK Cell-Depleted SCID Mice", Int. J. Cancer, vol. 78, 1998, pp. 480-485.
Harland et al., "Translation of mRNA Injected into Xenopus Oocytes Is Specifically Inhibited by Antisense RNA", The Journal of Cell Biology, vol. 101, Sep. 1985, pp. 1094-1099.
Haslinger et al., "Upstream promoter element of the human metallothionein-IIA gene can act like an enhancer element", Proc. Natl. Acad. Sci. USA, vol. 82, Dec. 1985, pp. 8572-8576.
Hauber et al., "Mutational Analysis of the trans-Activation-Responsive Region of the Human Immunodeficiency Virus Type I Long Terminal Repeat", Journal of Virology, Mar. 1988, vol. 62, No. 3, pp. 673-679.
Heise et al., "An adenovirus E1A mutant that demonstrates potent and selective systemic anti-tumoral efficacy", Nature Medicine, vol. 6, No. 10, Oct. 2000, pp. 1134-1139.
Hellstrand et al, "Histamine and Cytokine Therpay", Acta Oncologica, vol. 37, No. 4, 1998, pp. 347-353.
Hen et al. , "A mutated polyoma virus enhancer which is active in undifferentiated embryonal carcinoma cells is not repressed by adenovirus-2 E1A products", Nature, vol. 321, May 1986, pp. 249-251.
Herr et al., "The SV40 Enhancer is Composed of Multiple Functional Elements That Can Compensate for One Another", Cell, vol. 45, May 9, 1986, pp. 461-470.
Hilton et al., "Saturation Mutagenesis of the WSxWS Motif of the Erythropoietin Receptor", The Journal of Biological Chemistry, vol. 271, No. 9, Mar. 1, 1996, pp. 4699-4708.
Hirochika et al., "Enhancers and trans-Acting E2 Transcriptional Factors of Papillomaviruses", Journal of Virology, vol. 61, No. 8, Aug. 1987, pp. 2599-2606.
Hirsch et al., "Identification of Positive and Negative Regulatory Elements Governing Cell-Type-Specific Expression of the Neural Cell Adhesion Molecule Gene", Molecular and Cellular Biology, vol. 10, No. 5, May 1990, pp. 1959-1968.
Holbrook et al., "cis-Acting Transcriptional Regulatory Sequences in the Gibbon Ape Leukemia Virus (GALV) Long Terminal Repeat", Virology, vol. 157, Mar. 1987, Issue 1, pp. 211-219.
Holden et al., "The molecular structure of insecticyanin from the tobacco hornworm *Manduca sexta* L. at 2.6 A resolution", The EMBO Journal, vol. 6, No. 6, 1987, pp. 1565-1570.
Horlick et al., "The Upstream Muscle-Specific Enhancer of the Rat Muscle Creatine Kinase Gene Is Composed of Multiple Elements" Molecular and Cellular Biology, Jun. 1989, vol. 9, No. 6, pp. 2396-2413.
Huang et al., "Glucocorticoid Regulation of the Ha-MuSV p21 Gene Conferred by Sequences from Mouse Mammary Tumor Virus", Cell., vol. 27, Dec. 1981, Part 1, pp. 245-255.
Hug et al., "Organization of the Murine Mx Gene and Characterization of Its Interferon-and Virus-Inducible Promoter", Molecular and Cellular Biology, Aug. 1988, vol. 8, No. 8, pp. 3065-3079.
Hui et al., "Pathways for Potentiation of Immunogenicity during Adjuvant-Assisted Immunizations with Plasmodium falciparum Major Merozoite Surface Protein 1", Infection and Immunity, Nov. 1998, vol. 66, No. 11, pp. 5329-5336.
Hwang et al., "Characterization of the S-Phase-Specific Transcription Regulatory Elements in a DNA Replication-Independent Testis-Specific H2B (TH2B) Histone Gene", Molecular and Cellular Biology, vol. 10, No. 2, Feb. 1990, pp. 585-592.
Imagawa et al., "Transcription Factor AP-2 Mediates Induction by Two Different Signal-Transduction Pathways" Protein Kinase C and cAMP, Cell., vol. 51, Oct. 23, 1987, pp. 251-260.
Imbra et al., "Phorbol ester induces the transcriptional stimulatory activity of the SV40 enhancer", Nature, vol. 323, Oct. 9, 1986, pp. 555-558.
Imler et al., "Negative Regulation Contributes to Tissue Specificity of the Immunoglobulin Heavy-Chain Enhancer", Molecular and Cellular Biology, Jul. 1987, vol. 7, No. 7, pp. 2558-2567.
Imperiale et al., "Adenovirus 5 E2 Transcription Unit: an E1A-Inducible Promoter with an Essential Element That Functions Independently of Position or Orientation", Molecular and Cellular Biology, vol. 4, No. 5, May 1984, pp. 875-882.
Innis et al., "DNA sequencing with Thermus aquaticus DNA polymerase and direct sequencing of polymerase chain reaction-amplified DNA", Proc. Natl. Acad. Sci. USA, vol. 85, Dec. 1988, pp. 9436-9440.
Inouye et al., "Up-promoter mutations in the Ipp gene of *Escherichia coli*", Nucleic Acids Research, vol. 13, No. 9, received Mar. 4, 1985, accepted Apr. 5, 1985, pp. 3101-3109.
Irie et al., "Regression of cutaneous metastatic melanoma by intralesional injection with human monoclonal antibody to ganglioside GD2", Proc. Natl. Acad. Sci. USA, vol. 83, Nov. 1986, pp. 8694-8698.
Jakobovits et al., "A Discrete Element 3' of Human Immunodeficiency Virus 1 (HIV-1) and HIV-2 mRNA Initiation Sites Mediates Transcriptional Activation by an HIV trans Activator", Molecular and Cellular Biology, Jun. 1988, vol.8, No. 6, pp. 2555-2561.
Jameel et al., "The Human Hepatitis B Virus Enhancer Requires trans-Acting Cellular Factor(s) for Activity", Molecular and Cellular Biology. Feb. 1986, vol. 6, No. 2, pp. 710-715.
Jaynes et al., "The Muscle Creatine Kinase Gene Is Regulated by Multiple Upstream Elements, Including a Muscle-Specific Enhancer", Molecular and Cellular Biology, Jan. 1988, vol. 8, No. 1, pp. 62-70.
Johnson et al., "Protein kinase inhibitor prevents pulmonary edema in response to H2O2", American Journal of Physiology, vol. 256, 1989, pp. H1012-H1022.
Ju et al., "Interleukin-18 gene transfer increases antitumor effects of suicide gene therapy through efficient induction of antitumor immunity", Gene Therapy, 2000, vol. 7, pp. 1672-1679.
Kadesch et al., "Effects of the Position of the Simian Virus 40 Enhancer on Expression of Multiple Transcription Units in a Single Plasmid", Molecular and Cellular Biology, Jul. 1986, vol. 6, No. 7, pp. 2593-2601.
Kaeppler et al., Silicon carbide fiber-mediated DNA delivery into plant cells, Plant Cell Reports, 1990, vol. 9, pp. 415-418.
Kaneda et al., "Increased Expression of DNA Cointroduced with Nuclear Protein in Adult Rat Liver", Science, vol. 243, No. 4889, Jan. 20, 1989, pp. 375-378.
Karin et al., Metal-Responsive Elements Act as Positive Modulators of Human Metallothionein-IIa Enhancer Activity, Molecular and Cellular Biology, Feb. 1987, vol. 7. No. 2, pp. 606-613.
Katinka et al., "Expression of Polyoma Early Functions in Mouse Embryonal Carcinoma Cells Depends on Sequence Rearrangements in the Beginning of the Late Region", Cell, vol. 20, Jun. 1980, pp. 393-399.
Katinka et al., "Polyoma DNA sequences involved in control of viral gene expression in murine embryonal carcinoma cells", Nature, vol. 290, Apr. 1981, pp. 720-722.
Kato et al., "Expression of Hepatitis B Virus Surface Antigen in Adult Rat Liver", The Journal of Biological Chemistry, vol. 266, No. 6, Feb. 25, 1991, pp. 3361-3364.
Kawamoto et al., "Identification of the Human Beta-Actin Enhancer and Its Binding Factor", Molecular and Cellular Biology, Jan. 1988, vol. 8, No. 1, pp. 267-272.

(56) References Cited

OTHER PUBLICATIONS

Kerr et al., "Apoptosis: A Basic biological Phenomenon with Wide-Ranging Implications in Tissue Kinetics", Br. J. Cancer, received for publication Apr. 1972, published 1972, vol. 26, pp. 239-257.

Kerschner et al., "Identification and Characterization of Bahia Grande, Reed Ranch and Muir Springs Viruses, Related Members of the Family Rhabdoviridae with Widespread Distribution in the United States", J. Gen. Virology, Jun. 1986 vol. 67, No. 6, pp. 1081-1089.

Kiledjian et al., "Identification and Characterization of Two Functional Domains within the Murine Heavy-Chain Enhancer", Molecular and Cellular Biology, Jan. 1988, vol. 8, No. 1, pp. 145-152.

Kinoh et al., "Generation of a recombinant Sendai virus that is selectively activated and lyses human tumor cells expressing matrix metalloproteinases", Gene Therapy, 2004, published online Apr. 15, 2004, vol. 11, pp. 1137-1145.

Klamut et al., "Molecular and Functional Analysis of the Muscle-Specific Promoter Region of the Duchenne Muscular Dystrophy Gene", Molecular and Cellular Biology, Jan. 1990, vol. 10, No. 1, pp. 193-205.

Koch et al., "Anatomy of a New B-Cell-Specific Enhancer", Molecular and Cellular Biology, Jan. 1989, vol. 9, No. 1, pp. 303-311.

Kraus et al., "Alternative promoter usage and tissue specific expression of the mouse somatostatin receptor 2 gene", FEBS Letters 428, May 29, 1998, Issue 3, pp. 165-170.

Kriegler et al., "Enhanced Transformation by a Simian Virus 40 Recombinant Virus Containing a Harvey Murine Sarcoma Virus Long Terminal Repeat", Molecular and Cellular Biology, Mar. 1983, vol. 3, No. 3, pp. 325-339.

Kriegler et al., "Transformation Mediated by the SV40 T Antigens: Separation of the Overlapping SV40 Early Genes with a Retroviral Vector", Cell., vol. 38, Sep. 1984, pp. 483-491.

Kriegler et al., "A Novel Form of TNF/Cachectin Is a Cell Surface Cytotoxic Transmembrane Protein: Ramifications for the Complex Physiology of TNF", Cell., vol. 53, Apr. 8, 1988, pp. 45-53.

Kuhl et al., "Reversible Silencing of Enhancers by Sequences Derived from the Human IFN-alpha Promoter", Cell., vol. 50, Sep. 25, 1987, pp. 1057-1069.

Kunz et al., "Identifications of the promoter sequences involved in the interleukin-6 dependent expression of the rat alpha2-macroglobulin gene", Nucleic Acids Research, vol. 17, No. 3, 1989, accepted for publication Jan. 13, 1989, pp. 1121-1138.

Kwoh et al., "Transcription-based amplification system and detection of amplified human immunodeficiency virus type 1 with a bead-based sandwich hybridization format", Proc. natl. Acad. Sci. USA, vol. 86, Feb. 1989, pp. 1173-1177.

Kyte et al., "A Simple Method for Displaying the Hydropathic Character of a Protein", Journal Molecular Biology, 1982, vol. 157, pp. 105-132.

Lareyre et al., "A 5-Kilbase pair Promoter Fragment of the Murine Epididymal Retinoic Acid-binding Protein Gene Drives the Tissue-specific, Cell-specific, and Androgen-regulated Expression of a Foreign Gene in the Epididymis of Transgenic Mice", The Journal of Biological Chemistry, vol. 274, No. 12, Mar. 19, 1999, pp. 8282-8290.

Larsen et al., "Repression mediates cell-type-specific expression of the rat growth hormone gene", Proc. Natl. Acad. Sci, USA, vol. 83, Nov. 1986, pp. 8283-8287.

Laspia et al., "HIV-1 Tat Protein Increases Transcriptional Initiation and Stabilizes Elongation", Cell., vol. 59, Oct. 20, 1989, pp. 283-292.

Latimer et al., "Highly Conserved Upstream Regions of the alphal-Antitrypsin Gene in Two Mouse Species Govern Liver-Specific Expression by Different Mechanisms", Molecular and Cellular Biology, Feb. 1990, vol. 10, No. 2, pp. 760-769.

Lawson et al., "Recombinant vesicular stomatitis viruses from DNA", Proc. Natl. Acad. Sci. USA, vol. 92, May 1995, pp. 4477-4481.

Lee et al., "The Highly Basic Ribosomal Protein L41 Interacts with the beta Subunit of Protein Kinase CKII and Stimulates Phosphorylation of DNA Topoisomerase IIalpha by CKII", Biochemical and Biophysical Research Communications, vol. 238, Received Jul. 29, 1997, published 1997, pp. 462-467.

Lee et al., "Glucocorticoids regulate expression of dihydrofolate reductase cDNA in mouse mammary tumour virus chimaeric plasmids", Nature, vol. 294, Nov. 19, 1981, pp. 228-232.

Lee et al., "Functional Analysis of the steroid hormone control region of mouse mammary tumour virus", Nucleic Acids Research, vol. 12, No. 10, accepted for publication Apr. 17, 1984, published 1984, pp. 4191-4206.

Levenson et al., "Internal Ribosomal Entry Site-Containing Retroviral Vectors with Green Fluorescent Protein and Drug Resistance Markers", Human Gene Therapy, May 20, 1998, vol. 9, pp. 1233-1236.

Levinson et al., "Activation of SV40 genome by 72-base pair tandem repeats of Moloney sarcoma virus", Nature, vol. 295, Feb. 18, 1982, pp. 568-572.

Logg et al., "A Uniquely Stable Replication-Competent Retrovirus Vector Achieves Efficient Gene Delivery in Vitro and in Solid Tumors", Human Gene Therapy, vol. 12, May 20, 2001, pp. 921-932.

Luria et al., "Promoter and enhancer elements in the rearranged alpha chain gene of the human T cell receptor", The EMBO Journal, Nov. 1987, vol. 6, No. 11, pp. 3307-3312.

Lusky et al., "Transient replication of bovine papilloma virus type 1 plasmids: cis and trans requirements", Proc. Natl. Acad. Sci. USA, Jun. 1986, vol. 83, pp. 3609-3613.

Lusky et al., "Bovine Papilloma Virus Contains an Activator of Gene Expression at the Distal End of the Early Transcription Unit", Molecular and Cellular Biology, Jun. 1983, vol. 3, No. 6, pp. 1108-1122.

Macejak et al., "Internal initiation of translation mediated by the 5' leader of a cellular mRNA", Letters to Nature, vol. 353, Sep. 5, 1991, pp. 90-94.

Majors et al., "A small region of the mouse mammary tumor virus long terminal repeat confers glucocorticoid hormone regulation on a linked heterologous gene", Proc. Natl. Acad. Sci, USA, vol. 80, Oct. 1983, pp. 5866-5870.

McNeall et al., "Hyperinducible gene expression from a metallothionein promoter containing additional metal-responsive elements", Gene, accepted for publication Nov. 3, 1988, published 1989, vol. 76, pp. 81-88.

Miksicek et al., "Glucocorticoid Responsiveness of the Transcriptional Enhancer of Moloney Murine Sarcoma Virus", Cell., Jul. 18, 1986, vol. 46. pp. 283-290.

Mineta et al., "Attenuated multi-mutated herpes simplex virus-1 for the treatment of malignant gliomas", Nature Medicine, vol. 1, No. 9, Sep. 1995,pp. 938-943.

Mitchell et al., "Active Specific Immunotherapy of Melanoma With Allogeneic Cell Lysates", NY Acad. Sci., 1993, vol. 690, pp. 153-166.

Mordacq et al., "Co-localization of elements required for phorbol ester stimulation and glucocorticoid repression of proliferin gene expression", Genes & Development, accepted for publication Apr. 7, 1989, published 1989, vol. 3, pp. 760-769.

Moreau et al., "The SV40 72 base repair repeat has a striking effect on gene expression both in SV40 and other chimeric recombinants", Nucleic Acids Research, vol. 9, No. 22, 1981, received for publication Oct. 16, 1981, published 1981, pp. 6047-6088.

Muesing et al., "Regulation of mRNA Accumulation by a Human Immunodeficiency Virus Trans-Activator Protein", Cell., vol. 48, Feb. 27, 1987, pp. 691-701.

Nakaya et al., "Recombinant Newcastle Disease Virus as a Vaccine Vector", Journal of Virology, Dec. 2001, vol. 75, No. 23, pp. 11868-11873.

Ng et al., "Regulation of the human beta-actin promoter by upstream and intron domains", Nucleic Acids Research, vol. 17., No. 2, 1989, accepted for publication Dec. 20, 1988, pp. 601-615.

(56) References Cited

OTHER PUBLICATIONS

Nicolau et al., "Liposome-Mediated DNA Transfer in Eukaryotic Cells, Dependence of the transfer Efficiency Upon the Type of Liposomes Used and the Host Cell Cycle Stage", Biochimica et Biophysica Acta, vol. 721, Received for publication Mar. 31, 1982, published 1982, pp. 185-190.
Nicolau et al., "Liposomes as Carriers for in Vivo Gene Transfer and Expression", Methods in Enzymology, vol. 149, 1987, pp. 157-176.
Nomoto et al., "Cloning and Characterization of the alternative promoter regions of the human LIMK2 gene responsible for alternative transcripts with tissue-specific expression", Gene, vol. 236, accepted for publication Jun. 24, 1999, published 1999, pp. 259-271.
Ohara et al., "One-sided polymerase chain reaction: The amplification of cDNA", Proc. Natl. Acad. Sci. USA, Aug. 1989, vol. 86, pp. 5673-5677.
Omirulleh et al., "Activity of a chimeric promoter with the doubled CaMV 35S enhancer element in protoplast-derived cells and transgenic plants in maize", Plant Molecular Biology, vol. 21, accepted for publication Oct. 4, 1992, published 1993, pp. 415-428.
Ornitz et al., "Promoter and Enhancer Elements from the Rat Elastase I Gene Function Independently of Each Other amd of Heterologous Enhancers", Molecular and Cellular Biology, Oct. 1987, vol. 7, No. 10, pp. 3466-3472.
Ondek et al., "Discrete elements within the SV40 enhancer region display different cell-specific enhancer activities", The EMBO Journal, Apr. 1987, vol. 6, No. 4, pp. 1017-1025.
Palmiter et al., "Differential Regulation of Metallothionein-Thymidine Kinase Fusion Genes in Transgenic Mice and Their Offspring", Cell., Jun. 1982, vol. 29, pp. 701-710.
Palmiter et al., "Dramatic Growth of Mice that Develop from Eggs Microinjected with Metallothionein-Growth Hormone Fusion Genes", Nature, Dec. 16, 1982, vol. 300, pp. 611-615.
Pech et al., "Functional Identification of Regulatory Elements within the Promoter Region of Platelet-Derived Growth Faction 2", Molecular and Cellular Biology, Feb. 1989, vol. 9, No. 2, pp. 396-405.
Pelletier et al., "Internal initiation of translation of eukaryotic mRNA directed by a sequence derived from poliovirus RNA", Nature, vol. 334, Jul. 28, 1988, pp. 320-325.
Perez-Stable et al., "Roles of Fetal G-gamma-Globin Promoter Elements and the Adult beta-Globin 3' Enhancer in the Stage-Specific Expression of Globin Genes", Molecular and Cellular Biology, Mar. 1990, vol. 10, No. 3, pp. 1116-1125.
Picard et al., "A lymphocyte-specific enhancer in the mouse immunoglobulin k gene", Nature, Jan. 5, 1984, vol. 307, pp. 80-82.
Pietras et al., "Remission of human breast cancer xenografts on therapy with humanized monoclonal antibody to HER-2 receptor and DNA-reactive drugs", Oncogene, accepted for publication May 18, 1998, published 1998, pp. 2235-2249.
Pinkert et al., "An albumin enhancer located 10kb upstream functions along with its promoter to direct efficient, liver-specific expression in transgenic mice", Genes & Development, accepted for publication Mar. 4, 1987, vol. 1, published 1987, pp. 268-276.
Ponta et al., "Hormonal response region in the mouse mammary tumor virus along terminal repeat can be dissociated from the proviral promoter and has enhancer properties", Proc. Natl., Acad. Sci. USA, Feb. 1985, vol. 82, pp. 1020-1024.
Porton et al., "Immunoglobulin Heavy-Chain Enhancer is Required to Maintain Transfected y2A Gene Expression in a Pre-B-Cell Line", Molecular and Cellular Biology, Mar. 1990, vol. 10, No. 3, pp. 1076-1083.
Qin et al., "Interferon-beta gene therapy inhibits tumor formation and causes regression of established tumors in immune-deficient mice", Proc. Natl. Acad. Sci. USA, Nov. 1998, vol. 95, pp. 1411-14416.
Queen et al., "Immunoglobulin Gene Transcription Is Activated by Downstream Sequence Elements", Cell, Jul. 1983, vol. 33, pp. 741-748.
Quinn et al., "Multiple Components Are Required for Sequence Recognition of the AP1 Site in the Gibbon Ape Leukemia Virus Enhancer", Molecular and Cellular Biology, Nov. 1989, vol. 9, No. 11, pp. 4713-4721.
Ravindranath et al., Role of Gangliosides in Active Immunotherapy with Melanoma Vaccine, Intern. Rev. Immunology, vol. 7, accepted for publication Apr. 26, 1991, published 1991, pp. 303-329.
Redondo et al., "A T Cell-Specific Transcriptional Enhancer Within the Human T Cell Receptor delta Locus", Science, New Series, vol. 247, No. 4947, Mar. 9, 1990, pp. 1225-1229.
Reisman et al., "Induced Expression from the Moloney Murine Leukemia Virus Long Terminal Repeat during Differentiation of Human Myeloid Cells Is Mediated Through Its Transcriptional Enhancer", Molecular and Cellular Biology, Aug. 1989, vol. 9, No. 8, pp. 3571-3575.
Resendez, Jr. et al., "Identification of Highly Conserved Regulatory Domains and Protein-Binding Sites in the Promoters of the Rat and Human Genes Encoding the Stress-Inducible 78-Kilodalton Glucose-Regulated Protein", Molecular and Cellular Biology, Oct. 1988, vol. 8, No. 10, pp. 4579-4584.
Rippe et al., "Regulatory Elements in the 5'-Flanking Region and the First Intron Contribute to Transcriptional Control of the Mouse Alpha 1 Type I Collagen Gene", Molecular and Cellular Biology, May 1989, vol. 9, No. 5, pp. 2224-2227.
Rittling et al., "AP-1/jun binding sites mediate serum inducibility of the human vimentin promoter", Nucleic Acids Research, vol. 17, No. 4, accepted for publication Dec. 27, 1988, published 1989, pp. 1619-1633.
Rodriguez et al., "Regulated Expression of Nuclear Genes by T3 RNA Polymerase and Iac Repressor, Using Recombinant Vaccinia Virus Vectors", Journal of Virology, Oct. 1990, vol. 64, No. 10, pp. 4851-4857.
Rosen et al., "The Location of Cis-Acting Regulatory Sequences in the Human T Cell Lymphotropic Virus Type III (HTLV-III/LAV) Long Terminal Repeat", Cell, Jul. 1985, vol. 41, pp. 813-823.
Rosenberg et al., "Experience with the Use of High-Dose Interleukin-2 in the Treatment of 652 Cancer Patients", 109th Annual Meeting of the American Surgical Association, Colorado Springs, Colorado, Apr. 10-12, 1989, pp. 474-484.
Sakai et al., "Hormone-mediated repression: a negative glucocorticoid response element from the bovine prolactin gene", Genes & Development, accepted for publication Jul. 13, 1988, published 1988, pp. 1144-1154.
Sanjuan et al., "The contribution of epistasis to the architecture of fitness in an RNA virus", PNAS, Oct. 26, 2004, vol. 101, No. 43, pp. 15376-15379.
Satake et al., "Biological Activities of Oligonucleotides Spanning the F9 Point Mutation within the Enhancer Region of Polyomavirus DNA", Journal of Virology, Mar. 1988, vol. 62, No. 3, pp. 970-977.
Schaffner et al., "Redundancy of Information in Enhancers as a Principle of Mammalian Transcription Control", J. Mol. Biol., submitted for publication Dec. 10, 1987, published 1988, vol. 201, pp. 81-90.
Schnell et al., "Infectious rabies viruses from cloned cDNA", The EMBO Journal, Sep. 15, 1994, vol. 13, No. 18, pp. 4195-4203.
Searle et al., "Building a Metal-Responsive Promoter with Synthetic Regulatory Elements", Molecular and Cellular Biology, Jun. 1985, vol. 5, No. 6, pp. 1480-1489.
Shafren et al., "Systemic Therapy of Malignant Human Melanoma Tumors by a Common Cold-Producing Enterovirus, Coxsackievirus A21", Clinical Cancer Research, Jan. 1, 2004, vol. 10, pp. 53-60.
Sharp et al., "HIV TAR: An RNA Enhancer", Cell, Oct. 20, 1989, vol. 59, pp. 229-230.
Shaul et al., "Multiple nuclear proteins in liver cells are bound to hepatitis B virus enhancer element and its upstream sequences", The EMBO Journal, Jul. 1, 1987, vol. 6, No. 7, pp. 1913-1920.
Sherman et al., "Class II Box Consensus Sequences in the HLA-DR alpha Gene: Transcriptional Function and Interaction with Nuclear Proteins", Molecular and Cellular Biology, Jan. 1989, vol. 9, No. 1, pp. 50-56.
Sleigh et al., "SV40 enhancer activation during retinoic acid-induced differentiation of F9 embryonal carcinoma cells", The EMBO Journal, Dec. 30, 1985, vol. 4, No. 13B, pp. 3831-3837.

(56) References Cited

OTHER PUBLICATIONS

Spalholz et al., "Transactivation of a Bovine Papilloma Virus Transcriptional Regulatory Element by the E2 Gene Product", Cell, vol. 42, Aug. 1985, pp. 183-191.
Spandau et al., "trans-Activation of Viral Enhancers by the Hepatitis B Virus X Protein", Journal of Virology, Feb. 1988, vol. 62, No. 2, pp. 427-434.
Spandidos et al., "Host-specificities of papillomavirus, Moloney murine sarcoma virus and simian virus 40 enhancer sequences,", The EMBO Journal, 1983, vol. 2, No. 7, pp. 1193-1199.
Stephens et al., "The bovine papillomavirus genome and its uses as a eukaryotic vector", Biochem. J., 1987, vol. 248, pp. 1-11.
Stillman et al., "Replication and Amplification of Novel Vesicular Stomatitis Virus Minigenomes Encoding Viral Structural Proteins", Journal of Virology, May 1995, vol. 69, No. 5, pp. 2946-2953.
Stojdl et al., "VSV strains with defects in their ability to shutdown innate immunity are potent systemic anti-cancer agents", Cancer Cell, Oct. 2003, vol. 4, p. 263-275.
Stojdl et al., "Exploiting tumor-specific defects in the interferon pathway with a previously unknown oncolytic virus", Nature Medicine, vol. 6, No. 7, Jul. 2000, pp. 821-825.
Stuart et al., "Identification of multiple metal regulatory elements in mouse metallothionein-I promoter by assaying synthetic sequences", Nature, vol. 317, Oct. 31, 1985, pp. 828-831.
Sullivan et al., "Transcriptional Enhancers in the HLA-DQ Subregion", Molecular and Cellular Biology, Sep. 1987, vol. 7, No. 9, pp. 3315-3319.
Swartzendruber et al., "Neoplastic Differentiation: Interaction of Simian Virus 40 and Polyoma Virus with Murine Teratocarcinoma Cells in Vitro", J. Cell. Physio., 1975, vol. 85, pp. 179-188.
Takada et al., "A system for functional analysis of Ebola virus glycoprotein", Proc. Natl. Acad. Sci. USA, vol. 94, Dec. 1997, pp. 14764-14769.
Takebe et al., "Sr alpha Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, Jan. 1988, vol. 8, No. 1, pp. 466-472.
Tavernier et al., "Deletion mapping of the inducible promoter of human IFN-beta gene", Nature, vol. 301, Feb. 17, 1983, pp. 634-636.
Taylor et al., "Factor Substitution in a Human HSP70 Gene Promoter: TATA-Dependent and TATA-Independent Interactions", Molecular and Cellular Biology, Jan. 1990, vol. 10, No. 1, pp. 165-175.
Taylor et al., "E1a Transactivation of Human HSP70 Gene Promoter Substitution Mutants Is Independent of the Composition of Upstream and TATA Elements", Molecular and Cellular Biology, Jan. 1990, vol. 10, No. 1, pp. 176-183.
Taylor et al., "Stimulation of the Human Heat Shock Protein 70 Promoter in Vitro by Simian Virus 40 Large T Antigen", The Journal of Biological Chemistry, Sep. 25, 1989, vol. 264, No. 27, pp. 16160-16164.
Terstegen et al., "The Vesicular Stomatitis Virus Matrix Protein Inhibits Glycoprotein 130-Dependent STAT Activation", Journal of Immunology, 2001, vol. 167, pp. 5209-5216.
Thiesen et al., "A DNA Element Responsible for the Different Tissue Specificities of Friend and Moloney Retroviral Enhancers", Journal of Virology, Feb. 1988, vol. 62, No. 2, pp. 614-618.
Travassos Da Rosa et al., "Two New Rhabdoviruses (Rhabdoviridae) Isolated from Birds During Surveillance for Arboviral Encephalitis, Northeastern United States", Emerging Infectious Diseases, vol. 8, No. 6, Jun. 2002, pp. 614-618.
Treisman, "Identification of a Protein-Binding Site That Mediates Transcriptional REsponse of the c-fos Gene to Serum Factors", Cell, vol. 46, Aug. 15, 1986, pp. 567-574.
Tronche et al., "The Rat Albumin Promoter: Cooperation with Upstream Elements Is Required when Binding of APF/HNF1 to the Proximal Element Is Partially Impaired by Mutation or Bacterial Methylation", Molecular and Cellular Biology, Nov. 1989, vol. 9, No. 11, pp. 4759-4766.
Trudel et al., "A 3' enhancer contributes to the stage-specific expression of the human beta-globin gene", Genes & Development, 1987, accepted for publication Sep. 4, 1987, vol. 1, pp. 954-961.
Tsujimoto et al., "Clustering of breakpoints on chromosome 11 in human B-cell neoplasms with the t(11 ; 14) chromosome translocation", Nature, vol. 315, May 23, 1985, pp. 340-343.
Tsujimoto et al., "Analysis of the structure, transcripts and protein products of bci-2, the gene involved in human follicular lymphoma", Proc. Natl. Acad. Sco. USA, vol. 83, Jul. 1986, pp. 5214-5218.
Tsumaki et al., "Modular Arrangement of Cartilage-and Neural Tissue-specific cis-Elements in the Mouse alpha 2(XI) Collagen Promoter", The Journal of Biological Chemistry, vol. 273, No. 36, Sep. 4, 1998, pp. 22861-22864.
Unno et al., "Oncolytic Viral Therapy for Cervical and Ovarian Cancer Cells by Sindbis Virus AR339 Strain", Clin Cancer Res., Jun. 15, 2005, vol. 11, No. 12, pp. 4553-4560.
Vanice et al., "Properties of the Human Hepatitis B Virus Enhancer: Position Effects and Cell-Type Nonspecificity", Journal of Virology, Apr. 1988, vol. 62, No. 4, pp. 1305-1313.
Vasseur et al., "Isolation and characterization of polyoma virus mutants able to develop in embryonal carcinoma cells", Proc. Natl. Acad. Sci. USA, vol. 77, No. 2, Feb. 1980, pp. 1068-1072.
Walker et al., "Strand displacement amplification—an isothermal, in vitro DNA amplification technique", Nucleic Acids Research, accepted for publication Mar. 10, 1992, published 1992, vol. 20, No. 7, pp.1691-1696.
Wang et al., "SV40 Enhancer-Binding Factors Are Required at the Establishment but Not the Maintenance Step of the Enhancer-Dependent Transcriptional Activation", Cell, vol. 47, Oct. 24, 1986, pp. 241-247.
Warren et al., "A Rapid Screen of Active Site Mutants in Glycinamide Ribonucleotide Transformylase", Biochemistry, Jul. 9, 1996, vol. 35, No. 27, pp. 8855-8862.
Weber et al., "An SV40 "Enhancer Trap" Incorporated Exogenous Enhancers or Generates Enhancers from Its Own Sequences", cell., vol. 36, Apr. 1984, pp. 983-992.
Weinberger et al., "Localization of a Repressive Sequence Contributing to B-Cell Specificity in the Immunoglobulin Heavy-Chain Enhancer", Molecular and Cellular Biology, Feb. 1988, vol. 8, No. 2, pp. 988-992.
Wells et al., "Selectivity and antagonism of chemokine receptors", Journal of Leukocyte Biology, vol. 59, Jan. 1996, pp. 53-60.
Whelan et al., "Efficient recovery of infectious vesicular stomatitis virus entirely from cDNA clones", Proc. Natl. Acad. Sci, USA, vol. 92, Aug. 1995, pp. 8388-8392.
Winoto et al., "alpha beta Lineage-Specific Expression of a the alpha T Cell Receptor Gene by Nearby Silencers", Cell, vol. ss59, Nov. 17, 1989, pp. 649-655.
Wong et al., "Appearance of beta-lactamase activity in animal cells upon liposome-mediated gene transfer", Gene, vol. 10, accepted for publication Dec. 20, 1979, published 1980, pp. 87-94.
Wu et al., "CCR5 Levels and Expression Pattern Correlate with Infectability by Macrophage-tropic HIV-1, In Vitro", J. Exp. Med, vol. 185, No. 9, May 5, 1997, pp. 1681-1691.
Yelton et al., "Affinity Maturation of the BR96 Anti-Carcinoma Antibody by Codon-Based Mutagenesis", Journal of Immunology, vol. 155, No. 4, 1995, pp. 1994-2004.
Yutzey et al., "An Internal Regulatory Element Controls Troponin I Gene Expression", Molecular and Cellular Biology, Apr. 1989, vol. 9, No. 4, pp. 1397-1405.
Zheng et al., "ATP-Binding Site of Human Brain Hexokinase as Studied by Molecular Modeling and Site-Directed Mutagenesis", Biochemistry, submitted for publication Aug. 6, 1996, published 1996, vol. 35, pp. 13157-13164.
Zhao-Emonet et al., "Deletional and mutational analysis of the human CD4 gene promoter: characterization of a minimal tissue-specific promoter", Biochimica et Biophysica Acta, vol. 1442, accepted for publication Jul. 28, 1998, published 1998, pp. 109-119.

(56) References Cited

OTHER PUBLICATIONS

Sawyer et al., "Carboxyl-carboxylate interactions in proteins", Nature, vol. 295, Jan. 7, 1982, pp. 79-80.
Chang et al., "Glucose-Regulated Protein (GRP94 and GRP78) Genes Share Common Regulatory Domains and Are Coordinately Regulated by Common trans-Acting Factors", Molecular and Cellular Biology, May 1989, vol. 9, No. 5, pp. 2153-2162.
Mouras et al., "Localization by in situ hybridization of a low copy chimaeric resistance gene introduced into plants by direct gene transfer", Mol. Gen. Genet, 1987, vol. 207, pp. 204-209.
Travassos Da Rosa et al., "Carajas and Maraba Viruses, Two New Vesiculoviruses Isolated from Phlebotomine Sand Flies in Brazil", American Journal Trop. Med. Hyg., vol. 33, No. 5, 1984, accepted for publication Mar. 2, 1984, pp. 999-1006.
Lin et al., "Chromosome localization of two human serine protease genes to region 14q11.2-q12 by in situ hybridization", Cytogenet. Cell Genet., vol. 53. 1990. pp. 169-171.
Bajorin et al., "Comparison of Criteria for Assigning Germ Cell Tumor Patients to "Good Risk" and "Poor Risk" Studies", Journal of Clinical Oncology, vol. 6, No. 5, May 1988, pp. 786-792.
Morton et al., "Technical Details of Intraoperative Lymphatic Mapping for Early Stage Melanoma", Arch. Surg. vol. 127, Apr. 1992, pp. 392-399.
Chiocca, "The host response to cancer virotherapy", Current Opinion in Molecular Therapeutics, Feb. 2008, vol. 10, No. 1, pp. 38-45.
Tronche et al., "Anatomy of the Rat Albumin Promoter", Molecular Biology Med., received for publication Jul. 12, 1989, published 1990, vol. 7, pp. 173-185.
Hensel et al., "PMA-Responsive 5' Flanking Sequences of the Human tNF Gene", Lymphokine Research, vol. 8, No. 3, 1989, pp. 347-351.
Frohman et al., "Rapid production of full-length cDNAs from rare transcripts: Amplification using a single gene-specific oligonucleotide primer", Proc. Natl. Acad. Sci, USA, vol. 85, Dec. 1988, pp. 8998-9002.
Mitchell et al., "Active-Specific Immunotherapy for Melanoma", Journal of Clinical Oncology, vol. 8, No. 5, May 1990, pp. 856-869.
Fraley et al., "The Sev System: A New Disarmed TI Plasmid Vector System for Plant Transformation", Bio/Technology, vol. 3, Jul. 1985, pp. 629-635.
Irie et al., "Human Monoclonal Antibody to Ganglioside GM2 for Melanoma Treatment", The Lancet, vol. 333, Issue 8641, Apr. 1989, 2 pages.
Rosenberg et al., "Special Report Use of Tumor-Infiltrating Lmphcytes and Interleukin-2 in the Immunotherapy of Patients with Metastatic Melanoma", The New England Journal of Medicine, Dec. 22, 1988, pp. 1676-1680.
Usdin et al., "SP6 RNA Polymerase Containing Vaccinia Virus for Rapid Expression of Cloned Genes in Tissue Culture", Biotechniques, Feb. 1993, vol. 14, No. 2, pp. 222-224.
Brun et al., "Identification of Genetically Modified Maraba Virus as an Oncolytic Rhabdovirus",Molecular Therapy, EPUF, Jun. 15, 2010, vol. 18, No. 8., pp. 1440-1449.
International Patent Application No. PCT/IB2010/003396, International Search Report dated Jul. 12, 2011.
Irie Takashi et al: "Modifications of the PSAP region of the matrix protein lead to attenuation of vesicular stomatitis virus in vitro and in vivo", Journal of General Virology, Society for General Microbiology, Spencers Wood, GB, vol. 88, No. Pt. 9, Sep. 1, 2007, pp. 2559-2567, XP 002569284, ISSN: 0022-1317, DOI: 10.1099/VIR.0.83096-0.
European Search Report dated Aug. 19, 2013, issued in respect of corresponding European Application No. 10835567.8.
International Search Report and Written Opinion issued on corresponding International Application No. PCT/CA2012/050893 dated Aug. 28, 2013.
International Preliminary Report on Patentability issued on corresponding International Patent Application No. PCT/CA2012/050893 dated Jun. 25, 2015.
Beyer, R.J. et al. "Oncoretrovirus and Lentivirus Vectors Pseudotyped with Lymphocytic Choriomeningitis Virus Glycoprotein: Generation, Concentration, and Broad Host Range" Journal of Virology. 2002. vol. 76, No. 3, pp. 1488-1495.
Watson, D.J. et al. "Targeted Transduction Patterns in the Mouse Brain by Lentivirus Vectors Pseudotyped with VSV, Ebola, Mokola, LCMV, or MuLVEnvelope Proteins" Molecular Therapy. 2002. vol. 5, No. 5, pp. 528-537.
Office Action issued on the corresponding Russian Patent Application No. 2015128078 dated Oct. 13, 2015.
Final Office Action issued a against corresponding U.S. Appl. No. 14/123,057 dated Oct. 30, 2015.
Reasons for Rejection issued against Japanese corresponding application No. P2012-542635 dated Mar. 3, 2015, with its English translation.
International Preliminary Report on Patentability issued on corresponding International Patent Application No. PCT/CA2014/050118 dated Sep. 3, 2015.
Pol, J. et al.: "Use of oncolytic rhabdoviruses as potent tumour vaccine boosters". Abstract 145, Association for Cancer Immunotherapy (CIMT) 10th Annual Meeting, May 23-25, 2012.
Palacios et al., "Farmington virus, complete genome", Genbank Accession #HM627182.
International Search Report and Written Opinion issued on corresponding International Application No. PCT/CA2012/050385 dated Aug. 24, 2012.
Extended European Search Report and Opinion issued on corresponding European Patent Application No. 12796050.8 dated Nov. 21, 2014.
Alcami et al., "The Vaccinia Virus Soluble Alpha/Beta Interferon (IFN) Receptor Binds to the Cell Surface and Protects Cells from the Antiviral Effects of IFN", Journal of Virology,Dec. 2000, p. 11230-11239 vol. 74, No. 23.
Alcami et al., "Vaccinia Virus Encodes a Soluble Type I Interferon Receptor of Novel Structure and Broad Species Specificity", Cell, vol. 61, 551-560, May 19, 1995.
Second Office Action issued against corresponding Mexican Patent Application No. MX/a/2012/006508 dated Jul. 28, 2015.
Office Action issued on the corresponding Japanese Patent Application No. P2012-542635 dated Jan. 26, 2016 with English translation.
Abschuetz et al., "Oncolytic murine autonomous parvovirus, a candidate vector for glioma gene therapy, is innocuous to normal and immunocompetent mouse glial cells", Cell Tissue Res. published online May 3, 2006, vol. 325, pp. 423-426.
Almendro et al., "Cloning of the Human Platelet Endothelial Cell Adhesion Molecule-1 Promoter and Its Tissue-Specific Expression", The Journal of Immunology, 157(12), Dec. 1996, pp. 5411-5421.
Altomonte et al., "Enhanced oncolytic potency of vesicular stomatitis virus through vector-mediated inhibition of NK and NKT cells", Cancer Gene Therapy, 2009, published online Oct. 10, 2008, vol. 16, pp. 266-278.
Angel et al., "Phorbol Ester-Inducible Genes Contain a Common Cis Element Recognized by a TPA-Modulated Trans-Action Factor", Cell, vol. 49, Jun. 19, 1987, pp. 729-739.
Angel et al., "12-0-Tetradecanoyl-Phorbol-13-Acetate Induction of the Human Collagenase Gene Is Mediated by an Inducible Enhancer Element Located in the 5'-Flanking Region", Molecular and Cellular Biology, Jun. 1987, vol. 7, No. 6, pp. 2256-2266.
Austin-Ward et al., "Gene Therapy and its applications", Rev. Med. Chile, vol. 126, No. 7, Jul. 1998, pp. 838-845.
Bakhshi et al., "Cloning the Chromosomal Breakpoint of t(14;18) Human Lymphomas: Clustering around Jh on Chromosome 14 and near a Transcriptional Unit on 18", Cell, vol. 41, Jul. 1985, pp. 899-906.
Banerji et al., "Expression of a beta-Globin Gene Is Enhanced by Remote SV40 DNA Sequences", Cell., vol. 27, Dec. 1981, Part 1, pp. 299-308.
Banerji et al., "A Lymphocyte-Specific Cellular Enhancer Is Located Downstream of the Joining Region in Immunoglobulin Heavy Chain Genes", Cell., vol. 33, Jul. 1983, pp. 729-740.

(56) References Cited

OTHER PUBLICATIONS

Bermann et al., "A Genetically Engineered Influenza A Virus with ras-Dependent Oncolytic Properties", Cancer Research, 2001, vol. 61, pp. 8188-8193.
Berkhout et al., "Tat Trans-Activates the Human Immunodeficiency Virus through a Nascent RNA Target", Cell., vol. 59, Oct. 20, 1989, pp. 273-282.
Blanar et al., "A gamma-interferon-induced factor that binds the interferon response sequence of the MHC class I gene, H-2Kb", The EMBO Journal, vol. 8, No. 4, Apr. 1989, pp. 1139-1144.
Bodine et al., "An enhancer element lies 3' to the human A gamma globin gene", The EMBO Journal. vol. 6, No. 10, Oct. 1987, pp. 2997-3004.
Boshart et al., "A Very Strong Enhancer is Located Upstream of an Immediate Early Gene of Human Cytomegalovirus", Cell., vol. 41, Jun. 1985, pp. 521-530.
Bosze et al., "A transcriptional enhancer with specificity for erythroid cells is located in the long terminal repeat of the Friend murine leukemia virus", The EMBO Journal, vol. 5, No. 7, Jul. 1986, pp. 1615-1623.
Braddock et al., "HIV-1 TAT "Activates" Presynthesized Rna in the Nucleus", Cell, vol. 58, Jul. 28, 1989, pp. 269-279.
Braisted et al., "Minimizing a binding domain from protein A", Proc. Natl. Acad. Sci. USA, vol. 93, Jun. 1996, pp. 5688-5692.
Bukowski et al., "Signal transduction abnormalities in T lymphocytes from patients with advanced renal carcinoma: clinical relevant and effects of cytokine therapy", Clinical Cancer Research, vol. 4, No. 10, Oct. 1998, pp. 2337-2347.
Bulla et al., "The hepatitis B virus enhancer modulates transcription of the hepatitis B virus surface antigen gene from an internal location", Journal of Virology, vol. 4, Apr. 1988, p. 1437-1441.
Burton et al., "Human Antibodies from Combinatorial Libraries", Advances in Immunology, vol. 57, 1994, pp. 191-280.
Campbell et al., "Functional analysis of the individual enhancer core sequences of polyomavirus: cell-specific uncoupling of DNA replication from transcription", Molecular and Cellular Biology, May 1988, vol. 8, No. 5, pp. 1993-2004.
Campere et al., "Postnatal repression of the alpha-fetoprotein gene is enhancer independent", Genes & Development, vol. 3, 1989, revised version accepted for publication Feb. 15, 1989, pp. 537-546.
Campo et al., Transcriptional control signals in the genome of bovine papillomavirus type 1, Nature, vol. 303, May 1983, pp. 77-80.
Carbonelli et al., "A plasmid vector for isolation of strong promoters in *Escherichia coli*", FEMS Microbiology Letters, vol. 177, Aug. 1999, pp. 75-82.
Celander et al., "Glucocorticoid regulation of murine leukemia virus transcription elements is specified by determinants within the viral enhancer region", Journal of Virology, Feb. 1987, vol. 6, No. 2, pp. 269-275.
Celander et al., "Regulatory Elements with in the Murine Leukemia Virus Enhancer Regions Mediate Clucocorticoid Responsiveness", Journal of Virology, vol. 62, now. 4, Apr. 1988, pp. 1314-1322.
Chandler et al., "RNA splicing specificity determined by the coordinated action of RNA recognition motifs in SR proteins", Proc. Natl. Acad. Sci. USA, vol. 94, Apr. 1997, pp. 3596-3601.
Chaterjee et al., "Negative regulation of the thyroid-stimulating hormone alpha gene by thyroid hormone: Receptor interaction adjacent to the TATA box", Proc. Natl. Acad. Sci, USA, vol. 86, Dec. 1989, pp. 9114-9118.
Chen et al., "High-efficiency transformation of mammalian cells by plasmid DNA", Molecular and Cellular Biology, Aug. 1987, vol. 7, No. 8, pp. 2745-2752.
Choi et al., "An Altered Pattern of Cross-Resistance in Multidrug-Resistant Human Cells Results from Spontaneous Mutations in the mdr1 (P-Glycoprotein) Gene," Cell, vol. 53, May 20, 1988, pp. 519-529.
Christodoulides et al., "Immunization with recombinant class I outermembrane protein from Neisseria meningitidis: influence of liposomes and adjuvants on antibody avidity, recognition of native protein and the induction of a bactericidal immune response against meningococci", Microbiology, vol. 144, No. 11, Nov. 1998, pp. 3027-3037.
Cleary et al., "Nucleotide sequence of a t(14;18) chromosomal breakpoint in follicular lymphoma and demonstration of a breakpoint-cluster region near a transcriptionally active locus of chromosome 18", Proc. Natl. Acad. Sci., USA, vol. 82, Nov. 1985, pp. 7439-7443.
Cleary et al., "Detection of a Second t(14;18) Breakpoint Cluster Region in Human Follicular Lymphomas", J. Exp. Med., vol. 164(1), Jul. 1986, pp. 315-320.
Cocea, "Duplication of a Region in the Multiple Cloning Site of a Plasmid Vector to Enhance Cloning-Mediated Addition of Restriction Sites to a DNA Fragment", Biotechniques, vol. 23(5), Nov. 1997, pp. 814-816.
Coffey et al., "Reovirus Therapy of Tumors with Activated Ras Pathway", Science, vol. 282, No. 5392, Nov. 13, 1998, pp. 1332-1334.
Cohen et al., "Serotonin Receptor Activation of Phosphoinositide Turnover in Uterine, Fundal, Vascular, and Tracheal Smooth Muscle", Journal of Cardiovascular Pharmacology, 1987, accepted for publication Nov. 7, 1986, vol. 10, pp. 176-181.
Connor et al., "Role of Residues 121 to 124 Vesicular Stomatitis Virus Matrix Protein in Virus Assembly and Virus-Host Interaction", Journal of Virology, Apr. 2006, vol. 80, No. 8, pp. 3701-3711.
Costa et al., "The cell-specific enhancer of the mouse transthyretin (prealbumin) gene binds a common factor at one site and a liver-specific factor(s) at two other sites", Molecular and Cellular Biology, Jan. 1988, vol. 8, No. 1, pp. 81-90.
Cripe et al., "Transcriptional regulation of the human papillomavirus-16 E6-E7 promoter by a heratinocyte-dependent enhancer, and by viral E2 trans-activator and repressor gene products: implications for cervical carcinogenesis", The EMBO Journal, vol. 6, No. 12, Dec. 1, 1987, pp. 3745-3753.
Culotta et al., "Fine Mapping of a Mouse Metallothionein Gene Metal Response Element", Molecular and Cellular Biology, Mar. 1989, vol. 9, No. 3, pp. 1376-1380.
Culver et al., In Vivo Gene Transfer with Retroviral Vector-Producer Cells for Treatment of Experimental Brain Tumors, Science, vol. 256, No. 5063, Jun. 12, 1992, pp. 1550-1552.
Cunningham et al., "High-Resolution Epitope Mapping of hGH-Receptor Interactions by Alanine-Scanning Mutagenesis", Science, vol. 244, No. 4908, Jun. 2, 1989, pp. 1081-1085.
Cybinski et al., "Isolation of Tibrogargan Virus, a New Australian Rhabdovirus, from Culicoides Brevitarsis", Veterinary Microbiology, 1980, accepted for publication Jun. 26, 1980, vol. 5, pp. 301-308.
Dandolo et al., "Regulation of polyoma virus transcription in murine embryonal carcinoma cells", Journal of Virology, Jul. 1983, vol. 47, No. 1, pp. 55-64.
Davidson et al., "Intralesional Cytokine Therapy in Cancer: A Pilot Study of GM-CSF Infusion in Mesothelioma", Journal of Immunotherapy, 1998, accepted for publication May 5, 1997, vol. 21, No. 5, pp. 389-398.
Deschamps et al., "Indentification of a Transcriptional Enhancer Element Upstream from the Proto-Oncogene fos", Science, vol. 230, No. 4730, Dec. 6, 1985, pp. 1174-1177.
de Villiers et al., "Polyoma virus DNA replication requires an enhancer", Nature, vol. 312, No. 5991, Nov. 15, 1984, pp. 242-246.
Dhar et al., "Effect of Preexisting Immunity on Oncolytic Adenovirus Vector INGN 007 Antitumor Efficacy in Immunocompetent and Immunosuppressed Syrian Hamsters", Journal of Virology, Mar. 2009, vol. 83, No. 5, pp. 2130-2139.
Dilman, "Perceptions of Herceptin: A Monoclonal Antibody for the Treatment of Breast Cancer", Cancer Biotherapy & Radiopharmaceuticals, vol. 14, No. 1, Feb. 1999, pp. 5-10.
Doherty et al., "Isolation of Arboviruses from Mosquitoes, Biting Midges, Sandflies and Vertebrates Collected in Queensland, 1969 and 1970", Transactions of the Royal Society of Tropical Medicine and Hygiene, vol. 67, No. 4, 1973, pp. 536-543.
Needleman et al., "A General Method Applicable to the Search for Similarities in the Amino Acid Sequence of Two Proteins," Journal of Molecular Biology, vol. 48, Mar. 1970, pp. 443-453.

(56) References Cited

OTHER PUBLICATIONS

Australian Patent Application No. 2010329551, Notice of Acceptance dated Jan. 30, 2016.
Australian Patent Application No. 2016202789, Examination Report No. 1 dated Dec. 22, 2016.
Botstein et al., "Strategies and Applications of in Vitro Mutagenesis," Science, Sep. 1985, vol. 229 (4719), pp. 1193-1201.
Bridle et al., "Immunotherapy Can Reject Intracranial Tumor Cells without Damaging the Brain Despite Sharing the Target Antigen," Journal of Immonology, Apr. 2010, vol. 184 (8), pp. 4269-4275.
Bridle et al., "Vesicular Stomatitis Virus as a Novel Cancer Vaccine Vector to Prime Antitumor Immunity Amenable to Rapid Boosting with Adenovirus," Molecular Therapy, Oct. 2009, vol. 17 (10), pp. 1814-1821.
Bruggen et al., "Database of T cell-Defined Human Tumor Antigens: the 2013 Update," Cancer Immunity, Jul. 2013, vol. 13, pp. 15.
Canadian Patent Application No. 2,836,117, Office Action dated May 5, 2016.
Cary et al., "Oncolytic Vesicular Stomatitis Virus Induces Apoptosis in U87 Glioblastoma Cells by a Type II Death Receptor Mechanism and Induces Cell Death and Tumor Clearance In Vivo," Journal of Virology, Jun. 2011, vol. 85 (12), pp. 5708-5717.
Diallo et al., "Propagation, Purification, and In Vivo Testing of Oncolytic Vesicular Stomatitis Virus Strains," Methods in Molecular Biology, Aug. 2012, vol. 797, pp. 127-140.
European Patent Application No. 10835567.8, Intention to Grant dated Apr. 13, 2016.
Hausen, "Papillomavirus Infections—A Major Cause of Human Cancers," Biochimica et Biophysica Acta, Oct. 1996, vol. 1288 (2), pp. F55-F78.
Hoffmann et al., "Fusion-Active Glycoprotein G Mediates the Cytotoxicity of Vesicular Stomatitis Virus M Mutants Lacking Host Shut-Off Activity," Journal of General Virology, Nov. 2010, vol. 91 (Pt 11), pp. 2782-2793.
Hubert et al., "STEAP: A Prostate-Specific Cell-Surface Antigen Highly Expressed in Human Prostate Tumors," Proceedings of the National Academy of Sciences, Dec. 1999, vol. 96 (25), pp. 14523-14528.
Humme et al., "The EBV Nuclear Antigen 1 (EBNA1) Enhances B Cell Immortalization Several Thosuandfold," Proceedings of the National Academy of Sciences, Sep. 2003, vol. 100 (19), pp. 10989-10994.
International Patent Application No. PCT/IB2010/003396, International Preliminary Report on Patentability dated Jun. 21, 2012.
Israel Patent Application No. 220221, Office Action and English translation dated Nov. 16, 2016.
Japanese Patent Application No. 2016-105211, Notice of Reasons for Rejection and English Translation dated May 31, 2017.
Kruisbeek et al., "Mechanisms Underlying T-Cell Tolerance," Current Opinion in Imuunology, Apr. 1996, vol. 8 (2), pp. 233-244.
Lane et al., "Vaccination-Induced Autoimmune Vitaligo is a Consequence of Secondary Trauma to the Skin," Cancer Research, Feb. 2004, vol. 64 (4), pp. 1509-1514.
Levitskaya et al., "Inhibition of Antigen Processing by the Internal Repeat Region of the Epstein-Barr Virus Nuclear Entigen-1," Nature, Jun. 1995, vol. 375 (6533), pp. 685-688.
Lun et al., "Effects of Intravenously Administered Recombinant Vesicular Stomatitis Virus (VSV ~M51) on Multifocal and Invasive Gliomas," Journal of the National Cancer Institute, Nov. 2006, vol. 98 (21), pp. 1546-1557.
Mahoney et al., "Virus-Tumor Interactome Screen Reveals ER Stress Response Can Reprogram Resistant Cancers for Oncolytic Virus-Triggered Caspase-2 Cell Death," Cancer Cell, Oct. 2011, vol. 20 (40) pp. 443-456.
Medina et al., "Development of a Manufacturing Process for an Oncolytic Vaccine," European Society of Gene and Cell Therapy French Society of Cell and Gene Therapy, Collaborative Congress 2012, Selected Oral Presentations, A49, OR052, Oct. 25-29, 2012.
Mexican Patent Application No. MX/a/2016/001812, Office Action dated May 19, 2017—English Translation Available.
Morris, "Epitope Mapping: B-Cell Epitopes," Encyclopedia of Life Sciences, Sep. 2007, pp. 1-3.
Muik et al., "Pseudotyping Vesicular Stomatitis Virus With Lymphocytic Choriomeningitis Virus Glycoproteins Enhances Infectivity for Glioma Cells and Minimizes Neurotropism," Journal of Virology, Jun. 2011, vol. 85 (11), pp. 5679-5684.
Ng et al., "Development of a FLP/FRT System for Generating Helper-Dependent Adenoviral Vectors," Molecular Therapy, May 2001, vol. 3 (5), pp. 809-815.
Nicholaou et al., "Directions in the Immune Targeting of Cancer: Lessons Learned from the Cancer-Testis Ag NY-ESO-1," Immunology and Cell Biology, Jun. 2006, vol. 84, pp. 303-317.
Ozduman et al., "Systemic Vesicular Stomatitis Virus Selectively Destroys Multifocal Glioma and Metastatic Carcinoma in Brain," The Journal of Neuroscience, Feb. 2008, vol. 28(8), pp. 1882-1893.
De Plaen et al., "Structure, Chromosomal Localization, and Expression of 12 Genes of the MAGE Family," Immunogenetics, Sep. 1994, vol. 40 (5), pp. 360-369.
Pol et al., "Maraba Virus as a Potent Oncolytic Vaccine Vector," Molecular Therapy, Feb. 2014, vol. 22 (2), pp. 420-429.
Pol et al., "Oncolytic Viruses: A Step into Cancer Immunotherapy," Virus Adaptation and Treatment, Dec. 2012, vol. 4, pp. 1-21.
Power et al., "Carrier Cell-Based Delivery of an Oncolytic Virus Circumvents Antivial Immunity," Molecular Therapy, Jan. 2007, vol. 15 (1), pp. 123-130.
Russell et al., "Oncolytic Virotherapy," Nature Biotechnology, Jul. 2012, vol. 30 (7), pp. 1-13.
Silva et al., "PLAC1, a Trophoblast-Specific Cell Surface Protein, is Expressed in a Range of Human Tumors and Elicits Spontaneous Antibody Responses," Cancer Immunity, Nov. 2007, vol. 7, pp. 18.
Stemmer, "DNA Shuffling by Random Fragmentation and Reassembly: In Vitro Recombination for Molecular Evolution," Proceedings of the National Academy of Sciences of the United States of America, Oct. 1994, vol. 91 (22), pp. 10747-10751.
Stockinger, "T Lymphocyte Tolerance: from Thymic Deletion to Peripheral Control Mechanisms," Advances in Immunology, Dec. 1999, vol. 71, pp. 229-265.
Sur et al., "Vesicular Stomatitis Virus Infection and Neuropathogenesis in the Murine Model are Associated with Apoptosis," Veterinary Pathology, Sep. 2003, vol. 40 (5), pp. 512-520.
Thompson et al., "Clustal W: Improving the Sensitivity of Progressive Multiple Sequence Alignment Through Sequence Weighting, Position-Specific Gap Penalties and Weight Matrix Choice," Nudeic Acids Research, Nov. 1994, vol. 22 (22), pp. 4673-4680.
Tyler et al., "Neural Stem Cells Target Intracranial Glioma to Deliver an Oncolytic Adenovirus in Vivo," Gene Therapy, Feb. 2009, vol. 16 (2), pp. 262-278.
Walboomers et al., "Human Papillomavirus is a Necessary Cause of Invasive Cervical Cancer Worldwide," Journal of Pathology, Sep. 1999, vol. 189 (1), pp. 12-19.
Rudikoff et al., "Single amino acid substitution altering antigen-binding specificity," Proceedings of the National Academy of Sciences, Mar. 1982, vol. 79 (6), pp. 1979-1983.
Watson et al., "Transduction of the Choroid Plexus and Ependyma in Neonatal Mouse Brain by Vesicular Stomatitis Virus Glycoprotein-Pseudotyped Lentivirus and Adena-Associated Virus Type 5 Vectors," Human Gene Therapy, Jan. 2005, vol. 16 (1), pp. 49-56.
Wollmann et al., "Some Attenuated Variants of Vesicular Stomatitis Virus Show Enhanced Oncolytic Activity against Human Glioblastoma Cells relative to Normal Brain Cells," Journal of Virology, Feb. 2010, vol. 84 (3), pp. 1563-1573.
Wollmann et al., "Oncolytic Virus Therapy for Glioblastoma Multiforme—Concepts and Candidates," The Cancer Journal, Jan. 2012, vol. 18 (1), pp. 69-81.
Young et al., "Epstein-Barr Virus: 40 Years on," Nature Reviews Cancer, Oct. 2004, vol. 4, pp. 757-768.
Zhang et al., "Oncolytic Therapeutic Potency of Farmington Virus and Modified Maraba Virus in Immunocompetent Intracranial

(56) References Cited

OTHER PUBLICATIONS

Glioma Models and in Mice Bearing Human Brain Tumor Initiating Cells Models," Neuro-Oncology, Nov. 2011, vol. 13(suppl 3), pp. iii107-iii120.
Pearson, "Silent Mutations Speak Up," Nature, Dec. 2006.
Kaufman et al, "Oncolytic Viruses: a New Class of Immunotherapy drugs", Nature Review Drug Discovery, Sep. 2015, vol. 14 (9), pp. 642-662.
Heiber, "Characterization and Development of Vesicular Stomatitis Virus for Use as an Oncolytic Vector," Open Access Dissertation, Paper 600, Aug. 2011, 124 pages.
Ferguson et al., "Systemic Delivery of Oncolytic Viruses: Hopes and Hurdles," Advances in Virology, vol. 2012 (2), Jan. 2012, pp. 1-14.
Ikeda et al., "Oncolytic Virus Therapy of Multiple Tumors in the Brain Requires Suppression of Innate and Elicited Antiviral Responses," Nature Medicine, vol. 5 (8), Aug. 1999, pp. 881-887.
Palacios et al., "Characterization of Farmington Virus, a Novel Virus From Birds That Is Distantly Related to Members of the Family Rhabdoviridae," Virology Journal, vol. 10 (219), Jul. 2013, pp. 10.
Stylli et al., "Mouse Models of Glioma," Journal of Clinical Neuroscience, vol. 22 (4), Apr. 2015, pp. 619-626.
Parato et al., "Recent Progress in the Battle between Oncolytic Viruses and Tumours," Nature Reviews Cancer, vol. 5, Dec. 2005, pp. 965-976.
Tesh et al., "Efficacy of Killed Virus vaccine, Live Attenuated Chimeric Virus Vaccine, and Passive Immunization for Prevention of West Nile Virus Encephalitis in Hamster Model," Emerging Infectious Diseases, Dec. 2002, vol. 8 (12), pp. 1392-1397.
Tesh et al., "Immunization with Heterologous Flaviviruses Protective Against Fatal West Nile Encephalitis," Emerging Infectious Diseases, Mar. 2002, vol. 8 (3), pp. 614-618.
Office Action issued against corresponding Chinese Application No. 201080063490.X dated Dec. 23, 2013, along with an English translation.
Office Action issued against corresponding Chinese Application No. 201080063490.X dated May 13, 2013, along with an English translation.
Restriction Requirement issued on parent U.S. Appl. No. 13/514,837 dated Jan. 14, 2014.
Office Action issued on parent U.S. Appl. No. 13/514,837 dated Aug. 1, 2014.
Sanjuan, Rafael et al. "The contribution of epistasis to the architecture of fitness in an RNA virus." Proc. Natl. Acad. Sci., vol. 101, issue 43, pp. 15376-15379, Oct. 26, 2004, with supporting information.
Whelan, Sean P.J., et al. "Efficient recovery of infectious vesicular stomatitis virus entirely from cDNA clones." Proc. Natl. Acad. Sci. USA, vol. 92, pp. 8388-8392, Aug. 1995, Biochemistry.
Notice of Allowance issued on parent U.S. Appl. No. 13/514,837 dated Feb. 2, 2015.
Examination Report No. 1 issued against corresponding Australian Patent Application No. 2010329551, dated May 15, 2014.
Third Office Action issued on corresponding Chinese Patent Application No. 201080063490.X, dated Aug. 13, 2014, with English translation.
Office Action issued on corresponding Israeli Patent Application No. 220221 dated Feb. 25, 2015, along with an English translation.
International Search Report and Written Opinion from International Application No. PCT/CA2014/050534 dated Aug. 28, 2014.
LeBoeuf et al., "Synergistic interaction between oncolytic viruses augments tumor killing", Molecular Therapy, May 2010, vol. 18, pp. 888-895.
Fu et al., "Incorporation of the B18R gene of vaccinia virus into an oncolytic herpes simplex virus improves antitumor activity", Molecular Therapy, Oct. 2012, vol. 20, pp. 1871-1881.
LeBoeuf et al., "Model-based rational design of an oncolytic virus with improved therapeutic potential," Nature Communications, vol. 4: 1974, pp. 1-8.
International Search Report and Written Opinion from International Application No. PCT/CA2014/050563 dated Aug. 29, 2014.
Morrissey, D. et al. (2010) Tumor Targeting with Systematically Administered Bacteria. Curr Gene Ther 10: 3-14.
Yu, Y.A., et al. (Jan. 8, 2010) Establishment and Characterization of Conditions Required for Tumor Colonization by Intravenously Delivered Bacteria. Biotech Bioeng 100:567-578.
Office Action issued on corresponding European Patent Application No. 10835567.8 dated Jun. 16, 2015.
Fourth Office Action issued on corresponding Chinese Patent Application No. 201080063490.X, dated Jan. 22, 2015.
Notice of Reasons for Rejection issued on corresponding Japanese Patent Application No. 2012-542635 dated Feb. 27, 2015, with English translation of text.
Office Action issued on Mexican Patent Application No. MX/a/2012/006508 dated Feb. 27, 2015, with English summary.
Bridle et al., "Potentiating Cancer Immunotherapy Using an Oncolytic Virus," Molecular Therapy, Aug. 2010, vol. 18 (8), pp. 1430-1439.
Banerjee et al. "Transcription and Replication of Rhabdoviruses," Microbiological Reviews, Mar. 1987, vol. 51 (1), pp. 66-87.
Pinschewer et al., "Kinetics of Protective Antibodies are Determined by the Viral Surface Antigen," The Journal of Clinical Investigation, Oct. 2004, vol. 114 (7), pp. 988-993.
Israel Patent Application No. IL251307, Office Action dated Nov. 12, 2017—English Translation Available.
Australian Patent Application No. 2016202789, Office Action dated Nov. 20, 2017.

\* cited by examiner

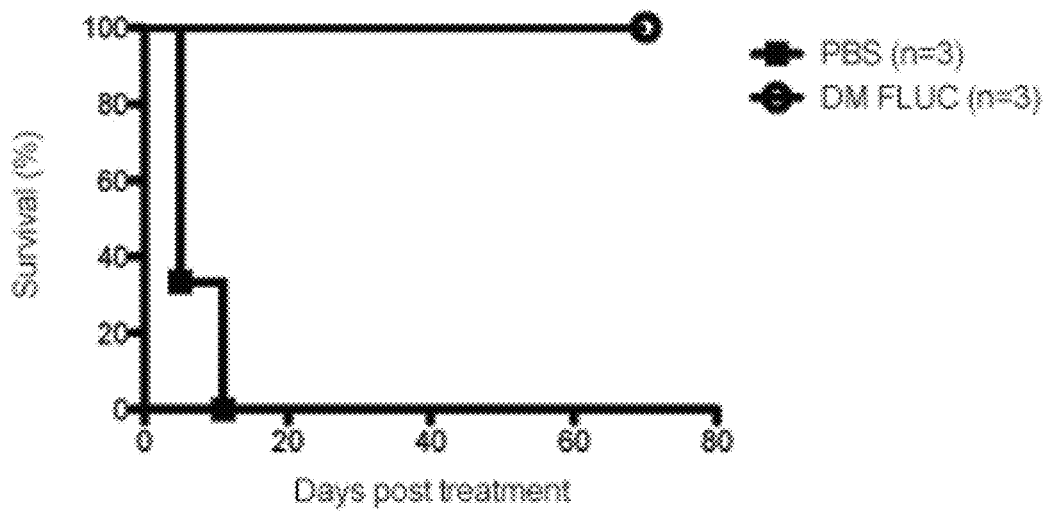
Fig. 4A(ii)
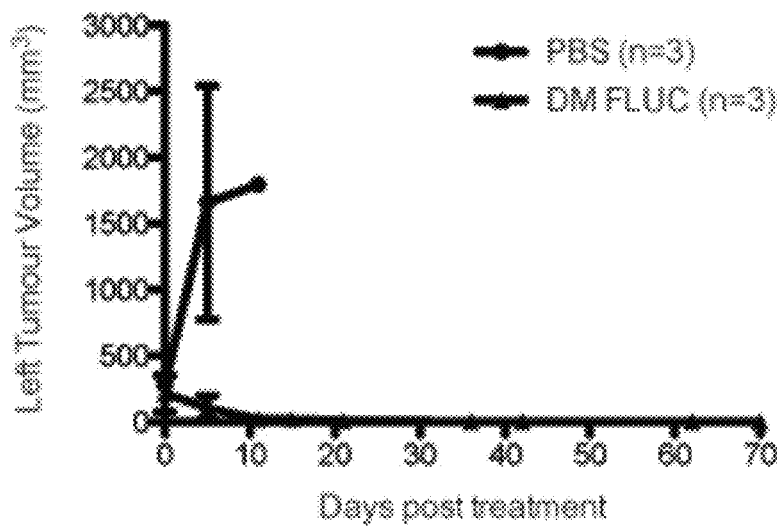
Fig. 4A(iii)

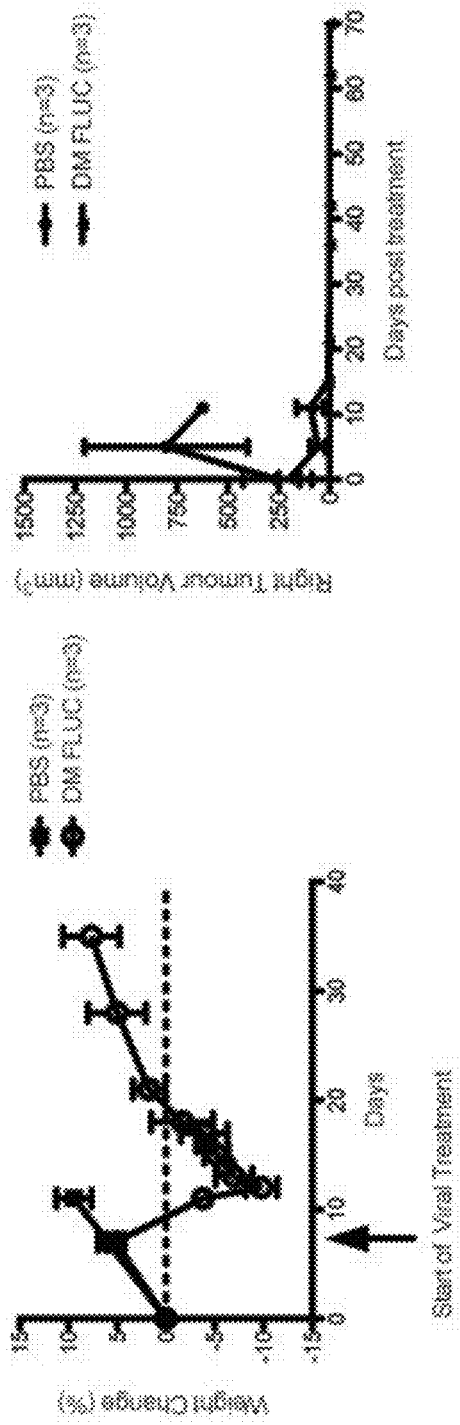
Fig. 4A(iv)

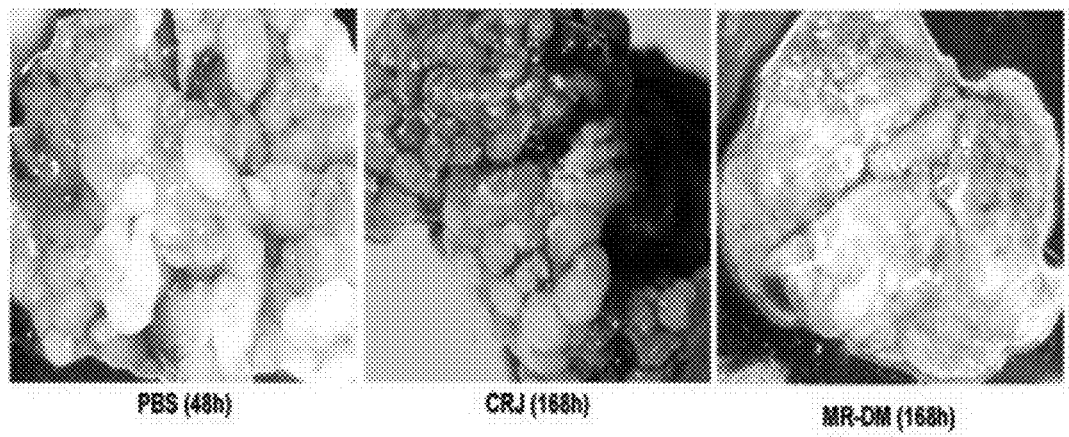
Fig. 4B(i)
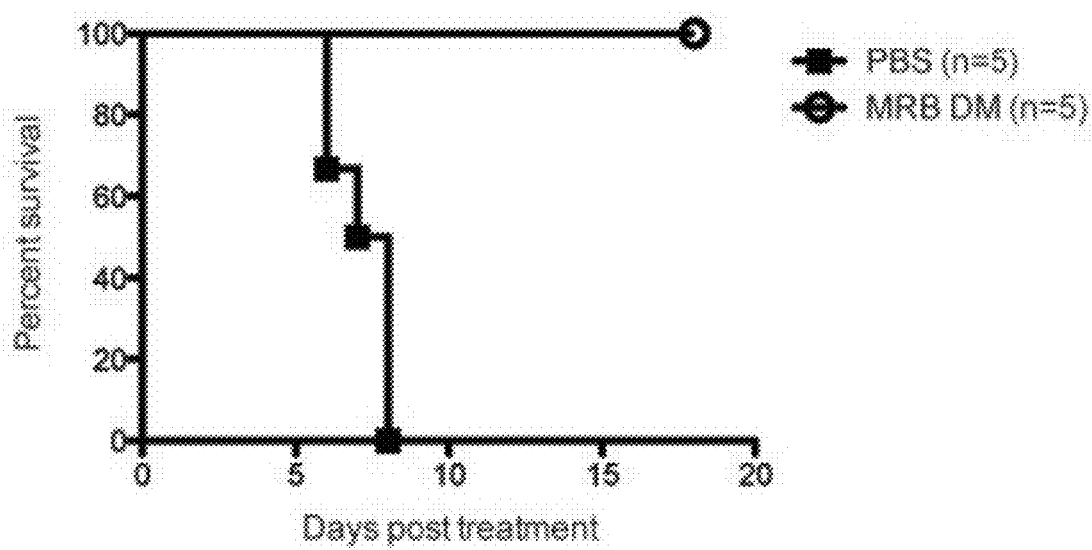
Fig. 4B(ii)

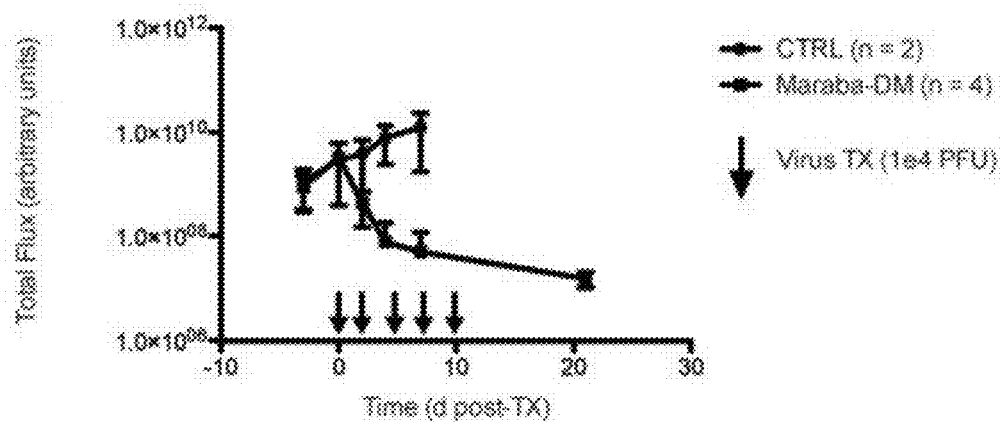
Fig. 4C(ii)
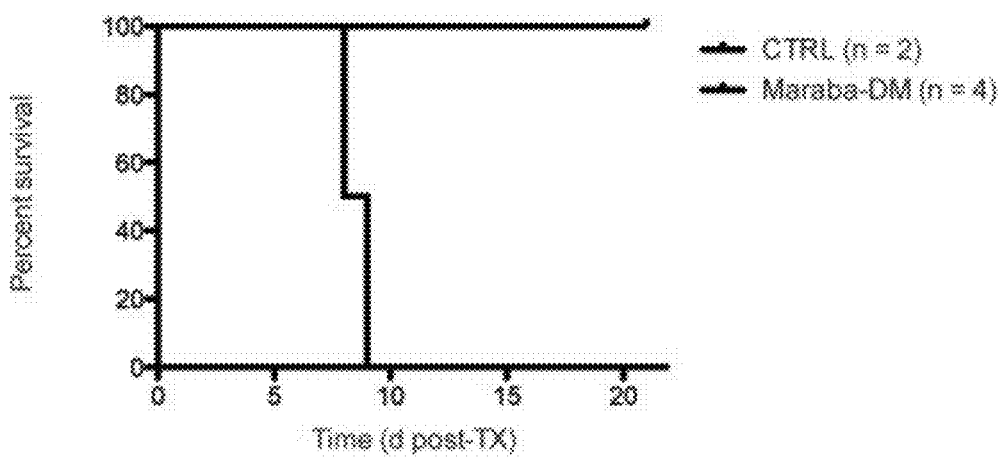
Fig. 4C(iii)

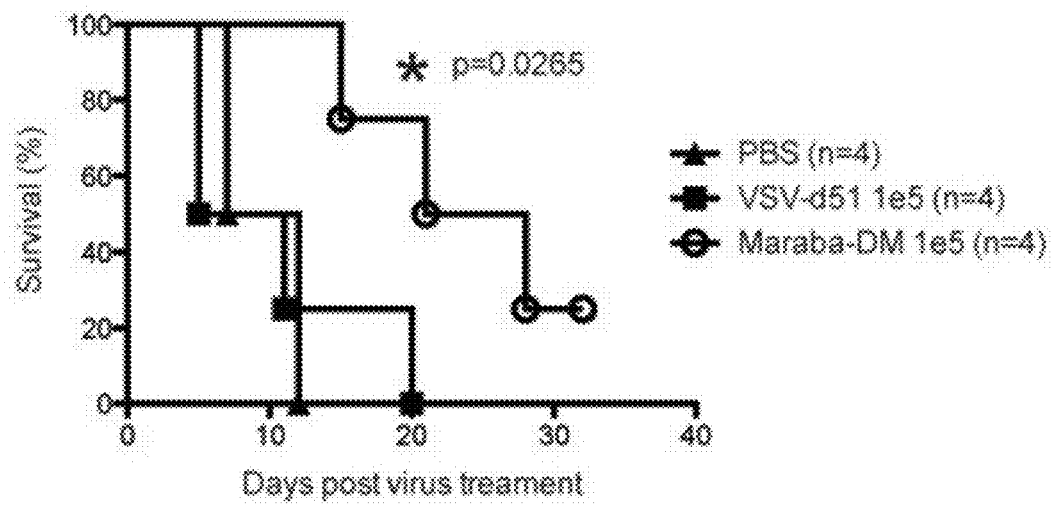
Fig. 4D(i)
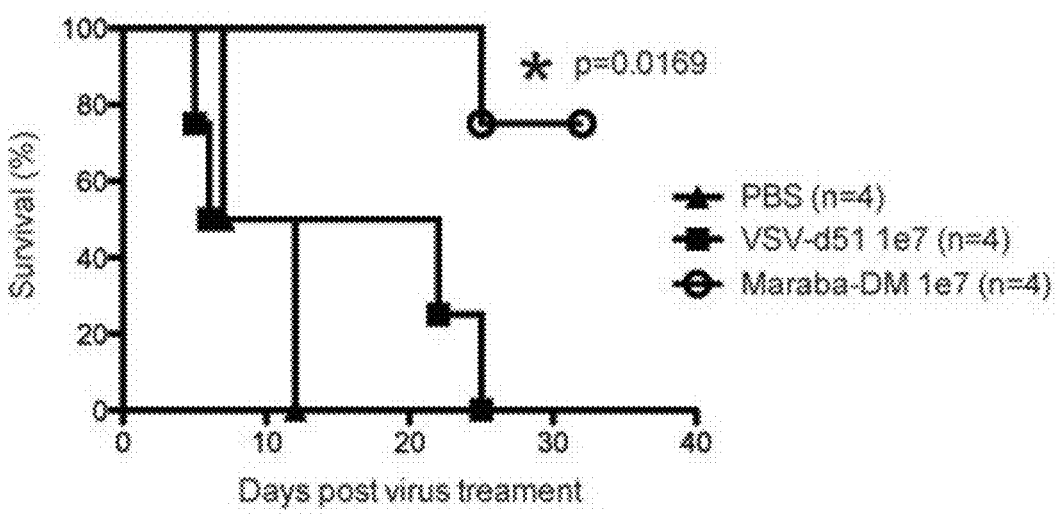
Fig. 4D(ii)

Fig. 5(i)

ONCOLYTIC RHABDOVIRUS

CROSS REFERENCE TO RELATED APPLICATIONS

This application is a divisional application of U.S. patent application Ser. No. 13/514,837 filed Jun. 8, 2012, which is a national phase entry of PCT/IB2010/003396 filed on Dec. 10, 2010, which claims priority to U.S. Provisional Patent application Ser. No. 61/285,461 filed Dec. 10, 2009, which are all incorporated herein by reference.

INCORPORATION OF SEQUENCE LISTING

A computer readable form of the Sequence Listing "PAT_7141AW-2_SequenceListing.txt", submitted via EFS-WEB and created on May 12, 2015, is herein incorporated by reference.

BACKGROUND OF THE INVENTION

I. Field of the Invention

This invention relates generally to virology and medicine. In certain aspects the invention relates to oncolytic viruses, particularly oncolytic rhabdoviruses.

II. Background

A number of viruses have been shown to replicate in and kill a wide variety of tumor cells in vitro (Sindbis virus (Unno et al., 2005); Sendai virus (Kinoh et al., 2004); Coxackie virus (Shafren et al., 2004); Herpes simplex virus (Mineta et al., 1995); Parvovirus (Abschuetz et al., 2006); Adenovirus (Heise et al., 2000); Polio virus (Gromeier et al., 2000); Newcastle disease virus; Vesicular stomatitis virus (Stojdl et al., 2000); Meales virus (Grote et al., 2001); Reovirus (Coffey et al., 1998); Retrovirus (Logg et al., 2001); Vaccinia (Timiryasova et al., 1999); and Influenza (Bergmann et al., 2001)). In addition, such viruses have demonstrated efficacy in treating animal models of cancer. There remains a need for additional therapeutics to treat cancer.

SUMMARY OF THE INVENTION

Described herein is a novel oncolytic platform and a recombinant system to genetically manipulate Maraba virus. Maraba double mutant ("DM") has been generated and demonstrates safety and efficacy by systemic delivery in multiple tumor models, both immunocompetent and human xenograft.

Several newly identified rhabdoviruses are much more efficient at killing particular cancers or cancer cell lines than VSV. Also, VSV and attenuated mutants of VSV are neurovirulent and cause CNS pathology in rodents and primates. Several rhabdoviruses do not infect the CNS (i.e., Muir Springs and Bahia Grande: Kerschner et al., 1986), and demonstrate a more acceptable safety profile. In addition, therapies based on the novel rhabdoviruses can be used to treat cancers of the CNS, both primary and secondary. The rhabdoviruses of the invention (and/or other oncolytic agents) can be used in succession to bypass the host immune response against a particular therapeutic virus(es). This would allow prolonged therapy and improve efficacy.

Embodiments of the invention include compositions and methods related to rhabdoviruses and their use as anti-cancer therapeutics. Such rhabdoviruses possess tumor cell killing properties in vitro and in vivo.

As used herein, rhabdovirus can be Maraba virus or an engineered variant of Maraba virus. The viruses described herein can be used in combination with other rhabdoviruses. Other rhabdovirus include one or more of the following viruses or variants thereof: Carajas virus, Chandipura virus, Cocal virus, Isfahan virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, *Entamoeba* virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. In certain aspects, rhabdovirus can refer to the supergroup of Dimarhabdovirus (defined as rhabdovirus capable of infection both insect and mammalian cells). In specific embodiments, the rhabdovirus is not VSV. In particular aspects the rhabdovirus is a Carajas virus, Maraba virus, Farmington, Muir Springs virus, and/or Bahia grande virus, including variants thereof. Any 1, 2, 3, 4, 5, 6, 7, 8, 9, 10, 11 12 13, 14, 15, 20, 25, 30, 35, 40, 45, 50, 55, 60, 65, 70, 75, 80, 85 or more, including all integers or ranges there between, of these virus can be specifically excluded from the claim scope.

One embodiment of the invention includes methods and compositions comprising an oncolytic Maraba virus encoding a variant M and/or G protein having an amino acid identity of at least or at most 20, 30, 40, 50, 60, 65, 70, 75, 80, 85, 90, 92, 94, 96, 98, 99, 100%, including all ranges and percentages there between, to the M or G protein of Maraba virus. In certain aspects amino acid 242 of the Maraba G protein is mutated. In further aspects amino acid 123 of the M protein is mutated. In still further aspects both amino acid 242 of the G protein (SEQ ID NO:5) and amino acid 123 of the M protein (SEQ ID NO:4) are mutated. Amino acid 242 can be substituted with an arginine (Q242R) or other amino acid that attenuates the virus. Amino acid 123 can be substituted with a tryptophan (L123W) or other amino acid that attenuates the virus. In certain aspects two separate mutations individually attenuate the virus in normal healthy cells. Upon combination of the mutants the virus becomes more virulent in tumor cells than the wild type virus. Thus, the therapeutic index of the Maraba DM is increased unexpectedly.

Methods and compositions of the invention can include a second therapeutic virus, such as an oncolytic or replication defective virus. Oncolytic typically refers to an agent that is capable of killing, lysing, or halting the growth of a cancer cell. In terms of an oncolytic virus the term refers to a virus that can replicate to some degree in a cancer cell, cause the death, lysis (oncolysis), or cessation of cancer cell growth and typically have minimal toxic effects on non-cancer cells.

A second virus includes, but is not limited to an adenovirus, a vaccinia virus, a Newcastle disease virus, an alphavirus, a parvovirus, a herpes virus, a rhabdovirus, a rhabdovirus and the like. In other aspects, the composition is a pharmaceutically acceptable composition. The composition may also include a second anti-cancer agent, such as a chemotherapeutic, radiotherapeutic, or immunotherapeutic.

Further embodiments of the invention include methods of killing a hyperproliferative cell comprising contacting the cell with an isolated oncolytic rhabdovirus composition described herein.

Still further methods include the treatment of a cancer patient comprising administering an effective amount of an oncolytic rhabdovirus composition described herein.

In certain aspects of the invention, a cell may be comprised in a patient and may be a hyperproliferative, neoplastic, pre-cancerous, cancerous, metastatic, or metastasized cell. A rhabdovirus (e.g., Maraba virus) can be administered to a patient having a cell susceptible to killing by at least one rhabdovirus or a therapeutic regime or composition including a rhabdovirus. Administration of therapeutic compositions may be done 1, 2, 3, 4, 5, 6, 7, 8, 9, 10 or more times with 1, 2, 3, 4, 5, 6, 7, 8, 9, 10 or more rhabdovirus or recombinant rhabdovirus, alone or in various combinations. The composition administered can have 10, 100, $10^3$, $10^4$, $10^5$, $10^6$, $10^7$, $10^8$, $10^9$, $10^{10}$, $10^{11}$, $10^{12}$, $10^{13}$, $10^{14}$, or more viral particles or plaque forming units (pfu). Administration can be by intraperitoneal, intravenous, intra-arterial, intramuscular, intradermal, subcutaneous, or intranasal administration. In certain aspects, the compositions are administered systemically, particularly by intravascular administration, which includes injection, perfusion and the like. The methods of invention can further comprise administering a second anti-cancer therapy, such as a second therapeutic virus. In certain aspects a therapeutic virus can be an oncolytic virus, more particularly a Maraba virus. In other aspects, a second anti-cancer agent is a chemotherapeutic, a radiotherapeutic, an immunotherapeutic, surgery or the like.

Embodiments of the invention include compositions and methods related to a rhabdoviruses comprising a heterologous G protein (pseudotyped virus) and their use as anticancer therapeutics. Such rhabdoviruses possess tumor cell killing properties in vitro and in vivo. Thus, a Maraba virus as described herein may be further modified by association of a heterologous G protein as well. As used herein, a heterologous G protein includes rhabdovirus G protein. Rhabdoviruses will include one or more of the following viruses or variants thereof: Carajas virus, Chandipura virus, Cocal virus, Isfahan virus, Maraba virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, *Entamoeba* virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. In certain aspects, rhabdovirus can refer to the supergroup of Dimarhabdovirus (defined as rhabdovirus capable of infection both insect and mammalian cells). In particular aspects the rhabdovirus is a Carajas virus, Maraba virus, Muir Springs virus, and/or Bahia grande virus, including variants thereof.

Further embodiments of the invention include methods of killing a hyperproliferative cell comprising administering or contacting the cell with an oncolytic Maraba virus composition. Still further methods include the treatment of a cancer patient comprising administering an effective amount of such a viral composition.

In certain aspects of the invention, a cell may be comprised in a patient and may be a hyperproliferative, neoplastic, pre-cancerous, cancerous, metastatic, or metastasized cell. A virus of the invention can be administered to a patient having a cell susceptible to killing by at least one virus or a therapeutic regime or composition including a virus. Administration of therapeutic compositions may be done 1, 2, 3, 4, 5, 6, 7, 8, 9, 10 or more times with 1, 2, 3, 4, 5, 6, 7, 8, 9, 10 or more virus, alone or in various combinations. The composition administered can have 10, 100, $10^3$, $10^4$, $10^5$, $10^6$, $10^7$, $10^8$, $10^9$, $10^{10}$, $10^{11}$, $10^{12}$, $10^{13}$, $10^{14}$, or more viral particles or plaque forming units (pfu). Administration can be by intraperitoneal, intravenous, intra-arterial, intramuscular, intradermal, subcutaneous, or intranasal administration. In certain aspects, the compositions are administered systemically, particularly by intravascular administration, which includes injection, perfusion and the like. The methods of invention can further comprise administering a second anti-cancer therapy, such as a second therapeutic virus. In particular aspects a therapeutic virus can be an oncolytic virus such as a Maraba virus as described herein. In other aspects, a second anti-cancer agent is a chemotherapeutic, a radiotherapeutic, an immunotherapeutic, surgery or the like.

Other embodiments of the invention are discussed throughout this application. Any embodiment discussed with respect to one aspect of the invention applies to other aspects of the invention as well, and vice versa. The embodiments in the Detailed Description and Example sections are understood to be non-limiting embodiments of the invention that are applicable to all aspects of the invention.

The terms "inhibiting," "reducing," or "preventing," or any variation of these terms, when used in the claims and/or the specification includes any measurable decrease or complete inhibition to achieve a desired result, e.g., treatment of cancer. Desired results include but are not limited to palliation, reduction, slowing, or eradication of a cancerous or hyperproliferative condition or symptoms related to a cancer, as well as an improved quality or extension of life.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2B) Illustration of the Maraba genome Engineered Maraba virus as an oncolytic agent outlining the various mutation sites for our single mutants (L123W, V221Y, Q242R) and double mutant (Q242R L123W). (FIG. 2C) Mutations in the G and M protein attenuate the ability of Maraba to kill GM38 cells. Viability assays were performed in GM38 cells at 72 hours post-infection with Maraba, and the indicated Maraba mutants. (FIG. 2D) Engineering L123W mutation into Q242R Maraba mutant reverts plaque sizes to a wild-type phenotype. Plaque assay was performed in SNB19 cells infected with wild-type Maraba, single and DM variants. The diameter was measured and plaque area calculated using the following formula $A=\pi r^2$. (FIG. 2E) Maraba and Maraba variants are highly lytic in a variety of tumor cell lines. Images of PC3, ES2, A549 and SW620 cells 48 hours post infection with wild type Maraba and Maraba variants. (FIG. 2F) Cells infected with WT Maraba and the Maraba variants were assayed using resazurin for viability. Viability is dramatically reduced in all treated cell lines 48 hours post-infection with Maraba and its variants.

(FIG. 3A) The Q242R mutant blocks interferon similar to wild-type Maraba. (FIG. 3B) The L123W mutant, V221Y, Maraba ΔM51, and the double mutant L123W-M/Q242R-G allow interferon to be produced following infection of PC3 cells. (FIG. 3C) rMaraba blocks nuclear/cytoplasmic transport of IFN-β. IFN-β mRNA induction is not detected in the cytoplasmic fraction after infection with rMaraba or Maraba Q242R as determined by qRTPCR. Cells infected with 451M, L123W and Maraba DM show IFN β mRNA induction in the cytoplasm following infection.

FIGS. 4A-4D. Systemic delivery of Maraba DM is efficacious in syngeneic and xenograft mouse tumor models. (FIG. 4A) Maraba DM is effective at treating a CT-26 bilateral tumor model (i) DMGFP and DM-FLUC replicate selectively at the tumor site 24 hours post IV injection ($5\times10^8$ pfu). (ii) Durable survival of Balb/C mice with bilateral CT26 tumors post Maraba DM treatment. (iii) Tumor volumes were calculated on a biweekly basis. Error bars denote SEM. (iv) Mouse weights measured prior to and after treatment with Maraba DM and control. Error bars denote SEM. (FIG. 4B) Systemic treatment of disseminated CT-26 tumors. (i) CT-26 lung tumors were treated intravenously with either PBS, Carajas virus or Maraba DM at day 10 post tumor implantation. At day 17 animals were sacrificed and lung images were captured. (ii) Effective tumor treatment with 6 intravenous doses of Maraba DM ($5\times10^8$ pfu/dose). (FIG. 4C) Maraba DM is efficacious in a human ovarian (ES-2) xenograft model (IP injections, $1\times10^4$ pfu/dose). (i) IVIS images demonstrating a rapid tumor regression following virus treatment. (ii) Bioluminescent flux plot quantifying a significant reduction in abdominal tumor burden in response to virus treatment. (iii) Kaplan Meier plot demonstrates enhanced survival post virus treatment. (FIG. 4D) Maraba DM is superior to VSV 451 in treating ES-2 xenograft tumors (IV injections, $1\times10^5$-$1\times10^7$ pfu/dose). (i-ii) Kaplan Meier plots demonstrate enhanced survival in animals treated with Maraba DM as compared to VSV 451.

DETAILED DESCRIPTION OF THE INVENTION

Figure 1A:
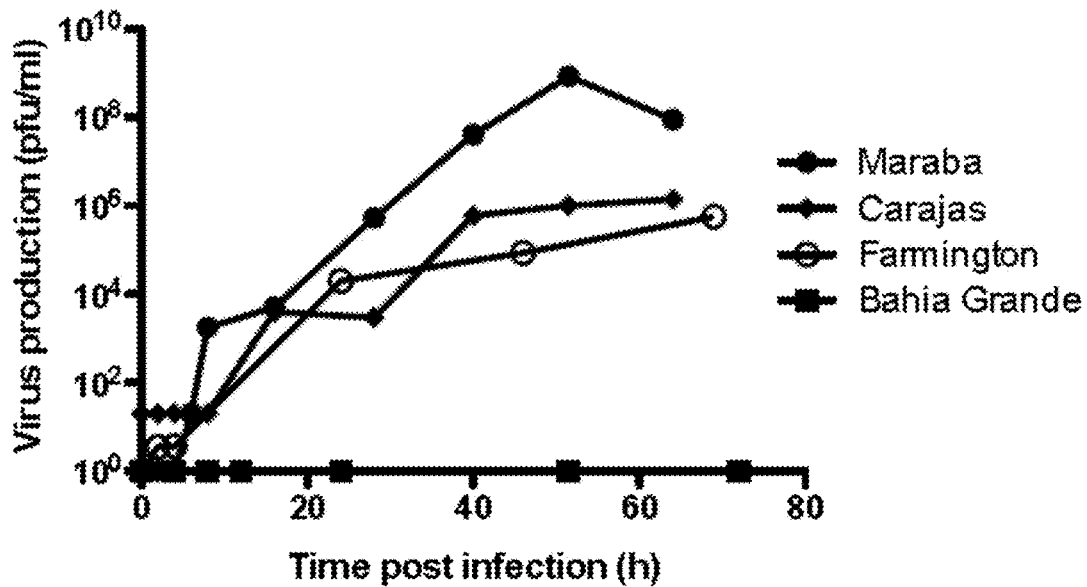
FIGS. 1A-1B. Novel Rhabdovirus Maraba demonstrate high viral productivity in cancer cells. A one step growth curve was used to quantify the viral productivity of Maraba, Carajas, Farmington and Bahia Grande in FIG. 1A NCI H226 and FIG. 1B SNB19 cells. Maraba consistently replicates to higher titers in both cell lines as compared to the other viruses.

Aspects of the invention are based on the killing by rhabdovirus (e.g., Maraba virus) or pseudotyped rhabdovirus of several kinds or types cancer cells. Some of the advantages of these oncolytic rhabdoviruses and recombinant rhabdoviruses include the following: (1) Antibodies to the inventive rhabdoviruses will be rare to non-existent in most populations of the world. (2) rhabdoviruses replicate more quickly than other oncolytic viruses such as adenovirus, reovirus, measles, parvovirus, retrovirus, and HSV. (3) Rhabdovirus grow to high titers and are filterable through 0.2 micron filter. (4) The oncolytic rhabdoviruses and recombinants thereof have a broad host range, capable of infecting many different types of cancer cells and are not limited by receptors on a particular cell (e.g., coxsackie, measles, adenovirus). (5) The rhabdovirus of the invention are amenable to genetic manipulation. (6) The rhabdovirus also has a cytoplasmic life cycle and do not integrate in the genetic material of a host cell, which imparts a more favorable safety profile.

As described herein, a novel oncolytic virus was identified to serve as a platform to build effective virus based cancer therapies. The Rhabdovirdae were screened for a virus with properties that contributed to strong oncolytic effects. Systemic delivery is an anticipated method of administration and is one beneficial aspect in treating disseminated cancers in the clinical setting. In certain aspects, a virus is delivered intravenously and can initiate infection at disparate tumor sites. It is postulated that one of the in vivo limitations to effective therapy could be that virus delivery to the tumor bed may be limiting. In fact, dose thresholds below which virus is not effectively delivered to the tumor in mouse models have been observed, and these doses were not efficacious (Stojdl et al., 2003). Thus, the inventors were interested in finding viruses capable of killing tumor cells at low multiplicities of infection ("MOI"), replicate quickly, and to produce large numbers of progeny to maximize the probability and magnitude of tumor bed infection. To this end a multiwell plate assay was designed to identify viruses capable of killing a wide array of tumor cells at lowMOI. Subsequent to the MOI assays, the most potent viruses were assayed for growth kinetics and burst size. Maraba virus was identified as a promising candidate.

The full genome sequence of Maraba (SEQ ID NO:1) and Carajas (CRJ) (SEQ ID NO:7) were obtained.

Once Maraba virus was identified as a candidate, the inventors conducted genetic engineering studies to improve its tumor selectivity. Two interesting mutations were originally identified in studies to monitor RNA virus fitness in changing environments. In a previous report, both L123W and H242R (Q242R in Maraba) were individually able to increase VSV replication in BHK 21 cells. Additionally, it was reported that the combination of the two mutations retained this fitness phenotype. The L123W/Q242R mutations provide a virus with a therapeutic index of at least 3 logs ($EC_{50}<10^{-3}$ MOI on some tumor cells; $EC_{50}=3$ MOI on GM38 fibroblasts). The Q242R and L123W mutations are attenuating on normal fibroblasts. The L123W mutation seems to function much the same as ΔM51 and V221Y, resulting in a deficit in the ability to block nuclear/cytoplasmic transport thereby inhibiting the host IFN transcriptional cascade. To the best of the inventors knowledge, this is the first demonstration of a role for this region of the matrix protein in mitigating host innate immune defenses. Previously, mutations in this region have been reported to affect translation of virus mRNA (Connor et al., 2006). The Q242R mutation severely reduces Maraba virus cytolysis of normal cells, but in an IFN independent manner. These properties form the basis of a potent tumor selectivity that results in a significant increase in therapeutic index for this novel Maraba based oncolytic virus platform.

As predicted from in vitro results, the Maraba DM variant was significantly less toxic than the wild type virus when delivered intravenously into Balb/C mice. The maximum tolerated dose ("MTD") was 100 fold greater than the WT virus. This allowed dosing well below the MTD to achieve significant tumor regressions in both tumor models. In the CT26 model for example, 6 doses of Maraba DM virus were sufficient to provide complete durable cures in all mice. Particularly important for the clinical setting, Maraba DM was effective at treating both a human xenograft tumor and an immunocompetent syngeneic tumor model by systemic delivery. Virus replication was demonstrated at the tumor site in the CT26 tumor model following intravenous injection, consistent with viral mediated oncolysis as a contributor to efficacy. In fact, Maraba DM appeared to be more effective than previous candidates VSV ΔM51 in the ES2 xenograft model. This is consistent with the in vitro data demonstrating Maraba DM to be more effective at killing tumor cells than even WT virus. Several studies have definitively demonstrated that the host immune response plays a positive and negative role in oncolytic virus efficacy (Dhar et al., 2008; Altomonte et al., 2008; Endo et al., 2008; Chiocca, 2008).

Embodiments of the invention include compositions and methods related to Maraba viruses or pseudotyped rhabdoviruses and their use as anti-cancer therapeutics.

I. Family Rhabdoviridae (Rhabdovirus)

The archetypal rhabdoviruses are rabies and vesicular stomatitis virus (VSV), the most studied of this virus family. Although these viruses share similar morphologies, they are very different in their life cycle, host range, and pathology. Rhabdovirus is a family of bullet shaped viruses having non-segmented (−)sense RNA genomes. There are greater than 250 Rhabdoviruses known that infect mammals, fish, insects, and plants.

The family Rhabdovirus includes, but is not limited to: Carajas virus, Chandipura virus (AF128868/gi:4583436, AJ810083/gi:57833891, AY871800/gi:62861470, AY871799/gi:62861468, AY871798/gi:62861466, AY871797/gi:62861464, AY871796/gi:62861462, AY871795/gi:62861460, AY871794/gi:62861459, AY871793/gi:62861457, AY871792/gi:62861455, AY871791/gi:62861453), Cocal virus (AF045556/gi:2865658), Isfahan virus (AJ810084/gi:57834038), Maraba virus (SEQ ID NO:1-6), Carajas virus (SEQ ID NO:7-12, AY335185/gi:33578037), Piry virus (D26175/gi:442480, Z15093/gi:61405), Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus (DQ457103/gi191984805), Perinet virus (AY854652/gi:71842381), Tupaia virus (NC_007020/gi:66508427), Farmington, Bahia Grande virus (SEQ ID NO:13-18), Muir Springs virus, Reed Ranch virus, Hart Park virus, Flanders virus (AF523199/gi:25140635, AF523197/gi:25140634, AF523196/gi:25140633, AF523195/gi:25140632, AF523194/gi:25140631, AH012179/gi:25140630), Kamese virus, Mosqueiro virus, Mossuril virus, Barur virus, Fukuoka virus (AY854651/gi:71842379), Kern Canyon virus, Nkolbisson virus, Le Dantec virus (AY854650/gi:71842377), Keuraliba virus, Connecticut virus, New Minto virus, Sawgrass virus, Chaco virus, Sena Madureira virus, Timbo virus, Almpiwar virus (AY854645/gi:71842367), Aruac virus, Bangoran virus, Bimbo virus, Bivens Arm virus, Blue crab virus, Charleville virus, Coastal Plains virus, DakArK 7292 virus, *Entamoeba* virus, Garba virus, Gossas virus, Humpty Doo virus (AY854643/gi:71842363), Joinjakaka virus, Kannamangalam virus, Kolongo virus (DQ457100/gi191984799 nucleoprotein (N) mRNA, partial cds); Koolpinyah virus, Kotonkon virus (DQ457099/gi191984797, AY854638/gi:71842354); Landjia virus, Manitoba virus, Marco virus, Nasoule virus, Navarro virus, Ngaingan virus (AY854649/gi:71842375), Oak-Vale virus (AY854670/gi:71842417), Obodhiang virus (DQ457098/gi191984795), Oita virus (AB116386/gi:46020027), Ouango virus, Parry Creek virus (AY854647/gi:71842371), Rio Grande cichlid virus, Sandjimba virus (DQ457102/gi191984803), Sigma virus (AH004209/gi:1680545, AH004208/gi:1680544, AH004206/gi:1680542), Sripur virus, Sweetwater Branch virus, Tibrogargan virus (AY854646/gi:71842369), Xiburema virus, Yata virus, Rhode Island, Adelaide River virus (U10363/gi:600151, AF234998/gi:10443747, AF234534/gi:9971785, AY854635/gi:71842348), Berrimah virus (AY854636/gi:71842350]), Kimberley virus (AY854637/gi:71842352), or Bovine ephemeral fever virus (NC_002526/gi:10086561).

A. Rhabdoviral Genome

Typically the rhabdovirus genome is approximately 11-15 kb with an approximately 50 nucleotide 3' leader and an approximately 60 nucleotide non-translated 5' region of a (−) sense viral RNA (vRNA). Typically, rhabdovirus vRNA has 5 genes encoding 5 proteins. Rhabdoviruses have a conserved polyadenylation signal at the end of each gene and a short intergenic region between each of the 5 genes. All Rhabdoviruses contain at least five genes which encode the nucleocapsid protein (N), Phosphoprotein (P, also designated NS), matrix protein (M), glycoprotein (G), and large protein (L). Typically these genes are ordered on negative sense vRNA as follows: 3'-N-P-M-G-(X)-L-5' (SEQ ID NO:29). The order of the genes is important as it dictates the proportion of proteins synthesized. Any manipulations of a Rhabdovirus genome will typically include at least five transcription domains to maintain ability to infect and replicate at high levels. Rhabdoviruses have an endogenous RNA polymerase for transcription of plus sense messenger RNA (mRNA). The X gene does not occur in all Rhabdoviruses. The X gene encodes a nonstructural protein found in the fish infectious hematopoietic necrosis virus (GenBank DQ164103/gi|76262981; DQ164102/gi|76262979; DQ164101/gi|76262977; DQ164100/gi|76262975; DQ164099/gi|76262973; AB250935/gi|112821165; AB250934/gi|112821163; AB250933/gi|112821161; AB250932/gi|112821159; AB250931/gi|112821157; AB250930/gi|112821155; AB250929/gi|112821153; AB250928/gi|112821151; AB250927/gi|112821149, describing the G protein encoding nucleotide sequence), a nonstructural glycoprotein in the bovine ephemeral fever virus and a pseudogene in the rabies virus. The extra (X) gene has been found in different locations on the Rhabdovirus genome. Synthesis of the M protein in infected cells is cytopathic to the cell, and will eventually result in cell death.

Transmission of rhabdovirus varies depending on virus/host, but most are transmitted by direct contact—e.g., transmission of rabies by animal bites or insect vector. There is a long incubation period in vivo, but this is not reflected in the kinetics of virus replication in culture. The G protein spikes bind to receptors on the surface of host cells and the viruses enters the cell by endocytosis and fusion with the membrane of the vesicle, mediated by the G protein.

With no intent to be limited to a particular theory, the receptor molecules for rhabdoviruses are believed to be phospholipids or carbohydrates rather than specific proteins. Rhabdoviral replication occurs in the cytoplasm—both the L and NS proteins are necessary for transcription—neither function alone. Five monocistronic mRNAs are produced, capped at the 5' end and polyadenylated at the 3' end and each containing the leader sequence from the 3' end of the vRNA at the 5' end of the message. These mRNAs are made by sequential transcription of the ORFs in the virus genome and it has been shown that the intergenic sequence is responsible for termination and re-initiation of transcription by the polymerase between each gene, thus producing separate transcripts.

Progeny vRNA is made from a (+) sense intermediate. The genome is replicated by the L+P polymerase complex (as in transcription), but additional host cell factors are also required. It is characteristic of Rhabdoviruses that these events all occur in a portion of the cytoplasm which acts as a virus 'factory' and appears as a characteristic cytoplasmic inclusion body.

B. Viral Protein Variants

In certain embodiments, a Maraba virus or a rhabdovirus will comprise a variant of one or more of the N, P, M, G, and/or L proteins. In certain aspects of the invention these viral protein variants can be comprised in a therapeutic virus, or a proteinaceous composition, which is further defined below. Proteinaceous compositions include viral particles and other compositions having one or more viral protein components. These polypeptide variant(s) can be engineered or selected for a modification in one or more physiological or biological characteristics, such as host cell range, host cell specificity, toxicity to non-target cells or organs, replication, cytotoxicity to a target cell, killing of cancer cells, stasis of cancer cells, infectivity, manufacturing parameters, size of virus particle, stability of viral particles, in vivo clearance, immunoreactivity, and the like. These polypeptide variants can be engineered by using a variety of methodologies known in the art, including various mutagenesis techniques. In certain aspects, the N, P, M, G, and/or L proteins can be heterologous to a virus (e.g., a VSV may comprise a Isfahan G protein or variant thereof).

C. Recombinant Rhabdoviruses

Recombinant rhabdovirus can be produced (1) entirely using cDNAs or (2) a combination of cDNAs transfected into a helper cell, or (3) cDNAs transfected into a cell, which is further infected with a minivirus providing in trans the remaining components or activities needed to produce either an infectious or non-infectious recombinant rhabdovirus. Using any of these methods (e.g., minivirus, helper cell line, or cDNA transfection only), the minimum components required are an RNA molecule containing the cis-acting signals for (1) encapsidation of the genomic (or antigenomic) RNA by the Rhabdovirus N protein, and (2) replication of a genomic or antigenomic (replicative intermediate) RNA equivalent.

By a replicating element or replicon, the inventors mean a strand of RNA minimally containing at the 5' and 3' ends the leader sequence and the trailer sequence of a rhabdovirus. In the genomic sense, the leader is at the 3' end and the trailer is at the 5' end. Any RNA placed between these two replication signals will in turn be replicated. The leader and trailer regions further must contain the minimal cis-acting elements for purposes of encapsidation by the N protein and for polymerase binding which are necessary to initiate transcription and replication.

For preparing engineered rhabdoviruses a minivirus containing the G gene would also contain a leader region, a trailer region and a G gene with the appropriate initiation and termination signals for producing a G protein mRNA. If the minivirus further comprises a M gene, the appropriate initiation and termination signals for producing the M protein mRNA must also present.

For any gene contained within the engineered rhabdovirus genome, the gene would be flanked by the appropriate transcription initiation and termination signals which will allow expression of those genes and production of the protein products. Particularly a heterologous gene, which is a gene that is typically not encoded by a rhabdovirus as isolated from nature or contains a rhabdovirus coding region in a position, form or context that it typically is not found, e.g., a chimeric G-protein.

To produce "non-infectious" engineered Rhabdovirus, the engineered Rhabdovirus must have the minimal replicon elements and the N, P, and L proteins and it must contain the M gene (one example is the ΔG or G-less construct, which is missing the coding region for the G protein). This produces virus particles that are budded from the cell, but are non-infectious particles. To produce "infectious" particles, the virus particles must additionally comprise proteins that can mediate virus particle binding and fusion, such as through the use of an attachment protein or receptor ligand. The native receptor ligand of rhabdoviruses is the G protein.

A "suitable cell" or "host cell" means any cell that would permit assembly of the recombinant rhabdovirus. One method to prepare infectious virus particles, an appropriate cell line (e.g., BHK cells) is first infected with vaccinia virus vTF7-3 (Fuerst et al., 1986) or equivalent which encodes a T7 RNA polymerase or other suitable bacteriophage polymerase such as the T3 or SP6 polymerases (see Usdin et al., 1993 or Rodriguez et al., 1990). The cells are then transfected with individual cDNA containing the genes encoding the G, N, P, L and M Rhabdovirus proteins. These cDNAs will provide the proteins for building a recombinant Rhabdovirus particle. Cells can be transfected by any method known in the art (e.g., liposomes, electroporation, etc.).

Also transfected into the cell line is a "polycistronic cDNA" containing the rhabdovirus genomic RNA equivalent. If the infectious, recombinant rhabdovirus particle is intended to be lytic in an infected cell, then the genes encoding for the N, P, M and L proteins must be present as well as any heterologous nucleic acid segment. If the infectious, recombinant rhabdovirus particle is not intended to be lytic, then the gene encoding the M protein is not included in the polycistronic DNA. By "polycistronic cDNA" it is meant a cDNA comprising at least transcription units containing the genes which encode the N, P and L proteins. The recombinant rhabdovirus polycistronic DNA may also contain a gene encoding a protein variant or polypeptide fragment thereof, or a therapeutic nucleic acid. Alternatively, any protein to be initially associated with the viral particle first produced or fragment thereof may be supplied in trans.

Another embodiment contemplated is a polycistronic cDNA comprising a gene encoding a reporter protein or fluorescent protein (e.g., green fluorescent protein and its derivatives, β-galactosidase, alkaline phosphatase, luciferase, chloramphenicol acetyltransferase, etc.), the N-P-L or N-P-L-M genes, and/or a fusion protein or a therapeutic nucleic acid. Another polycistronic DNA contemplated may contain a gene encoding a protein variant, a gene encoding a reporter, a therapeutic nucleic acid, and/or either the N-P-L genes or the N-P-L-M genes.

The first step in generating a recombinant rhabdovirus is expression of an RNA that is a genomic or antigenomic equivalent from a cDNA. Then that RNA is packaged by the N protein and then replicated by the P/L proteins. The virus thus produced can be recovered. If the G protein is absent from the recombinant RNA genome, then it is typically supplied in trans. If both the G and the M proteins are absent, then both are supplied in trans.

For preparing "non-infectious rhabdovirus" particles, the procedure may be the same as above, except that the polycistronic cDNA transfected into the cells would contain the N, P and L genes of the Rhabdovirus only. The polycistronic cDNA of non-infectious rhabdovirus particles may additionally contain a gene encoding a reporter protein or a therapeutic nucleic acid. For additional description regarding methods of producing a recombinant rhabdovirus lacking the gene encoding the G protein, see Takada et al. (1997).

1. Culturing of Cells to Produce Virus

Transfected cells are usually incubated for at least 24 hr at the desired temperature, usually about 37° C. For non-infectious virus particles, the supernatant is collected and the virus particles isolated. For infectious virus particles, the supernatant containing virus is harvested and transferred to fresh cells. The fresh cells are incubated for approximately 48 hours, and the supernatant is collected.

2. Purification of the Recombinant Rhabdovirus

The terms "isolation" or "isolating" a Rhabdovirus means the process of culturing and purifying the virus particles such that very little cellular debris remains. One example would be to take the virion containing supernatant and pass them through a 0.1-0.2 micron pore size filter (e.g., Millex-GS, Millipore) to remove the virus and cellular debris. Alternatively, virions can be purified using a gradient, such as a sucrose gradient. Recombinant rhabdovirus particles can then be pelleted and resuspended in whatever excipient or carrier is desired. Titers can be determined by indirect immunofluorescence using antibodies specific for particular proteins.

3. Methods of Making Recombinant Rhabdoviruses Using cDNAs and a Minivirus or a Helper Cell Line Both "miniviruses" and "helper cells" (also known as "helper cell lines") provide the same thing: to provide a source of rhabdovirus proteins for rhabdovirus virion assembly. One example of a rhabdovirus minivirus is the VSV minivirus which expresses only the G and M protein, as reported by Stillman et al., (1995). Helper viruses and miniviruses are used as methods of providing rhabdovirus proteins that are not produced from transfected DNA encoding the genes for rhabdovirus proteins.

When using a minivirus, cells are infected with vaccinia virus as described above for purposes of providing T7 RNA polymerase. The desired polycistronic RNA, and plasmids containing the N, P and L genes are transfected into cells. The transfection mix is removed after approximately 3 hrs, and cells are infected with the minivirus at a multiplicity of infection (m.o.i.) of about 1. The minivirus supplies the missing G and/or M proteins. The polycistronic RNA transfected into the cell will depend on whether an infectious or non-infectious recombinant rhabdovirus is wanted.

Alternatively, a minivirus could be used to provide the N, P, and L genes. The minivirus could also be used to produce the M protein in addition to N, P, and L. The minivirus also can produce the G protein.

When using a helper cell line, the genes encoding the missing rhabdovirus proteins are produced by the helper cell line. The helper cell line has N, P, L, and G proteins for production of recombinant rhabdovirus particles which does not encode wild-type G protein. The proteins are expressed from genes or DNAs that are not part of the recombinant virus genome. These plasmids or other vector system is stably incorporated into the genome of the cell line. The proteins are then produced from the cell's genome and not from a replicon in the cytoplasm. The helper cell line can then be transfected with a polycistronic DNA and plasmid cDNAs containing the other rhabdovirus genes not expressed by the helper virus. The polycistronic RNA used will depend on whether an infectious or non-infectious recombinant rhabdovirus is desired. Otherwise, supply of missing gene products (e.g., G and/or M) would be accomplished as described above.

II. Viral Compositions

The present invention concerns rhabdoviruses that are advantageous in the study and treatment of hyperproliferative or neoplastic cells (e.g., cancer cells) and hyperproliferative or neoplastic conditions (e.g., cancer) in a patient. It may concern, but is not limited to, rhabdoviruses with a reduced neurovirulence, e.g., rhabdoviruses such as Maraba virus. In certain aspects rhabdovirus that encode or contain one or more protein components (N, P, M, G, and/or L proteins) or a nucleic acid genome distinct from those of VSV (i.e., at least or at most 10, 20, 40, 50, 60, 70, 80% identical at the amino acid or nucleotide level), and/or that have been constructed with one or more mutations or variations as compared to a wild-type virus or viral proteins such that the virus has desirable properties for use against cancer cells, while being less toxic or non-toxic to non-cancer cells than the virus as originally isolated or VSV. The teachings described below provide various examples of protocols for implementing methods and compositions of the invention. They provide background for generating mutated or variant viruses through the use of bioselection or recombinant DNA or nucleic acid technology.

A. Proteinaceous Compositions

Proteinaceous compositions of the invention include viral particles and compositions including the viral particles, as well as isolated polypeptides. In certain embodiments, the present invention concerns generating or isolating rhabdovirus (e.g., Maraba virus), pseudotyped or oncolytic rhabdoviruses (rhabdoviruses that lyse, kill, or retard growth of cancer cells). In certain embodiments, rhabdoviruses will be engineered to include polypeptide variants of rhabdovirus proteins (N, P, M, G, and/or L) and/or therapeutic nucleic acids that encode therapeutic polypeptides. Other aspects of the invention include the isolation of rhabdoviruses that lack one or more functional polypeptides or proteins. In other embodiments, the present invention concerns rhabdoviruses and their use in combination with or included within proteinaceous compositions as part of a pharmaceutically acceptable formulation.

As used herein, a "protein" or "polypeptide" refers to a molecule comprising polymer of amino acid residues. In some embodiments, a wild-type version of a protein or polypeptide are employed, however, in many embodiments of the invention, all or part of a viral protein or polypeptide is absent or altered so as to render the virus more useful for the treatment of a patient. The terms described above may be used interchangeably herein. A "modified protein" or "modified polypeptide" or "variant protein" or "variant polypeptide" refers to a protein or polypeptide whose chemical structure or amino acid sequence is altered with respect to the wild-type or a reference protein or polypeptide. In some embodiments, a modified protein or polypeptide has at least one modified activity or function (recognizing that proteins or polypeptides may have multiple activities or functions). The modified activity or function may be reduced, diminished, eliminated, enhanced, improved, or altered in some other way (such as infection specificity) with respect to that activity or function in a wild-type protein or polypeptide, or the characteristics of virus containing such a polypeptide. It is contemplated that a modified protein or polypeptide may be altered with respect to one activity or function yet retain wild-type or unaltered activity or function in other respects. Alternatively, a modified protein may be completely non-functional or its cognate nucleic acid sequence may have been altered so that the polypeptide is no longer expressed at all, is truncated, or expresses a different amino acid sequence as a result of a frameshift or other modification.

In certain embodiments the size of a recombinant protein or polypeptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. It is contemplated that polypeptides may be modified by truncation, rendering them shorter than their corresponding unaltered form or by fusion or domain shuffling which may render the altered protein longer.

As used herein, an "amino molecule" refers to any amino acid, amino acid derivative, or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties. Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including the expression of proteins, polypeptides, or peptides through standard molecular biological techniques, the isolation of proteinaceous compounds from natural sources, or the chemical synthesis of proteinaceous materials. The nucleotide and polypeptide sequences for various rhabdovirus genes or genomes have been previously disclosed, and may be found at computerized databases known to those of ordinary skill in the art. One such database is the National Center for Biotechnology Information's GenBank and Gen-Pept databases, which can be accessed via the internet at ncbi.nlm.nih.gov/. The coding regions for these known genes and viruses may be amplified and/or expressed using the techniques disclosed herein or as would be know to those of ordinary skill in the art.

B. Functional Aspects

When the present application refers to the function or activity of viral proteins or polypeptides, it is meant to refer to the activity or function of that viral protein or polypeptide under physiological conditions, unless otherwise specified. For example, the G protein is involved in specificity and efficiency of binding and infection of particular cell types. Determination of which molecules possess this activity may be achieved using assays familiar to those of skill in the art, such as infectivity assays, protein binding assays, plaque assays and the like.

C. Variants of Viral Polypeptides

Amino acid sequence variants of the polypeptides of the present invention can be substitutional, insertional or deletion variants. A mutation in a gene encoding a viral polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids (i.e., segment) of a polypeptide, as compared to a wild-type or unaltered polypeptide or other reference polypeptide. Various polypeptides encoded by rhabdoviruses may be identified by reference to GenBank Accession Numbers and the related public database entries for each of the viruses disclosed herein, all GenBank entries related to the family rhabdoviridae are incorporated herein by reference.

Deletion variants lack one or more residues of the native, unaltered or wild-type protein. Individual residues can be deleted, or all or part of a domain (such as a catalytic or binding domain) can be deleted. A stop codon may be introduced (by substitution or insertion) into an encoding nucleic acid sequence to generate a truncated protein. Insertional mutants typically involve the addition of material at a non-terminal point in the polypeptide, a specific type of insert is a chimeric polypeptide that include homologous or similar portions of a related protein in place of the related portion of a target protein. This may include the insertion of an immunoreactive epitope or simply one or more residues. Terminal additions, typically called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The term "functionally equivalent codon" is used herein to refer to codons that encode the same amino acid, such as the six codons for arginine or serine, and also refers to codons that encode biologically equivalent amino acids (see Table 1, below).

TABLE 1

| Codon Table | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids or 5' or 3' sequences, and yet still be essentially as set as forth herein, including having a certain biological activity. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a N, P, L, M, or G protein to create an equivalent, or even an improved, molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of rhabdovirus without appreciable loss of biological utility or activity of interest, as discussed below.

In making such changes, the hydropathic index of amino acids may be considered. The importance of the hydropathic amino acid index in conferring a biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine *−0.5); cysteine (−1.0); methionine (−1.3); valine (−1.5); leucine (−1.8); isoleucine (−1.8); tyrosine (2.3); phenylalanine (−2.5); tryptophan (−3.4). It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

III. Nucleic Acid Molecules

The present invention includes polynucleotides isolatable from cells that are capable of expressing all or part of a viral protein or polypeptide. In some embodiments of the invention, it concerns all or parts of a viral genome that has been specifically mutated or altered to generate a virus or viral polypeptide, e.g., a pseudotyped or rhabdoviral polypeptide or virus, with certain properties and/or characteristics. The polynucleotides may encode a peptide or polypeptide containing all or part of a viral or heterologous amino acid sequence or be engineered so they do not encode such a viral polypeptide or encode a viral polypeptide having at least one function or activity added, increased, reduced, diminished, or absent. Recombinant proteins can be purified from expressing cells to yield active proteins. The genome of rhabdovirus members may be found in GenBank Accession Numbers in the NCBI database or similar databases, each of which is incorporated herein by reference.

A. Polynucleotides Encoding Native or Modified Proteins

As used herein, the term "RNA, DNA, or nucleic acid segment" refers to a RNA, DNA, or nucleic acid molecule that has been isolated free of total genomic DNA or other contaminants. Therefore, a nucleic acid segment encoding a polypeptide refers to a nucleic acid segment that contains wild-type, polymorphic, or mutant polypeptide-coding sequences yet is isolated away from, or purified free from, genomic nucleic acid(s). Included within the term "nucleic acid segment" are polynucleotides, nucleic acid segments smaller than a polynucleotide, and recombinant vectors, including, for example, plasmids, cosmids, phage, viruses, and the like.

As used in this application, the term "rhabdovirus polynucleotide" can refer to pseudotyped or rhabdoviral nucleic acid molecule encoding at least one rhabdovirus polypeptide. In certain embodiments the polynucleotide has been isolated free of other nucleic acids. Similarly, a Maraba virus, Carajas virus, Muir Springs virus and/or Bahia Grande virus polynucleotide refers to a nucleic acid molecule encoding a Maraba virus, Carajas virus, Muir Springs virus and/or Bahia Grande virus polypeptide that has been isolated from other nucleic acids. A "rhabdovirus genome" or a Maraba virus, Carajas virus, Muir Springs virus and/or Bahia Grande virus genome refers to a VSV or a nucleic acid molecule that can be provided to a host cell to yield a viral particle, in the presence or absence of a helper virus or complementing coding regions supplying other factors in trans. The genome may or may have not been recombinantly mutated as compared to wild-type or an unaltered virus.

The term "cDNA" is intended to refer to DNA prepared using RNA as a template. There may be times when the full or partial genomic sequence is preferred.

It also is contemplated that a particular polypeptide from a given species may be represented by natural variants that have slightly different nucleic acid sequences but, nonetheless, encode the same protein (see Table 1 above).

Similarly, a polynucleotide encoding an isolated or purified wild-type, or modified polypeptide refers to a DNA segment including wild-type or mutant polypeptide coding sequences and, in certain aspects, regulatory sequences, isolated substantially away from other naturally occurring genes or protein encoding sequences. In this respect, the term "gene" is used for simplicity to refer to a nucleic acid unit encoding a protein, polypeptide, or peptide (including any sequences required for proper transcription, post-translational modification, or localization). As will be understood by those in the art, this functional term includes genomic sequences, cDNA sequences, and smaller engineered nucleic acid segments that express, or may be adapted to express, proteins, polypeptides, domains, peptides, fusion proteins, and mutants. A nucleic acid encoding all or part of a native or modified polypeptide may contain a contiguous nucleic acid of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs.

In particular embodiments, the invention concerns isolated nucleic acid segments and recombinant vectors incorporating nucleic acid sequences that encode a wild-type or mutant rhabdovirus polypeptide(s) that includes within its amino acid sequence a contiguous amino acid sequence in accordance with, or essentially corresponding to a native polypeptide. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated nucleic acid segments and recombinant vectors incorporating nucleic acid sequences that encode a polypeptide or peptide that includes within its amino acid sequence a contiguous amino acid sequence in accordance with, or essentially corresponding to one or more rhabdovirus polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol.

It is contemplated that the nucleic acid constructs of the present invention may encode full-length polypeptide(s) from any source or encode a truncated or modified version of the polypeptide(s), for example a truncated rhabdovirus polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide or segment thereof that is not the same as the modified polypeptide or found associated with or encoded by the naturally occurring virus.

In a non-limiting example, one or more nucleic acid construct may be prepared that include a contiguous stretch of nucleotides identical to or complementary to a particular viral segment, such as a rhabdovirus N, P, M, G, or L gene. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges). It will be readily understood that "intermediate lengths" and "intermediate ranges," as used herein, means any length or range including or between the quoted values (i.e., all integers including and between such values).

The nucleic acid segments used in the present invention encompass modified nucleic acids that encode modified polypeptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity or lack thereof of the protein, to reduce toxicity effects of the protein in vivo to a subject given the protein, or to increase the efficacy of any treatment involving the protein or a virus comprising such protein.

In certain other embodiments, the invention concerns isolated nucleic acid segments and recombinant vectors that include within their sequence a contiguous nucleic acid sequence from that shown in sequences identified herein (and/or incorporated by reference). Such sequences, however, may be mutated to yield a protein product whose activity is altered with respect to wild-type.

It also will be understood that this invention is not limited to the particular nucleic acid and amino acid sequences of these identified sequences. Recombinant vectors and isolated nucleic acid segments may therefore variously include rhabdovirus-coding regions themselves, coding regions bearing selected alterations or modifications in the basic coding region, or they may encode larger polypeptides that nevertheless include rhabdovirus-coding regions, or may encode biologically functional equivalent proteins or peptides that have variant amino acids sequences.

The nucleic acid segments of the present invention can encode rhabdovirus proteins and peptides that are the biological functional equivalent of, or variants or mutants of rhabdovirus that increase the therapeutic benefit of the virus. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site directed mutagenesis techniques, e.g., to introduce improvements in cancer cell binding of a viral protein.

B. Mutagenesis of Rhabdovirus Polynucleotides

In various embodiments, the rhabdovirus polynucleotide may be altered or mutagenized. Alterations or mutations may include insertions, deletions, point mutations, inversions, and the like and may result in the modulation, activation and/or inactivation of certain proteins or molecular mechanisms, as well as altering the function, location, or expression of a gene product, in particular rendering a gene product non-functional. Where employed, mutagenesis of a polynucleotide encoding all or part of a rhabdovirus may be accomplished by a variety of standard, mutagenic procedures (Sambrook et al., 2001). Mutation is the process whereby changes occur in the quantity or structure of an organism. Mutation can involve modification of the nucleotide sequence of a single gene, blocks of genes or whole genomes. Changes in single genes may be the consequence of point mutations which involve the removal, addition or substitution of a single nucleotide base within a DNA sequence, or they may be the consequence of changes involving the insertion or deletion of large numbers of nucleotides.

1. Random Mutagenesis a. Insertional Mutagenesis

Insertional mutagenesis is based on the inactivation of a gene via insertion of a known nucleic acid fragment. Because it involves the insertion of some type of nucleic acid fragment, the mutations generated are generally loss-of-function, rather than gain-of-function mutations. However, there are several examples of insertions generating gain-of-function mutations. Insertional mutagenesis may be accomplished using standard molecular biology techniques.

b. Chemical Mutagenesis

Chemical mutagenesis offers certain advantages, such as the ability to find a full range of mutations with degrees of phenotypic severity, and is *facile* and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the 04 position of thymine induced by exposure to n-nitrosourea results in TA to CG transitions.

c. Radiation Mutagenesis

Biological molecules are degraded by ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible. Ionizing radiation causes DNA damage, generally proportional to the dose rate.

In the present invention, the term "ionizing radiation" means radiation comprising particles or photons that have sufficient energy or can produce sufficient energy to produce ionization (gain or loss of electrons). An exemplary and preferred ionizing radiation is an x-radiation. The amount of ionizing radiation needed in a given cell or for a particular molecule generally depends upon the nature of that cell or molecule and the nature of the mutation target. Means for determining an effective amount of radiation are well known in the art.

d. In Vitro Scanning Mutagenesis

Random mutagenesis also may be introduced using error prone PCR. The rate of mutagenesis may be increased by performing PCR in multiple tubes with dilutions of templates. One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

2. Site-Directed Mutagenesis

Structure-guided site-specific mutagenesis represents a powerful tool for the dissection and engineering of protein-ligand interactions (Wells, 1996; Braisted et al., 1996). The technique provides for the preparation and testing of sequence variants by introducing one or more nucleotide sequence changes into a selected DNA.

C. Vectors

To generate mutations in a rhabdovirus genome, native and modified polypeptides may be encoded by a nucleic acid molecule comprised in a vector. The term "vector" is used to refer to a carrier nucleic acid molecule into which an exogenous nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (2001) and Ausubel et al. (1994), both incorporated herein by reference.

In addition to encoding a modified polypeptide such as modified N protein, P protein, M protein, G protein, or L protein, a vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body. Alternatively, the targeting molecule alters the tropism of an organism, such as rhabdovirus for certain cell types, e.g., cancer cells.

The term "expression vector" refers to a vector containing a nucleic acid sequence coding for at least part of a gene product capable of being transcribed. In some cases, RNA molecules are translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements that bind regulatory proteins and molecules, such as RNA polymerase and other transcription factors. The phrases "operatively positioned," "operatively coupled," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression.

In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-specific, cell selective (i.e., more active in one cell type as compared to another), inducible, and/or useful under the appropriate conditions to direct high level expression of the introduced nucleic acid segment, such as is advantageous in the large-scale production of recombinant proteins and/or peptides. The promoter may be heterologous or endogenous.

Several elements/promoters that may be employed, in the context of the present invention, to regulate the expression of a gene. This list is not intended to be exhaustive of all the possible elements involved in the promotion of expression but, merely, to be exemplary thereof. Also provided are examples of inducible elements, which are regions of a nucleic acid sequence that can be activated in response to a specific stimulus. Promoter/Enhancer (References) include: Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990); Immunoglobulin Light Chain (Queen et al., 1983; Picard et al., 1984); T Cell Receptor (Luria et al., 1987; Winoto et al., 1989; Redondo et al.; 1990); HLA DQ α and/or DQ β (Sullivan et al., 1987); β Interferon (Goodbourn et al., 1986; Fujita et al., 1987; Goodbourn et al., 1988); Interleukin-2 (Greene et al., 1989); Interleukin-2 Receptor (Greene et al., 1989; Lin et al., 1990); MHC Class II 5 (Koch et al., 1989); MHC Class II HLA-DRα (Sherman et al., 1989); 13-Actin (Kawamoto et al., 1988; Ng et al.; 1989); Muscle Creatine Kinase (MCK) (Jaynes et al., 1988; Horlick et al., 1989; Johnson et al., 1989); Prealbumin (Transthyretin) (Costa et al., 1988); Elastase I (Omitz et al., 1987); Metallothionein (MTII) (Karin et al., 1987; Culotta et al., 1989); Collagenase (Pinkert et al., 1987; Angel et al., 1987); Albumin (Pinkert et al., 1987; Tronche et al., 1989, 1990); α-Fetoprotein (Godbout et al., 1988; Campere et al., 1989); γ-Globin (Bodine et al., 1987; Perez-Stable et al., 1990); β-Globin (Trudel et al., 1987); c-fos (Cohen et al., 1987); c-HA-ras (Triesman, 1986; Deschamps et al., 1985); Insulin (Edlund et al., 1985); Neural Cell Adhesion Molecule (NCAM) (Hirsh et al., 1990); α1-Antitrypain (Latimer et al., 1990); H2B (TH2B) Histone (Hwang et al., 1990); Mouse and/or Type I Collagen (Ripe et al., 1989); Glucose-Regulated Proteins (GRP94 and GRP78) (Chang et al., 1989); Rat Growth Hormone (Larsen et al., 1986); Human Serum Amyloid A (SAA) (Edbrooke et al., 1989); Troponin I (TN I) (Yutzey et al., 1989); Platelet-Derived Growth Factor (PDGF) (Pech et al., 1989); Duchenne Muscular Dystrophy (Klamut et al., 1990); SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988); Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988); Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989); Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987); Hepatitis B Virus (Bulla et al., 1986; Jameel et al., 1986; Shaul et al., 1987; Spandau et al., 1988; Vannice et al., 1988); Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989); Cytomegalovirus (CMV) (Weber et al., 1984; Boshart et al., 1985; Foecking et al., 1986); and Gibbon Ape Leukemia Virus (Holbrook et al., 1987; Quinn et al., 1989).

Inducible Elements (Element/Inducer (References)) include: MT II/Phorbol Ester (TNFA), Heavy metals (Palmiter et al., 1982; Has linger et al., 1985; Searle et al., 1985; Stuart et al., 1985; Magana et al., 1987, Karin et al., 1987; Angel et al., 1987b; McNeal et al., 1989); MMTV (mouse mammary tumor virus)/Glucocorticoids (Huang et al., 1981; Lee et al., 1981; Majors et al., 1983; Chandler et al., 1983; Lee et al., 1984; Ponta et al., 1985; Sakai et al., 1988); β-Interferon/poly(rI)x, poly(rc) (Tavernier et al., 1983); Adenovirus 5 E2/E1A (Imperiale et al., 1984); Collagenase/Phorbol Ester (TPA) (Angel et al., 1987a); Stromelysin/Phorbol Ester (TPA) (Angel et al., 1987b); SV40/Phorbol Ester (TPA) (Angel et al., 1987b); Murine MX Gene/Interferon, Newcastle Disease Virus (Hug et al., 1988); GRP78 Gene/A23187 (Resendez et al., 1988); α-2-Macroglobulin/IL-6 (Kunz et al., 1989); Vimentin/Serum (Rittling et al., 1989); MHC Class I Gene H-2 κb/Interferon (Blanar et al., 1989); HSP70/E1A, SV40 Large T Antigen (Taylor et al., 1989, 1990a, 1990b); Proliferin/Phorbol Ester-TPA (Mordacq et al., 1989); Tumor Necrosis Factor/PMA (Hensel et al., 1989); and Thyroid Stimulating Hormone α Gene/Thyroid Hormone (Chatterjee et al., 1989).

The identity of tissue-specific or tissue-selective (i.e., promoters that have a greater activity in one cell as compared to another) promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996), and the SM22α promoter.

Additional viral promoters, cellular promoters/enhancers and inducible promoters/enhancers that could be used in combination with the present invention are listed herein. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest. Alternatively, a tissue-specific promoter for cancer gene therapy (Table 2) or the targeting of tumors (Table 3) may be employed with the nucleic acid molecules of the present invention.

TABLE 2

Candidate Tissue-Specific Promoters for Cancer Gene Therapy

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adeno-carcinomas cells | Type II pneumocytes; Clara |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastro-intestinal, and genito-urinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g.: Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 3

Candidate Promoters for Use with a Tissue-Specific Targeting of Tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colo-rectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpres-sion in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs of the present invention will generally comprise at least one termination signal. A "termination signal" or "terminator" is comprised of the RNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In negative sense RNA viruses, including rhabdoviruses, termination is defined by a RNA motif. Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

5. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

D. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors or viruses (which does not qualify as a vector if it expresses no exogenous polypeptides). A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KCB, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*. Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

E. Expression Systems

Numerous expression systems exist that comprise at least all or part of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

F. Nucleic Acid Detection

In addition to their use in directing the expression of poxvirus proteins, polypeptides and/or peptides, the nucleic acid sequences disclosed herein have a variety of other uses. For example, they have utility as probes or primers for embodiments involving nucleic acid hybridization. They may be used in diagnostic or screening methods of the present invention. Detection of nucleic acids encoding rhabdovirus or rhabdovirus polypeptide modulators are encompassed by the invention.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified and are well known (see Sambrook et al., 2001; WO 90/07641; and U.S. Pat. No. 5,882,864).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used. Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety. Qbeta Replicase, described in PCT Application No. PCT/US87/00880, may also be used as an amplification method in the present invention. Isothermal amplification as described by Walker et al. (1992) can also be used. As well as Strand Displacement Amplification (SDA), disclosed in U.S. Pat. No. 5,916,779.

Other nucleic acid amplification procedures include transcription-based amplification systems (TAS), including nucleic acid sequence based amplification (NASBA) and 3 SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. Other amplification methods include "RACE" and "one-sided PCR" (Frohman, 1990; Ohara et al., 1989).

3. Detection of Nucleic Acids

Following any amplification, it may be desirable to separate and/or isolate the amplification product from the template and/or the excess primer. In one embodiment, amplification products are separated by agarose, agarose-acrylamide, or polyacrylamide gel electrophoresis using standard methods (Sambrook et al., 2001).

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

Typical visualization methods includes staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic nucleic acids, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art. One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations (for example see U.S. Pat. No. 4,946,773. Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

G. Methods of Gene Transfer

Suitable methods for nucleic acid delivery to effect expression of compositions of the present invention are believed to include virtually any method by which a nucleic acid (e.g., DNA or RNA, including viral and nonviral vectors) can be introduced into an organelle, a cell, a tissue or an organism, as described herein or as would be known to one of ordinary skill in the art. Such methods include, but are not limited to, direct delivery of nucleic acid such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Through the application of techniques such as these, organelle(s), cell(s), tissue(s) or organism(s) may be stably or transiently transformed.

H. Lipid Components and Moieties

In certain embodiments, the present invention concerns compositions comprising one or more lipids associated with a nucleic acid, an amino acid molecule, such as a peptide, or another small molecule compound. In any of the embodiments discussed herein, the molecule may be either a rhabdovirus polypeptide or a rhabdovirus polypeptide modulator, for example a nucleic acid encoding all or part of either a rhabdovirus polypeptide, or alternatively, an amino acid molecule encoding all or part of rhabdovirus polypeptide modulator. A lipid is a substance that is characteristically insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or amino acid molecule, such as a peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid/virus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-virus complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type, or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. Thus, it is contemplated that lipid compositions of the present invention may comprise any of the lipids, lipid types, or other components in any combination or percentage range.

IV. Pharmaceutical Formulations and Treatment Regimens

In an embodiment of the present invention, a method of treatment for a hyperproliferative or neoplastic disease, such as cancer, by the delivery of a rhabdovirus, such as Maraba virus, Carajas virus, Muir Springs virus, and/or Bahia Grande virus, is contemplated. Examples of cancer contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions, pre-neoplastic lesions in the lung, colon cancer, melanoma, bladder cancer and any other cancers or tumors that may be treated, including metastatic or systemically distributed cancers.

An effective amount of the pharmaceutical composition, generally, is defined as that amount sufficient to detectably and repeatedly to slow, ameliorate, reduce, minimize, or limit the extent of the disease or its symptoms. More rigorous definitions may apply, including elimination, eradication, or cure of disease.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

A. Administration

To kill cells, inhibit cell growth, inhibit metastasis, decrease tumor or tissue size, and otherwise reverse, stay, or reduce the malignant phenotype of tumor cells, using the methods and compositions of the present invention, one would generally contact a hyperproliferative or neoplastic cell with a therapeutic composition such as a virus or an expression construct encoding a polypeptide. The routes of administration will vary, naturally, with the location and nature of the lesion, and include, e.g., intradermal, transdermal, parenteral, intravascular, intravenous, intramuscular, intranasal, subcutaneous, regional, percutaneous, intratracheal, intraperitoneal, intraarterial, intravesical, intratumoral, inhalation, perfusion, lavage, direct injection, alimentary, and oral administration and formulation.

To effect a therapeutic benefit with respect to a vascular condition or disease, one would contact a vascular cell with the therapeutic compound. Any of the formulations and routes of administration discussed with respect to the treatment or diagnosis of cancer may also be employed with respect to vascular diseases and conditions.

Intratumoral injection, or injection into the tumor vasculature is contemplated for discrete, solid, accessible tumors. Local, regional or systemic administration is also contemplated, particularly for those cancers that are disseminated or are likely to disseminated systemically. The viral particles may be administering by at least or at most 1, 2, 3, 4, 5, 6, 7, 8, 9, 10 injections.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a rhabdovirus polypeptide or a rhabdovirus, which may or may not harbor a mutation, that is advantageous for treatment of cancer or cancer cells. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 1, 2, 3, 4, 5, 6 or more dose application over a 1, 2, 3, 4, 5, 6-week period or more. A two-week regimen may be repeated one, two, three, four, five, six or more times. During a course of treatment, the need to complete the planned dosings may be re-evaluated.

The treatments may include various "unit doses." Unit dose is defined as containing a predetermined quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) or viral particles for viral constructs. Unit doses range from $10^3$, $10^4$, $10^5$, $10^6$, $10^7$, $10^8$, $10^9$, $10^{10}$, $10^{11}$, $10^{12}$, $10^{13}$ pfu or vp and higher. Alternatively, depending on the kind of virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

B. Injectable Compositions and Formulations

The preferred method for the delivery of an expression construct or virus encoding all or part of a rhabdovirus genome to cancer or tumor cells in the present invention is via intravascular injection. However, the pharmaceutical compositions disclosed herein may alternatively be administered intratumorally, parenterally, intravenously, intrarterially, intradermally, intramuscularly, transdermally or even intraperitoneally as described in U.S. Pat. Nos. 5,543,158, 5,641,515 and 5,399,363 (each specifically incorporated herein by reference in its entirety).

Injection of nucleic acid constructs may be delivered by syringe or any other method used for injection of a solution, as long as the expression construct can pass through the particular gauge of needle required for injection (for examples see U.S. Pat. Nos. 5,846,233 and 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards required by governments of the countries in which the compositions are being used.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

C. Combination Treatments

The compounds and methods of the present invention may be used in the context of hyperproliferative or neoplastic diseases/conditions including cancer and atherosclerosis. In order to increase the effectiveness of a treatment with the compositions of the present invention, such as rhabdoviruses, it may be desirable to combine these compositions with other agents effective in the treatment of those diseases and conditions. For example, the treatment of a cancer may be implemented with therapeutic compounds of the present invention and other anti-cancer therapies, such as anti-cancer agents or surgery.

Various combinations may be employed; for example, a rhabdovirus, such as Maraba virus, is "A" and the secondary anti-cancer therapy is "B", which may include a second rhabdovirus or other oncolytic virus:

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/B/B B/A/A/A A/B/A/A A/A/B/A

Administration of the therapeutic virus or viral constructs of the present invention to a patient will follow general protocols for the administration of that particular secondary therapy, taking into account the toxicity, if any, of the virus treatment. It is expected that the treatment cycles would be repeated as necessary. It also is contemplated that various standard therapies, as well as surgical intervention, may be applied in combination with the described cancer or tumor cell therapy.

1. Anti-Cancer Therapy

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with virus or viral construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the virus and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that poxvirus therapy could be used similarly in conjunction with chemotherapeutic, radiotherapeutic, immunotherapeutic, or other biological intervention, in addition to other pro-apoptotic or cell cycle regulating agents.

Alternatively, a viral therapy may precede or follow the other treatment by intervals ranging from minutes to weeks. In embodiments where the other agent and virus are applied separately to the cell, one would generally ensure that a significant period of time did not expire between the time of each delivery, such that the agent and virus would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

b. Radiotherapy

Other factors that cause DNA damage and have been used extensively include what are commonly known as γ-rays, X-rays, proton beams, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of certain rhabdovirus or rhabdovirus polypeptides would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. Tumor cell lysates may also be used in an antigenic composition.

An alternative aspect of immunotherapy is to combine anticancer effects with immune stimulatory effects. Immune stimulating molecules include: cytokines such as IL-2, IL-4, IL-12, GM-CSF, IFNγ, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000).

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. Nos. 5,801,005 and 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor (Dillman, 1999). Combination therapy of cancer with herceptin and chemotherapy has been shown to be more effective than the individual therapies. Thus, it is contemplated that one or more anti-cancer therapies may be employed with the rhabdovirus-related therapies described herein.

(1) Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie and Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

(2) Active Immunotherapy

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti ganglioside or anticarbohydrate antibodies.

(3) Adoptive Immunotherapy

In adoptive immunotherapy, the patient's circulating lymphocytes, or tumor infiltrated lymphocytes, are isolated in vitro, activated by lymphokines such as IL 2 or transduced with genes for tumor necrosis, and readministered (Rosenberg et al., 1988; 1989). To achieve this, one would administer to an animal, or human patient, an immunologically effective amount of activated lymphocytes in combination with an adjuvant incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

d. Genes

In yet another embodiment, the secondary treatment is a gene therapy in which a therapeutic polynucleotide is administered before, after, or at the same time as a rhabdovirus is administered. Delivery of a rhabdovirus in conjunction with a vector encoding one of the following gene products will have a combined anti-cancer effect on target tissues. Alternatively, the rhabdovirus may be engineered as a viral vector to include the therapeutic polynucleotide. A variety of proteins are encompassed within the invention, some of which are described below. Table 4 lists various genes that may be targeted for gene therapy of some form in combination with the present invention.

(1) Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

(2) Inhibitors of Cellular Proliferation

The tumor suppressor oncogenes function to inhibit excessive cellular proliferation. The inactivation of these genes destroys their inhibitory activity, resulting in unregulated proliferation. Tumor suppressors include p53, p16 and C-CAM. Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

(3) Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl 2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl 2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl 2 (e.g., BclXL, BclW, BclS, Mc1-1, A1, Bfl-1) or counteract Bcl 2 function and promote cell death (e.g., Bax, Bak, Bik, Bim, Bid, Bad, Harakiri).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, pre-cancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing ability of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as viral therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body.

Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment V. Examples The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

A. Results

Maraba Virus Demonstrates Potent Oncolytic Properties In Vitro.

Figure 5I:
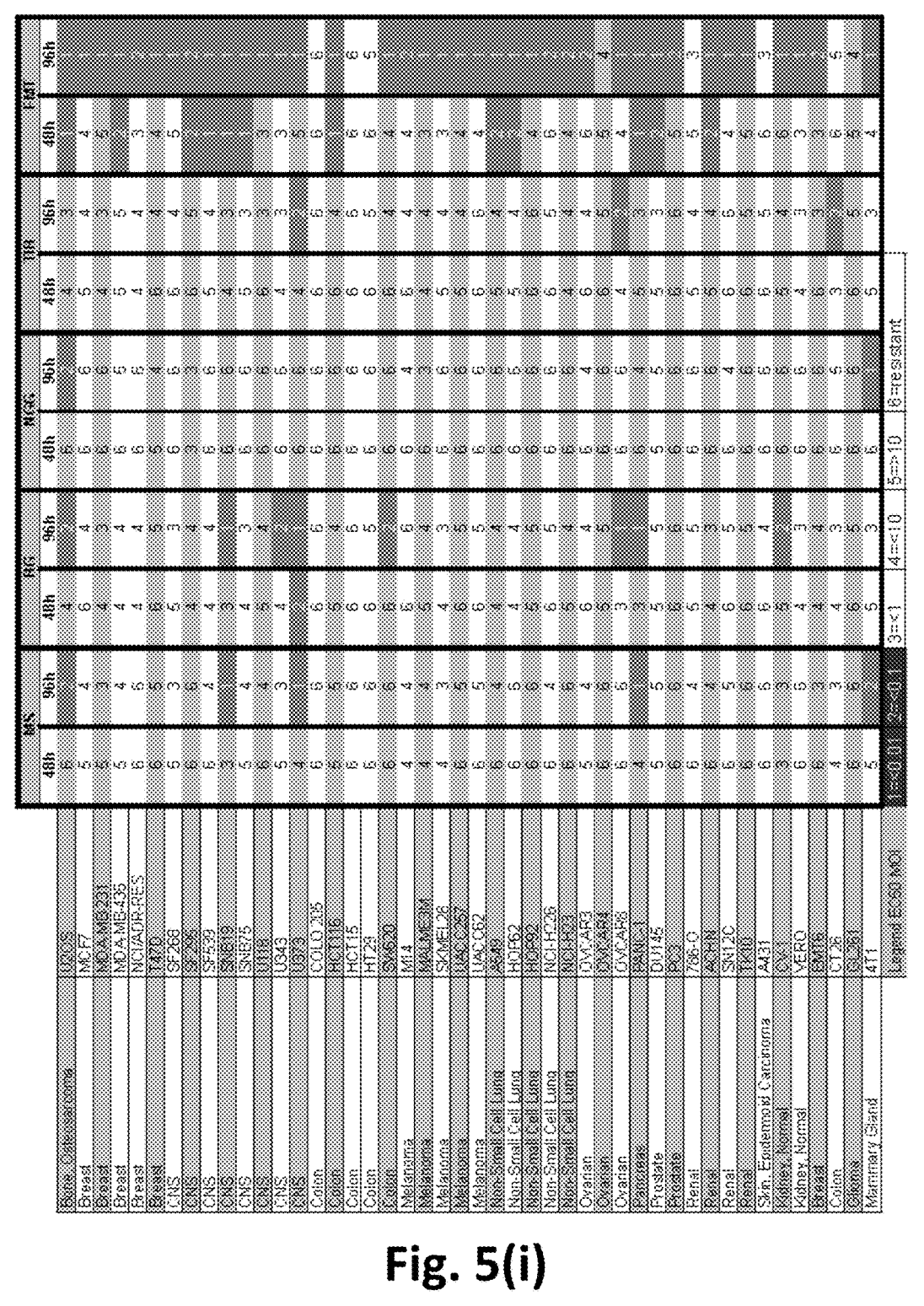
Figure 5:
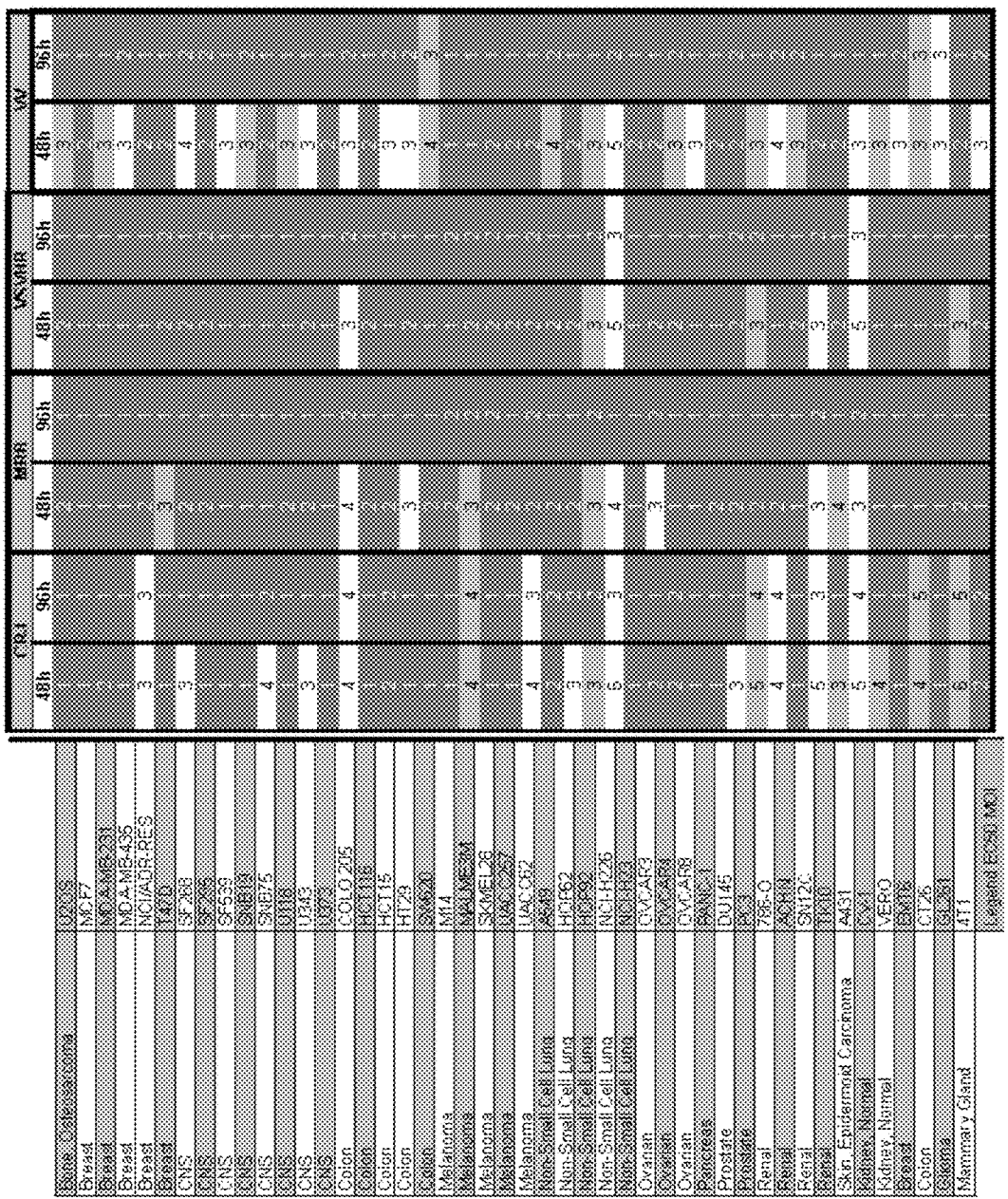
FIG. 5. Rhabdovirus mediated cell killing on the NCI 60 cell panel Cells from the NCI 60 cell panel were plated in 96 well plates to a confluency of 90%. These cells were infected at log dilutions with various rhabdoviruses, as indicated. After 48 hours or 96 hours post infection with engineered Maraba vrus as an oncolytic agent, the monolayers were washed, fixed and stained with 1% crystal violet solution. Stained monolayers were subsequently solubilized in 1% SDS in water to create homogenous lysates. Absorbance was read at 595 nm and to score for viable cells. MOI EC50 were scored in ranges as indicated in the figure.

The rhabdovirus family is vast and genetically and geographically diverse. The inventors selected a panel of rhabdoviruses with previously documented capacity to replicate in mammalian cells as a starting point. Seven viruses were selected for in vitro screening to identify those with potent tumor cell cytolytic capacity (Table 4). Cell killing assays were performed in 96 well format on cell lines from the NCI 60 tumor cell panel and an assortment of mouse tumor lines (FIG. 5). Several species were demonstrated to be highly lytic on human tumor lines with EC50 scores of less than 0.1 MOI by plaque forming units (pfu) for the majority of cell lines tested. In particular, Maraba (Travassos da Rosa et al., 1984), Carajas (CRJ) (Travassos da Rosa et al., 1984) and Farmington virus (FMT) (Travassos da Rosa et al., 2002) appeared to be very effective at killing human tumor lines from all cancer indications represented in the cell panel. A notable exception was observed for FMT virus having difficulty killing cell lines derived from colon tumors. Interestingly, not all rhabdoviruses possess the capacity to efficiently kill cancer cells. Viruses such as Muir Springs (MS)(Kerschner et al., 1986), Bahia Grande (BG)(Kerschner et al., 1986), Ngaingin (NGG) (Doherty et al., 1973) and Tibrogargan (TIB) (Cybinski et al., 1980) showed activity in a very small proportion of tumor cells. Presently, the mechanisms governing the restriction of these viruses remain unknown.

TABLE 4

Novel Strains of uncharacterized Rhabdoviruses are highly lytic on NCI 60 cell panel *percent of NCI 60 cell lines by tumour type deemed highly sensitive to virus infection. Bracketed numbers denote the number of cell lines tested within each cancer indication grouping. Virus was scored as highly lytic to a cell line with an EC50 <0.1 MOI following 96 hours of infection.

|  | MS | BG | NGG | TIB | FMT | CRJ | MRB | VSV | VV |
|---|---|---|---|---|---|---|---|---|---|
| Breast (5) | 0* | 0 | 0 | 0 | 100 | 80 | 100 | 100 | 100 |
| CNS (8) | 25 | 38 | 0 | 13 | 100 | 100 | 100 | 100 | 100 |
| Colon (5) | 0 | 20 | 0 | 0 | 40 | 80 | 100 | 100 | 80 |
| Melanoma (5) | 0 | 0 | 0 | 0 | 100 | 60 | 100 | 100 | 100 |
| Lung (5) | 0 | 0 | 0 | 0 | 100 | 80 | 100 | 80 | 100 |
| Ovarian (3) | 0 | 33 | 0 | 33 | 67 | 100 | 100 | 100 | 100 |
| Prostate (2) | 0 | 0 | 0 | 0 | 100 | 50 | 100 | 100 | 100 |
| Renal (4) | 0 | 0 | 0 | 0 | 75 | 50 | 100 | 100 | 100 |
| Total (37) | 6 | 14 | 0 | 5 | 86 | 78 | 100 | 97 | 97 |

*Percent of NCI 60 panel cell lines by tumour type deemed highly sensitive to virus infection. Bracketed numbers denote the number of cell lines tested within each cancer indication grouping. Virus was scored as highly lytic to a cell line with an EC50 <0.1 MOI following 96 hours of infection.

Figure 1B:
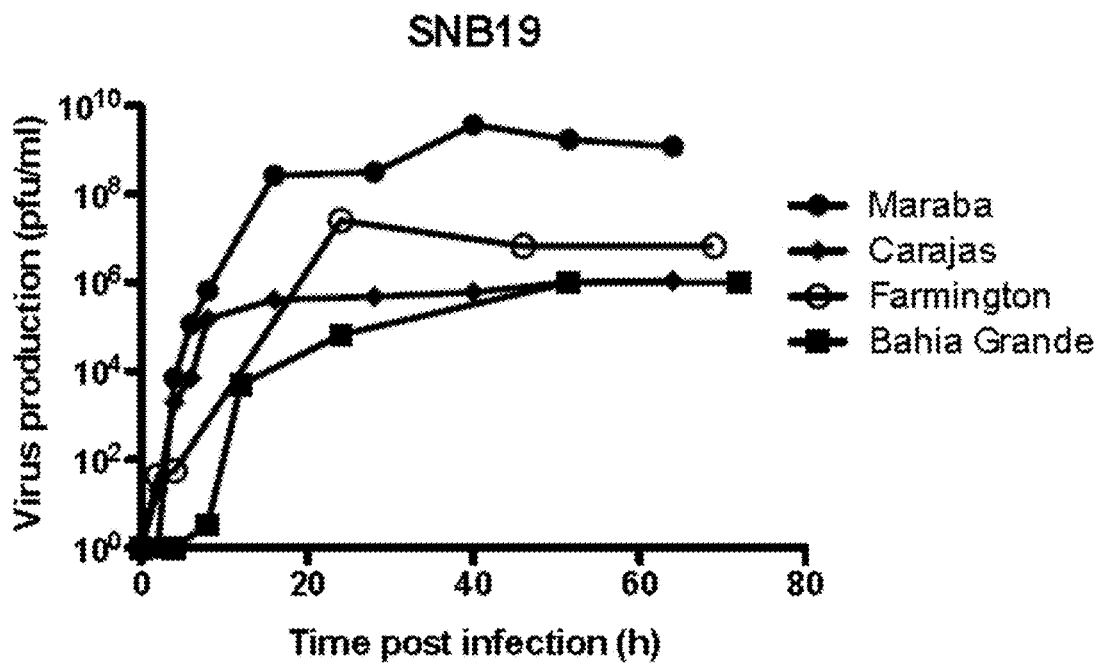

To further characterize these viruses, single step growth curves were performed on both a susceptible cell line (SNB19) as well as a relatively resistant cell line (NCI H226) to monitor the rates of replication and to quantify virus burst sizes. The inventors were unable to detect virus following infection of NCI H226 cells with BG virus, which is consistent with the observation that BG is only poorly cytolytic on this cell line. However, BG was able to replicate to a similar degree as FMT and CRJ on the SNB19 cells, again correlating with its cytolytic capacity. Both FMT and CRJ produced progeny with similar kinetics and with equivalent burst sizes when assayed on NCI H226 cells. FMT appeared to replicate to higher titers than CRJ on SNB19 cells although both clearly produced sufficient progeny to result in rapid killing of this susceptible cell line (FIG. 1A and FIG. 1B). MRB produced virus with equal or faster kinetics than the other 3 strains, and to a much higher titer than the other viruses on both SNB19 and NCI H226 cells.

MRB virus demonstrated good cytolytic activity against tumor lines, rapid virus production, and large burst size. These are all properties that contribute to good oncolytic activity. Maraba was selected as a oncolytic virus to develop further.

Maraba Virus.

Figure 2A:
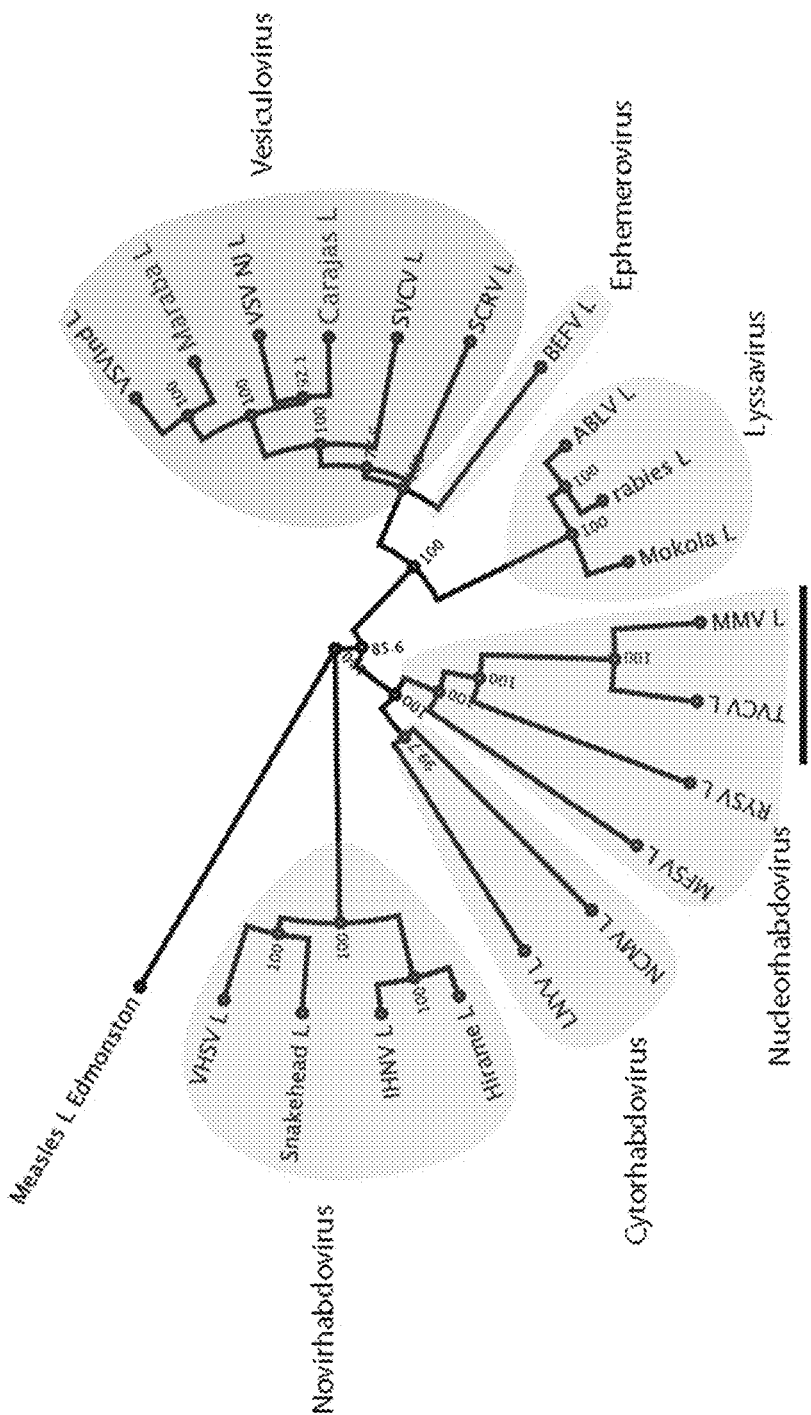
FIGS. 2A-2F. Maraba mutants retain their killing potency in cancer cells yet are attenuated on normal cells.
Figure 2B:
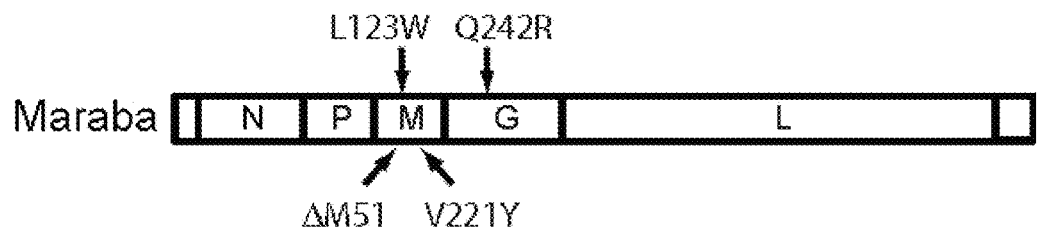

As a prelude to genetically manipulating Maraba virus, a "shot gun" sequencing approach was employed to obtain the full length genomic sequence for this strain. Subsequent phylogenetic analysis was performed by aligning the amino acid sequence of the Maraba L protein to members of the 6 known genera of the rhabdovirus family (FIG. 2A). The virus has the expected genomic structure common to other rhabdoviruses, with 5 discrete cistrons separated by transcriptional stop/start sequences responsible for delineating the virus's N, P, M, G and L genes (FIG. 2B).

Engineered Maraba Virus Mutants Show Improved Cancer Cell Selectivity.

The full length anti-genomic sequence was cloned into a T7 promoter driven vector and the N, P and L genes into CMV promoter driven expression constructs. This strategy has been used successfully to develop reverse genetic systems for several negative strand RNA viruses (Schnell et al., 1994; Whelan et al., 1995; Lawson et al., 1995; Nakaya et al., 2001). The resulting virus was rescued by transfection of the genome construct, N, P and L plasmids into A549 cells previously infected with vaccinia virus expressing T7 polymerase and named rMaraba WT (recombinant Maraba wild type).

The inventors introduced mutations to improve the tumor selective killing properties of wild type maraba virus. The inventors had previously demonstrated that a deletion of methionine 51 in the M protein of VSV rendered the virus defective for blocking the interferon response in infected cells (Stojdl et al., 2003). Similarly, the inventors had shown that a double mutation in VSV M protein at amino acids V221F and S226R also rendered the virus unable to block nuclear cytoplasmic transport of host mRNAs and thereby allowed the host cell to propagate an IFN response (Stojdl et al., 2003). Considering the Glasgow strain of VSV also has a S226R variation in its matrix protein, it was hypothesized that the attenuating phenotype for the V221F S226R double mutant may arise from the mutation at V221F alone. Thus, the inventors constructed and rescued the ΔM51 Maraba recombinant virus, and V221Y Maraba mutant strain as possible attenuated variants (FIG. 2B).

Two other mutations reportedly improved the replication of VSV on BHK-21 cells (M protein L123W and L protein H242R) (Sanjuan et al., 2004). Aligning the Maraba sequence to VSV, the corresponding mutation to be L123W and Q242R in the Maraba sequence of the M and L proteins, respectively. Recombinant Maraba viruses where constructed with the M protein L123W or the G protein Q242R single mutations, or both L123W and Q242R (hereafter referred to as Maraba DM) (FIG. 2B).

Figure 2C:
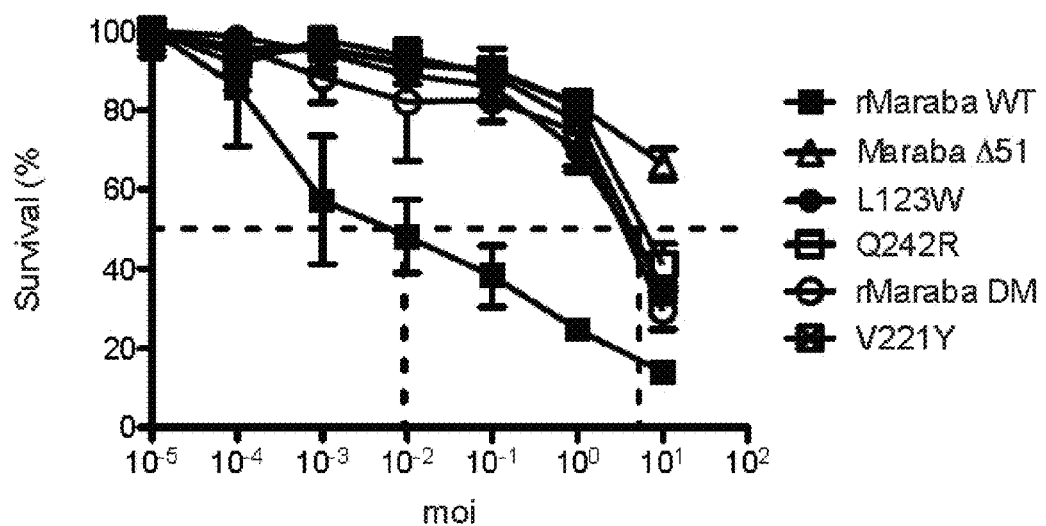
Figure 2D:
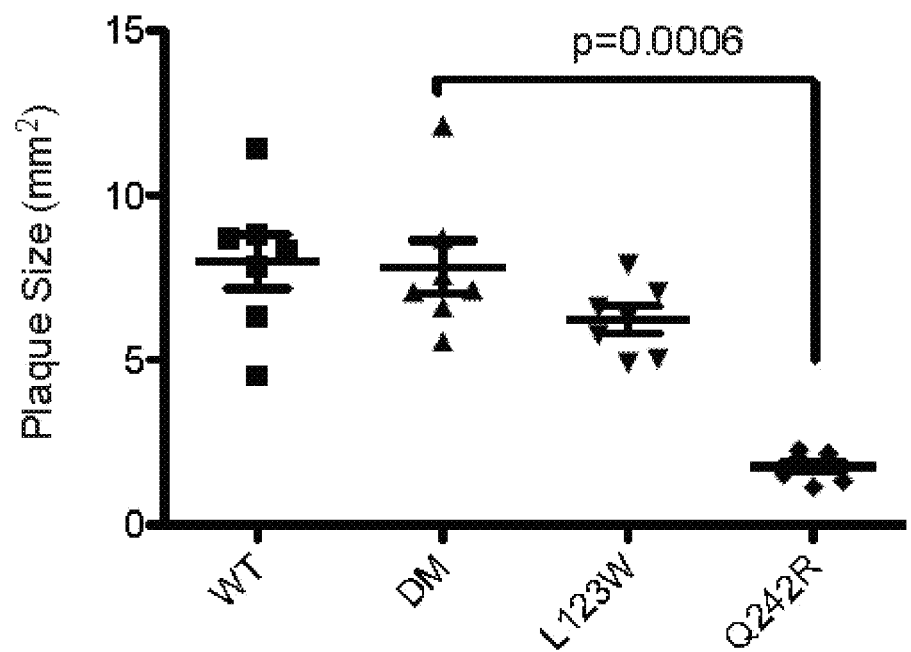

Cytotoxicity of our rMaraba WT and mutant strains were tested on primary human skin fibroblasts (GM38 cells) to detect and quantify any attenuation resulting from the engineered mutations (FIG. 2C). The ΔM51 maraba virus is attenuated on these primary cells ($EC_{50}$>>10 MOI) compared to rMaraba WT ($EC_{50}$=0.01 MOI). The V221Y was also attenuated, although to a slightly lesser degree than the ΔM51 ($EC_{50}$=3 MOI). Surprisingly, both the L123W and the Q242R mutants were also highly attenuated ($EC_{50}$=3 MOI). Furthermore, the double mutant combining both L123W and Q242R mutations was equally attenuated as compared to the single mutants, resulting in a 100 fold increase in $EC_{50}$ after 72 hour infection of primary human fibroblasts ($EC_{50}$=3 MOI). These results were surprising given that both mutations were expected to improve replication, not attenuate the virus. These phenotypes correlated with plaque formation as well. Following infection of GM38 fibroblasts, small but detectable plaques became visible one week after infection with rMaraba WT. However, no plaques were visible over the same time frame for the various Maraba single mutants or Maraba DM. This again demonstrated the severely attenuated nature of V221Y, L123W and Maraba DM on normal primary fibroblasts. In contrast, large plaques formed on a tumor line (SNB19) following just 24 hours of infection with either rMaraba WT, V221Y, L123W or Maraba DM (FIG. 2D). The Q242R mutant however made smaller plaques as compared to the other strains, suggesting this mutation may slightly impair replication of this strain in tumor cells as well. Interestingly however, the double mutant, which contains the Q242R mutation, clearly demonstrated no such impairment on malignant cells (FIG. 2D).

Figure 2E:
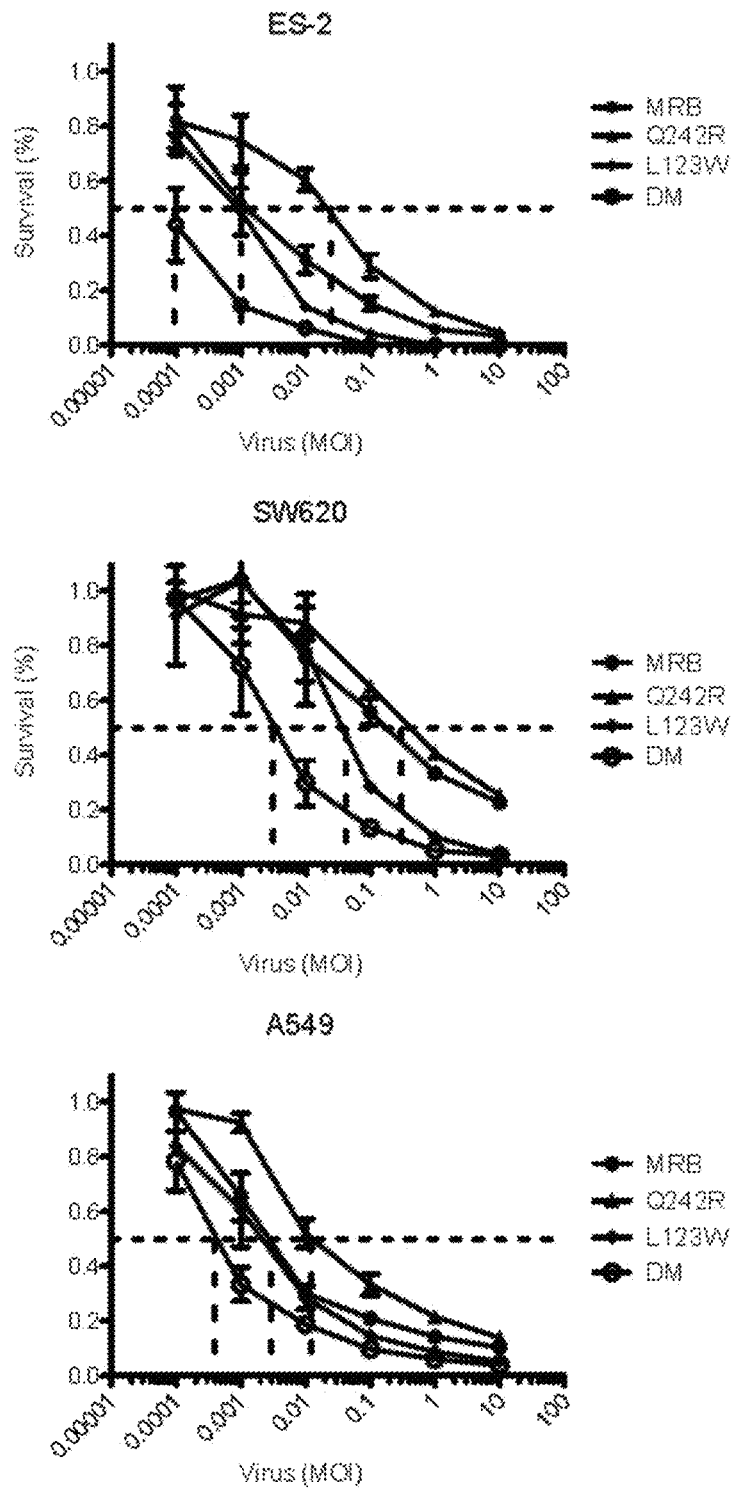
Figure 2F:
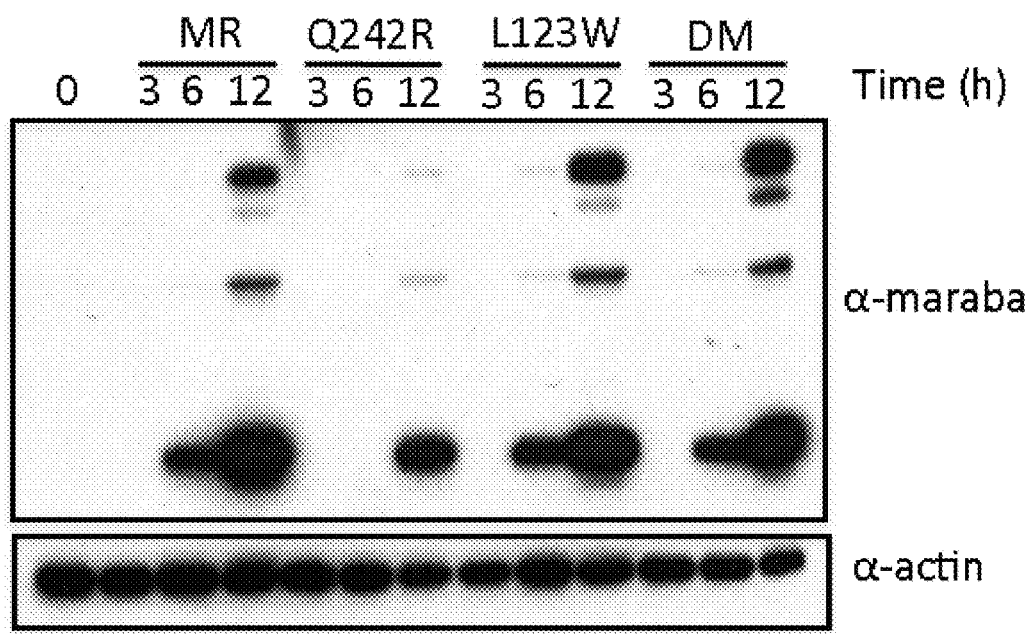

In contrast to our observation on normal fibroblasts, all of the mutant strains remained highly lytic when assayed on a panel of malignant cell lines (FIG. 2E). After 48 hours of exposure to virus, lytic capacity of the various strains was quantified using Alamar Blue vital dye (FIG. 2E). The L123W strain appeared to be as cytolytic as the rMaraba WT on tumor cells and thereby demonstrated an improved in vitro therapeutic index compared to WT strain. Maraba Q242R was very cytolytic on all three tumor lines albeit appeared to be less cytolytic than its parental rMaraba WT strain; in line with our plaque size observations. The double mutant however, demonstrated an interesting reversal of this phenotype as it showed no impairment in cytotoxicity due to the Q242R mutation it harbours. In fact, Maraba DM consistently appeared to be the most lytic strain on cancer cell lines (FIG. 2E), even more cytolytic than the parental WT. It appears that the combination of L123W and Q242R gives rise to a Maraba strain that is selectively hyper-virulent only on cancer cells yet remains attenuated on normal fibroblasts. This was also evident when viral protein production was assayed over time in OVCAR4 human ovarian carcinoma cells (FIG. 2F). rMaraba WT and the L123W strains showed rapid viral protein induction, while the Q242R mutant lagged behind. Here again the Q242R L123W double mutant Maraba showed no impairment in viral protein kinetics.

Maraba Mutants are Variably Defective in Blocking Host IFN Anti Viral Responses.

Figure 3A:
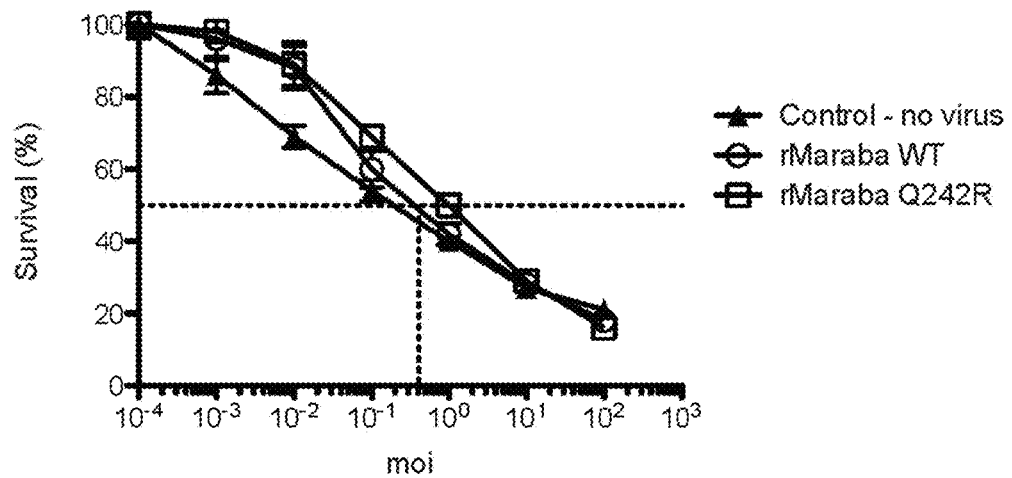
FIGS. 3A-3C. Maraba mutants vary in their ability to block interferon production. PC-3 cells were infected with the Maraba variants and the supernatant was used to protect Vero cells from subsequent infection with wild type Maraba virus.
Figure 3B:
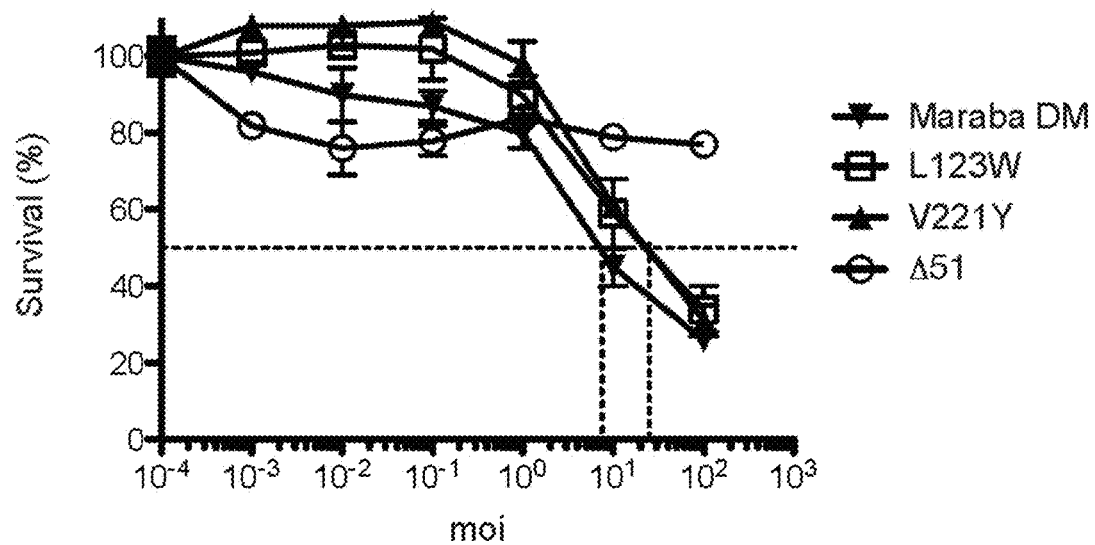
Figure 3C:
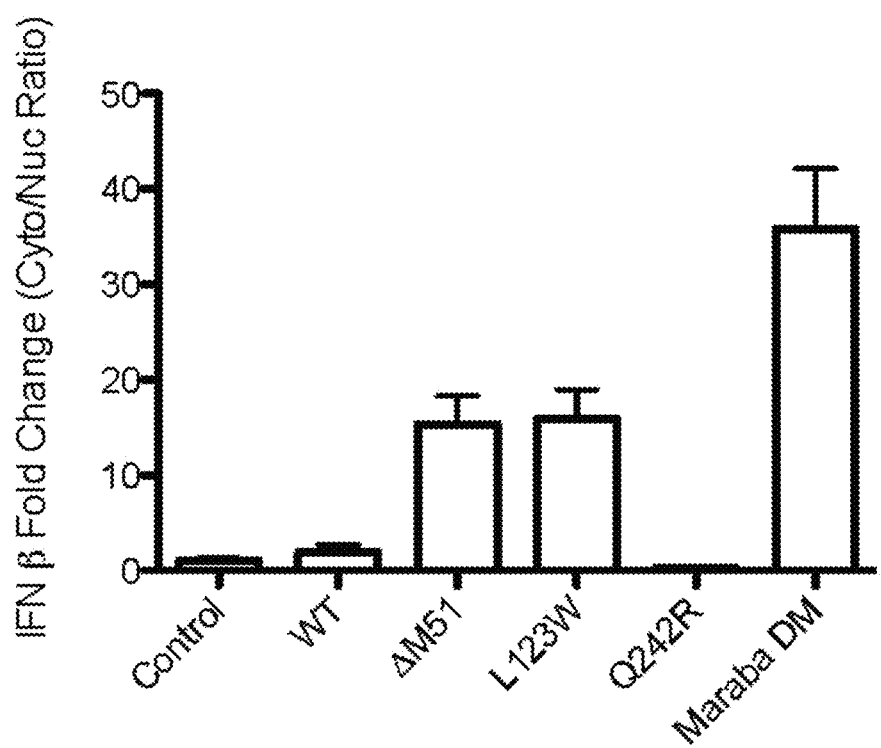

Having established several Maraba mutant strains as being selectively attenuated in normal primary fibroblasts, the inventors sought to understand whether this attenuation was due to defects in innate immune blockade. For example, ΔM51 and V221 mutations had previously been shown in VSV to render the virus unable to block nuclear/cytoplasmic mRNA transport, thereby inhibiting the host IFN transcriptional cascade. When PC3 cells were either mock infected, or infected with rMaraba WT, the inventors could detect no IFN production, consistent with the ability of the parental virus to block innate immune responses (FIG. 3A). As expected, the ΔM51 and V221Y mutants did show defects in the ability to block IFN production as measured in bioassay (FIG. 3B). Interestingly, the L123W mutant also demonstrated a defect in its ability to block IFN production to a similar magnitude as the V221Y mutant (FIG. 3B). The Q242R mutant, however, was similar to the WT virus in its ability to block cytokine production in PC3 cells, thus concluding that this mutant has no defect in IFN blockade. Therefore, the profound attenuation of the Q242R mutant appears to be unrelated host IFN responses. When the two single mutations are combined in the Maraba DM variant, the resulting virus was indistinguishable from the L123W single mutant (FIG. 3B). Furthermore, it was observed that interferon beta mRNA transport from the nuclear compartment to the cytoplasm was blocked following infection with either WT Maraba or the Q242R mutant (FIG. 3C). These results are consistent with previous reports that indicate certain viruses rely on their matrix proteins to inhibit the IFN transcriptional cascade by several mechanisms including blocking mRNA transport to the cytoplasm (Ferran and Lucas-Lenard, 1997; Terstegen et al., 2001; Stojdl et al., 2003). These results indicate that Maraba virus employs the same strategy. In contrast, Maraba ΔM51, the L123W strain and Maraba DM all showed a "leak" of IFN beta mRNA detectable in the cytoplasm following virus infection, and this deficit in mRNA blockade correlated with the viruses' ability to block IFN responses as measured in the bioassay (FIG. 2B).

Maraba DM in Less Toxic In Vivo.

The LD50 and maximum tolerable doses (MTD) were determined for Maraba WT and several attenuated strains. Since the desired therapeutic route of administration to treat disseminated tumors is intravenous administration mice were treated at a range of doses intravenously with either WT virus, or two mutant strains. The inventors observed that Maraba virus is well tolerated following intravenous injection in to Balb/C mice. As predicted from the in vitro data (FIG. 2C), Maraba DM has a MTD 2 logs higher than the parental WT Maraba (Table 5). Animals that received lethal doses of either WT, V221Y or DM display signs of CNS infection and had significant titers of virus in their brains (data not shown). At doses below the MTD, mice generally showed transient weight loss, dehydration, piloerection consistent with a virus infection. These symptoms resolved within 3-4 days post infection and no virus was detected in the brains of these mice scarified at day 12 post infection.

TABLE 5

| Intravenous Single Dose Toxicity of rMaraba virus strains | | |
|---|---|---|
| IntraVenous | LD50[a] (LOG10) | MTD[b] (LOG10) |
| rMaraba | 8.45 | 7 |
| rMaraba DM | 9.45 | 9 |
| rMaraba V221Y | 95 | 9 |

[a]Single Dose LD50 assayed in Balb/C mice (5-8 weeks old female) and calculated using the Spearman Karber method.
[b]Maximal Tolerable Dose (MTD) is equal to the highest dose not resulting in durable morbidity as measured by behaviour and weight.
[a]Single Dose LD50 assayed in Balb/C mice (5-8 weeks old female) and calculated using the spearman Karber method.
[b]Maximal Tolerable Dose (MTD) is equal to the highest dose not resulting in durable morbidity as measured by behavior and weight.

Maraba DM is Efficacious in Syngeneic and Xenograft Tumor Models.

Figure 4A:
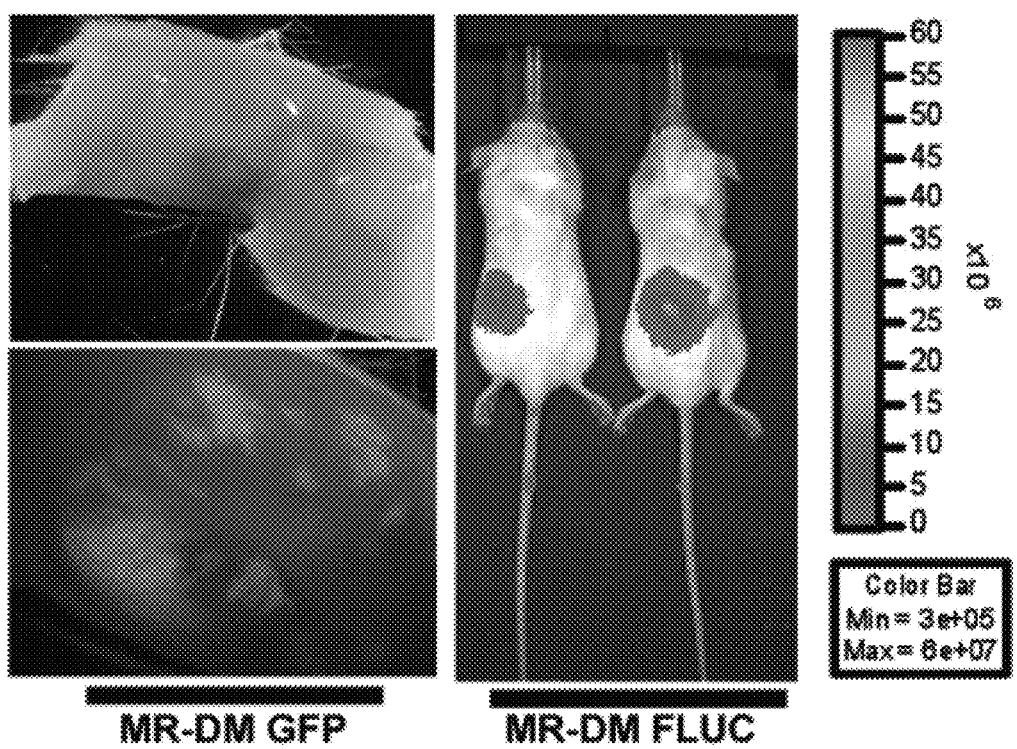

The inventors sought to determine whether Maraba DM is efficacious in in vivo mouse models of cancer. Maraba DM strains were engineered to expressing GFP or firefly luciferase and their replication in subcutaneous CT26 tumors following systemic administration was examined. The inventors observed Maraba DM virus to be delivered to tumor beds and to replicate in tumor tissue using both bioluminescent imaging in whole animals, and fluorescent microscopy in tumor explants (FIG. 4A(i)). Next, the efficacy of Maraba DM on a bilateral CT26 subcutaneous tumor model was examined (FIG. 4A(ii) and (iii)). Specifically animals with bilateral tumors reaching a size of 10-600 mm3 were treated intravenously with Maraba DM thrice weekly for 2 weeks. Five days after the first treatment, control animals treated with saline reached endpoint with tumors reaching a size of 750 mm3 or greater. However, animals that received 6 systemic doses of Maraba DM responded to treatment with complete tumor regression by day 35, leading to durable cures in 100% of the animals (FIG. 4A(ii) and (iii)). Finally, intravenous Maraba DM treatment was well tolerated in the animals, with no mortality and minimal morbidity. Piloerection, mild dehydration and transient weight loss was observed (FIG. 4A(iv)) but all resolved within 2 weeks of first treatment.

The inventors also sought to determine the utility of Maraba DM to reduce tumor burden in a disseminated disease model. Therefore, CT-26 cells were injected intravenously into Balb/C mice to induce disseminated lung tumors. While saline (PBS) and Carajas treated animals display a massive tumor burden, Maraba DM animals show little to no tumor burden and displaying a normal lung phenotype (FIG. 4B(i)). Moreover, Maraba DM also lead to a significant prolongation in survival when administered systemically thrice weekly for two weeks FIG. 4B(ii). This data is consistent with the observations in the subcutaneous model and further demonstrates the potency of Maraba DM to effectively treat an aggressive subcutaneous or disseminated syngeneic tumor model.

Figure 4C:
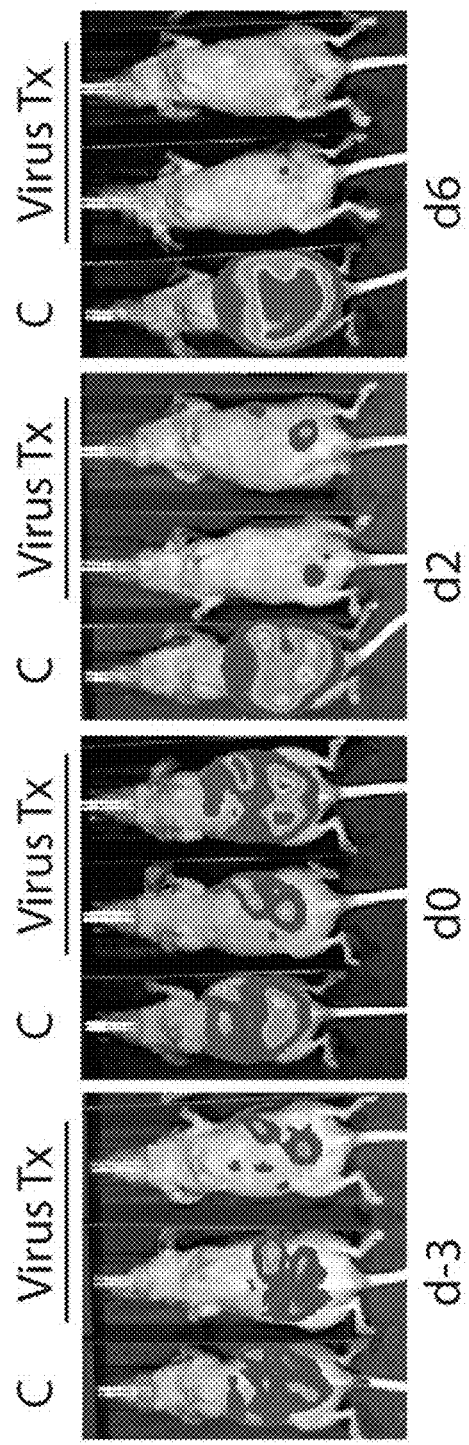

To complement these studies of viral efficacy in immunocompetent animals, Maraba DM was tested using a bioluminescent human ES-2 ovarian xenograft model. Even at a very low doses ($1 \times 10^4$ pfu), animals treated with Maraba DM had a significant decrease in tumor burden (FIG. 4C(i-iii)). In contrast, control treated mice rapidly developed ascites with increasing tumor burden until reaching endpoint. Systemic treatment of ES2 tumor bearing mice using low and high doses of virus demonstrated a dose dependent tumor response (FIG. 4D(i-ii)). The inventors tested Maraba DM against previously developed oncolytic virus strain (VSV ΔM51), and at both dose levels Maraba DM showed superior efficacy to VSV ΔM51.

B. Materials and Methods

Cell Lines.

Human A549 lung carcinoma, human Hela cervical carcinoma, murine CT26 colon carcinoma (American Type Tissue Collection), human GM38 primary fibroblasts (National Institute of General Medical Sciences Mutant Cell Repository, Camden, N.J.) and cell lines from the NCI 60 cell panel obtained from the Developmental Therapeutics Program, National Cancer Institute (Bethesda, Md.), were propagated in Dulbecco's modified Eagle's medium (Hyclone, Logan, Utah) supplemented with 10% fetal calf serum (Cansera, Etobicoke, Ontario, Canada). NCI 60 cell panel In Vitro Cytotoxicity Screen.

Cells from the NCI 60 cell panel were plated in 96 well plates to a confluency of 90%. These cells were infected at log dilutions with various rhabdoviruses, as indicated. After 96 hours post infection, the monolayers were washed, fixed and stained with 1% crystal violet solution. Stained monolayers were subsequently solubilized in 1% SDS in water to create homogenous lysates. Absorbance was read at 595 nm and to score for viable cells.

Single Step Growth Curves.

NCI226 cells and SNB19 cells were infected with the indicated viruses at a multiplicity of infection of 5 pfu/cell for 1 hour. Cells were then washed with PBS and incubated at 37° C. Aliquots (100 μL) were taken at time 0, 4, 8, 12, 16, 24, 48 and 72 hour time points and titered on Vero cells.

Sequencing and Cloning of Maraba Rhabdovirus.

Maraba rhabdovirus was amplified on Vero cells and RNA was isolated from purified virus by standard techniques (Trizol+RNAeasy®, Invitrogen). With the exception of the 5' and 3' terminal ends, the virus sequence was obtained using the mRNA Complete cloning kit (Invitrogen). The 3' and 5' end sequencing was completed following T4 RNA ligase mediated ligation of T7 DNA primers to either end followed by RT-PCR and cloning into pCR2.1-TOPO® (Invitrogen). The viral cDNA was amplified in a single RT-PCR reaction (yielding a >11 kbp fragment) and cloned into a modified LC-KAN vector (Lucigen Corporation) carrying a T7 promoter upstream of the 5'-anti-genomic leader sequence and immediately downstream of the 3'-terminator a modified HDV ribozyme and T7 polymerase termination signal sequence.

Phylogenetic Analysis.

Phylogenetic relationships between rhabdoviruses based on a Muscle alignment of L protein amino acid sequences, and using the paramyxovirus Measles Edmonston strain as the outgroup. The tree was generated by the neighbor-joining method and bootstrap values (indicated for each branch node) were estimated using 1000 tree replicas. Branch lengths are proportional to genetic distances. The scale bar corresponds to substitutions per amino acid site.

Recombinant Maraba Rescue System.

A549 lung carcinoma cells seeded at a $3.0 \times 10^5$ cells per well in 6-well plates were infected 24 h later at a multiplicity of infection (MOI) of 10 with Vaccinia virus expressing the T7 RNA polymerase in OptiMeM medium for 1.5 h. Following removal of the Vaccinia virus, each well was transfected with LC-KAN Maraba (2 μg) together with pCI-Neo constructs encoding for Maraba N (1 μg), P (1.25 μg) and L (0.25 μg) with lipofectamine 2000 (5 μL per well) according to the manufacturer's instructions. The transfection reagent was removed 5 h later and replaced with DMEM containing 10% FBS. 48 h following the transfection, medium was collected (pooled from 2 plates), filtered (0.2 μm) to remove contaminating Vaccinia virus and 1 mL was used to infect SNB-19 glioblastoma cells in each well of a 6-well plate. Cytopathic effects visible 24-48 h later were indicative of a successful rescue, which was confirmed by purifying viral RNA and RT-PCR with Maraba specific primers. All viruses underwent 3 rounds of plaque purification (on SNB-19 cells), before scale up, purification on sucrose cushion and resuspension in PBS containing 15% glucose.

Mutagenesis and Maraba Variants.

Single phosphorylated mutagenic primers (45-55 bp) were used with the high fidelity Phusion enzyme (NEB) to create the panel of LC-KAN Maraba mutants described within. Briefly, a PCR reaction was carried out with 100 ng of mutagenic primer and 100 ng DNA template with hotstart addition of enzyme (98° C.-2 min, 80° C. hold—add enzyme) and typical PCR setup (98° C.-10 sec, 55° C.-30 sec, 72° C. for 7 min for 30 cycles). Dimethyl sulfoxide (DMSO) was added in the range of 0 to 6% in increments of 2%. The parental plasmid was digested with Dpn I (NEB) (37° C. for 1 h) and 4 μL of the 25 μL DpnI-digested PCR mixture was used to transform TOP-10® competent cells (Invitrogen). Positive clones were screened by introduction of noncoding change restriction site changes (adding or removing) followed by sequencing. The different attenuated mutants described here include deletion of Met-51 in the M protein (ΔM51), Leu-123 to Trp in the M protein (L123W), Val-221 to Tyr in the M protein (V221Y), Gln-242 to Arg in the G protein (Q242R), and double mutant Leu-123 to Trp in the M protein and Gln-242 to Arg in the G protein (Maraba DM).

Viability Assays.

The indicated cell lines were plated at a density of 10,000 cells/well into 96 well plates. The next day cells were infected with the indicated viruses at various multiplicity of infections (0.0001-10 pfu/cell). Following a 48 hour incubation Alamar Blue (Resazurin sodium salt (Sigma-Aldrich)) was added to a final concentration of 20 μg/ml. After a 6 hour incubation the absorbance was read at a wavelength of 573 nm.

Plaque Assays.

Vero cells were plated at a density of $5\times10^5$ cells per/well of a 6 well dish. The next day 100 µl of serial viral dilutions were prepared and added for 1 hour to Vero cells. After viral adsorption 2 ml of agarose overlay was added (1:1 1% agarose: 2×DMEM and 20% FCS). Plaques were counted the following day.

Interferon Bioassay.

PC-3 cells were infected with rMarabaWT, ΔM51, V221Y, L123W, Q242R, or Maraba DM at a multiplicity of infection of 3 pfu/cell for 24 hours. The following day supernatant was acid neutralized with 0.25N HCl overnight at 4° C. followed by the addition of 0.25 NaOH to adjust the pH to 7. Vero cells were incubated with the neutralized supernatant for 24 hours and subsequently infected rMaraba WT with a multiplicity of infection ranging from 0.0001 to 100 pfu/cell. Any interferon secreted by the PC-3 cells in response to Maraba or the attenuated mutants would subsequently protect the Vero cells from infection with Maraba. After 24 hours, survival was quantitated using a crystal violet assay. Briefly cells were incubated with 1% crystal violet solution, washed, dried, resuspended in 1% SDS and read at a wavelength of 595 nm.

Quantitative RT-PCR to Detect Nuclear and Cytoplasmic Interferon.

Nuclear and cytoplasmic RNA was separated as described previously. Briefly OVCAR4 cells either mock treated or infected with Maraba, ΔM51, L123W, Q242R or Maraba DM were harvested in PBS, pelleted, and resuspended in 200 µl of Lysis buffer (25 mM Tris [pH 7.4], 15 mM NaCl, 12.5 mM $MgCl_2$ 5% sucrose, and 1% NP-40). The lysates were incubated at 4° C. for 10 min with occasional vortexing. Nuclei were collected by centrifugation at 1000×g for 3 min. The supernatant (cytoplasmic fraction) was collected while nuclear fraction was washed once with 250 µl of lysis buffer followed by total RNA extraction using the Qiagen RNeasy kit (as per manufacturer's instructions; Qiagen). QRTPCR of IFN-beta mRNA was performed using the Quantitect SYBR Green RT-PCR kit from Qiagen with previously described primers. IFN-beta was assayed from nuclear and cytoplasmic fractions and normalized to HPRT mRNA from the same compartment. Normalized values were normalized again to values from uninfected nuclear and cytoplasmic fractions respectively, to determine fold induction values in each compartment, following virus infection. Plotted values indicate the ratio of normalized mRNA induction from the cytoplasmic to nuclear compartments. All QPCR values were calculated using the delta CT method.

Determination of In Vivo Toxicity.

Groups of 3-5 Balb/C mice (6-8 weeks old) were injected once intravenously in half log increments of virus ranging from $3\times10^6$ pfu-$3\times10^9$ pfu. The animals were monitored for signs of distress including weight loss, morbidity, piloerection, hind-limb paralysis and respiratory distress.

Bilateral Subcutaneous Tumor Model.

Murine CT26 colon cancer cells ($3\times10^5$) were injected in the right and left flanks of 6-8 week old Balb/C mice. Tumors were allowed to grow to a size of 10-600 $mm^3$ followed by 6 total (thrice weekly) intravenous injections of either 51VSV or MR-SDM at a dose of $5\times10^8$ pfu. Tumors were measured twice weekly after initial injection. Animals were monitored for piloerection, weight loss, morbidity, hind leg paralysis and respiratory distress. When tumor burden exceeded a size of 750 $mm^3$ animals were euthanized. The following formula was used to calculate tumor volume $(L\times W^2)/2$.

Imaging Maraba DM Virus in a Subcutaneous Tumor Model.

Maraba DM was adapted for fluorescent or bioluminescent imaging by genetically engineering in eGFP or firefly luciferase (FLUC) respectively. DM-GFP and DM-FLUC was injected IV ($1\times10^8$) into Balb/C animals bearing subcutaneous CT-26 tumors. Twenty-four hours post infection DM-GFP infected animals were euthanized and their tumors were extracted and imaged under a Nikon fluorescent microscope. Animals infected with DM-FLUC were injected with luciferin and underwent live imaging using the IVIS Xenogen 200 system.

CT-26 Lung Tumor Model.

Lung tumors were established by a single intravenous injection of $3\times10^5$ CT-26 colon cancer cells into 6-8 week old Balb/C animals. Generally mice develop severe respiratory distress, piloerection and hunched phenotype at day 16-18 at which point they are euthanized. Mice were either IV treated with PBS, carajas, or Maraba DM ($5\times10^8$ pfu) treated at day 10, 12 and 14, 17, 19 and 21. Some animals were sacrificed at day 17 and images were captured on a Nikon dissecting microscope. The remaining animals were monitored for survival.

Ovarian Xenograft Model.

Human ovarian ES-2 cells were adapted for bioluminescent imaging at which time $1\times10^6$ ES-2 cells were injected intraperitoneally into 6-8 week old athymic CD-1 nude mice. Untreated CD-1 animals develop ascites at about day 15-17. Intraperitoneal and intravenous (tail vein) injections were performed on day 8, 9, 12, 14 and 16 with $1\times10^4$-$1\times10^7$ pfu of Maraba DM or VSV 451. Tumor imaging was captured with a Xenogen 200 IVIS system (Caliper LS, USA).

Statistics.

For plaque size determinations, one way ANOVA was performed using the Bonferroni multiple comparison's test to derive a P value (Graphpad Prism). For Kaplan Meier plots, survival plots were compared using Mantel-Cox Log rank analysis (Graphpad Prism).

REFERENCES

U.S. Pat. No. 4,554,101
U.S. Pat. No. 4,683,195
U.S. Pat. No. 4,683,202
U.S. Pat. No. 4,684,611
U.S. Pat. No. 4,800,159
U.S. Pat. No. 4,879,236
U.S. Pat. No. 4,883,750
U.S. Pat. No. 4,946,773
U.S. Pat. No. 4,952,500
U.S. Pat. No. 5,220,007
U.S. Pat. No. 5,279,721
U.S. Pat. No. 5,284,760
U.S. Pat. No. 5,302,523
U.S. Pat. No. 5,322,783
U.S. Pat. No. 5,354,670
U.S. Pat. No. 5,366,878
U.S. Pat. No. 5,384,253
U.S. Pat. No. 5,389,514
U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318

U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,635,377
U.S. Pat. No. 5,641,515
U.S. Pat. No. 5,656,610
U.S. Pat. No. 5,702,932
U.S. Pat. No. 5,736,524
U.S. Pat. No. 5,739,169
U.S. Pat. No. 5,780,448
U.S. Pat. No. 5,789,166
U.S. Pat. No. 5,789,215
U.S. Pat. No. 5,798,208
U.S. Pat. No. 5,801,005
U.S. Pat. No. 5,824,311
U.S. Pat. No. 5,830,650
U.S. Pat. No. 5,830,880
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,225
U.S. Pat. No. 5,846,233
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,846,945
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,871,986
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,925,565
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624

Abschuetz et al., *Cell Tissue Res.*, 325(3):423-36, 2006.
Almendro et al., *J. Immunol.*, 157(12):5411-5421, 1996.
Altomonte et al., *Cancer Gene Ther.*, 16(3):266-78, 2008.
Angel et al., *Cell*, 49:729, 1987a.
Angel et al., *Mol. Cell. Biol.*, 7:2256, 1987b.
Austin-Ward and Villaseca, *Revista Medica de Chile*, 126 (7):838-845, 1998.
Ausubel et al., In: *Current Protocols in Molecular Biology*, John, Wiley & Sons, Inc, NY, 1994.
Bajorin et al., *J. Clin. Oncol.*, 6(5):786-792, 1988.
Bakhshi et al., *Cell*, 41(3):899-906, 1985.
Banerji et al., *Cell*, 27 (2 Pt 1):299-308, 1981.
Banerji et al., *Cell*, 33(3):729-740, 1983.
Bergmann et al., *Cancer Res.*, 61(22):8188-93, 2001.
Berkhout et al., *Cell*, 59:273-282, 1989.
Blanar et al., *EMBO J.*, 8:1139, 1989.
*Blood*. 2001 Jun. 15; 97(12):3746-54
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Braisted and Wells, *Proc. Natl. Acad. Sci. USA*, 93(12): 5688-5692, 1996.
Bukowski et al., *Clinical Cancer Res.*, 4(10):2337-2347, 1998.
Bulla and Siddiqui, *J. Virology*, 62:1437, 1986.
Burton and Barbas, *Adv. Immunol.*, 57:191-280, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75-82, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Chiocca, *Curr. Opin. Mol. Ther.*, 10:38-45, 2008.
Choi et al., *Cell*, 53:519, 1988.
Christodoulides et al., *Microbiology*, 144 (Pt 11):3027-3037, 1998.
Cleary and Sklar, *Proc. Natl. Acad. Sci. USA*, 82(21):7439-7443, 1985.
Cleary et al., *J. Exp. Med.*, 164(1):315-320, 1986.
Cocea, *Biotechniques*, 23(5):814-816, 1997.

Coffey et al., *Science,* 282(5392):1332-4, 1998.
Cohen and Wittenauer, *J. Cardiovasc. Pharmacol.,* 10:176-181, 1987.
Connor et al., *J. Virol.,* 80:3701-3711, 2006.
Costa et al., *Mol. Cell. Biol.,* 8:81-90, 1988.
Cripe et al., *EMBO J.,* 6:3745, 1987.
Culotta and Hamer, *Mol. Cell. Biol.,* 9:1376-1380, 1989.
Culver et al., *Science,* 256(5063):1550-1552, 1992.
Cunningham et al., *Science,* 244(4908):1081-1085, 1989.
Cybinski et al., *Veterinary Microbiol.,* 5:301-308, 1980.
Dandolo et al., *J. Virology,* 47:55-64, 1983.
Davidson et al., *J. Immunother.,* 21(5):389-398, 1998.
de Villiers et al., *Nature,* 312(5991):242-246, 1984.
Deschamps et al., *Science,* 230:1174-1177, 1985.
Dhar et al., *J. Virol.,* 83(5):2130-2139, 2008.
Dillman, *Cancer Biother. Radiopharm.,* 14(1):5-10, 1999.
Doherty et al. *Trans. R Soc. Trop. Med. Hyg.,* 67:536-543, 1973.
Edbrooke et al., *Mol. Cell. Biol.,* 9:1908-1916, 1989.
Edlund et al., *Science,* 230:912-916, 1985.
Endo et al. *Oncogene,* 27:2375-2381, 2008.
European Appln. 320 308
European Appln. 329 822
Fechheimer, et al., *Proc Natl. Acad. Sci. USA,* 84:8463-8467, 1987.
Feng and Holland, *Nature,* 334:6178, 1988.
Ferran and Lucas-Lenard, *J. Virol.,* 71:371-377, 1997.
Firak and Subramanian, *Mol. Cell. Biol.,* 6:3667, 1986.
Foecking and Hofstetter, *Gene,* 45(1):101-105, 1986.
Fraley et al., *Bio/Technology,* 3:629-635, 1985.
Frohman, In: *PCR Protocols: A Guide To Methods And Applications,* Academic Press, N.Y., 1990.
Fuerst et al., Proc Natl Acad Sci USA 83, 8122-8126, 1986.
Fujita et al., *Cell,* 49:357, 1987.
GB Appln. 2 202 328
Gilles et al., *Cell,* 33:717, 1983.
Gloss et al., *EMBO J.,* 6:3735, 1987.
Godbout et al., *Mol. Cell. Biol.,* 8:1169, 1988.
Goodbourn and Maniatis, *Proc. Natl. Acad. Sci. USA,* 85:1447, 1988.
Goodbourn et al., *Cell,* 45:601, 1986.
Gopal, *Mol. Cell Biol.,* 5:1188-1190, 1985.
Graham and Van Der Eb, *Virology,* 52:456-467, 1973.
Greene et al., *Immunology Today,* 10:272, 1989.
Gromeier et al., *Proc. Natl. Acad. Sci. USA,* 97(12):6803-8, 2000.
Grosschedl and Baltimore, *Cell,* 41:885, 1985.
Grote et al., *Blood.,* 97(12):3746-54, 2001.
Hanibuchi et al., *Int. J. Cancer,* 78(4):480-485, 1998.
Harland and Weintraub, *J. Cell Biol.,* 101(3):1094-1099, 1985.
Haslinger and Karin, *Proc. Natl. Acad. Sci. USA,* 82:8572, 1985.
Hauber and Cullen, *J. Virology,* 62:673, 1988.
Heise et al., *Nat. Med.,* 6(10):1134-9, 2000.
Hellstrand et al., *Acta Oncologica,* 37(4):347-353, 1998.
Hen et al., *Nature,* 321:249, 1986.
Hensel et al., *Lymphokine Res.,* 8:347, 1989.
Herr and Clarke, *Cell,* 45:461, 1986.
Hilton et al., *J. Biol. Chem.,* 271(9):4699-4708, 1996.
Hirochika et al., *J. Virol.,* 61:2599, 1987.
Hirsch et al., *Mol. Cell. Biol.,* 10:1959, 1990.
Holbrook et al., *Virology,* 157:211, 1987.
Holden et al., *EMBO J.,* 6:1565-1570, 1987.
Horlick and Benfield, *Mol. Cell. Biol.,* 9:2396, 1989.
Huang et al., *Cell,* 27:245, 1981.
Hug et al., *Mol. Cell. Biol.,* 8:3065-3079, 1988.
Hui and Hashimoto, *Infection Immun.,* 66(11):5329-5336, 1998.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Innis et al., *Proc. Natl. Acad. Sci. USA,* 85(24):9436-9440, 1988.
Inouye and Inouye, *Nucleic Acids Res.,* 13:3101-3109, 1985.
Irie and Morton, *Proc. Natl. Acad. Sci. USA,* 83(22):8694-8698, 1986.
Irie et al., *Lancet.,* 1(8641):786-787, 1989.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., *Amer. J. Physiol.,* 256:H1012-1022, 1989.
Ju et al., *Gene Ther.,* 7(19):1672-1679, 2000.
Kadesch and Berg, *Mol. Cell. Biol.,* 6:2593, 1986.
Kaeppler et al., *Plant Cell Reports,* 9:415-418, 1990.
Kaneda et al., *Science,* 243:375-378, 1989.
Karin et al., *Mol. Cell. Biol.,* 7:606, 1987.
Katinka et al., *Cell,* 20:393, 1980.
Katinka et al., *Nature,* 290:720, 1981.
Kato et al, *J. Biol. Chem.,* 266:3361-3364, 1991.
Kawamoto et al., *Mol. Cell. Biol.,* 8:267, 1988.
Kerr et al., *Br. J. Cancer,* 26(4):239-257, 1972.
Kerschner et al., *J. Gen. Virol.,* 67 (Pt 6):1081-1089, 1986.
Kiledjian et al., *Mol. Cell. Biol.,* 8:145, 1988.
Kinoh et al., *Gene Ther.,* 11(14):1137-45, 2004.
Klamut et al., *Mol. Cell. Biol.,* 10:193, 1990.
Koch et al., *Mol. Cell. Biol.,* 9:303, 1989.
Kraus et al. *FEBS Lett.,* 428(3):165-170, 1998.
Kriegler and Botchan, In: *Eukaryotic Viral Vectors,* Gluzman (Ed.), Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984.
Kriegler et al., *Cell,* 53:45, 1988.
Kriegler et al., In: *Cancer Cells 2/Oncogenes and Viral Genes,* Van de Woude et al. eds, Cold Spring Harbor, Cold Spring Harbor Laboratory, 1984.
Kriegler et al., In: *Gene Expression,* Alan Liss (Ed.), Hamer and Rosenberg, New York, 1983.
Kuhl et al., *Cell,* 50:1057, 1987.
Kunz et al., *Nucl. Acids Res.,* 17:1121, 1989.
Kwoh et al., *Proc. Natl. Acad. Sci. USA,* 86:1173, 1989.
Kyte and Doolittle, *J. Mol. Biol.,* 157(1):105-132, 1982.
Lareyre et al., *J. Biol. Chem.,* 274(12):8282-8290, 1999.
Larsen et al., *Proc. Natl. Acad. Sci. USA.,* 83:8283, 1986.
Laspia et al., *Cell,* 59:283, 1989.
Latimer et al., *Mol. Cell. Biol.,* 10:760, 1990.
Lawson et al., *Proc. Natl. Acad. Sci. USA,* 92:4477-4481, 1995.
Lee et al., *Biochem. Biophys. Res. Commun.,* 238(2):462-467, 1997.
Lee et al., *Nature,* 294:228, 1981.
Lee et al., *Nucleic Acids Res.,* 12:4191-206, 1984.
Levenson et al., *Hum. Gene Ther.,* 9(8):1233-1236, 1998.
Levinson et al., *Nature,* 295:79, 1982.
Lin et al., *Cytogenet. Cell Genet.,* 53:169-171, 1990.
Logg et al., *Hum. Gene Ther.,* 12(8):921-32, 2001.
Luria et al., *EMBO J.,* 6:3307, 1987.
Lusky and Botchan, *Proc. Natl. Acad. Sci. USA,* 83:3609, 1986.
Lusky et al., *Mol. Cell. Biol.,* 3:1108, 1983.
Macejak and Sarnow, *Nature,* 353:90-94, 1991.

Majors and Varmus, *Proc. Natl. Acad. Sci. USA.*, 80:5866, 1983.
McNeall et al., *Gene,* 76:81, 1989.
Miksicek et al., *Cell,* 46:203, 1986.
Mineta et al., *Nat. Med.,* 1(9):938-43, 1995.
Mitchell et al., *Ann. NY Acad. Sci.,* 690:153-166, 1993.
Mitchell et al., *J. Clin. Oncol.,* 8(5):856-869, 1990.
Mordacq and Linzer, *Genes and Dev.,* 3:760, 1989.
Moreau et al., *Nucl. Acids Res.,* 9:6047, 1981.
Morton et al., *Arch. Surg.,* 127:392-399, 1992.
Muesing et al., *Cell,* 48:691, 1987.
Muir Springs and Bahia Grande: J Gen Virol. 1986 June; 67 (Pt 6):1081-9
Nakaya et al., *J. Virol.,* 75:11868-11873, 2001.
Ng et al., *Nuc. Acids Res.,* 17:601, 1989.
Nicolau and Sene, *Biochim. Biophys. Acta,* 721:185-190, 1982.
Nicolau et al., *Methods Enzymol.,* 149:157-176, 1987.
Nomoto et al., *Gene,* 236(2):259-271, 1999.
Ohara et al., *Proc. Natl. Acad. Sci. USA,* 86:5673-5677, 1989.
Omirulleh et al., *Plant Mol. Biol.,* 21(3):415-428, 1993.
Omitz et al., *Mol. Cell. Biol.* 7:3466, 1987.
Oncol Res. 1999; 11(3):133-44.
Ondek et al., *EMBO J.,* 6:1017, 1987.
Palmiter et al., *Cell,* 29:701, 1982.
Palmiter et al., *Nature,* 300:611, 1982.
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 94/09699
PCT Appln. WO 95/06128
Pech et al., *Mol. Cell. Biol.,* 9:396, 1989.
Pelletier and Sonenberg, *Nature,* 334(6180):320-325, 1988.
Perez-Stable and Constantini, *Mol. Cell. Biol.,* 10:1116, 1990.
Picard and Schaffner, *Nature,* 307:83, 1984.
Pietras et al., *Oncogene,* 17(17):2235-2249, 1998.
Pinkert et al., *Genes and Dev.,* 1:268, 1987.
Ponta et al., *Proc. Natl. Acad. Sci. USA.,* 82:1020, 1985.
Porton et al., *Mol. Cell. Biol.,* 10:1076, 1990.
Potrykus et al., *Mol. Gen. Genet.,* 199(2):169-177, 1985.
Qin et al., *Proc. Natl. Acad. Sci. USA,* 95(24):14411-14416, 1998.
Queen and Baltimore, *Cell,* 35:741, 1983.
Quinn et al., *Mol. Cell. Biol.,* 9:4713, 1989.
Ravindranath and Morton, *Intern. Rev. Immunol.,* 7: 303-329, 1991.
Redondo et al., *Science,* 247:1225, 1990.
Reisman and Rotter, *Mol. Cell. Biol.,* 9:3571, 1989.
Remington's Pharmaceutical Sciences" 15th Edition, pages 1035-1038 and 1570-1580, 1990.
Resendez Jr. et al., *Mol. Cell. Biol.,* 8:4579, 1988.
Rippe et al., *Mol. Cell. Biol.,* 9(5):2224-22277, 1989.
Rittling et al., *Nuc. Acids Res.,* 17:1619, 1989.
Rodriguez et al. (1990) *J. Virol.,* 64:4851-4857, 1990.
Rodriguez et al., *J. Virol.,* 64:4851-4857, 1990.
Rosen et al., *Cell,* 41:813, 1988.
Rosenberg et al., *Ann. Surg.,* 210(4):474-548, 1989.
Rosenberg et al., *N. Engl. J. Med.,* 319:1676, 1988.
Sakai et al., *Genes and Dev.,* 2:1144, 1988.
Sambrook and Russell, Molecular Cloning: A Laboratory Manual 3$^{rd}$ Ed., Cold Spring Harbor Laboratory Press, 2001.
Sanjuan et al., *Proc. Natl. Acad. Sci. USA,* 101(43):15376-15379, 2004.
Satake et al., *J. Virology,* 62:970, 1988.
Schaffner et al., *J. Mol. Biol.,* 201:81, 1988.
Schnell et al., *EMBO J.,* 13:4195-4203, 1994.
Searle et al., *Mol. Cell. Biol.,* 5:1480, 1985.
Shafren et al., *Clin. Cancer Res.,* 10 (1 Pt 1):53-60, 2004.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Stephens and Hentschel, *Biochem. J.,* 248:1, 1987.
Stillman et al., *J. Virol.,* 69:2946-2953, 1995.
Stojdl et al., *Cancer Cell.,* 4(4):263-75, 2003.
Stojdl et al., *Nat Med.,* 6(7):821-5, 2000.
Stuart et al., *Nature,* 317:828, 1985.
Sullivan and Peterlin, *Mol. Cell. Biol.,* 7:3315, 1987.
Swartzendruber and Lehman, *J. Cell. Physiology,* 85:179, 1975.
Takada et al., *Proc. Natl. Acad. Sci. USA,* 94(26):14764-14769, 1997.
Takebe et al., *Mol. Cell. Biol.,* 8:466, 1988.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Terstegen et al., *J. Immunol.,* 167:5209-5216, 2001.
Thiesen et al., *J. Virology,* 62:614, 1988.
Timiryasova et al., *Oncol. Res.,* 11(3):133-44, 1999.
Travassos da Rosa et al., *Am. J. Trop. Med. Hyg.,* 33:999-1006, 1984.
Travassos da Rosa et al., *Emerging Infect. Dis.,* 8:614-618, 2002.
Treisman, *Cell,* 46(4):567-174, 1986
Tronche et al., *Mol. Biol. Med.,* 7:173, 1990.
Tronche et al., *Mol. Cell Biol.,* 9(11):4759-4766, 1989.
Trudel and Constantini, *Genes and Dev.,* 6:954, 1987.
Tsujimoto and Croce, *Proc. Natl. Acad. Sci. USA,* 83(14):5214-5218, 1986.
Tsujimoto et al., *Nature,* 315:340-343, 1985.
Tsumaki et al., *J. Biol. Chem.,* 273(36):22861-22864, 1998.
Unno et al., *Clin. Cancer Res.,* 11(12):4553-60, 2005.
Usdin et al., *Bio. Techniques.,* 14:222-224, 1993.
Vannice and Levinson, *J. Virology,* 62:1305, 1988.
Vasseur et al., *Proc. Natl. Acad. Sci. USA.,* 77:1068, 1980.
Walker et al., *Nucleic Acids Res.* 20(7):1691-1696, 1992.
Wang and Calame, *Cell,* 47:241, 1986.
Warren et al., *Biochemistry,* 35(27):8855-8862, 1996.
Weber et al., *Cell,* 36:983, 1984.
Weinberger et al., *Mol. Cell. Biol.,* 8:988, 1984.
Wells et al., *J. Leukoc. Biol.,* 59(1):53-60, 1996.
Whelan et al., *Proc. Natl. Acad. Sci. USA,* 92:8388-8392, 1995.
Winoto and Baltimore, *Cell,* 59:649, 1989.
Wong et al., *Gene,* 10:87-94, 1980.
Wu et al., *J. Exp. Med.,* 185:1681-1691, 1997.
Yelton et al., *J. Immunol.,* 155(4):1994-2004, 1995.
Yutzey et al., *Mol. Cell. Biol.,* 9:1397-1405, 1989.
Zeng et al., *Biochemistry,* 35(40):13157-13164, 1996.
Zhao-Emonet et al., *Biochim. Biophys. Acta,* 1442 (2-3): 109-119, 1998.

The invention claimed is:

1. An attenuated Maraba virus comprising:
a G protein having an amino acid sequence that is at least 95% identical to the amino acid sequence of SEQ ID NO:5 and an arginine at the position corresponding to position 242 of SEQ ID NO:5.

2. A method of killing a hyperproliferative cell comprising contacting the cell with an isolated oncolytic Maraba virus encoding:
a G protein having an amino acid sequence that is at least 95% identical to the amino acid sequence of SEQ ID NO:5 and an arginine at the position corresponding to position 242 of SEQ ID NO:5.

3. The method of claim 2, wherein the cell is comprised in a patient.

4. The method of claim 3, wherein the cell is a cancer cell.

5. The method of claim 4, wherein the cancer cell is a metastatic cancer cell.

6. The method of claim 3, wherein the oncolytic Maraba virus is administered to the patient.

7. The method of claim 6, wherein the oncolytic Maraba virus is administered by intraperitoneal, intravenous, intra-arterial, intramuscular, intradermal, intratumoral subcutaneous, or intranasal administration.

8. The method of claim 2, further comprising administering a second anti-cancer therapy.

9. The method of claim 8, wherein the second cancer therapy is chemotherapeutic, radiotherapeutic, or immunotherapeutic.

10. A method for treating a cancer patient comprising administering an effective amount of an isolated oncolytic Maraba virus encoding:
a G protein having an amino acid sequence that is at least 95% identical to the amino acid sequence of SEQ ID NO:5 and an arginine at the position corresponding to position 242 of SEQ ID NO:5.

11. The method of claim 10, wherein the oncolytic Maraba virus is administered intraperitoneal, intravenous, intra-arterial, intramuscular, intradermal, intratumoral, subcutaneous, or intranasal administration.

12. The method of claim 10, further comprising administering a second cancer therapy.

13. The method of claim 12, wherein the second cancer therapy is chemotherapy, radiotherapy, immunotherapy, or surgery.

14. A composition comprising an isolated oncolytic Maraba virus having a nucleic acid segment encoding:
a G protein having an amino acid sequence that is at least 95% identical to the amino acid sequence of SEQ ID NO:5 and an arginine at the position corresponding to position 242 of SEQ ID NO:5.

15. The composition of claim 14, wherein the composition is a pharmaceutically acceptable composition.

16. The composition of claim 15, further comprising a second anti-cancer agent.

17. The composition of claim 16, wherein the second anti-cancer agent is a chemotherapeutic, radiotherapeutic, or immunotherapeutic.

18. The attenuated Maraba virus of claim 1, wherein the G protein has an amino acid sequence that is 100% identical to the amino acid sequence of SEQ ID NO: 5 except for an arginine at the position corresponding to position 242 of SEQ ID NO: 5.

19. The method of claim 2, wherein the G protein has an amino acid sequence that is 100% identical to the amino acid sequence of SEQ ID NO: 5 except for an arginine at the position corresponding to position 242 of SEQ ID NO: 5.

20. The method of claim 10, wherein the G protein has an amino acid sequence that is 100% identical to the amino acid sequence of SEQ ID NO: 5 except for an arginine at the position corresponding to position 242 of SEQ ID NO: 5.

21. The composition of claim 14, wherein the G protein has an amino acid sequence that is 100% identical to the amino acid sequence of SEQ ID NO: 5 except for an arginine at the position corresponding to position 242 of SEQ ID NO: 5.

* * * * *

SEQUENCE LISTING

<160> NUMBER OF SEQ ID NOS: 29

<210> SEQ ID NO 1
<211> LENGTH: 11068
<212> TYPE: DNA
<213> ORGANISM: Maraba Virus

<400> SEQUENCE: 1

| | | | | | |
|---|---|---|---|---|---|
| ctgttacagt | caagagagtc | attgatgatt | cactcatcac | ccccaaattg | cctgcgaatg | 60 |
| aggaccctgt | ggagtaccct | gctgattatt | tcaaaaagtc | ccgtgatatt | ccggtgtaca | 120 |
| taaacacgac | caaaagtttg | tctgatttgc | ggggctatgt | ttatcaaggc | ctaaagtcag | 180 |
| gcaacatctc | tataattcat | gtcaacagtt | atctgtatgc | agcattaaaa | gagatcagag | 240 |
| gaaaattgga | cagagattgg | atcacctttg | gtatccaaat | cggaaaaaca | ggagatagcg | 300 |
| tggggatatt | cgatttactg | accctaaaac | ctctagatgg | tgttttacca | gatggggtgt | 360 |
| ctgatgctac | tcgaactagc | tcagacgatg | catggcttcc | actgtatcta | ttggggttat | 420 |
| acagagttgg | tcgaacacag | atgccagaat | acaggaagaa | gctgatggat | ggtctgatta | 480 |
| atcaatgtaa | gatgatcaat | gagcagtttg | aaccactgtt | gccagaagga | agagatgtct | 540 |
| ttgatgtctg | gggaaatgac | agcaattaca | caaagattgt | ggccgctgta | gatatgttct | 600 |
| tccatatgtt | caaaaagcat | gagaaggcct | ctttcaggta | tggcacaata | gtgtcaagat | 660 |
| ttaaggattg | tgcagcattg | gctacatttg | gtcatctgtg | taagatcact | ggtatgtcca | 720 |
| ctgaagatgt | gacaacttgg | attctaaaca | gggaggtggc | tgatgagatg | gttcaaatga | 780 |
| tgtacccagg | acaggagata | gataaggctg | attcttacat | gccttatcta | atcgacttag | 840 |
| gtctgtcctc | aaaatctcca | tatccatcag | ttaaaaatcc | agctttccat | ttttggggtc | 900 |
| aattgaccgc | attgttactg | agatcaacca | gagccagaaa | tgcacgtcag | ccggatgaca | 960 |
| tcgagtatac | atccctgacc | actgctgggc | tgttgtatgc | atatgccgtt | ggttcgtctg | 1020 |
| cagacctggc | tcaacaattc | tacgttgggg | acaacaagta | tgtgccagaa | actggagatg | 1080 |
| gaggattaac | caccaatgca | ccgccacaag | ggcgagatgt | ggtcgagtgg | cttagttggt | 1140 |
| ttgaagatca | aaacagaaaa | cctaccccag | acatgctcat | gtatgctaag | agagctgtca | 1200 |
| gtgctttaca | aggattgagg | gagaagacga | ttggcaagta | cgccaagtca | gagttttgaca | 1260 |
| aatgacaact | cactcaccat | atgtattact | acctttgctt | catatgaaaa | aaactaacag | 1320 |
| cgatcatgga | tcagctatca | aaggtcaagg | aattccttaa | gacttacgcg | cagttggatc | 1380 |
| aagcagtaca | agagatggat | gacattgagt | ctcagagaga | ggaaaagact | aattttgatt | 1440 |
| tgtttcagga | agaaggattg | gagattaagg | agaagccttc | ctattatcgg | gcagatgaag | 1500 |
| aagagattga | ttcagatgaa | gacagcgtgg | atgatgcaca | agacttaggg | atacgtacat | 1560 |
| caacaagtcc | catcgagggg | tatgtggatg | aggagcagga | tgattatgag | gatgaggaag | 1620 |
| tgaacgtggt | gtttacatcg | gactggaaac | agcctgagct | ggaatccgac | ggggatggga | 1680 |
| aaactctccg | attgacgata | ccagatggat | tgactgggga | gcagaagtcg | caatggcttg | 1740 |
| ccacgattaa | ggcagttgtt | cagagtgcta | atattggaa | catctcagaa | tgttcatttg | 1800 |
| agagttatga | gcaaggggtt | ttgattagag | agacaaat | gactcctgat | gtctacaaag | 1860 |
| tcactcctgt | tttaaatgct | ccaccggttc | aaatgacagc | taatcaagat | gtttggtctc | 1920 |
| tcagcagcac | tccatttaca | tttttgccca | agaaacaagg | tgtgactcca | ttgaccatgt | 1980 |
| ccttagaaga | actcttcaac | acccgaggtg | aattcatatc | tctgggagga | aacgggaaaa | 2040 |
| tgagtcaccg | ggaggccatc | attctagggt | tgagacacaa | gaagctctat | aatcaagcca | 2100 |

```
gactaaagta taacttagct tgaatatgaa aaaaactaac agatatcaaa agatatctct   2160
aactcagtcc attgtgttca gttcaatcat gagctctctc aagaaaattt tgggtattaa   2220
agggaaaggg aagaaatcta agaaattagg tatggctccc ccaccctatg aagaagagac   2280
tccaatggaa tattctccaa gtgcacctta tgataagtca ttgtttggag tcgaagatat   2340
ggatttccat gatcaacgtc aactccgata tgagaaattt cacttctcat gaagatgac   2400
tgtgagatca aacaaaccat ttcgaaatta tgatgacgtt gcagcagcgg tgtccaattg   2460
ggatcatatg tacatcggca tggcaggaaa acgtccttt tataagatat tagcattcat    2520
gggttctact ctattgaagg ctacaccagc tgtcttggct gaccaaggac agccagaata   2580
tcatgctcac tgtgagggac gagcttactt gccgcatcgg ttagggccga cccctccgat   2640
gttgaatgtc cctgaacatt ttcgccgtcc atttaacatc ggattattca gagggacaat   2700
cgacataacc ctggtacttt tcgatgatga atctgtagat tctgccccgg tcatatggga   2760
tcattttaat gcatccagat tgagcagctt cagagaaaag gctttgttgt ttggtttgat   2820
tctagaaaag aaagccactg ggaattgggt attggactct attagtcatt tcaagtaatt   2880
atcacaagtg ttgaggtgat gggcagacta tgaaaaaaac taacagggtt caaacactct   2940
tgatcgaggt acccagttat atttgttaca acaatgttga gactttttct cttttgtttc   3000
ttggccttag gagcccactc caaatttact atagtattcc ctcatcatca aaagggaat    3060
tggaagaatg tgccttccac atatcattat tgcccttcta gttctgacca gaattggcat   3120
aatgatttga ctggagttag tcttcatgtg aaaattccca aaagtcacaa agctatacaa   3180
gcagatggct ggatgtgcca cgctgctaaa tgggtgacta cttgtgactt cagatggtac   3240
ggacccaaat acatcacgca ttccatacac tctatgtcac ccaccctaga acagtgcaag   3300
accagtattg agcagacaaa gcaaggagtt tggattaatc caggctttcc ccctcaaagc   3360
tgcggatatg ctacagtgac ggatgcgagg gtggttgttg tacaagcaac acctcatcat   3420
gtgttggttg atgagtacac aggagaatgg attgactcac aattggtggg gggcaaatgt   3480
tccaaggagg tttgtcaaac ggttcacaac tcgaccgtgt ggcatgctga ttacaagatt   3540
acagggctgt gcgagtcaaa tctggcatca gtggatatca ccttcttctc tgaggatggt   3600
caaaagacgt cttgggaaa accgaacact ggattcagga gtaattactt tgcttacgaa    3660
agtggagaga aggcatgccg tatgcagtac tgcacacaat gggggatccg actaccttct   3720
ggagtatggt ttgaattagt ggacaaagat ctcttccagg cggcaaaatt gcctgaatgt   3780
cctagaggat ccagtatctc agctccttct cagacttctg tggatgttag tttgatacaa   3840
gacgtagaga ggatcttaga ttactctcta tgccaggaga cgtggagtaa gatacgagcc   3900
aagcttcctg tatctccagt agatctgagt tatctcgccc caaaaaatcc agggagcgga   3960
ccggccttca ctatcattaa tggcactttg aaatatttcg aaacaagata catcagagtt   4020
gacataagta atcccatcat ccctcacatg gtgggaacaa tgagtggaac cacgactgag   4080
cgtgaattgt ggaatgattg gtatccatat gaagacgtag agattggtcc aaatggggtg   4140
ttgaaaactc ccactggttt caagtttccg ctgtacatga ttgggcacgg aatgttggat   4200
tccgatctcc acaaatcctc ccaggctcaa gtcttcgaac atccacacgc aaaggacgct   4260
gcatcacagc ttcctgatga tgagacttta tttttggtg acacaggact atcaaaaaac    4320
ccagtagagt tagtagaagg ctggttcagt agctggaaga gcacattggc atcgttcttt   4380
ctgattatag gcttgggggt tgcattaatc ttcatcattc gaattattgt tgcgattcgc   4440
```

```
tataaataca agggaggaa gacccaaaaa atttacaatg atgtcgagat gagtcgattg    4500
ggaaataaat aacagatgac gcatgagggt cagatcagat ttacagcgta agtgtgatat    4560
ttaggattat aaaggttcct tcattttaat ttgttacaga ctgtatgaaa aaaactcatc    4620
aacagccatc atggatgtta acgattttga gttgcatgag gactttgcat tgtctgaaga    4680
tgactttgtc acttcagaat ttctcaatcc ggaagaccaa atgacatacc tgaatcatgc    4740
cgattataat ttgaattctc ccttaatcag cgatgatatt gatttcctga tcaagaaata    4800
taatcatgag caaattccga aaatgtggga tgtaaagaat tgggagggag tgttagagat    4860
gttgacagcc tggcaagcca gtccaatttt atctagcact atgcataagt gggtgggaaa    4920
gtggctcatg tctgatgatc atgacgcaag ccaaggcttc agttttcttc atgaagtgga    4980
caaagaagct gatctgacgt tgaggtggt ggagacattc attagaggat ggggaggtcg    5040
agaattgcag tacaagagga agacacatt tccggactcc tttagagttg cagcctcatt    5100
gtgtcaaaaa ttccttgatt tgcacaaact cactctgata atgaattcag tctctgaagt    5160
cgaacttacc aacctagcaa agaattttaa aggaaaaaac aggaaagcaa aaagcggaaa    5220
tctgataacc agattagggg ttcccagttt aggtcctgct tttgtgactc agggatgggt    5280
gtacatgaag aagttggaaa tgattatgga tcggaatttt ttgttgatgt tgaaagacgt    5340
tatcatcggg aggatgcaga cgatcctgtc catgatctca agagatgata atctcttctc    5400
cgagtctgat atctttactg tattaaagat ataccggata ggggataaga tattagaaag    5460
gcaagggaca aagggttacg acttgatcaa aatgattgag cctatttgta acttaaagat    5520
gatgaatctg gcacgtaaat atcgtcctct catccctaca tttcctcatt ttgaaaaaca    5580
tattgctgac tctgttaagg aaggatcgaa aatagacaaa gggattgagt ttatatatga    5640
tcacattatg tcaatccctg gtgtggactt gaccttagtt atttacggat catttcggca    5700
ctggggtcat ccttttatca actactatga gggcttagag aagctacaca agcaggttac    5760
aatgcccaag actattgaca gagaaatatgc agaatgtctt gctagtgatc tggcaagaat    5820
cgttcttcag caacaattca atgaacataa gaaatggttt gttgatgtag ataaagtccc    5880
acaatcccat cctttcaaaa gccatatgaa agagaatact tggcctactg cagcccaagt    5940
tcaggattac ggcgatcgct ggcatcagct cccactcatc aaatgcttcg aaatcccaga    6000
tttgttagat ccatcgatca tctactcaga caaaagtcat tccatgaacc ggtctgaagt    6060
actacgacat gtaagactta cacctcatgt gcccattcca agcaggaaag tattgcagac    6120
aatgttggag actaaggcaa cagactggaa agagtttttta aagaaaattg acgaagaggg    6180
gttagaggat gatgatcttg tcataggact caaagggaaa gagagagaat taaaaattgc    6240
gggaagattc ttttcttga tgtcctggaa gctcagagag tattttgtca tcactgagta    6300
tttgattaag acgcactttg tcccgatgtt taaagggttg accatggcgg atgacttgac    6360
agcggtgata aagaagatga tggacacatc ttcaggacaa ggcttagata attatgaatc    6420
catttgtata gccaaccata ttgactatga gaagtggaac aatcatcaaa gaaaagagtc    6480
gaacgggccc gtgttcaagg tgatgggtca attcttggga tatccacgtc tgattgagag    6540
aactcatgaa ttttttgaga agagtctgat atattacaat ggacgaccag atctgatgcg    6600
ggttcgagga aattctctag tcaacgcctc atctttaaat gtctgctggg agggtcaagc    6660
tgggggatta gaaggactgc gacagaaggg atggagtatt ctaaatttgc ttgtcattca    6720
gagagaagca aaaataagga acaccgcccg gaaagtgcta gctcaaggtg acaatcaggt    6780
gatatgtact cagtataaaa cgaagaaatc ccggaatgat attgagctta aggcagctct    6840
```

```
aacacagatg gtatctaata atgagatgat tatgtctgcg attaaatcag gcaccgagaa      6900
actgggtctt ttgattaatg atgatgagac aatgcaatct gctgattacc tcaattacgg      6960
gaaggttccc attttcagag gagtaatcag aggccttgag acaaaaagat ggtcacgcgt      7020
gacctgtgtg acaaatgatc agattccaac gtgtgcgaac attatgagct ctgtgtcaac      7080
taatgcatta actgtagccc attttgccga gaatccagtc aatgccatca ttcagtataa      7140
ctactttgga acatttgcaa ggctactgct gatgatgcat gaccccgctc tgaggatctc      7200
tctgtatgaa gtccaatcaa aaattccagg acttcacagt ttgacattta aatattctat      7260
gttgtatctg gatccttcga taggaggagt ctccggaatg tcactctcga gattcctcat      7320
aagatcattt ccagatccag tgacagaaag tttggcgttc tggaaattta ccactctca       7380 tgcaagaagc gattcattaa aggagatatg tgcagttttt ggaaatcctg aaattgcaag      7440
atttcggcta actcatgtcg ataaattggt ggaagaccca acctcattga acatagctat      7500
gggaatgagt cctgctaatc tattaaagac agaggtaaaa aaatgtctac tggaatcaag      7560
gcagagcatc aagaaccaga ttgtaagaga tgctactatt tacctacacc atgaggaaga      7620
caaacttcgt agtttcttat ggtccataac accactgttc cctcggttct tgagtgaatt      7680
caaatctggg acattcatcg gagtagcaga tggcctgatc agcttatttc agaactctag      7740
gactattcga aattcttttta aaagcgtta tcacagggaa cttgatgatt taataatcaa      7800
gagcgaagtt tcctcactta tgcatttggg taagctacat ttgaggcgag gctcagttcg      7860
tatgtggact tgctcttcta ctcaggctga tcttctccga ttccggtcat ggggaagatc      7920
tgttatagga accacagtcc ctcatccctt agagatgtta ggacaacatt ttaaaaagga      7980
gactccttgc agtgcttgca acatatccgg attagactat gtatctgtcc actgtccgaa      8040
tgggattcat gacgttttttg aatcacgtgg tccactccct gcatatttgg gttctaaaac      8100
atccgaatca acttcgatct tgcagccgtg ggagagagag agtaaagtac cgttgattaa      8160
gcgtgccaca aggcttcgtg atgcaatttc atggtttgtg tctcccgact ctaacttggc      8220
ctcaactatc cttaagaaca taaatgcatt aacaggagaa gaatggtcaa gaagcagca       8280 tggatttaaa aggacgggat cggcgttaca caggttctcc acatccagga tgagtcatgg      8340
tggttttgct tctcagagta cggctgcctt gactagattg atggcaacta ctgacactat      8400
gagagatctg ggagaacaga actatgattt cctgtttcag cgacattat tgtatgctca       8460 aataaccaca actgtagtca ggaatggatc atttcatagc tgcacggacc attaccatat      8520
aacctgcaaa tcttgtctga gggccattga tgagattacc ttggattcag cgatggaata      8580
tagccctcca gatgtatcat cagttttaca atcttggagg aatggagaag gctcttgggg      8640
acatgaagtg aaacaaatat acccagttga aggtgactgg aggggactat ctcctgttga      8700
acaatcttat caagtcggac gctgtatcgg gtttctgttc ggtgatctgg cgtatagaaa      8760
atcatcccat gcagatgata gctccatgtt tccgttatct atacaaaaca aagtcagagg      8820
aagaggcttt ttaaagggc ttatggatgg gttaatgaga gccagttgtt gccaggtgat       8880
ccatcgtcga agcttagccc atctgaagag accggctaat gcagtctatg gagggctgat      8940
ttatttgata gacaaattga gtgcatctgc ccctttttctt tcactgacga gacatggacc      9000
tttaagggaa gaattagaaa ctgttccaca taagataccg acttcttatc ctacgagcaa      9060
ccgagatatg ggggtgatag ttcgtaatta ttttaaatat cagtgcagac tggtagaaaa      9120
aggtcggtac aagacacatt atcctcaatt gtggcttttc tcagatgtgc tgtccattga      9180
```

| | |
|---|---|
| tttcttagga cccctgtcta tatcttcaac tctattgggt attctgtata aacagacgtt | 9240 |
| atcttctcga gacaaaaatg agttgagaga actcgctaac ttgtcttcat tgttgagatc | 9300 |
| aggagaagga tgggaagata tccatgtcaa attcttctct aaggacactt tactctgccc | 9360 |
| tgaagagatc cgacatgcgt gcaaatttgg gattgctaag gaatccgctg ttttaagcta | 9420 |
| ttatcctcct tggtctcaag agtcttatgg aggcatcacc tcgatcccg tatattttc | 9480 |
| gaccaggaag tatcccaaaa ttttagatgt ccctcctcgg gttcaaaacc cattggtctc | 9540 |
| gggtctacga ttggggcaac tccctactgg agcacattat aagattagga gcattgtaaa | 9600 |
| gaacaagaac cttcgttata gagatttcct tagttgtggg gatggatctg ggggatgac | 9660 |
| cgcggcacta ttgagagaaa acagacaaag taggggaatc ttcaacagcc tgttagagtt | 9720 |
| agccggatct cttatgagag gagcatctcc agagcctcca agtgcactgg agacgctcgg | 9780 |
| gcaagaacga tctaggtgtg tgaatggaag cacatgttgg gagtactcat ctgacctaag | 9840 |
| ccaaaaagag acatgggatt acttcttaag attgaagaga ggcctgggtt tgaccgtgga | 9900 |
| cttaatcacc atggacatgg aggtcagaga ccctaataca agtttgatga tagaaaagaa | 9960 |
| cctcaaagtt tatctgcatc agatattaga accaactggt gtcttaatat ataaaacata | 10020 |
| cgggacccat attgcgacac aaacagataa tatcctgacg ataatcggtc ctttctttga | 10080 |
| gacggttgac ctagtccagt ccgaatacag cagctcacaa cgtccgaggtctatttgt | 10140 |
| aggacgaggc ttgcgctctc atgttgacga accctgggtg gactggccat ccttaatgga | 10200 |
| caattggaga tccatttatg cttttcatga tcctactaca gaatttatca gagcaaaaaa | 10260 |
| agtctgtgaa attgacagtc ttataggcat tccggctcaa ttcattccag acccatttgt | 10320 |
| aaatctcgag accatgctac agatagttgg tgttccaaca ggagtttcgc atgccgcagc | 10380 |
| tctattatca tcacaatatc caaatcaatt ggtcacaacg tcaatatttt atatgacact | 10440 |
| cgtgtcttat tataatgtaa accatattcg aagaagcccc aagcctttct ctcctccgtc | 10500 |
| tgatggagtc tcacagaaca ttggttcagc catagtcgga ctaagttttt gggtgagttt | 10560 |
| gatggagaat gatctcggat tatacaaaca ggctctaggt gcaataaaga cgtcattccc | 10620 |
| tattagatgg tcctctgtcc agaccaagga tgggtttaca caagaatgga gaactaaagg | 10680 |
| aaacggaatt cctaaagatt gtcgtctctc agactctttg gctcagatag gaaactggat | 10740 |
| cagagcgatg gaattggtta ggaacaaaac gaggcaatca ggattttctg aaaccctatt | 10800 |
| tgatcaattc tgcggacttg cagaccatca cctcaaatgg cggaagttgg gaaacagaac | 10860 |
| aggaattatt gattggctaa ataatagaat ttcatccatt gacaaatcca tcttggtgac | 10920 |
| caaaagtgat ctgcatgacg agaactcatg gagggagtga agatgtattc ttccacctct | 10980 |
| cattgggtga tacccatata tgaaaaaaac tataagtact ttaaactctc tttgttttt | 11040 |
| aatgtatatc tggttttgtt gtttccgt | 11068 |

<210> SEQ ID NO 2
<211> LENGTH: 422
<212> TYPE: PRT
<213> ORGANISM: Maraba Virus N

<400> SEQUENCE: 2

Met Ser Val Thr Val Lys Arg Val Ile Asp Asp Ser Leu Ile Thr Pro
1               5                   10                  15

Lys Leu Pro Ala Asn Glu Asp Pro Val Glu Tyr Pro Ala Asp Tyr Phe
            20                  25                  30

Lys Lys Ser Arg Asp Ile Pro Val Tyr Ile Asn Thr Thr Lys Ser Leu

```
                35                  40                  45
Ser Asp Leu Arg Gly Tyr Val Tyr Gln Gly Leu Lys Ser Gly Asn Ile
 50                  55                  60

Ser Ile Ile His Val Asn Ser Tyr Leu Tyr Ala Ala Leu Lys Glu Ile
 65                  70                  75                  80

Arg Gly Lys Leu Asp Arg Asp Trp Ile Thr Phe Gly Ile Gln Ile Gly
                 85                  90                  95

Lys Thr Gly Asp Ser Val Gly Ile Phe Asp Leu Leu Thr Leu Lys Pro
                100                 105                 110

Leu Asp Gly Val Leu Pro Asp Gly Val Ser Asp Ala Thr Arg Thr Ser
                115                 120                 125

Ser Asp Asp Ala Trp Leu Pro Leu Tyr Leu Leu Gly Leu Tyr Arg Val
130                 135                 140

Gly Arg Thr Gln Met Pro Glu Tyr Arg Lys Lys Leu Met Asp Gly Leu
145                 150                 155                 160

Ile Asn Gln Cys Lys Met Ile Asn Glu Gln Phe Glu Pro Leu Leu Pro
                165                 170                 175

Glu Gly Arg Asp Val Phe Asp Val Trp Gly Asn Asp Ser Asn Tyr Thr
                180                 185                 190

Lys Ile Val Ala Ala Val Asp Met Phe Phe His Met Phe Lys Lys His
                195                 200                 205

Glu Lys Ala Ser Phe Arg Tyr Gly Thr Ile Val Ser Arg Phe Lys Asp
210                 215                 220

Cys Ala Ala Leu Ala Thr Phe Gly His Leu Cys Lys Ile Thr Gly Met
225                 230                 235                 240

Ser Thr Glu Asp Val Thr Thr Trp Ile Leu Asn Arg Glu Val Ala Asp
                245                 250                 255

Glu Met Val Gln Met Met Tyr Pro Gly Gln Glu Ile Asp Lys Ala Asp
                260                 265                 270

Ser Tyr Met Pro Tyr Leu Ile Asp Leu Gly Leu Ser Ser Lys Ser Pro
                275                 280                 285

Tyr Pro Ser Val Lys Asn Pro Ala Phe His Phe Trp Gly Gln Leu Thr
290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ala Gln Gln Phe Tyr Val Gly Asp
                340                 345                 350

Asn Lys Tyr Val Pro Glu Thr Gly Asp Gly Leu Thr Thr Asn Ala
                355                 360                 365

Pro Pro Gln Gly Arg Asp Val Val Glu Trp Leu Ser Trp Phe Glu Asp
370                 375                 380

Gln Asn Arg Lys Pro Thr Pro Asp Met Leu Met Tyr Ala Lys Arg Ala
385                 390                 395                 400

Val Ser Ala Leu Gln Gly Leu Arg Glu Lys Thr Ile Gly Lys Tyr Ala
                405                 410                 415

Lys Ser Glu Phe Asp Lys
                420

<210> SEQ ID NO 3
<211> LENGTH: 265
<212> TYPE: PRT
<213> ORGANISM: Maraba Virus P
```

```
<400> SEQUENCE: 3

Met Asp Gln Leu Ser Lys Val Lys Glu Phe Leu Lys Thr Tyr Ala Gln
1               5                   10                  15

Leu Asp Gln Ala Val Gln Glu Met Asp Asp Ile Glu Ser Gln Arg Glu
            20                  25                  30

Glu Lys Thr Asn Phe Asp Leu Phe Gln Glu Glu Gly Leu Glu Ile Lys
        35                  40                  45

Glu Lys Pro Ser Tyr Tyr Arg Ala Asp Glu Glu Ile Asp Ser Asp
    50                  55                  60

Glu Asp Ser Val Asp Asp Ala Gln Asp Leu Gly Ile Arg Thr Ser Thr
65              70                  75                  80

Ser Pro Ile Glu Gly Tyr Val Asp Glu Gln Asp Asp Tyr Glu Asp
                85                  90                  95

Glu Glu Val Asn Val Val Phe Thr Ser Asp Trp Lys Gln Pro Glu Leu
                100                 105                 110

Glu Ser Asp Gly Asp Gly Lys Thr Leu Arg Leu Thr Ile Pro Asp Gly
            115                 120                 125

Leu Thr Gly Glu Gln Lys Ser Gln Trp Leu Ala Thr Ile Lys Ala Val
130                 135                 140

Val Gln Ser Ala Lys Tyr Trp Asn Ile Ser Glu Cys Ser Phe Glu Ser
145                 150                 155                 160

Tyr Glu Gln Gly Val Leu Ile Arg Glu Arg Gln Met Thr Pro Asp Val
                165                 170                 175

Tyr Lys Val Thr Pro Val Leu Asn Ala Pro Pro Val Gln Met Thr Ala
            180                 185                 190

Asn Gln Asp Val Trp Ser Leu Ser Ser Thr Pro Phe Thr Phe Leu Pro
        195                 200                 205

Lys Lys Gln Gly Val Thr Pro Leu Thr Met Ser Leu Glu Glu Leu Phe
    210                 215                 220

Asn Thr Arg Gly Glu Phe Ile Ser Leu Gly Gly Asn Gly Lys Met Ser
225                 230                 235                 240

His Arg Glu Ala Ile Ile Leu Gly Leu Arg His Lys Lys Leu Tyr Asn
                245                 250                 255

Gln Ala Arg Leu Lys Tyr Asn Leu Ala
            260                 265

<210> SEQ ID NO 4
<211> LENGTH: 229
<212> TYPE: PRT
<213> ORGANISM: Maraba Virus M

<400> SEQUENCE: 4

Met Ser Ser Leu Lys Lys Ile Leu Gly Ile Lys Gly Lys Gly Lys Lys
1               5                   10                  15

Ser Lys Lys Leu Gly Met Ala Pro Pro Pro Tyr Glu Glu Thr Pro
            20                  25                  30

Met Glu Tyr Ser Pro Ser Ala Pro Tyr Asp Lys Ser Leu Phe Gly Val
        35                  40                  45

Glu Asp Met Asp Phe His Asp Gln Arg Gln Leu Arg Tyr Glu Lys Phe
    50                  55                  60

His Phe Ser Leu Lys Met Thr Val Arg Ser Asn Lys Pro Phe Arg Asn
65              70                  75                  80

Tyr Asp Asp Val Ala Ala Ala Val Ser Asn Trp Asp His Met Tyr Ile
                85                  90                  95
```

```
Gly Met Ala Gly Lys Arg Pro Phe Tyr Lys Ile Leu Ala Phe Met Gly
            100                 105                 110

Ser Thr Leu Leu Lys Ala Thr Pro Ala Val Leu Ala Asp Gln Gly Gln
            115                 120                 125

Pro Glu Tyr His Ala His Cys Glu Gly Arg Ala Tyr Leu Pro His Arg
            130                 135                 140

Leu Gly Pro Thr Pro Met Leu Asn Val Pro Glu His Phe Arg Arg
145                 150                 155                 160

Pro Phe Asn Ile Gly Leu Phe Arg Gly Thr Ile Asp Ile Thr Leu Val
                    165                 170                 175

Leu Phe Asp Asp Glu Ser Val Asp Ser Ala Pro Val Ile Trp Asp His
                180                 185                 190

Phe Asn Ala Ser Arg Leu Ser Ser Phe Arg Glu Lys Ala Leu Leu Phe
            195                 200                 205

Gly Leu Ile Leu Glu Lys Lys Ala Thr Gly Asn Trp Val Leu Asp Ser
            210                 215                 220

Ile Ser His Phe Lys
225

<210> SEQ ID NO 5
<211> LENGTH: 512
<212> TYPE: PRT
<213> ORGANISM: Maraba Virus G

<400> SEQUENCE: 5

Met Leu Arg Leu Phe Leu Phe Cys Phe Leu Ala Leu Gly Ala His Ser
1               5                   10                  15

Lys Phe Thr Ile Val Phe Pro His His Gln Lys Gly Asn Trp Lys Asn
            20                  25                  30

Val Pro Ser Thr Tyr His Tyr Cys Pro Ser Ser Asp Gln Asn Trp
            35                  40                  45

His Asn Asp Leu Thr Gly Val Ser Leu His Val Lys Ile Pro Lys Ser
50                  55                  60

His Lys Ala Ile Gln Ala Asp Gly Trp Met Cys His Ala Ala Lys Trp
65                  70                  75                  80

Val Thr Thr Cys Asp Phe Arg Trp Tyr Gly Pro Lys Tyr Ile Thr His
                85                  90                  95

Ser Ile His Ser Met Ser Pro Thr Leu Glu Gln Cys Lys Thr Ser Ile
            100                 105                 110

Glu Gln Thr Lys Gln Gly Val Trp Ile Asn Pro Gly Phe Pro Pro Gln
            115                 120                 125

Ser Cys Gly Tyr Ala Thr Val Thr Asp Ala Glu Val Val Val Gln
            130                 135                 140

Ala Thr Pro His His Val Leu Val Asp Glu Tyr Thr Gly Glu Trp Ile
145                 150                 155                 160

Asp Ser Gln Leu Val Gly Gly Lys Cys Ser Lys Glu Val Cys Gln Thr
                165                 170                 175

Val His Asn Ser Thr Val Trp His Ala Asp Tyr Lys Ile Thr Gly Leu
            180                 185                 190

Cys Glu Ser Asn Leu Ala Ser Val Asp Ile Thr Phe Phe Ser Glu Asp
            195                 200                 205

Gly Gln Lys Thr Ser Leu Gly Lys Pro Asn Thr Gly Phe Arg Ser Asn
            210                 215                 220

Tyr Phe Ala Tyr Glu Ser Gly Glu Lys Ala Cys Arg Met Gln Tyr Cys
```

```
                    225                 230                 235                 240
Thr Gln Trp Gly Ile Arg Leu Pro Ser Gly Val Trp Phe Glu Leu Val
                245                 250                 255

Asp Lys Asp Leu Phe Gln Ala Ala Lys Leu Pro Glu Cys Pro Arg Gly
                260                 265                 270

Ser Ser Ile Ser Ala Pro Ser Gln Thr Ser Val Asp Ser Leu Ile
            275                 280                 285

Gln Asp Val Glu Arg Ile Leu Asp Tyr Ser Leu Cys Gln Glu Thr Trp
        290                 295                 300

Ser Lys Ile Arg Ala Lys Leu Pro Val Ser Pro Val Asp Leu Ser Tyr
305                 310                 315                 320

Leu Ala Pro Lys Asn Pro Gly Ser Gly Pro Ala Phe Thr Ile Ile Asn
                325                 330                 335

Gly Thr Leu Lys Tyr Phe Glu Thr Arg Tyr Ile Arg Val Asp Ile Ser
                340                 345                 350

Asn Pro Ile Ile Pro His Met Val Gly Thr Met Ser Gly Thr Thr Thr
                355                 360                 365

Glu Arg Glu Leu Trp Asn Asp Trp Tyr Pro Tyr Glu Asp Val Glu Ile
370                 375                 380

Gly Pro Asn Gly Val Leu Lys Thr Pro Thr Gly Phe Lys Phe Pro Leu
385                 390                 395                 400

Tyr Met Ile Gly His Gly Met Leu Asp Ser Asp Leu His Lys Ser Ser
                405                 410                 415

Gln Ala Gln Val Phe Glu His Pro His Ala Lys Asp Ala Ala Ser Gln
                420                 425                 430

Leu Pro Asp Asp Glu Thr Leu Phe Phe Gly Asp Thr Gly Leu Ser Lys
                435                 440                 445

Asn Pro Val Glu Leu Val Glu Gly Trp Phe Ser Trp Lys Ser Thr
                450                 455                 460

Leu Ala Ser Phe Phe Leu Ile Ile Gly Leu Gly Val Ala Leu Ile Phe
465                 470                 475                 480

Ile Ile Arg Ile Ile Val Ala Ile Arg Tyr Lys Tyr Lys Gly Arg Lys
                485                 490                 495

Thr Gln Lys Ile Tyr Asn Asp Val Glu Met Ser Arg Leu Gly Asn Lys
                500                 505                 510

<210> SEQ ID NO 6
<211> LENGTH: 2109
<212> TYPE: PRT
<213> ORGANISM: Maraba Virus L

<400> SEQUENCE: 6

Met Asp Val Asn Asp Phe Glu Leu His Glu Asp Phe Ala Leu Ser Glu
1               5                   10                  15

Asp Asp Phe Val Thr Ser Glu Phe Leu Asn Pro Glu Asp Gln Met Thr
                20                  25                  30

Tyr Leu Asn His Ala Asp Tyr Asn Leu Asn Ser Pro Leu Ile Ser Asp
            35                  40                  45

Asp Ile Asp Phe Leu Ile Lys Lys Tyr Asn His Glu Gln Ile Pro Lys
        50                  55                  60

Met Trp Asp Val Lys Asn Trp Glu Gly Val Leu Glu Met Leu Thr Ala
65                  70                  75                  80

Trp Gln Ala Ser Pro Ile Leu Ser Ser Thr Met His Lys Trp Val Gly
                85                  90                  95
```

```
Lys Trp Leu Met Ser Asp Asp His Asp Ala Ser Gln Gly Phe Ser Phe
            100                 105                 110

Leu His Glu Val Asp Lys Glu Ala Asp Leu Thr Phe Glu Val Val Glu
        115                 120                 125

Thr Phe Ile Arg Gly Trp Gly Gly Arg Glu Leu Gln Tyr Lys Arg Lys
        130                 135                 140

Asp Thr Phe Pro Asp Ser Phe Arg Val Ala Ala Ser Leu Cys Gln Lys
145                 150                 155                 160

Phe Leu Asp Leu His Lys Leu Thr Leu Ile Met Asn Ser Val Ser Glu
                165                 170                 175

Val Glu Leu Thr Asn Leu Ala Lys Asn Phe Lys Gly Lys Asn Arg Lys
            180                 185                 190

Ala Lys Ser Gly Asn Leu Ile Thr Arg Leu Arg Val Pro Ser Leu Gly
        195                 200                 205

Pro Ala Phe Val Thr Gln Gly Trp Val Tyr Met Lys Lys Leu Glu Met
210                 215                 220

Ile Met Asp Arg Asn Phe Leu Leu Met Leu Lys Asp Val Ile Ile Gly
225                 230                 235                 240

Arg Met Gln Thr Ile Leu Ser Met Ile Ser Arg Asp Asp Asn Leu Phe
                245                 250                 255

Ser Glu Ser Asp Ile Phe Thr Val Leu Lys Ile Tyr Arg Ile Gly Asp
            260                 265                 270

Lys Ile Leu Glu Arg Gln Gly Thr Lys Gly Tyr Asp Leu Ile Lys Met
        275                 280                 285

Ile Glu Pro Ile Cys Asn Leu Lys Met Met Asn Leu Ala Arg Lys Tyr
290                 295                 300

Arg Pro Leu Ile Pro Thr Phe Pro His Phe Glu Lys His Ile Ala Asp
305                 310                 315                 320

Ser Val Lys Glu Gly Ser Lys Ile Asp Lys Gly Ile Glu Phe Ile Tyr
                325                 330                 335

Asp His Ile Met Ser Ile Pro Gly Val Asp Leu Thr Leu Val Ile Tyr
            340                 345                 350

Gly Ser Phe Arg His Trp Gly His Pro Phe Ile Asn Tyr Tyr Glu Gly
        355                 360                 365

Leu Glu Lys Leu His Lys Gln Val Thr Met Pro Lys Thr Ile Asp Arg
370                 375                 380

Glu Tyr Ala Glu Cys Leu Ala Ser Asp Leu Ala Arg Ile Val Leu Gln
385                 390                 395                 400

Gln Gln Phe Asn Glu His Lys Lys Trp Phe Val Asp Val Asp Lys Val
                405                 410                 415

Pro Gln Ser His Pro Phe Lys Ser His Met Lys Glu Asn Thr Trp Pro
            420                 425                 430

Thr Ala Ala Gln Val Gln Asp Tyr Gly Asp Arg Trp His Gln Leu Pro
        435                 440                 445

Leu Ile Lys Cys Phe Glu Ile Pro Asp Leu Leu Asp Pro Ser Ile Ile
450                 455                 460

Tyr Ser Asp Lys Ser His Ser Met Asn Arg Ser Glu Val Leu Arg His
465                 470                 475                 480

Val Arg Leu Thr Pro His Val Pro Ile Pro Ser Arg Lys Val Leu Gln
                485                 490                 495

Thr Met Leu Glu Thr Lys Ala Thr Asp Trp Lys Glu Phe Leu Lys Lys
            500                 505                 510

Ile Asp Glu Glu Gly Leu Glu Asp Asp Asp Leu Val Ile Gly Leu Lys
```

```
            515                 520                 525
Gly Lys Glu Arg Glu Leu Lys Ile Ala Gly Arg Phe Phe Ser Leu Met
        530                 535                 540

Ser Trp Lys Leu Arg Glu Tyr Phe Val Ile Thr Glu Tyr Leu Ile Lys
545                 550                 555                 560

Thr His Phe Val Pro Met Phe Lys Gly Leu Thr Met Ala Asp Asp Leu
                565                 570                 575

Thr Ala Val Ile Lys Lys Met Met Asp Thr Ser Ser Gly Gln Gly Leu
            580                 585                 590

Asp Asn Tyr Glu Ser Ile Cys Ile Ala Asn His Ile Asp Tyr Glu Lys
        595                 600                 605

Trp Asn His Gln Arg Lys Glu Ser Asn Gly Pro Val Phe Lys Val
610                 615                 620

Met Gly Gln Phe Leu Gly Tyr Pro Arg Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val Arg Gly Asn Ser Leu Val Asn Ala Ser Ser Leu Asn Val Cys
            660                 665                 670

Trp Glu Gly Gln Ala Gly Gly Leu Glu Gly Leu Arg Gln Lys Gly Trp
        675                 680                 685

Ser Ile Leu Asn Leu Leu Val Ile Gln Arg Glu Ala Lys Ile Arg Asn
690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asn Asp Ile Glu Leu Lys Ala Ala
                725                 730                 735

Leu Thr Gln Met Val Ser Asn Asn Glu Met Ile Met Ser Ala Ile Lys
            740                 745                 750

Ser Gly Thr Glu Lys Leu Gly Leu Leu Ile Asn Asp Asp Glu Thr Met
        755                 760                 765

Gln Ser Ala Asp Tyr Leu Asn Tyr Gly Lys Val Pro Ile Phe Arg Gly
770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Val Asn Ala
            820                 825                 830

Ile Ile Gln Tyr Asn Tyr Phe Gly Thr Phe Ala Arg Leu Leu Leu Met
        835                 840                 845

Met His Asp Pro Ala Leu Arg Ile Ser Leu Tyr Glu Val Gln Ser Lys
850                 855                 860

Ile Pro Gly Leu His Ser Leu Thr Phe Lys Tyr Ser Met Leu Tyr Leu
865                 870                 875                 880

Asp Pro Ser Ile Gly Gly Val Ser Gly Met Ser Leu Ser Arg Phe Leu
                885                 890                 895

Ile Arg Ser Phe Pro Asp Pro Val Thr Glu Ser Leu Ala Phe Trp Lys
            900                 905                 910

Phe Ile His Ser His Ala Arg Ser Asp Ser Leu Lys Glu Ile Cys Ala
        915                 920                 925

Val Phe Gly Asn Pro Glu Ile Ala Arg Phe Arg Leu Thr His Val Asp
930                 935                 940
```

-continued

```
Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Leu Glu Ser
                965                 970                 975

Arg Gln Ser Ile Lys Asn Gln Ile Val Arg Asp Ala Thr Ile Tyr Leu
            980                 985                 990

His His Glu Glu Asp Lys Leu Arg Ser Phe Leu Trp Ser Ile Thr Pro
        995                 1000                1005

Leu Phe Pro Arg Phe Leu Ser Glu Phe Lys Ser Gly Thr Phe Ile
    1010                1015                1020

Gly Val Ala Asp Gly Leu Ile Ser Leu Phe Gln Asn Ser Arg Thr
    1025                1030                1035

Ile Arg Asn Ser Phe Lys Lys Arg Tyr His Arg Glu Leu Asp Asp
    1040                1045                1050

Leu Ile Ile Lys Ser Glu Val Ser Ser Leu Met His Leu Gly Lys
    1055                1060                1065

Leu His Leu Arg Arg Gly Ser Val Arg Met Trp Thr Cys Ser Ser
    1070                1075                1080

Thr Gln Ala Asp Leu Leu Arg Phe Arg Ser Trp Gly Arg Ser Val
    1085                1090                1095

Ile Gly Thr Thr Val Pro His Pro Leu Glu Met Leu Gly Gln His
    1100                1105                1110

Phe Lys Lys Glu Thr Pro Cys Ser Ala Cys Asn Ile Ser Gly Leu
    1115                1120                1125

Asp Tyr Val Ser Val His Cys Pro Asn Gly Ile His Asp Val Phe
    1130                1135                1140

Glu Ser Arg Gly Pro Leu Pro Ala Tyr Leu Gly Ser Lys Thr Ser
    1145                1150                1155

Glu Ser Thr Ser Ile Leu Gln Pro Trp Glu Arg Glu Ser Lys Val
    1160                1165                1170

Pro Leu Ile Lys Arg Ala Thr Arg Leu Arg Asp Ala Ile Ser Trp
    1175                1180                1185

Phe Val Ser Pro Asp Ser Asn Leu Ala Ser Thr Ile Leu Lys Asn
    1190                1195                1200

Ile Asn Ala Leu Thr Gly Glu Glu Trp Ser Lys Lys Gln His Gly
    1205                1210                1215

Phe Lys Arg Thr Gly Ser Ala Leu His Arg Phe Ser Thr Ser Arg
    1220                1225                1230

Met Ser His Gly Gly Phe Ala Ser Gln Ser Thr Ala Ala Leu Thr
    1235                1240                1245

Arg Leu Met Ala Thr Thr Asp Thr Met Arg Asp Leu Gly Glu Gln
    1250                1255                1260

Asn Tyr Asp Phe Leu Phe Gln Ala Thr Leu Leu Tyr Ala Gln Ile
    1265                1270                1275

Thr Thr Thr Val Val Arg Asn Gly Ser Phe His Ser Cys Thr Asp
    1280                1285                1290

His Tyr His Ile Thr Cys Lys Ser Cys Leu Arg Ala Ile Asp Glu
    1295                1300                1305

Ile Thr Leu Asp Ser Ala Met Glu Tyr Ser Pro Pro Asp Val Ser
    1310                1315                1320

Ser Val Leu Gln Ser Trp Arg Asn Gly Glu Gly Ser Trp Gly His
    1325                1330                1335
```

-continued

```
Glu Val Lys Gln Ile Tyr Pro Val Glu Gly Asp Trp Arg Gly Leu
1340                1345                1350

Ser Pro Val Glu Gln Ser Tyr Gln Val Gly Arg Cys Ile Gly Phe
    1355                1360                1365

Leu Phe Gly Asp Leu Ala Tyr Arg Lys Ser Ser His Ala Asp Asp
    1370                1375                1380

Ser Ser Met Phe Pro Leu Ser Ile Gln Asn Lys Val Arg Gly Arg
    1385                1390                1395

Gly Phe Leu Lys Gly Leu Met Asp Gly Leu Met Arg Ala Ser Cys
    1400                1405                1410

Cys Gln Val Ile His Arg Arg Ser Leu Ala His Leu Lys Arg Pro
    1415                1420                1425

Ala Asn Ala Val Tyr Gly Gly Leu Ile Tyr Leu Ile Asp Lys Leu
    1430                1435                1440

Ser Ala Ser Ala Pro Phe Leu Ser Leu Thr Arg His Gly Pro Leu
    1445                1450                1455

Arg Glu Glu Leu Glu Thr Val Pro His Lys Ile Pro Thr Ser Tyr
    1460                1465                1470

Pro Thr Ser Asn Arg Asp Met Gly Val Ile Val Arg Asn Tyr Phe
    1475                1480                1485

Lys Tyr Gln Cys Arg Leu Val Glu Lys Gly Arg Tyr Lys Thr His
    1490                1495                1500

Tyr Pro Gln Leu Trp Leu Phe Ser Asp Val Leu Ser Ile Asp Phe
    1505                1510                1515

Leu Gly Pro Leu Ser Ile Ser Ser Thr Leu Leu Gly Ile Leu Tyr
    1520                1525                1530

Lys Gln Thr Leu Ser Ser Arg Asp Lys Asn Glu Leu Arg Glu Leu
    1535                1540                1545

Ala Asn Leu Ser Ser Leu Leu Arg Ser Gly Glu Gly Trp Glu Asp
    1550                1555                1560

Ile His Val Lys Phe Phe Ser Lys Asp Thr Leu Leu Cys Pro Glu
    1565                1570                1575

Glu Ile Arg His Ala Cys Lys Phe Gly Ile Ala Lys Glu Ser Ala
    1580                1585                1590

Val Leu Ser Tyr Tyr Pro Pro Trp Ser Gln Glu Ser Tyr Gly Gly
    1595                1600                1605

Ile Thr Ser Ile Pro Val Tyr Phe Ser Thr Arg Lys Tyr Pro Lys
    1610                1615                1620

Ile Leu Asp Val Pro Pro Arg Val Gln Asn Pro Leu Val Ser Gly
    1625                1630                1635

Leu Arg Leu Gly Gln Leu Pro Thr Gly Ala His Tyr Lys Ile Arg
    1640                1645                1650

Ser Ile Val Lys Asn Lys Asn Leu Arg Tyr Arg Asp Phe Leu Ser
    1655                1660                1665

Cys Gly Asp Gly Ser Gly Gly Met Thr Ala Ala Leu Leu Arg Glu
    1670                1675                1680

Asn Arg Gln Ser Arg Gly Ile Phe Asn Ser Leu Leu Glu Leu Ala
    1685                1690                1695

Gly Ser Leu Met Arg Gly Ala Ser Pro Glu Pro Ser Ala Leu
    1700                1705                1710

Glu Thr Leu Gly Gln Glu Arg Ser Arg Cys Val Asn Gly Ser Thr
    1715                1720                1725

Cys Trp Glu Tyr Ser Ser Asp Leu Ser Gln Lys Glu Thr Trp Asp
```

-continued

```
                1730                1735                1740

Tyr Phe Leu Arg Leu Lys Arg Gly Leu Gly Leu Thr Val Asp Leu
    1745                1750                1755

Ile Thr Met Asp Met Glu Val Arg Asp Pro Asn Thr Ser Leu Met
    1760                1765                1770

Ile Glu Lys Asn Leu Lys Val Tyr Leu His Gln Ile Leu Glu Pro
    1775                1780                1785

Thr Gly Val Leu Ile Tyr Lys Thr Tyr Gly Thr His Ile Ala Thr
    1790                1795                1800

Gln Thr Asp Asn Ile Leu Thr Ile Ile Gly Pro Phe Phe Glu Thr
    1805                1810                1815

Val Asp Leu Val Gln Ser Glu Tyr Ser Ser Ser Gln Thr Ser Glu
    1820                1825                1830

Val Tyr Phe Val Gly Arg Gly Leu Arg Ser His Val Asp Glu Pro
    1835                1840                1845

Trp Val Asp Trp Pro Ser Leu Met Asp Asn Trp Arg Ser Ile Tyr
    1850                1855                1860

Ala Phe His Asp Pro Thr Thr Glu Phe Ile Arg Ala Lys Lys Val
    1865                1870                1875

Cys Glu Ile Asp Ser Leu Ile Gly Ile Pro Ala Gln Phe Ile Pro
    1880                1885                1890

Asp Pro Phe Val Asn Leu Glu Thr Met Leu Gln Ile Val Gly Val
    1895                1900                1905

Pro Thr Gly Val Ser His Ala Ala Ala Leu Leu Ser Ser Gln Tyr
    1910                1915                1920

Pro Asn Gln Leu Val Thr Thr Ser Ile Phe Tyr Met Thr Leu Val
    1925                1930                1935

Ser Tyr Tyr Asn Val Asn His Ile Arg Arg Ser Pro Lys Pro Phe
    1940                1945                1950

Ser Pro Pro Ser Asp Gly Val Ser Gln Asn Ile Gly Ser Ala Ile
    1955                1960                1965

Val Gly Leu Ser Phe Trp Val Ser Leu Met Glu Asn Asp Leu Gly
    1970                1975                1980

Leu Tyr Lys Gln Ala Leu Gly Ala Ile Lys Thr Ser Phe Pro Ile
    1985                1990                1995

Arg Trp Ser Ser Val Gln Thr Lys Asp Gly Phe Thr Gln Glu Trp
    2000                2005                2010

Arg Thr Lys Gly Asn Gly Ile Pro Lys Asp Cys Arg Leu Ser Asp
    2015                2020                2025

Ser Leu Ala Gln Ile Gly Asn Trp Ile Arg Ala Met Glu Leu Val
    2030                2035                2040

Arg Asn Lys Thr Arg Gln Ser Gly Phe Ser Glu Thr Leu Phe Asp
    2045                2050                2055

Gln Phe Cys Gly Leu Ala Asp His His Leu Lys Trp Arg Lys Leu
    2060                2065                2070

Gly Asn Arg Thr Gly Ile Ile Asp Trp Leu Asn Asn Arg Ile Ser
    2075                2080                2085

Ser Ile Asp Lys Ser Ile Leu Val Thr Lys Ser Asp Leu His Asp
    2090                2095                2100

Glu Asn Ser Trp Arg Glu
    2105

<210> SEQ ID NO 7
```

<211> LENGTH: 10716
<212> TYPE: DNA
<213> ORGANISM: Carajas Virus

<400> SEQUENCE: 7

```
cggccggtcg acgctgccta tttacttact gggtctttac cgtgttggaa kaacaaaact    60
gccggaatac cgaaagaagt tgatggaggg gttggaaatg cagtgtaaaa tcatgtatcc   120
tgactttgta ccaatcgttc cggaaggaat ggacttcttt gatgtgtggg gaaatgatag   180
taatttcacc aaaatagtcg ccgcagtgga tatgtttttc catatgttca aaaagcatga   240
gagagcatcc ctcagatatg aacaattgt ctccagattc aaggattgtg ctgcattggc    300
tacatttggc catgtatgta agtttccgg aatgtccaca gaggaggtca ccacttgggt    360
gctgaatagg gaagtggcag acgaattatg ccagatgatg ttccctggac aggaaataga   420
ccgagcggac tcatacatgc cgtatatgat agatttcggg ttgtctcaga aatcgccata   480
ttcctctgtc aaaaatccgt cttttcactt tgggggcaa cttgcagcac tactgctcag    540
atcaaccagg gcaaaaatg ccagacaacc tgatgacatt gaatacacat cactgactac    600
agcaggtcta cttcttgcgt atgctgtagg gtcatctgca gacatctctc aacagttcta   660
catgggagat gagaaatata tctcagaccc aagtgcgggt ggattaacct ccaatgcacc   720
tccgaaagga aggaatgtag ttgactggct cgggtggttt gaggatcaag gaggaaatat   780
cactccagat atgtacactt cgctaaaagg gctgtttgct ctttgcaagg gctgcgagat   840
aagaccattg gaaagtatgc caagggagag tttgacaagt gactccattc agatcaaatg   900
ctttactaca tgctgtatta tataaacta tgaaaaaaac taacagagat catggataat    960
ctctcgaaac ttaaggagta tatggggact acacccatc tagactctgc attgcaagat   1020
gcaaatgaat cagaagaatc tcgagatgaa aagagcaatt ttgatctttt cgatgaggaa   1080
agtaaggagg ttgcaagacc ttcttattat tctgcaattg atgaggagtc tgaccaggag   1140
gaaactgaat ccgatgatcc agatgaggag ctgaatgact caaatgccca tggggcggtg   1200
gatggatggg acgagacgtt gaacgagaat tctcagcctg acgacaatgt ctctgttgag   1260
ttcgctcgta catggtcaac accggtgatg gaatcttcgt cagagggaaa gactttgcat   1320
ttggctatgc cagatggact gaatccagat caagtcgcac agtggctgca gactgtcaag   1380
gctttgtttg agagtgccaa atattggaat ctgtccgaat gcaggatgga agtgctgctt   1440
gagggagtat taatcaaaga gagacaaatg actccagatc ttcagaaggt cacaccgaag   1500
ccgaacaatc ctcctccaga aagtatgcca tgcgatcctc tccctcccgc tatggacgtg   1560
tgggaggccg cgtctcaggt gtatacacta gagcccaagc gggcaaacct ggccccaatg   1620
gatgtaaagc tgaaagatct gttttcatct agggccgaat ttctctcagt cggaggatct   1680
ccccagatga gctggaaaga ggccattata ttgggtctaa gatacaagaa attgtataat   1740
caagctcgcc taaatatttc cctataggt ataccccata tgaaaaaaac taacagaatt    1800
caaaatgagt tctctcaaga aaatactcgg cctgaaaggc aagaaggagg aaaagtccaa   1860
aaagttggga cttcctcctc cttacgagat gccagcaaac aatgagttcg agccaaatgc   1920
tcctttagat cctgacatgt cggggcgga acatttggag attgaaagca gtctgccat    1980
gcgttatgag aaatttaagt ctctctgtca agatcacctt aggaccaatc gacctttgag   2040
aacttatgat gatgtgtgcc agattctatc caaatgggat gcaatgtatg tcggcatgat   2100
gggtaagcga ccgttctaca aggtattggt cttgatcgga tccagccact tgcaggctac   2160
acctgctata ctctcagatc gtggtcaacc agaatatcat atgtacttgg aagatagagg   2220
```

```
attcatcgca cacaggttgg ggttgacacc gccaatgtta agtgggccgg aaagttttag    2280
aagacctttc catgtcggtc tttacagagg gacaattgac attacagtaa atctcatgga    2340
cgacgaatca acggaatcag caccacaggt ttgggatcac ttcaatacca gatatgtgaa    2400
tcatttcctt gagcatgcaa agaggttcgg attggtcctg tccaagaaac caggtggcgg    2460
ctggatatta gatcaagcgg tctgtgcata atgcgaatat aatcatagtc tcatcagacg    2520
attatttata cattattcta ttctctctct tagttggtgg tagctatgaa aaaaactaac    2580
agagttcaaa actctacatc tcaactgcaa aggctatttt tcttaaaaaa acctttaat    2640
acagagtcat cattcaaaaa tgaagatgaa atggtcata gcaggattaa tcctttgtat    2700
agggatttta ccggctattg ggaaaataac aatttctttc ccacaaagct tgaaaggaga    2760
ttggaggcct gtacctaagg gatacaatta ttgtcctaca agtgcggata aaaatctcca    2820
tggtgatttg attgacatag gtctcagact tcgggcccct aagagcttca aagggatctc    2880
cgcagatgga tggatgtgcc atgcggcaag atggatcacc acctgtgatt tcagatggta    2940
tggacccaag tacatcaccc actcaattca ctctttcagg ccgagcaatg accaatgcaa    3000
agaagcaatc cggctgacta atgaagggaa ttggattaat ccaggtttcc ctccgcaatc    3060
ttgcggatat gcttctgtaa ccgactcaga atccgttgtc gtaaccgtga ccaagcacca    3120
ggtcctagta gatgagtact ccggctcatg gatcgatagt caattccccg gaggaagttg    3180
cacatccccc atttgcgata cagtgcacaa ctcgacactt tggcacgcgg accacaccct    3240
ggacagtatc tgtgaccaag aattcgtggc aatggacgca gttctgttca cagagagtgg    3300
caaatttgaa gagttcggaa accgaactc cggcatcagg agcaactatt ttccttatga    3360
gagtctgaaa gatgtatgtc agatggattt ctgcaagagg aaaggattca agctcccatc    3420
cggtgtctgg tttgaaatcg aggatgcaga gaaatctcac aaggcccagg ttgaattgaa    3480
aataaaacgg tgccctcatg gagcagtaat ctcagctcct aatcagaatg cagcagatat    3540
caatctgatc atggatgtgg aacgaattct agactactcc ctttgccaag caacttggag    3600
caaaatccaa aacaaggaag cgttgacccc catcgatatc agttatcttg gtccgaaaaa    3660
cccaggacca ggcccagcct tcaccataat aaatggaaca ctgcactact tcaatactag    3720
atacattcga gtggatattg cagggcctgt taccaaagag attacaggat tgtttcggg    3780
aacatctaca tctagggtgc tgtgggatca gtggtcccat atggagagaa ttccattgga    3840
cccaatggct tgctgaaaac cgccagcgga tacaaatatc cattgttcat ggttggtaca    3900
ggtgtgctgg atgcggacat ccacaagctg ggagaagcaa ccgtgattga acatccacat    3960
gccaaagagg ctcagaaggt agttgatgac agtgaggtta tattttttgg tgacaccgga    4020
gtctccaaga atccagtgga ggtagtcgaa ggatggttta gcggatggag aagctctttg    4080
atgagcatat ttggcataat tttgttgatt gtttgtttag tcttgattgt tcgaatcctt    4140
atagcccctta aatactgttg tgttagacac aaaaagagaa ctatttacaa agaggacctt    4200
gaaatgggtc gaattcctcg gagggcttaa ttacttataa ttacggactt taaatgtatg    4260
aaaaaaacta taacagaagt caaaatggac ttcttacccg ttgaacaaga ggaggactgg    4320
ggttatgcag aagatgattt ctctagctca gattatctag attttgaaga acgaatgaca    4380
tatttaaatc aggctgatta taatctaaac tcaccattga tatctgatga catttattac    4440
ctgagtcgaa aattccactc atatggcatc ccccccatgt ggaacctcaa agaatgggat    4500
ggaccattgg agatgttaaa atcatgtcaa gcagacccga ttccacatga tctgatgcac    4560
```

```
aaatggtttg gaacttggtt agaagacttt gatcacgact ctgcacaagg gatagtgttt    4620
ttaagggaag tagacaaaga ggcctccgag acctatgatt tagtggatac cttttttgaaa   4680
aattgggcag ggaaatccta tccttacaaa gcaaaggaga gatacttaga tcagatgaag    4740
atcattggcc ctttgtgtca aaagttcctt gatttgcaca agctgacatt gatcctcaat    4800
gctgttggtc ctgaagagtt gaaaaacctg ttacgaacat ttaagggaag aacgagagat    4860
ttatcgacca aagatccatg cactcggcta cgtgttccca gccttgggcc cgtattcata    4920
tgcaaaggct gggtctatat ccacaagcac aaaattttga tggaccgaaa tttcctgctt    4980
atgtgtaaag atgtcataat aggacgcatg cagaccctat tgtctatgat aggtagatct    5040
gacgatgcat tcactcagca agacttcttc acccttgtaa atatctacag acaggagat    5100
atcatcttac aagagaaagg aaatctggcc tatgacttaa tcaagatggt ggagcctatc    5160
tgcaatctga aattgatgaa attggcgaga gaatacagac cactgattcc ccctttttcca    5220
cattttgaaa atcatgttaa aaatgcagtg gacgaacaat ctaaggtctc gaggaggatc    5280
aaagttctct ttgagctgat tatggggaatc aaaaatgtgg atcttgtcct ggtgatctat    5340
ggatcattta ggcattgggg gcatccattc atagattatt tcgaaggatt aaacaagcta    5400
cataagcagg taaccatgtc gaaggagatt gacacggagt atgcaaatgc tctggcaagt    5460
gatttggcta gaatcgttct gactaaacag tttgactctg ttaagaagtg gtttgtagac    5520
aagacaaaaa tcccctctgc ccatcccttt ttcaagcata tcatggataa cacatggccc    5580
actgccgccc agatccaaga ctttggagac cactggcatg aactgccgtt aatcaagtgt    5640
tatgagatac ctgacctcat cgatccatct atcatctatt cagacaagag ccactcaatg    5700
aaccgatctg aggtgcttgg acatgtgagg agatcccctc atttgccaat accgagcaaa    5760
aaggtactcc agactatgct tgataccagg gcgacaaact gggttgagtt tctagaaatg    5820
gtagacaaac atggtcttga aaaggatgat ttgataattg gactcaaggg gaaagaacgt    5880
gagttaaaat tagcaggtag attttttttca ttgatgtcct ggaagttgag agaatacttc    5940
gttatcacgg aatatcttat aaaaacacat tttgtaccct tgtttaaggg gctgacgatg    6000
gcagatgatt taacttccgt catcaaaaag atgttggata gttcttccgg acagggaata    6060
gacgactact cttcagtgtg ttttgccaat catatagatt acgagaagtg gaataatcac    6120
cagagaaagg aatcaaacgg accagtgttt cgggtgatgg gccaattttt gggatacccca    6180
cgtttgattg aacgaaccca tgagttcttt gagaaaagtc tcatttatta taacaacaga    6240
ccggatctaa tgtgggtcaa tgaagacaca ctgattaatc gtacacaaca gcgagtatgt    6300
tgggaaggtc aggctggagg ccttgagggg ttgaggcaaa agggttggag tattctcaat    6360
cttcttgtga ttcagagaga ggcaaaaatt cgaaacacag cagtcaaggt attggcacaa    6420
ggggacaatc aggtcatctg tactcaatat aagacgaaga aatccagaga tcagagtgaa    6480
ctcatcaatg cattagatca aatggtgaaa acaacaaca aaattatgga ggaaataaag    6540
aagggaacga gcaaactggg actattgatt aacgatgatg agaccatgca atcggctgat    6600
tatttgaatt acggtaaagt tccaatattc cgtggggtaa ttagagggtt agagacaaaa    6660
agatggtccc gggtcacatg tgtgacaaat gatcaaattc caacgtgtgc caatctgatg    6720
gcttctgtct caactaatgc actaacagta gctcattttg cgtctaaccc aatcaattca    6780
atgatacagt acaattactt cggtaacttt tcccgactac tgttgtttat gcatgaccca    6840
gcactgcgaa gatcacttta cgatgtgcag aatgaaatac cggattgca cagtaagact    6900
ttcaaatatg caatgctata tttggaccca tctattggcg gcgtttcagg gatggcattg    6960
```

```
agtagattcc ttatacgtgc attcccggac cctgtaactg aaagcttatc tttctggaaa    7020
tttattcatg accatactga tgatgaatac ctcaaaagct tatcaattgc ctttgggaat    7080
cctgatatag cgaaattccg actagagcat atcagtaaac tgcttgagga tccaacttcc    7140
ctcaatatat ctatgggaat gagtccttca aatcttttga aaaccgaagt taaaaaatgt    7200
ctcattgaaa atagaacatc tatcaggaac gatattatca aagatgccac catctatttg    7260
aaccaagagg aagcaaaatt gaaaagcttc ttatggtcta tcaatccact gtttcctaga    7320
tttttgagtg agttcaaatc tggcaccttc ctgggagtat ccgaaggatt aatcagtcta    7380
ttccaaaatt ctcggaccat ccgaaattcc ttcaagggta agtatcggaa agagctggat    7440
cacttgatcg tgaagagtga aatttcttct ctcaaacatc tgggcggcat tcacttcaaa    7500
ttggggaatg ggaaaatttg gggatgctcg tcatcccaat cagatttgct tagatacaga    7560
tcctggggaa gaaaactggt gggaactaca attcctcatc ctttggaaat gcacggagca    7620
gcgagtccta aagaggctcc ttgcaccttg tgtaactgct ctggcctgac ttacatctct    7680
gttcattgcc cgaaaggaat tacagaggta ttttccagaa gaggacccct accggcgtac    7740
ctgggttcta agacatcgga gaccacttca attcttcagc cttgggaaaa agaaagtaag    7800
gttcctattg taagacgagc tactagactg agagatgcca tctcatggtt catagaccca    7860
gattctacac ttgctcaatc tattcttgac aacattaaat ctttgacagg ggaagagtgg    7920
ggaggaagac agcatgggta agagaact ggctctgcat tgcatagatt ttctacctca    7980
cgtatgagca atggagggtt tgcttctcaa agtcccgcgg cttttgacccg attgattgct    8040 acgactgaca ccatgcacga ttatggagac aagaattatg atttcatgtt ccaggcctct    8100
ttgttatacg cacagatgac tacatctata tccagatggg ggcatgtcgg ggcttgcaca    8160
gatcattacc atgtccgttg tgacagctgc attcgagaaa tacaagagat tgaattgaac    8220
actggagtcc agtactctcc ccccgatgtg tcttatgttt tgacaaaatg gcggaacggc    8280
tcaggttctt ggggtactgt caccaaacaa ctcatcccga agaaggaaa ctggaccgta    8340 ctctcgcctg cagaacaatc ctatcaagtt ggacggtgta tcggatttct gtacggagat    8400
ctagtacata agaaatcaca tcaagcggac gacagttcat tatttccgtt aagcatacaa    8460
cacaaagtga gagggagagg ttttcttgaa ggtcttttag atggaataat gagagctagc    8520
tgttgtcaag tcattcacag gagaagtgtc gcaaccttaa agcgtccggc aaatgctgtg    8580
tatgggggag tcatattctt gattgacaaa ttgagtatgt cagccccatt cttgtcttta    8640
acccgtactg gtcctatcag ggaagaacta gaaaatgtcc ctcacaaaat gccagcgtcc    8700
tacccaacta ataatcgaga tttggggatg accgtcagaa actacttcaa gtatcaatgt    8760
cgaatcattg agagaggaca gtataaatcc cattatccca caatttggtt attttccgat    8820
gtcttatcgg tggactttat tggtcctatg tccttgtcat ctggacttat gagattgtta    8880
tacaagaaca gtctcagtaa gaaagacaaa aatgagctcc gagacttggc aaatctttca    8940
tctcttctca gatcaggaga agaatgggat gatatacatg tcaaattttt ctctcaagac    9000
ttactctttt gttctcagga gatacgacat gcctgtaaat tcgggattat acgagacaaa    9060
gtaagtctag aagtggatca tgggtggggg aagaagcat atggaggatg tacagtgctt    9120
ccagtgttct acaggtctca gatttataag aaaagtttga ctgtacccc acgaattcaa    9180 aaccctatca tatctggact ccgcttgggg caacttccta caggagctca ttataagatc    9240
agatcaatca tcatgactct aaagatcaat tatcaggact tcctgtcatg tggagacggt    9300
```

```
tcagggggga tgactgcctg cttgctccgg ttaaaccta atagtcgggg aattttcaat    9360
agtttgctag aattagatgg agcattaatg agaggatcat ccccgagcc acccagtgcg    9420
ctagagacgt tggggagcca agaactcga tgtgtaaacg aggaacatg ttgggaacat    9480
ccctctgact tgagcgaccc caatacttgg aagtatttta ttggattgaa gagaggatta    9540
ggcttgcaga tcaatctgat tactatggat atggaagttc gagatccagt gatctcacac    9600
aaaattgaag caaacatccg agcatttctc tatgatcttt tagacccgga gggaaccctt    9660
atatacaaaa cgtatggcac atatctggca gaagaggaaa ggaatattct gacagaagta    9720
ggtcctttgt ttcacactac tgacttggtg caaactattt acagtagtgc ccagacttcg    9780
gaggtttact gtgtatgcag acggttaaag aaatatgctg atcaacaaca tgtggattgg    9840
tcattgttga ctgatggatg gtctcggtta tatgcgtttt ctgtgaatcg attggaattc    9900
caaagggctc agagtcttcg gaaactggac acactgcaag gaattccaag ctttttcata    9960
ccagatcctt ttgtcaatgc ggagacttta ttgcaaattg caggtgttcc aacagggatt   10020
tctcacacag ccgtattaca tggatcgtta cattctgaac aattgataac gcttggtatt   10080
ttcttctgtg cgctaatctc tcaccataca atgaacatca tacgaatatc acctgtcccc   10140
ccgtctcctc catccgatgg gtcaataagt agaatgtgtt ctgcaatcac agggatccta   10200
ttttgggtct ccttagtgga aaggacttg actctataca actcattgtt gtcaataata   10260
cagagatcct ttccaatccg atggtacaaa ataaggaga aaaacggatg gtcccaatgt   10320
tgggggggcaa atggagacgg gataccaaa gatactcgac taaatgattc gatggcgaac   10380
ataggaaaact ggataaggc tatggagttg ctttgcaata agaccgctca gatgcccttc   10440
tctcccaagt tgttcaatcg attggccgca caatatgaca gagaattaac atggaagaag   10500
gtgttggcta aaacaggact tgcagattta ctaacaggac aaatttcaca aattgatcga   10560
tcagttgcga atgtccggag cgagccgagt aatgagaact cttggcaaga ttagagcgat   10620
ccacaagtat gaaaaaaact aatcccatag ccattttaaa ttattgaaat tgatgaaatt   10680
ggcgtcgacc ggccgcgatt ctggakccga tgcgta                            10716
```

<210> SEQ ID NO 8
<211> LENGTH: 442
<212> TYPE: PRT
<213> ORGANISM: Carajas Virus N

<400> SEQUENCE: 8

```
Met Asn Ser Ile Val Lys Lys Val Ile Asp Asp Thr Val Ile Gln Pro
1               5                   10                  15

Lys Leu Pro Ala Asn Glu Asp Pro Val Glu Tyr Pro Ala Asp Tyr Phe
            20                  25                  30

Lys Thr Ser Lys Gln Ile Pro Leu Tyr Ile Asn Thr Lys Thr Leu
        35                  40                  45

Ala Glu Leu Arg Ala Phe Val Tyr Gln Gly Leu Lys Ala Gly Asn Pro
    50                  55                  60

Ser Ile Ile His Val Asn Ser Tyr Leu Tyr Leu Ala Leu Lys Asp Ile
65                  70                  75                  80

Lys Ala Thr Leu Glu Arg Asp Trp Thr Ser Phe Ser Ile Thr Ile Gly
                85                  90                  95

Lys Gln Gly Glu Glu Ile Thr Ile Phe Asn Leu Val Ser Val Arg Pro
            100                 105                 110

Leu Val Ile Thr Val Pro Asp Gly Arg Thr Asp Pro Asp Arg Ser Pro
        115                 120                 125
```

```
Asn Asp Asp Lys Trp Leu Pro Ile Tyr Leu Gly Leu Tyr Arg Val
            130                 135                 140

Gly Arg Thr Lys Leu Pro Glu Tyr Arg Lys Lys Leu Met Glu Gly Leu
145                 150                 155                 160

Glu Met Gln Cys Lys Ile Met Tyr Pro Asp Phe Val Pro Ile Val Pro
                165                 170                 175

Glu Gly Met Asp Phe Phe Asp Val Trp Gly Asn Asp Ser Asn Phe Thr
            180                 185                 190

Lys Ile Val Ala Ala Val Asp Met Phe Phe His Met Phe Lys Lys His
        195                 200                 205

Glu Arg Ala Ser Leu Arg Tyr Gly Thr Ile Val Ser Arg Phe Lys Asp
    210                 215                 220

Cys Ala Ala Leu Ala Thr Phe Gly His Val Cys Lys Val Ser Gly Met
225                 230                 235                 240

Ser Thr Glu Glu Val Thr Thr Trp Val Leu Asn Arg Glu Val Ala Asp
                245                 250                 255

Glu Leu Cys Gln Met Met Phe Pro Gly Gln Glu Ile Asp Arg Ala Asp
            260                 265                 270

Ser Tyr Met Pro Tyr Met Ile Asp Phe Gly Leu Ser Gln Lys Ser Pro
        275                 280                 285

Tyr Ser Ser Val Lys Asn Pro Ser Phe His Phe Trp Gly Gln Leu Ala
    290                 295                 300

Ala Leu Leu Leu Arg Ser Thr Arg Ala Lys Asn Ala Arg Gln Pro Asp
305                 310                 315                 320

Asp Ile Glu Tyr Thr Ser Leu Thr Thr Ala Gly Leu Leu Leu Ala Tyr
                325                 330                 335

Ala Val Gly Ser Ser Ala Asp Ile Ser Gln Gln Phe Tyr Met Gly Asp
            340                 345                 350

Glu Lys Tyr Ile Ser Asp Pro Ser Ala Gly Gly Leu Thr Ser Asn Ala
        355                 360                 365

Pro Pro Lys Gly Arg Asn Val Val Asp Trp Leu Gly Trp Phe Glu Asp
    370                 375                 380

Gln Gly Gly Asn Ile Thr Pro Asp Met Tyr Thr Ser Leu Lys Gly Leu
385                 390                 395                 400

Phe Ala Leu Cys Lys Gly Cys Glu Ile Arg Pro Leu Glu Ser Met Pro
                405                 410                 415

Arg Glu Ser Leu Thr Ser Asp Ser Ile Gln Ile Lys Cys Phe Thr Thr
            420                 425                 430

Cys Cys Ile Ile Tyr Asn Tyr Glu Lys Asn
        435                 440

<210> SEQ ID NO 9
<211> LENGTH: 261
<212> TYPE: PRT
<213> ORGANISM: Carajas Virus P

<400> SEQUENCE: 9

Met Gly Thr Tyr Thr His Leu Asp Ser Ala Leu Gln Asp Ala Asn Glu
1               5                   10                  15

Ser Glu Glu Ser Arg Asp Glu Lys Ser Asn Phe Asp Leu Phe Asp Glu
                20                  25                  30

Glu Ser Lys Glu Val Ala Arg Pro Ser Tyr Tyr Ser Ala Ile Asp Glu
            35                  40                  45

Glu Ser Asp Gln Glu Glu Thr Glu Ser Asp Asp Pro Asp Glu Glu Leu
```

```
                    50                  55                  60
Asn Asp Ser Asn Ala His Gly Ala Val Asp Gly Trp Asp Glu Thr Leu
 65                  70                  75                  80

Asn Glu Asn Ser Gln Pro Asp Asn Val Ser Val Glu Phe Ala Arg
                 85                  90                  95

Thr Trp Ser Thr Pro Val Met Glu Ser Ser Glu Gly Lys Thr Leu
                100                 105                 110

His Leu Ala Met Pro Asp Gly Leu Asn Pro Asp Gln Val Ala Gln Trp
                115                 120                 125

Leu Gln Thr Val Lys Ala Leu Phe Glu Ser Ala Lys Tyr Trp Asn Leu
                130                 135                 140

Ser Glu Cys Arg Met Glu Val Leu Leu Glu Gly Val Leu Ile Lys Glu
145                 150                 155                 160

Arg Gln Met Thr Pro Asp Leu Gln Lys Val Thr Pro Lys Pro Asn Asn
                165                 170                 175

Pro Pro Pro Glu Ser Met Pro Cys Asp Pro Leu Pro Ala Met Asp
                180                 185                 190

Val Trp Glu Ala Ala Ser Gln Val Tyr Thr Leu Glu Pro Lys Arg Ala
                195                 200                 205

Asn Leu Ala Pro Met Asp Val Lys Leu Lys Asp Leu Phe Ser Ser Arg
                210                 215                 220

Ala Glu Phe Leu Ser Val Gly Ser Pro Gln Met Ser Trp Lys Glu
225                 230                 235                 240

Ala Ile Ile Leu Gly Leu Arg Tyr Lys Lys Leu Tyr Asn Gln Ala Arg
                245                 250                 255

Leu Lys Tyr Ser Leu
                260

<210> SEQ ID NO 10
<211> LENGTH: 228
<212> TYPE: PRT
<213> ORGANISM: Carajas Virus M

<400> SEQUENCE: 10

Met Ser Ser Leu Lys Lys Ile Leu Gly Leu Lys Gly Lys Lys Glu Glu
 1                   5                  10                  15

Lys Ser Lys Lys Leu Gly Leu Pro Pro Tyr Glu Met Pro Ala Asn
                 20                  25                  30

Asn Glu Phe Glu Pro Asn Ala Pro Leu Asp Pro Asp Met Phe Gly Ala
                 35                  40                  45

Glu His Leu Glu Ile Glu Ser Lys Ser Ala Met Arg Tyr Glu Lys Phe
                 50                  55                  60

Lys Phe Ser Val Lys Ile Thr Leu Arg Thr Asn Arg Pro Leu Arg Thr
 65                  70                  75                  80

Tyr Asp Asp Val Cys Gln Ile Leu Ser Lys Trp Asp Ala Met Tyr Val
                 85                  90                  95

Gly Met Met Gly Lys Arg Pro Phe Tyr Lys Val Leu Val Leu Ile Gly
                100                 105                 110

Ser Ser His Leu Gln Ala Thr Pro Ala Ile Leu Ser Asp Arg Gly Gln
                115                 120                 125

Pro Glu Tyr His Met Tyr Leu Glu Asp Arg Gly Phe Ile Ala His Arg
                130                 135                 140

Leu Gly Leu Thr Pro Pro Met Leu Ser Gly Pro Glu Ser Phe Arg Arg
145                 150                 155                 160
```

```
Pro Phe His Val Gly Leu Tyr Arg Gly Thr Ile Asp Ile Thr Val Asn
                165                 170                 175

Leu Met Asp Asp Glu Ser Thr Glu Ser Ala Pro Gln Val Trp Asp His
            180                 185                 190

Phe Asn Thr Arg Tyr Val Asn His Phe Leu Glu His Ala Lys Arg Phe
            195                 200                 205

Gly Leu Val Leu Ser Lys Lys Pro Gly Gly Gly Trp Ile Leu Asp Gln
    210                 215                 220

Ala Val Cys Ala
225

<210> SEQ ID NO 11
<211> LENGTH: 519
<212> TYPE: PRT
<213> ORGANISM: Carajas Virus G

<400> SEQUENCE: 11

Met Val Ile Ala Gly Leu Ile Leu Cys Ile Gly Ile Leu Pro Ala Ile
1               5                   10                  15

Gly Lys Ile Thr Ile Ser Phe Pro Gln Ser Leu Lys Gly Asp Trp Arg
            20                  25                  30

Pro Val Pro Lys Gly Tyr Asn Tyr Cys Pro Thr Ser Ala Asp Lys Asn
        35                  40                  45

Leu His Gly Asp Leu Ile Asp Ile Gly Leu Arg Leu Arg Ala Pro Lys
    50                  55                  60

Ser Phe Lys Gly Ile Ser Ala Asp Gly Trp Met Cys His Ala Ala Arg
65                  70                  75                  80

Trp Ile Thr Thr Cys Asp Phe Arg Trp Tyr Gly Pro Lys Tyr Ile Thr
                85                  90                  95

His Ser Ile His Ser Phe Arg Pro Ser Asn Asp Gln Cys Lys Glu Ala
            100                 105                 110

Ile Arg Leu Thr Asn Glu Gly Asn Trp Ile Asn Pro Gly Phe Pro Pro
        115                 120                 125

Gln Ser Cys Gly Tyr Ala Ser Val Thr Asp Ser Glu Ser Val Val Val
    130                 135                 140

Thr Val Thr Lys His Gln Val Leu Val Asp Glu Tyr Ser Gly Ser Trp
145                 150                 155                 160

Ile Asp Ser Gln Phe Pro Gly Gly Ser Cys Thr Ser Pro Ile Cys Asp
                165                 170                 175

Thr Val His Asn Ser Thr Leu Trp His Ala Asp His Thr Leu Asp Ser
            180                 185                 190

Ile Cys Asp Gln Glu Phe Val Ala Met Asp Ala Val Leu Phe Thr Glu
        195                 200                 205

Ser Gly Lys Phe Glu Glu Phe Gly Lys Pro Asn Ser Gly Ile Arg Ser
    210                 215                 220

Asn Tyr Phe Pro Tyr Glu Ser Leu Lys Asp Val Cys Gln Met Asp Phe
225                 230                 235                 240

Cys Lys Arg Lys Gly Phe Lys Leu Pro Ser Gly Val Trp Phe Glu Ile
                245                 250                 255

Glu Asp Ala Glu Lys Ser His Lys Ala Gln Val Glu Leu Lys Ile Lys
            260                 265                 270

Arg Cys Pro His Gly Ala Val Ile Ser Ala Pro Asn Gln Asn Ala Ala
        275                 280                 285

Asp Ile Asn Leu Ile Met Asp Val Glu Arg Ile Leu Asp Tyr Ser Leu
    290                 295                 300
```

```
Cys Gln Ala Thr Trp Ser Lys Ile Gln Asn Lys Glu Ala Leu Thr Pro
305                 310                 315                 320

Ile Asp Ile Ser Tyr Leu Gly Pro Lys Asn Pro Gly Pro Gly Pro Ala
                325                 330                 335

Phe Thr Ile Ile Asn Gly Thr Leu His Tyr Phe Asn Thr Arg Tyr Ile
            340                 345                 350

Arg Val Asp Ile Ala Gly Pro Val Thr Lys Glu Ile Thr Gly Phe Val
        355                 360                 365

Ser Gly Thr Ser Thr Ser Arg Val Leu Trp Asp Gln Trp Phe Pro Tyr
    370                 375                 380

Gly Glu Asn Ser Ile Gly Pro Asn Gly Leu Leu Lys Thr Ala Ser Gly
385                 390                 395                 400

Tyr Lys Tyr Pro Leu Phe Met Val Gly Thr Gly Val Leu Asp Ala Asp
                405                 410                 415

Ile His Lys Leu Gly Glu Ala Thr Val Ile Glu His Pro His Ala Lys
            420                 425                 430

Glu Ala Gln Lys Val Val Asp Ser Glu Val Ile Phe Phe Gly Asp
        435                 440                 445

Thr Gly Val Ser Lys Asn Pro Val Glu Val Val Glu Gly Trp Phe Ser
    450                 455                 460

Gly Trp Arg Ser Ser Leu Met Ser Ile Phe Gly Ile Leu Leu Ile
465                 470                 475                 480

Val Cys Leu Val Leu Ile Val Arg Ile Leu Ile Ala Leu Lys Tyr Cys
                485                 490                 495

Cys Val Arg His Lys Lys Arg Thr Ile Tyr Lys Glu Asp Leu Glu Met
            500                 505                 510

Gly Arg Ile Pro Arg Arg Ala
        515

<210> SEQ ID NO 12
<211> LENGTH: 2109
<212> TYPE: PRT
<213> ORGANISM: Carajas Virus L

<400> SEQUENCE: 12

Met Asp Phe Leu Pro Val Glu Gln Glu Glu Asp Trp Gly Tyr Ala Glu
1               5                   10                  15

Asp Asp Phe Ser Ser Asp Tyr Leu Asp Phe Glu Arg Met Thr
                20                  25                  30

Tyr Leu Asn Gln Ala Asp Tyr Asn Leu Asn Ser Pro Leu Ile Ser Asp
            35                  40                  45

Asp Ile Tyr Tyr Leu Ser Arg Lys Phe His Ser Tyr Gly Ile Pro Pro
        50                  55                  60

Met Trp Asn Leu Lys Glu Trp Asp Gly Pro Leu Glu Met Leu Lys Ser
65                  70                  75                  80

Cys Gln Ala Asp Pro Ile Pro His Asp Leu Met His Lys Trp Phe Gly
                85                  90                  95

Thr Trp Leu Glu Asp Phe Asp His Asp Ser Ala Gln Gly Ile Val Phe
            100                 105                 110

Leu Arg Glu Val Asp Lys Glu Ala Ser Glu Thr Tyr Asp Leu Val Asp
        115                 120                 125

Thr Phe Leu Lys Asn Trp Ala Gly Lys Ser Tyr Pro Tyr Lys Ala Lys
    130                 135                 140

Glu Arg Tyr Leu Asp Gln Met Lys Ile Ile Gly Pro Leu Cys Gln Lys
```

```
                145                 150                 155                 160
        Phe Leu Asp Leu His Lys Leu Thr Leu Ile Leu Asn Ala Val Gly Pro
                        165                 170                 175
        Glu Glu Leu Lys Asn Leu Leu Arg Thr Phe Lys Gly Arg Thr Arg Asp
                        180                 185                 190
        Leu Ser Thr Lys Asp Pro Cys Thr Arg Leu Arg Val Pro Ser Leu Gly
                        195                 200                 205
        Pro Val Phe Ile Cys Lys Gly Trp Val Tyr Ile His Lys His Lys Ile
                        210                 215                 220
        Leu Met Asp Arg Asn Phe Leu Leu Met Cys Lys Asp Val Ile Ile Gly
        225                 230                 235                 240
        Arg Met Gln Thr Leu Leu Ser Met Ile Gly Arg Ser Asp Asp Ala Phe
                        245                 250                 255
        Thr Gln Gln Asp Phe Phe Thr Leu Val Asn Ile Tyr Arg Thr Gly Asp
                        260                 265                 270
        Ile Ile Leu Gln Glu Lys Gly Asn Leu Ala Tyr Asp Leu Ile Lys Met
                        275                 280                 285
        Val Glu Pro Ile Cys Asn Leu Lys Leu Met Lys Leu Ala Arg Glu Tyr
                        290                 295                 300
        Arg Pro Leu Ile Pro Pro Phe Pro His Phe Glu Asn His Val Lys Asn
        305                 310                 315                 320
        Ala Val Asp Glu Gln Ser Lys Val Ser Arg Arg Ile Lys Val Leu Phe
                        325                 330                 335
        Glu Leu Ile Met Gly Ile Lys Asn Val Asp Leu Val Leu Val Ile Tyr
                        340                 345                 350
        Gly Ser Phe Arg His Trp Gly His Pro Phe Ile Asp Tyr Phe Glu Gly
                        355                 360                 365
        Leu Asn Lys Leu His Lys Gln Val Thr Met Ser Lys Glu Ile Asp Thr
                        370                 375                 380
        Glu Tyr Ala Asn Ala Leu Ala Ser Asp Leu Ala Arg Ile Val Leu Thr
        385                 390                 395                 400
        Lys Gln Phe Asp Ser Val Lys Lys Trp Phe Val Asp Lys Thr Lys Ile
                        405                 410                 415
        Pro Ser Ala His Pro Phe Lys His Ile Met Asp Asn Thr Trp Pro
                        420                 425                 430
        Thr Ala Ala Gln Ile Gln Asp Phe Gly Asp His Trp His Glu Leu Pro
                        435                 440                 445
        Leu Ile Lys Cys Tyr Glu Ile Pro Asp Leu Ile Asp Pro Ser Ile Ile
                        450                 455                 460
        Tyr Ser Asp Lys Ser His Ser Met Asn Arg Ser Glu Val Leu Gly His
        465                 470                 475                 480
        Val Arg Arg Ser Pro His Leu Pro Ile Pro Ser Lys Lys Val Leu Gln
                        485                 490                 495
        Thr Met Leu Asp Thr Arg Ala Thr Asn Trp Val Glu Phe Leu Glu Met
                        500                 505                 510
        Val Asp Lys His Gly Leu Glu Lys Asp Leu Ile Ile Gly Leu Lys
                        515                 520                 525
        Gly Lys Glu Arg Glu Leu Lys Leu Ala Gly Arg Phe Phe Ser Leu Met
                        530                 535                 540
        Ser Trp Lys Leu Arg Glu Tyr Phe Val Ile Thr Glu Tyr Leu Ile Lys
        545                 550                 555                 560
        Thr His Phe Val Pro Leu Phe Lys Gly Leu Thr Met Ala Asp Asp Leu
                        565                 570                 575
```

-continued

```
Thr Ser Val Ile Lys Lys Met Leu Asp Ser Ser Gly Gln Gly Ile
            580                 585                 590

Asp Asp Tyr Ser Ser Val Cys Phe Ala Asn His Ile Asp Tyr Glu Lys
        595                 600                 605

Trp Asn Asn His Gln Arg Lys Glu Ser Asn Gly Pro Val Phe Arg Val
610                 615                 620

Met Gly Gln Phe Leu Gly Tyr Pro Arg Leu Ile Glu Arg Thr His Glu
625                 630                 635                 640

Phe Phe Glu Lys Ser Leu Ile Tyr Tyr Asn Asn Arg Pro Asp Leu Met
                645                 650                 655

Trp Val Asn Glu Asp Thr Leu Ile Asn Arg Thr Gln Gln Arg Val Cys
            660                 665                 670

Trp Glu Gly Gln Ala Gly Gly Leu Glu Gly Leu Arg Gln Lys Gly Trp
        675                 680                 685

Ser Ile Leu Asn Leu Leu Val Ile Gln Arg Glu Ala Lys Ile Arg Asn
    690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asp Gln Ser Glu Leu Ile Asn Ala
                725                 730                 735

Leu Asp Gln Met Val Lys Asn Asn Lys Ile Met Glu Glu Ile Lys
            740                 745                 750

Lys Gly Thr Ser Lys Leu Gly Leu Leu Ile Asn Asp Asp Glu Thr Met
        755                 760                 765

Gln Ser Ala Asp Tyr Leu Asn Tyr Gly Lys Val Pro Ile Phe Arg Gly
    770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Leu Met Ala Ser Val Ser
                805                 810                 815

Thr Asn Ala Leu Thr Val Ala His Phe Ala Ser Asn Pro Ile Asn Ser
            820                 825                 830

Met Ile Gln Tyr Asn Tyr Phe Gly Asn Phe Ser Arg Leu Leu Leu Phe
        835                 840                 845

Met His Asp Pro Ala Leu Arg Arg Ser Leu Tyr Asp Val Gln Asn Glu
    850                 855                 860

Ile Pro Gly Leu His Ser Lys Thr Phe Lys Tyr Ala Met Leu Tyr Leu
865                 870                 875                 880

Asp Pro Ser Ile Gly Gly Val Ser Gly Met Ala Leu Ser Arg Phe Leu
                885                 890                 895

Ile Arg Ala Phe Pro Asp Pro Val Thr Glu Ser Leu Ser Phe Trp Lys
            900                 905                 910

Phe Ile His Asp His Thr Asp Asp Glu Tyr Leu Lys Ser Leu Ser Ile
        915                 920                 925

Ala Phe Gly Asn Pro Asp Ile Ala Lys Phe Arg Leu Glu His Ile Ser
    930                 935                 940

Lys Leu Leu Glu Asp Pro Thr Ser Leu Asn Ile Ser Met Gly Met Ser
945                 950                 955                 960

Pro Ser Asn Leu Leu Lys Thr Glu Val Lys Lys Cys Leu Ile Glu Asn
                965                 970                 975

Arg Thr Ser Ile Arg Asn Asp Ile Ile Lys Asp Ala Thr Ile Tyr Leu
            980                 985                 990
```

-continued

```
Asn Gln Glu Glu Ala Lys Leu Lys  Ser Phe Leu Trp Ser  Ile Asn Pro
            995                 1000                1005

Leu Phe Pro Arg Phe Leu Ser  Glu Phe Lys Ser Gly  Thr Phe Leu
    1010                1015                1020

Gly Val Ser Glu Gly Leu Ile  Ser Leu Phe Gln Asn  Ser Arg Thr
    1025                1030                1035

Ile Arg Asn Ser Phe Lys Gly  Lys Tyr Arg Lys Glu  Leu Asp His
    1040                1045                1050

Leu Ile Val Lys Ser Glu Ile  Ser Ser Leu Lys His  Leu Gly Gly
    1055                1060                1065

Ile His Phe Lys Leu Gly Asn  Gly Lys Ile Trp Gly  Cys Ser Ser
    1070                1075                1080

Ser Gln Ser Asp Leu Leu Arg  Tyr Arg Ser Trp Gly  Arg Lys Leu
    1085                1090                1095

Val Gly Thr Thr Ile Pro His  Pro Leu Glu Met His  Gly Ala Ala
    1100                1105                1110

Ser Pro Lys Glu Ala Pro Cys  Thr Leu Cys Asn Cys  Ser Gly Leu
    1115                1120                1125

Thr Tyr Ile Ser Val His Cys  Pro Lys Gly Ile Thr  Glu Val Phe
    1130                1135                1140

Ser Arg Arg Gly Pro Leu Pro  Ala Tyr Leu Gly Ser  Lys Thr Ser
    1145                1150                1155

Glu Thr Thr Ser Ile Leu Gln  Pro Trp Glu Lys Glu  Ser Lys Val
    1160                1165                1170

Pro Ile Val Arg Arg Ala Thr  Arg Leu Arg Asp Ala  Ile Ser Trp
    1175                1180                1185

Phe Ile Asp Pro Asp Ser Thr  Leu Ala Gln Ser Ile  Leu Asp Asn
    1190                1195                1200

Ile Lys Ser Leu Thr Gly Glu  Glu Trp Gly Gly Arg  Gln His Gly
    1205                1210                1215

Tyr Lys Arg Thr Gly Ser Ala  Leu His Arg Phe Ser  Thr Ser Arg
    1220                1225                1230

Met Ser Asn Gly Gly Phe Ala  Ser Gln Ser Pro Ala  Ala Leu Thr
    1235                1240                1245

Arg Leu Ile Ala Thr Thr Asp  Thr Met His Asp Tyr  Gly Asp Lys
    1250                1255                1260

Asn Tyr Asp Phe Met Phe Gln  Ala Ser Leu Leu Tyr  Ala Gln Met
    1265                1270                1275

Thr Thr Ser Ile Ser Arg Trp  Gly His Val Gly Ala  Cys Thr Asp
    1280                1285                1290

His Tyr His Val Arg Cys Asp  Ser Cys Ile Arg Glu  Ile Gln Glu
    1295                1300                1305

Ile Glu Leu Asn Thr Gly Val  Gln Tyr Ser Pro Pro  Asp Val Ser
    1310                1315                1320

Tyr Val Leu Thr Lys Trp Arg  Asn Gly Ser Gly Ser  Trp Gly Thr
    1325                1330                1335

Val Thr Lys Gln Leu Ile Pro  Lys Glu Gly Asn Trp  Thr Val Leu
    1340                1345                1350

Ser Pro Ala Glu Gln Ser Tyr  Gln Val Gly Arg Cys  Ile Gly Phe
    1355                1360                1365

Leu Tyr Gly Asp Leu Val His  Lys Lys Ser His Gln  Ala Asp Asp
    1370                1375                1380

Ser Ser Leu Phe Pro Leu Ser  Ile Gln His Lys Val  Arg Gly Arg
```

-continued

```
            1385                1390                1395

Gly Phe Leu Glu Gly Leu Leu Asp Gly Ile Met Arg Ala Ser Cys
        1400                1405                1410

Cys Gln Val Ile His Arg Arg Ser Val Ala Thr Leu Lys Arg Pro
        1415                1420                1425

Ala Asn Ala Val Tyr Gly Gly Val Ile Phe Leu Ile Asp Lys Leu
        1430                1435                1440

Ser Met Ser Ala Pro Phe Leu Ser Leu Thr Arg Thr Gly Pro Ile
        1445                1450                1455

Arg Glu Glu Leu Glu Asn Val Pro His Lys Met Pro Ala Ser Tyr
        1460                1465                1470

Pro Thr Asn Asn Arg Asp Leu Gly Met Thr Val Arg Asn Tyr Phe
        1475                1480                1485

Lys Tyr Gln Cys Arg Ile Ile Glu Arg Gly Gln Tyr Lys Ser His
        1490                1495                1500

Tyr Pro Thr Ile Trp Leu Phe Ser Asp Val Leu Ser Val Asp Phe
        1505                1510                1515

Ile Gly Pro Met Ser Leu Ser Ser Gly Leu Met Arg Leu Leu Tyr
        1520                1525                1530

Lys Asn Ser Leu Ser Lys Lys Asp Lys Asn Glu Leu Arg Asp Leu
        1535                1540                1545

Ala Asn Leu Ser Ser Leu Leu Arg Ser Gly Glu Glu Trp Asp Asp
        1550                1555                1560

Ile His Val Lys Phe Phe Ser Gln Asp Leu Leu Phe Cys Ser Gln
        1565                1570                1575

Glu Ile Arg His Ala Cys Lys Phe Gly Ile Ile Arg Asp Lys Val
        1580                1585                1590

Ser Leu Glu Val Asp His Gly Trp Gly Lys Glu Ala Tyr Gly Gly
        1595                1600                1605

Cys Thr Val Leu Pro Val Phe Tyr Arg Ser Gln Ile Tyr Lys Lys
        1610                1615                1620

Ser Leu Thr Val Pro Pro Arg Ile Gln Asn Pro Ile Ile Ser Gly
        1625                1630                1635

Leu Arg Leu Gly Gln Leu Pro Thr Gly Ala His Tyr Lys Ile Arg
        1640                1645                1650

Ser Ile Ile Met Thr Leu Lys Ile Asn Tyr Gln Asp Phe Leu Ser
        1655                1660                1665

Cys Gly Asp Gly Ser Gly Gly Met Thr Ala Cys Leu Leu Arg Leu
        1670                1675                1680

Asn Pro Asn Ser Arg Gly Ile Phe Asn Ser Leu Leu Glu Leu Asp
        1685                1690                1695

Gly Ala Leu Met Arg Gly Ser Ser Pro Glu Pro Ser Ala Leu
        1700                1705                1710

Glu Thr Leu Gly Ser Gln Arg Thr Arg Cys Val Asn Gly Gly Thr
        1715                1720                1725

Cys Trp Glu His Pro Ser Asp Leu Ser Asp Pro Asn Thr Trp Lys
        1730                1735                1740

Tyr Phe Ile Gly Leu Lys Arg Gly Leu Gly Leu Gln Ile Asn Leu
        1745                1750                1755

Ile Thr Met Asp Met Glu Val Arg Asp Pro Val Ile Ser His Lys
        1760                1765                1770

Ile Glu Ala Asn Ile Arg Ala Phe Leu Tyr Asp Leu Leu Asp Pro
        1775                1780                1785
```

Glu Gly Thr Leu Ile Tyr Lys Thr Tyr Gly Thr Tyr Leu Ala Glu
    1790                1795                1800

Glu Glu Arg Asn Ile Leu Thr Glu Val Gly Pro Leu Phe His Thr
    1805                1810                1815

Thr Asp Leu Val Gln Thr Ile Tyr Ser Ser Ala Gln Thr Ser Glu
    1820                1825                1830

Val Tyr Cys Val Cys Arg Arg Leu Lys Lys Tyr Ala Asp Gln Gln
    1835                1840                1845

His Val Asp Trp Ser Leu Leu Thr Asp Gly Trp Ser Arg Leu Tyr
    1850                1855                1860

Ala Phe Ser Val Asn Arg Leu Glu Phe Gln Arg Ala Gln Ser Leu
    1865                1870                1875

Arg Lys Leu Asp Thr Leu Gln Gly Ile Pro Ser Phe Phe Ile Pro
    1880                1885                1890

Asp Pro Phe Val Asn Ala Glu Thr Leu Leu Gln Ile Ala Gly Val
    1895                1900                1905

Pro Thr Gly Ile Ser His Thr Ala Val Leu His Gly Ser Leu His
    1910                1915                1920

Ser Glu Gln Leu Ile Thr Leu Gly Ile Phe Phe Cys Ala Leu Ile
    1925                1930                1935

Ser His His Thr Met Asn Ile Ile Arg Ile Ser Pro Val Pro Pro
    1940                1945                1950

Ser Pro Pro Ser Asp Gly Ser Ile Ser Arg Met Cys Ser Ala Ile
    1955                1960                1965

Thr Gly Ile Leu Phe Trp Val Ser Leu Val Glu Lys Asp Leu Thr
    1970                1975                1980

Leu Tyr Asn Ser Leu Leu Ser Ile Ile Gln Arg Ser Phe Pro Ile
    1985                1990                1995

Arg Trp Tyr Lys Asn Lys Glu Lys Asn Gly Trp Ser Gln Cys Trp
    2000                2005                2010

Gly Ala Asn Gly Asp Gly Ile Pro Lys Asp Thr Arg Leu Asn Asp
    2015                2020                2025

Ser Met Ala Asn Ile Gly Asn Trp Ile Arg Ala Met Glu Leu Leu
    2030                2035                2040

Cys Asn Lys Thr Ala Gln Met Pro Phe Ser Pro Lys Leu Phe Asn
    2045                2050                2055

Arg Leu Ala Ala Gln Tyr Asp Arg Glu Leu Thr Trp Lys Lys Val
    2060                2065                2070

Leu Ala Lys Thr Gly Leu Ala Asp Leu Leu Thr Gly Gln Ile Ser
    2075                2080                2085

Gln Ile Asp Arg Ser Val Ala Asn Val Arg Ser Glu Pro Ser Asn
    2090                2095                2100

Glu Asn Ser Trp Gln Asp
    2105

<210> SEQ ID NO 13
<211> LENGTH: 12416
<212> TYPE: DNA
<213> ORGANISM: Bahia Grande

<400> SEQUENCE: 13
acaatattag ataaactcct ctacttctta actatcgtta gacatggccg ccgcaatact    60
tccagtttct cgtaacatgc ctgtcagaga aaggacagtg gcaggaagtg taacagcgcc   120

```
accagttcag tatccaagca cctggttcca agcccatgcc ggacaaaaag tttcaataac      180
tatttatcaa atactaatg cacgacaagc tttctccaga attactcaac tcagaaacaa       240
cggacaatgg gatgataaat tgatcgctac tttcatgaaa ggtgtcttgg atgaaaatgc     300
tgaatggttc caaagccctc ccctcattga ggactggatt gtaaatgaag cagtcatcgg     360
aagagtagat gacgtagttg cacccactgc acttgcacag tgggaagagg ttgaaaggcc    420
tcaaaacatg gatccagtac ccaatgagga aggagaactg gggactcgga ggtcatttt     480 cttggcatta atcaccatct acaggcaagt actgacaaga accatcaatg tggactacgg   540
ccaagaagtg agcagaagga taatagataa tttcaaagaa caacctttag gtatgtcaca   600
ggatgacata aatgaaatcc aggggtatga atcaaaagaa aggctaacta caaattatgt    660
gaaaatctta tgcatccttg atatgttctt caataagttt cagacccatg acaaaagcac    720
catcaggata gctactttac caacaagata tagaggatgt gctgcattca cttcatacgg   780
agaactagca ataagattgg gaattgaacc cataaagctg cccagtttga ttcttacagt    840
agcagtggcc aaagatttcg ataagatcaa tgtcaatgga gagcaagcag agcaattaga    900
tggatatttt ccatatcaat tagagttggg attagttaaa aagagtgctt attcagcagg   960
aaattgtcca tctttatact tatggatgca ccatagga caatgctcc atcaacaaag     1020 atcttatcga gccaatgttc ccaaaaatgt accagaccaa atgggaacaa taaattctgc    1080
aattgctgtt gccatgcagt ttgttgctgg gggagagttc agtatgcaat ttgtagggga   1140
tgcacgagtt caagaagcca tgagagaaat gcaaacagca gaagctgaat tgaatgagtt    1200
aagaatggct caggcaagag aaatgagagc tgcagcaaga ggagatgaag atgaagaagg    1260
ctctgaagat ggacttgatg atgaaaatga tggagaaggg gatgatgagt taccagctga   1320
aattgaacaa aatcctgaat atttaaatag agtcaacagg atcagagaat tacaagaaaa    1380
cctccaacaa tacaacgcaa cagtacaaca gcacactaat gcggtagaaa aagccgcact    1440
cagagcactc gcttatcttc aagaaaatgg aggaattgca gataaggaca agagagactt    1500
gggtataaga ttcaggaggt ttgctgatga agcggaaggt agagtcggta aattattagc    1560
cagtttgttc cctgccccga gataaatatt ctttcaggta tcattttctt attttttaaaa   1620 tatttttatcc agatttaat ttctttatct actgtattat tttattcaaa tatgtttca    1680 attaattttt tcttctttat atgttatatt ctatacat at gttaatgttc atgaaaaaaa   1740
caacaaatct cataagatac tcgtttaag aaatggctta ttcaactggt ttgattaaag     1800
gtgaagtgtc ccaaggattg tctaatgcat ttaaagatgc aggaatacat caaatagaat     1860
taaataaaga atatgacaat ttatcaattt tgggggccaa catgagtgca ttgaataaaa      1920
tgtttgacac agaagatgaa gggttatctg atactaatac taactcatca aaaaactcta    1980
ttttacaagc gagtgatatg ttcataggaa atgatgaata tgaatcagat gactctcatc    2040
attttctaag ctcacctagt ccagataaag gaagcagtga agaaggaagc aacctccaag   2100
aattcaattt tcagatacct agaaacaagg ttggaaaaga aaaggcatac aggaggggag   2160
tcattgatgt attggatttt ctacagagac acagatttat agaagaattc cgtatggaag   2220
gacttaatga ggatatagtc tgtatcatcc ctacaagagg aatgatcccc acaaaaacac    2280 ccctaccct ggatgacaaa attcatcttg ctaacgatca gtcaatagaa aagaagaaa      2340 tcctccaaaa agacaagaca tcaaaaccaa acaaaggaat caaacagcca acaagcaag    2400 aggcacaacc agtctctgaa tctcaaacag gaatgaagga agacaaaaaa gaacaaaagc   2460
caaagcaaaa ccaaattccc attaaaaaca acaggaaaaa tgaagactca aaagaagttg   2520
```

```
ctaagaccaa caaagataaa gaaaataaag tcagcaaagg aagtatgtca aagaatgaca    2580
aactaaaaga aggcaatata actgttccaa aacagggatt tgaaaagaag aaaacaaaac    2640
aaataaatga agaaggccac aaatcatttg attatgctaa tacatatggg acaaaagtca    2700
ctgtgaaaac tataaggtat tgtaagacat gcaatcctaa tactagaaaa aatgctacag    2760
tatatcttga ccatctttat gaacgccaca gtcatgaggt tgctttgatt aahagcttgg    2820
cttaccctct tttattttwt ttwwggttga wttaaattaa ctaattagat actttyttaa    2880
tacatgawaa wwacaacaaa tctaataaat tacattgaaa caaagatgtc tggtgtgatg    2940
agtatattta aaaggaagga caagaaaggg aatgagggtt ccaaagccct agccatacca    3000
gatgaaaaat cagtagtccc atctgcacct ccagacatct cagctatgga ttatgggagg    3060
tttggtttat tagggaggca aactctatta gaagaagatg aggaagaatc tagatgcatc    3120
actattatag atctagaagt cgatctacag atagaggtgt tatctaatag agaaactcga    3180 cttgtaaatag acttgattgc tcctttgtgt aatcttcaaa ctgattacat tggaaaagag    3240
aacacaaaag caatttggat aggattaact gtagtagcag cttttggagt gaaaagaacc    3300
attaagacaa aaaatcatca tgtatataaa gggtgtgtct ccagtggact taggcttttta    3360 atagactcag aaaaacaatt tgagctagat aagaggaata aatgstctca gcatctcagt    3420
tatctcacca atggtgtaaa aacagagtgg gccataagag gggagatgat caggacaaga    3480
gtaccttacc ttcctcagcc aggaagtgag gatgtgctta tgttttttagc agggatggga    3540 ataagttgtt attcaaatcc agatggtcat ttagtcctca aagtttgaaa ataacaaaa    3600 ttctttagag atcatattca gtatttatac cttagtaata ttgtggctca gatttaatga    3660
tgggagtgcc taaagtattt caattttggg ttagaatcag gacatgaaaa aaacaacaaa    3720
tctaattaac tatcatttag tacttagaac gaacttatct tctgttgaat catgatttcg    3780
aatatgtttt tcttgtttca actctcatta tttctacagt ttatagcagg agatgagtca    3840
ttagaaacaa taacagcccc tgaaactcct gaccctatac tcttaaaagg agatacaaaa    3900
tatctgttct tagtcccttc ttctgtcaaa aattggaaac cagctgacct gaatgaatta    3960
acatgccccc ccctaatctc gaaaccagat acttctgaaa tgacttattt ttccacagat    4020
gtgatggagt tacaaaaaca tcatgaattg gcaccagtag aagggtattt atgttcgggt    4080
ttgcgttaca aagtaatatg ttctgaagga tttttttggac aaaaaacaat agcaaaaag    4140 attgagaaca ttgaacctga tagtaaacaa tgccttgatg acttgtcaaa atttaagaat    4200
gatgattacc tactcccata tttcccttct gaagattgta attggatgaa agagactccc    4260
acccataaag attttatagt ttttcaaaaa cattttgtta aatatgaccc atacaataat    4320 ggttttatg atcctttact taaaaaagac tactgtgata ctcaagtctg tgagacagaa    4380
catgatcaaa ctatttggat aacagaaaag agtattgaaa atgaatgcat cttcaattat    4440
ccgattaaaa agcatatatt ccatacagct gactttggga aatgataat agattacgaa    4500 ttaaatcaat ggacttcagt ggaagatggg tgtttaatta actattgtgg aagagaggga    4560
ataaggttat ctaatgggat gttctttgta ggtaagttct ataaaaatct caataattta    4620
cagacctgta gtgctggaac aaaggtcagt tacaagcctt taacctccaa gctggaagaa    4680
attgaaaatg aaatcattct agatcaggaa agattattat gtcttgattc aattaggcaa    4740
atgacagcaa caaaaaaatt atcattttat tctttatcct ttctagaacc aaaatcttct    4800
agtaggcaca aggtctttag aattcataat aaaacactag aatataccga aaccgaatgg    4860
```

```
catccaatca tgtcgtttaa ttttgatgaa ccaaacaaaa ttggaattga caagaatggt    4920
aaatcagttt attggaatga atgggttcct agtggaatat ctgggctgtt atcagggttc    4980
aatggagtct acaaaaaaga aaatgaaact aaagtaacta ttgcccgatt agaaacaata    5040
aaagaagatt atgatagggga gatgatgata gatcacgagt tggtagaggt agaacatcct    5100
```
```
catccaatca tgtcgtttaa ttttgatgaa ccaaacaaaa ttggaattga caagaatggt    4920
aaatcagttt attggaatga atgggttcct agtggaatat ctgggctgtt atcagggttc    4980
aatggagtct acaaaaaaga aaatgaaact aaagtaacta ttgcccgatt agaaacaata    5040
aaagaagatt atgatagggga gatgatgata gatcacgagt tggtagaggt agaacatcct    5100
aaaattgtac acttaaaaag agagaacatc acaggatcta gagtcgaaat tgttaataaa    5160
gaacattctg atgtgagtgg ttggctgtca tcagtattga gtagttttg gggaaaaatc      5220
atgatgacaa taataagtat aatcttaatc gtaataatag gattagtttt aataaactgc    5280
tgcccaatta tatgcaaatc atgtattaaa cgttataaaa caaggaaga atcccgcaat      5340
agacatagat tggatagaga agataacggt agattgagga ggcaacatcg agttattttt    5400
aacaatcaat ccaatgatga agaaaatgcc attgaaatgg tagaatatac tgacactccc    5460
aggccattgc gaccgattcc tgatgccaca acatcagaca ctgagtcaag atcccccaca    5520
acagcccata gttttttcaa ccgttaaaaa ggtaggttat attatacttt tctctatacc    5580
tctaatagtc atcatcgtgt tttttgtgtt attagataga aaacatctca aatatatacc    5640
tttaaaggca tggaacactt caataattac aattaaagaa ccttattaaa attaaaaagt    5700
tttcttaaaa ataattctcc taattgattt taatttcatg aaaaaaacat taahaaatct    5760
aagtatmact saaatttagg gtatgcttgg tgtgttaaaa tggatttctc ttatgaacaa    5820
ttgctggatc ctatagatgt cttagaagaa gaattatatg aatttgattt cgaatatgat    5880
gattacactg atgatgatca gacacccctta cccaatatta agtacaaaaa cctagaaggt    5940
aaagactata atttaaactc acctctcatc agcgatgtga tcgattcagg aagagaatac    6000
ataattaatt ctaaaaagta cttttctcat gaaagaacaa atccggagtt ggaacaattt    6060
agtaaagctc taatggctat tgggttttct agatttgatt tacgaaaatc atcagaacat    6120
cataggtaca tgagttcata tatatatgga aatgagaaaa acatatgaa atcgaaata      6180
atacccagat ggaaagaagt cttagaactg actcgcaatc ctgtagaagt aacctctcat    6240
aagatattgg gatcaaaatc acaatctgat caagaaggat atataaatag attgcgatat    6300
attacagtag atggacctca tgcaagaaaa acaagattac accaagaatg ggaaaaattc    6360
tcaacattac attatataac gtatattatg aattcaaaag cctttagtga caacaaaaat    6420
tgggtgaggaa agtctttga gaccatagaa actagtgaag ttgaccctga ataattaca    6480
ataattggaa caggtttatc aaagaaagaa gtatcctgga ttatatctga aactttgca    6540
ttaaatgtta gaacaggttt atttgtctcc aaagatttct tgctgatgat taaagatgtc    6600
accttagcta gatgtatgag caaactgagt atgattaaca gaaagtctcc caacacaact    6660
tatgatatga taaaattttt ggatagtcta tatgaaagtg gtgacaaaat attgacaaga    6720
catggaaatt tagcttacaa gcatatcaag ttattggagg cagcttgtct agagagatgg    6780
aatcaattag ggcacaaatt tcgaccattg ataccaatct cttcaagcat gagtgatcat    6840
cttagaactc aattagaaga aaatcaagat ctctatatgg tgagtaggga attcttcgat    6900
ttgattggaa agattgaaga tccttgggtc gttgctcaag cgtatggaac attcaggcat    6960
tggggacatc catacattga ttatttaaat ggtctaaaag atctagaaaa aagagtaaat    7020
gaaaatatca aaattgataa aaattatgca gaaaaattgg ctagcgatct tgcgtttata    7080
gttctaaaag accaatttgg aaaacataaa agatggtttg ctaaacctaa taagaattg     7140
gatgaaaata tcccatgcg aaaatgcata gaaaacaatg tgtggcctaa cactaaagtt    7200
attttagact tcggagacaa ttggcataaa ttagaattat taccatgttt tgaaatccct    7260
```

```
gatgcaatag acctttctga cctatatagt gataaagctc attccatgca atacagtgaa    7320
gtattaaatt atgtaaaata caaaaaatcc aaaaagaata tccctgcctt acgtgttatc    7380
gggacattat tagaaaagga aaatccaaat ataaaagaat ttttacaaaa aataaacgat    7440
gaaggtttag atgatgatga tctgataata gggctgaaag caagaaaaga gaactgaaag    7500
ataaaggaag attttttctct cttatgagtt ggaatattag gttatatttt ktgattacag    7560
aatatttaat twwwttwcaw ttttktmcca ttgttttctg gcttaacagt agcggatgac    7620
ttaaatactg dcmsmmamrr attmttaagt gctacagaag acaaggtct agatgactat    7680 gaaagggtct acatagcaaa tagtttagat tatgaaaaat ggaacaacag gcagcgttat    7740
gaatctaatg aaccagtatt cacagtaatg gggaaatttt taggttatcc aaacttaata    7800
tcgtatactc ataagatttt tgaaagatca tttatctatt ataacggaag actagactta    7860
atgggagtag atggttacca tatttataat ttatttgatg ataaaatggt ctgttggcat    7920
ggtcaattgg gaggatttga aggtgtaaga caaaagggct ggagtgtttt aaattactta    7980
attttgcgaa gagaagctgc aacacgaaat actgcaccga aatttttagc ccaaggagac    8040
aatcaaattg tcattactca gtatacattg accagtaaaa gcactcaagc tataattgaa    8100
cgagaattga ggaatatttg ggaaaacaat gctcatataa tgcataggat acaacaagcg    8160
acaagtcgaa ttggattagt cataaataat gatgaagtgt taacttccgc agagttattg    8220
gtttacggta aaataccagt atttcgaggg aaattgttac ctttagaaac aaaaagatgg    8280
tctagagtca gtaccgtgac aaatgaacag ataccatcct tttctaattc attggctagt    8340
agtacaacta ctgctttggc ggttaatcaa cactcagaaa atcctatcga ggttatatct    8400
caacatcatt tctttagttc ttttgctggc acattagtaa catttgttaa tcctatctta    8460
ggttttgatc cgattaaata ttctcaattg tcagagagaa ataagaagtt attcttatta    8520
aggcttattt acaaagatcc aagtgttggg ggagtttgtg gaactaattt attaaggttt    8580
tttatatcaa gatttcctga tcctttgaca gagacattga catggtggaa atatattggtt    8640 gagaattcta aagataaaga ggttgttaaa attgcgctag aatgtggaaa tcctaagttt    8700
ggagggatta atgataagac attagctatg ttactcgaag accctatgtc actaaatata    8760
ccaggaggac tctcaagtga cacgatgata aaaacaaaa tttatgaagg tcttattcat    8820
caaatggggc ttaaattgat caaaaatgaa ttggttgtag aatctctaac cttctataat    8880
gattacaaag cacaatttgt aagatggtta ttctccataa gaccaatttt cccacgattc    8940
attagtgaat tttatacatc tacttatttt tatataacag aaagtgtcct tgccatattt    9000
caaaattcta gaaccattag aaaagttttc tcaaaaagat ttccgaaaga ggtttatctc    9060
acgatagtta aaggagaaca aatgtctata gatagcttat tgacaaccaa aagagggatt    9120
gttagggagg ctatttggaa atgttcagca acgaaagcag atgaaatgag aaaactatca    9180
tggggtagag atatggttgg aataacaaca cctcatccag ctgaattcac acaagaatta    9240
ttatgttcag acgggtgttc agaacctcac attgtagcca aaaaggttat ttactctgat    9300
agaaaattat ggactaaggg taagatgatg ccttaccttg gtactaaaac caaagagtcc    9360
acaagtatac ttcaaccatg ggaaaaaaga ttagagattc cattattgag gaaagcatgt    9420
gatttaagaa aagccattag gtggtttgta gaagataatt caaacttagc aaaatccatt    9480
tataaaaatt tagaaagtat gacaggaatt gatttaagag aagaacttcg aaactataaa    9540
agaactggta gtagcaaaca tagattaaga aactcgagag tctccaatga aggtaatccc    9600
```

```
gccataggtt ataataacct aacgtatgtc acagtaacaa ctgatagttt aggaaatatt   9660
aattccgaaa attatgattt catgtatcaa tctatcttat gctggtgtgg tgtattatcg   9720
tccctagcaa ccaatcgata tcgagaccat gagactactc attttcatct taaatgtaat   9780
gattgcttca gattggttaa agaggaaata ttagaggctc cttcagttta cccatttcct   9840
aatgtaagat cctctgtaag gagaatgctt acacaggata ttaaattaaa atatctgcca   9900
cgaatttctg cccctgatga aaacacctgg gatactctgg atgttgatca aaaaagttgg   9960
catattggga gagctcaagg gttttgtgg ggattaaatg tatttaccaa aaccactaaa  10020
gaggttgagg gtgacatttt cccaacttcc ataacgaaaa aagtcgaacc agaaaattac  10080
atggatggtt tacacagagg gttttgttta ggagctactc tctcccccat gtacacaaga  10140
tatggatcac tcagcaggat ggctagaaga aaattcgaag gagcatactg ggaaatcgta  10200
gatgaagcaa tgaaaactaa tctaccaaat atgattgatc amaaaaattt caaacctttc  10260
ctgagaagga caggaggtga tctaattaaa tcttatcctg cacgaaagga agagttggta  10320
cttgttttaa agaaatggtt cttacataaa atggtctctg aaagaaaaaa caattccata  10380
tgggaaagta aaagagtaat tgcctttgct gacatggaca ctgaatttgt attgtgtctc  10440
ttcagattag cggaaagcat actgaattgt tatcaaaatg aagctttatc tgctggtcag  10500
gctagggtct tagggaatgc aaaagagaca atagatctga tctcaaaata caataactca  10560
aacattaatg cagatgagat tgagcgattg cagcagatat tgatggcttc tgacctgaaa  10620
gatcatgaag ttgtagattc acaagctagg catgctgctt ctgacttacc tgaattggca  10680
aaatcagaaa attacaatga agtgattaaa tatgtagaat ttagaggtta tggtggtaaa  10740
accataagat tagaatatca acctagtgat tgatagact ggaagggagg aatggttcaa  10800
gacctacaag tacctagatt gaagaaccct ttaatttctg gagtcagagt agtgcaatat  10860
agcacaggag ctcattataa atataaagat atagaaagag aatttcaaat tgctggtgat  10920
ggtatattcg ctggtgatgg ttctggtggt atgggtgcaa accatctgag attacataaa  10980
tcagcccgcg ttatatttaa ctctaaatta gagttagaag gagaatcttt aaaagggtta  11040 gccctgcag gacctggagc ttacacggtc tcaggtgaag atgttgtgga agatgtgtc  11100 aattacacaa cttgctggga agaagcttct gatctgagtg acgaaaaaac ttggaagaat  11160
ttttttaggc tcataaaaga gtactcatta gatatagaag tgttttgctg tgatgctgaa  11220
gtccaagacc catatatcac aaacaaaatt gaatctaata tattgaaata catatctttg  11280
atccttaata aaagaactgg aactttaatt tacaaaactt atttcaatag attattggat  11340
cccaatacta taaccccactt tttgggaatg ttttttccata gatgttacgg atttctccct  11400
actactcaag gatcctttac ctctgaaatt tacattgtct gtcaatatcc aaagacactt  11460
gactctacaa gcaaaacaga gttaacctat actagtttat ttaatattta tcagaacata  11520
agagtgatgg aaacttatca aaatgaattt gatagagcat gtagtttatt gtttctgat   11580 atgacggaag gtcttattga taaaacacca tttttagatc ctgaagaatt ggctatttc   11640 ctgacaacag tgggattgga tacggggtgg gctttactaa tagcagaaca attacagata  11700
tcttgctcaa acaaattaca tccaataatc atattatgga ttttaggctt tataatttcc  11760
agacacttag tgagtataac atcttggttt cgtagaggaa caaaattccc tccttctatc  11820
cagttgcaaa aaatgttagc tgctctattt ggaatctggt atggagtctc ttatattatg  11880
aatgatgcag agagttactc aaggattcct gtattgtaca atcaagagat ttatttctca  11940
ttaggcttga ctaatatggt atataggaaa aaagatgaca tggaattggg tcaattttca  12000
```

```
acttggaaga taggacctgg tgataatagt aaactcatag atataggtcc caaagcgggt   12060
ataactcaga caatgataag agctattgta gtcttgtata aaggagaaca tataacttct   12120
attgtgacta aggaagataa agtagaagga gatagaattt taagcttatt tggaaaagga   12180
ttgaatctta aaactttaat ggagcgaaca ggaataaatt atttgcaaat aggggaaaga   12240
aatcctcaag aaattccata tacgttagag gaagaagtat tggaagaagt ggtagaagaa   12300
aatacaggag aatttgatca atcataaaca gataaaggaa atraaaaaaa aaaaaatata   12360
tattgaaata ataaagctta aagaacaaga tcttgaaatt gtgaactact aagtat        12416
```

<210> SEQ ID NO 14
<211> LENGTH: 513
<212> TYPE: PRT
<213> ORGANISM: Bahia Grande N

<400> SEQUENCE: 14

```
Met Ala Ala Ala Ile Leu Pro Val Ser Arg Asn Met Pro Val Arg Glu
1               5                   10                  15

Arg Thr Val Ala Gly Ser Val Thr Ala Pro Pro Val Gln Tyr Pro Ser
                20                  25                  30

Thr Trp Phe Gln Ala His Ala Gly Gln Lys Val Ser Ile Thr Ile Tyr
            35                  40                  45

Gln Asn Thr Asn Ala Arg Gln Ala Phe Ser Arg Ile Thr Gln Leu Arg
    50                  55                  60

Asn Asn Gly Gln Trp Asp Asp Lys Leu Ile Ala Thr Phe Met Lys Gly
65                  70                  75                  80

Val Leu Asp Glu Asn Ala Glu Trp Phe Gln Ser Pro Pro Leu Ile Glu
                85                  90                  95

Asp Trp Ile Val Asn Glu Ala Val Ile Gly Arg Val Asp Asp Val Val
            100                 105                 110

Ala Pro Thr Ala Leu Ala Gln Trp Glu Glu Val Glu Arg Pro Gln Asn
        115                 120                 125

Met Asp Pro Val Pro Asn Glu Glu Gly Glu Leu Gly Thr Arg Arg Ser
    130                 135                 140

Phe Phe Leu Ala Leu Ile Thr Ile Tyr Arg Gln Val Leu Thr Arg Thr
145                 150                 155                 160

Ile Asn Val Asp Tyr Gly Gln Glu Val Ser Arg Arg Ile Ile Asp Asn
                165                 170                 175

Phe Lys Glu Gln Pro Leu Gly Met Ser Gln Asp Asp Ile Asn Glu Ile
            180                 185                 190

Gln Gly Tyr Glu Ser Lys Glu Arg Leu Thr Thr Asn Tyr Val Lys Ile
        195                 200                 205

Leu Cys Ile Leu Asp Met Phe Phe Asn Lys Phe Gln Thr His Asp Lys
    210                 215                 220

Ser Thr Ile Arg Ile Ala Thr Leu Pro Thr Arg Tyr Arg Gly Cys Ala
225                 230                 235                 240

Ala Phe Thr Ser Tyr Gly Glu Leu Ala Ile Arg Leu Gly Ile Glu Pro
                245                 250                 255

Ile Lys Leu Pro Ser Leu Ile Leu Thr Val Ala Val Ala Lys Asp Phe
            260                 265                 270

Asp Lys Ile Asn Val Asn Gly Glu Gln Ala Glu Gln Leu Asp Gly Tyr
        275                 280                 285

Phe Pro Tyr Gln Leu Glu Leu Gly Leu Val Lys Lys Ser Ala Tyr Ser
    290                 295                 300
```

```
Ala Gly Asn Cys Pro Ser Leu Tyr Leu Trp Met His Thr Ile Gly Thr
305                 310                 315                 320

Met Leu His Gln Gln Arg Ser Tyr Arg Ala Asn Val Pro Lys Asn Val
            325                 330                 335

Pro Asp Gln Met Gly Thr Ile Asn Ser Ala Ile Ala Val Ala Met Gln
            340                 345                 350

Phe Val Ala Gly Gly Glu Phe Ser Met Gln Phe Val Gly Asp Ala Arg
            355                 360                 365

Val Gln Glu Ala Met Arg Glu Met Gln Thr Ala Glu Ala Glu Leu Asn
370                 375                 380

Glu Leu Arg Met Ala Gln Ala Arg Glu Met Arg Ala Ala Ala Arg Gly
385                 390                 395                 400

Asp Glu Asp Glu Glu Gly Ser Glu Asp Gly Leu Asp Asp Glu Asn Asp
            405                 410                 415

Gly Glu Gly Asp Asp Glu Leu Pro Ala Glu Ile Glu Gln Asn Pro Glu
            420                 425                 430

Tyr Leu Asn Arg Val Asn Arg Ile Arg Glu Leu Gln Glu Asn Leu Gln
            435                 440                 445

Gln Tyr Asn Ala Thr Val Gln Gln His Thr Asn Ala Val Glu Lys Ala
            450                 455                 460

Ala Leu Arg Ala Leu Ala Tyr Leu Gln Glu Asn Gly Gly Ile Ala Asp
465                 470                 475                 480

Lys Asp Lys Arg Asp Leu Gly Ile Arg Phe Arg Arg Phe Ala Asp Glu
            485                 490                 495

Ala Glu Gly Arg Val Gly Lys Leu Leu Ala Ser Leu Phe Pro Ala Pro
            500                 505                 510

Arg

<210> SEQ ID NO 15
<211> LENGTH: 353
<212> TYPE: PRT
<213> ORGANISM: Bahia Grande P

<400> SEQUENCE: 15

Met Ala Tyr Ser Thr Gly Leu Ile Lys Gly Glu Val Ser Gln Gly Leu
1               5                   10                  15

Ser Asn Ala Phe Lys Asp Ala Gly Ile His Gln Ile Glu Leu Asn Lys
            20                  25                  30

Glu Tyr Asp Asn Leu Ser Ile Leu Gly Ala Asn Met Ser Ala Leu Asn
            35                  40                  45

Lys Met Phe Asp Thr Glu Asp Glu Gly Leu Ser Asp Thr Asn Thr Asn
50                  55                  60

Ser Ser Lys Asn Ser Ile Leu Gln Ala Ser Asp Met Phe Ile Gly Asn
65                  70                  75                  80

Asp Glu Tyr Glu Ser Asp Ser His His Phe Leu Ser Ser Pro Ser
            85                  90                  95

Pro Asp Lys Gly Ser Ser Glu Glu Gly Ser Asn Leu Gln Glu Phe Asn
            100                 105                 110

Phe Gln Ile Pro Arg Asn Lys Val Gly Lys Glu Lys Ala Tyr Arg Arg
            115                 120                 125

Gly Val Ile Asp Val Leu Asp Phe Leu Gln Arg His Arg Phe Ile Glu
            130                 135                 140

Glu Phe Arg Met Glu Gly Leu Asn Glu Asp Ile Val Cys Ile Ile Pro
145                 150                 155                 160
```

```
Thr Arg Gly Met Ile Pro Thr Lys Thr Pro Thr Leu Asp Asp Lys
                165                 170                 175

Ile His Leu Ala Asn Asp Gln Ser Ile Glu Lys Glu Ile Leu Gln
            180                 185                 190

Lys Asp Lys Thr Ser Lys Pro Asn Lys Gly Ile Lys Gln Pro Asn Lys
        195                 200                 205

Gln Glu Ala Gln Pro Val Ser Glu Ser Gln Thr Gly Met Lys Glu Asp
    210                 215                 220

Lys Lys Glu Gln Lys Pro Lys Gln Asn Gln Ile Pro Ile Lys Asn Lys
225                 230                 235                 240

Gln Glu Asn Glu Asp Ser Lys Glu Val Ala Lys Thr Asn Lys Asp Lys
                245                 250                 255

Glu Asn Lys Val Ser Lys Gly Ser Met Ser Lys Asn Asp Lys Leu Lys
            260                 265                 270

Glu Gly Asn Ile Thr Val Pro Lys Gln Gly Phe Glu Lys Lys Thr
        275                 280                 285

Lys Gln Ile Asn Glu Glu Gly His Lys Ser Phe Asp Tyr Ala Asn Thr
    290                 295                 300

Tyr Gly Thr Lys Val Thr Val Lys Thr Ile Arg Tyr Cys Lys Thr Cys
305                 310                 315                 320

Asn Pro Asn Thr Arg Lys Asn Ala Thr Val Tyr Leu Asp His Leu Tyr
                325                 330                 335

Glu Arg His Ser His Glu Val Ala Leu Ile Lys Ser Leu Ala Tyr Pro
            340                 345                 350

Leu

<210> SEQ ID NO 16
<211> LENGTH: 220
<212> TYPE: PRT
<213> ORGANISM: Bahia Grande M
<220> FEATURE:
<221> NAME/KEY: misc_feature
<222> LOCATION: (160)..(160)
<223> OTHER INFORMATION: Xaa can be any naturally occurring amino acid

<400> SEQUENCE: 16

Met Ser Gly Val Met Ser Ile Phe Lys Arg Lys Asp Lys Lys Gly Asn
1               5                   10                  15

Glu Gly Ser Lys Ala Leu Ala Ile Pro Asp Glu Lys Ser Val Val Pro
            20                  25                  30

Ser Ala Pro Pro Asp Ile Ser Ala Met Asp Tyr Gly Arg Phe Gly Leu
        35                  40                  45

Leu Gly Arg Gln Thr Leu Leu Glu Glu Asp Glu Glu Ser Arg Cys
    50                  55                  60

Ile Thr Ile Ile Asp Leu Glu Val Asp Leu Gln Ile Glu Val Leu Ser
65                  70                  75                  80

Asn Arg Glu Thr Arg Leu Val Ile Asp Leu Ile Ala Pro Leu Cys Asn
                85                  90                  95

Leu Gln Thr Asp Tyr Ile Gly Lys Glu Asn Thr Lys Ala Ile Trp Ile
            100                 105                 110

Gly Leu Thr Val Val Ala Ala Phe Gly Val Lys Arg Thr Ile Lys Thr
        115                 120                 125

Lys Asn His His Val Tyr Lys Gly Cys Val Ser Ser Gly Leu Arg Leu
    130                 135                 140

Leu Ile Asp Ser Glu Lys Gln Phe Glu Leu Asp Lys Arg Asn Lys Xaa
```

```
                145                 150                 155                 160
Ser Gln His Leu Ser Tyr Leu Thr Asn Gly Val Lys Thr Glu Trp Ala
                165                 170                 175

Ile Arg Gly Glu Met Ile Arg Thr Arg Val Pro Tyr Leu Pro Gln Pro
                180                 185                 190

Gly Ser Glu Asp Val Leu Met Phe Leu Ala Gly Met Gly Ile Ser Cys
                195                 200                 205

Tyr Ser Asn Pro Asp Gly His Leu Val Leu Lys Val
                210                 215                 220

<210> SEQ ID NO 17
<211> LENGTH: 591
<212> TYPE: PRT
<213> ORGANISM: Bahia Grande G

<400> SEQUENCE: 17

Met Ile Ser Asn Met Phe Phe Leu Phe Gln Leu Ser Leu Phe Leu Gln
1               5                   10                  15

Phe Ile Ala Gly Asp Glu Ser Leu Glu Thr Ile Thr Ala Pro Glu Thr
                20                  25                  30

Pro Asp Pro Ile Leu Leu Lys Gly Asp Thr Lys Tyr Leu Phe Leu Val
                35                  40                  45

Pro Ser Ser Val Lys Asn Trp Lys Pro Ala Asp Leu Asn Glu Leu Thr
            50                  55                  60

Cys Pro Pro Leu Ile Ser Lys Pro Asp Thr Ser Glu Met Thr Tyr Phe
65              70                  75                  80

Ser Thr Asp Val Met Glu Leu Gln Lys His His Glu Leu Ala Pro Val
                85                  90                  95

Glu Gly Tyr Leu Cys Ser Gly Leu Arg Tyr Lys Val Ile Cys Ser Glu
                100                 105                 110

Gly Phe Phe Gly Gln Lys Thr Ile Ala Lys Lys Ile Glu Asn Ile Glu
                115                 120                 125

Pro Asp Ser Lys Gln Cys Leu Asp Asp Leu Ser Lys Phe Lys Asn Asp
            130                 135                 140

Asp Tyr Leu Leu Pro Tyr Phe Pro Ser Glu Asp Cys Asn Trp Met Lys
145             150                 155                 160

Glu Thr Pro Thr His Lys Asp Phe Ile Val Phe Gln Lys His Phe Val
                165                 170                 175

Lys Tyr Asp Pro Tyr Asn Asn Gly Phe Tyr Asp Pro Leu Leu Lys Lys
                180                 185                 190

Asp Tyr Cys Asp Thr Gln Val Cys Glu Thr Glu His Asp Gln Thr Ile
                195                 200                 205

Trp Ile Thr Glu Lys Ser Ile Glu Asn Glu Cys Ile Phe Asn Tyr Pro
            210                 215                 220

Ile Lys Lys His Ile Phe His Thr Ala Asp Phe Gly Lys Met Ile Ile
225             230                 235                 240

Asp Tyr Glu Leu Asn Gln Trp Thr Ser Val Glu Asp Gly Cys Leu Ile
                245                 250                 255

Asn Tyr Cys Gly Arg Glu Gly Ile Arg Leu Ser Asn Gly Met Phe Phe
                260                 265                 270

Val Gly Lys Phe Tyr Lys Asn Leu Asn Asn Leu Gln Thr Cys Ser Ala
            275                 280                 285

Gly Thr Lys Val Ser Tyr Lys Pro Leu Thr Ser Lys Leu Glu Glu Ile
            290                 295                 300
```

```
Glu Asn Glu Ile Ile Leu Asp Gln Glu Arg Leu Leu Cys Leu Asp Ser
305                 310                 315                 320

Ile Arg Gln Met Thr Ala Thr Lys Lys Leu Ser Phe Tyr Ser Leu Ser
                325                 330                 335

Phe Leu Glu Pro Lys Ser Ser Ser Arg His Lys Val Phe Arg Ile His
            340                 345                 350

Asn Lys Thr Leu Glu Tyr Thr Glu Thr Glu Trp His Pro Ile Met Ser
        355                 360                 365

Phe Asn Phe Asp Glu Pro Asn Lys Ile Gly Ile Asp Lys Asn Gly Lys
370                 375                 380

Ser Val Tyr Trp Asn Glu Trp Val Pro Ser Gly Ile Ser Gly Leu Leu
385                 390                 395                 400

Ser Gly Phe Asn Gly Val Tyr Lys Lys Glu Asn Glu Thr Lys Val Thr
                405                 410                 415

Ile Ala Arg Leu Glu Thr Ile Lys Glu Asp Tyr Asp Arg Glu Met Met
            420                 425                 430

Ile Asp His Glu Leu Val Glu Val Glu His Pro Lys Ile Val His Leu
        435                 440                 445

Lys Arg Glu Asn Ile Thr Gly Ser Arg Val Glu Ile Val Asn Lys Glu
450                 455                 460

His Ser Asp Val Ser Gly Trp Leu Ser Ser Val Leu Ser Ser Phe Trp
465                 470                 475                 480

Gly Lys Ile Met Met Thr Ile Ile Ser Ile Ile Leu Ile Val Ile Ile
                485                 490                 495

Gly Leu Val Leu Ile Asn Cys Cys Pro Ile Ile Cys Lys Ser Cys Ile
            500                 505                 510

Lys Arg Tyr Lys Thr Lys Glu Glu Ser Arg Asn Arg His Arg Leu Asp
        515                 520                 525

Arg Glu Asp Asn Gly Arg Leu Arg Arg Gln His Arg Val Ile Phe Asn
530                 535                 540

Asn Gln Ser Asn Asp Glu Glu Asn Ala Ile Glu Met Val Glu Tyr Thr
545                 550                 555                 560

Asp Thr Pro Arg Pro Leu Arg Pro Ile Pro Asp Ala Thr Thr Ser Asp
                565                 570                 575

Thr Glu Ser Arg Ser Pro Thr Thr Ala His Ser Phe Phe Asn Arg
            580                 585                 590

<210> SEQ ID NO 18
<211> LENGTH: 2175
<212> TYPE: PRT
<213> ORGANISM: Bahia Grande L

<400> SEQUENCE: 18

Met Asp Phe Ser Tyr Glu Gln Leu Leu Asp Pro Ile Asp Val Leu Glu
1               5                   10                  15

Glu Glu Leu Tyr Glu Phe Asp Phe Glu Tyr Asp Asp Tyr Thr Asp Asp
                20                  25                  30

Asp Gln Thr Pro Leu Pro Asn Ile Lys Tyr Lys Asn Leu Glu Gly Lys
            35                  40                  45

Asp Tyr Asn Leu Asn Ser Pro Leu Ile Ser Asp Val Ile Asp Ser Gly
        50                  55                  60

Arg Glu Tyr Ile Ile Asn Ser Lys Lys Tyr Phe Ser His Glu Arg Thr
65                  70                  75                  80

Asn Pro Glu Leu Glu Gln Phe Ser Lys Ala Leu Met Ala Ile Gly Phe
                85                  90                  95
```

-continued

```
Ser Arg Phe Asp Leu Arg Lys Ser Ser Glu His His Arg Tyr Met Ser
            100                 105                 110
Ser Tyr Ile Tyr Gly Asn Glu Lys Lys His Met Lys Ile Glu Ile Ile
        115                 120                 125
Pro Arg Trp Lys Glu Val Leu Glu Leu Thr Arg Asn Pro Val Glu Val
130                 135                 140
Thr Ser His Lys Ile Leu Gly Ser Lys Ser Gln Ser Asp Gln Glu Gly
145                 150                 155                 160
Tyr Ile Asn Arg Leu Arg Tyr Ile Thr Val Asp Gly Pro His Ala Arg
                165                 170                 175
Lys Thr Arg Leu His Gln Glu Trp Glu Lys Phe Ser Thr Leu His Tyr
            180                 185                 190
Ile Thr Tyr Ile Met Asn Ser Lys Ala Phe Ser Asp Asn Lys Asn Trp
        195                 200                 205
Val Arg Glu Val Phe Glu Thr Ile Glu Thr Ser Glu Val Asp Pro Glu
210                 215                 220
Ile Ile Thr Ile Ile Gly Thr Gly Leu Ser Lys Lys Glu Val Ser Trp
225                 230                 235                 240
Ile Ile Ser Glu Asn Phe Ala Leu Asn Val Arg Thr Gly Leu Phe Val
                245                 250                 255
Ser Lys Asp Phe Leu Leu Met Ile Lys Asp Val Thr Leu Ala Arg Cys
            260                 265                 270
Met Ser Lys Leu Ser Met Ile Asn Arg Lys Ser Pro Asn Thr Thr Tyr
        275                 280                 285
Asp Met Ile Lys Phe Leu Asp Ser Leu Tyr Glu Ser Gly Asp Lys Ile
290                 295                 300
Leu Thr Arg His Gly Asn Leu Ala Tyr Lys His Ile Lys Leu Leu Glu
305                 310                 315                 320
Ala Ala Cys Leu Glu Arg Trp Asn Gln Leu Gly His Lys Phe Arg Pro
                325                 330                 335
Leu Ile Pro Ile Ser Ser Ser Met Ser Asp His Leu Arg Thr Gln Leu
            340                 345                 350
Glu Glu Asn Gln Asp Leu Tyr Met Val Ser Arg Glu Phe Phe Asp Leu
        355                 360                 365
Ile Gly Lys Ile Glu Asp Pro Trp Val Ala Gln Ala Tyr Gly Thr
370                 375                 380
Phe Arg His Trp Gly His Pro Tyr Ile Asp Tyr Leu Asn Gly Leu Lys
385                 390                 395                 400
Asp Leu Glu Lys Arg Val Asn Glu Asn Ile Lys Ile Asp Lys Asn Tyr
                405                 410                 415
Ala Glu Lys Leu Ala Ser Asp Leu Ala Phe Ile Val Leu Lys Asp Gln
            420                 425                 430
Phe Gly Lys His Lys Arg Trp Phe Ala Lys Pro Asn Lys Glu Leu Asp
        435                 440                 445
Glu Asn Asn Pro Met Arg Lys Cys Ile Glu Asn Asn Val Trp Pro Asn
450                 455                 460
Thr Lys Val Ile Leu Asp Phe Gly Asp Asn Trp His Lys Leu Glu Leu
465                 470                 475                 480
Leu Pro Cys Phe Glu Ile Pro Asp Ala Ile Asp Leu Ser Asp Leu Tyr
                485                 490                 495
Ser Asp Lys Ala His Ser Met Gln Tyr Ser Glu Val Leu Asn Tyr Val
            500                 505                 510
```

```
Lys Tyr Lys Lys Ser Lys Lys Asn Ile Pro Ala Leu Arg Val Ile Gly
        515                 520                 525

Thr Leu Leu Glu Lys Glu Asn Pro Asn Ile Lys Glu Phe Leu Gln Lys
    530                 535                 540

Ile Asn Asp Glu Gly Leu Asp Asp Asp Leu Ile Ile Gly Leu Lys
545                 550                 555                 560

Ala Lys Glu Arg Glu Leu Lys Asp Lys Gly Arg Phe Phe Ser Leu Met
                565                 570                 575

Ser Trp Asn Ile Arg Leu Tyr Phe Val Ile Thr Glu Tyr Leu Ile Lys
                580                 585                 590

Leu His Phe Val Pro Leu Phe Ser Gly Leu Thr Val Ala Asp Asp Leu
            595                 600                 605

Asn Thr Val Thr Lys Lys Leu Leu Ser Ala Thr Glu Gly Gln Gly Leu
            610                 615                 620

Asp Asp Tyr Glu Arg Val Tyr Ile Ala Asn Ser Leu Asp Tyr Glu Lys
625                 630                 635                 640

Trp Asn Asn Arg Gln Arg Tyr Glu Ser Asn Glu Pro Val Phe Thr Val
                645                 650                 655

Met Gly Lys Phe Leu Gly Tyr Pro Asn Leu Ile Ser Tyr Thr His Lys
            660                 665                 670

Ile Phe Glu Arg Ser Phe Ile Tyr Tyr Asn Gly Arg Leu Asp Leu Met
            675                 680                 685

Gly Val Asp Gly Tyr His Ile Tyr Asn Leu Phe Asp Asp Lys Met Val
            690                 695                 700

Cys Trp His Gly Gln Leu Gly Gly Phe Glu Gly Val Arg Gln Lys Gly
705                 710                 715                 720

Trp Ser Val Leu Asn Tyr Leu Ile Leu Arg Arg Glu Ala Ala Thr Arg
                725                 730                 735

Asn Thr Ala Pro Lys Phe Leu Ala Gln Gly Asp Asn Gln Ile Val Ile
            740                 745                 750

Thr Gln Tyr Thr Leu Thr Ser Lys Ser Thr Gln Ala Ile Ile Glu Arg
            755                 760                 765

Glu Leu Arg Asn Ile Trp Glu Asn Asn Ala His Ile Met His Arg Ile
    770                 775                 780

Gln Gln Ala Thr Ser Arg Ile Gly Leu Val Ile Asn Asn Asp Glu Val
785                 790                 795                 800

Leu Thr Ser Ala Glu Leu Leu Val Tyr Gly Lys Ile Pro Val Phe Arg
                805                 810                 815

Gly Lys Leu Leu Pro Leu Glu Thr Lys Arg Trp Ser Arg Val Ser Thr
            820                 825                 830

Val Thr Asn Glu Gln Ile Pro Ser Phe Ser Asn Ser Leu Ala Ser Ser
            835                 840                 845

Thr Thr Thr Ala Leu Ala Val Asn Gln His Ser Glu Asn Pro Ile Glu
    850                 855                 860

Val Ile Ser Gln His His Phe Ser Ser Phe Ala Gly Thr Leu Val
865                 870                 875                 880

Thr Phe Val Asn Pro Ile Leu Gly Phe Asp Pro Ile Lys Tyr Ser Gln
                885                 890                 895

Leu Ser Glu Arg Asn Lys Lys Leu Phe Leu Leu Arg Leu Ile Tyr Lys
                900                 905                 910

Asp Pro Ser Val Gly Gly Val Cys Gly Thr Asn Leu Leu Arg Phe Phe
            915                 920                 925

Ile Ser Arg Phe Pro Asp Pro Leu Thr Glu Thr Leu Thr Trp Trp Lys
```

```
                  930                 935                 940
Ile Leu Val Glu Asn Ser Lys Asp Lys Glu Val Val Lys Ile Ala Leu
945                 950                 955                 960

Glu Cys Gly Asn Pro Lys Phe Gly Gly Ile Asn Asp Lys Thr Leu Ala
                965                 970                 975

Met Leu Leu Glu Asp Pro Met Ser Leu Asn Ile Pro Gly Gly Leu Ser
            980                 985                 990

Ser Asp Thr Met Ile Lys Asn Lys Ile Tyr Glu Gly Leu Ile His Gln
        995                1000                1005

Met Gly Leu Lys Leu Ile Lys Asn Glu Leu Val Val Glu Ser Leu
    1010                1015                1020

Thr Phe Tyr Asn Asp Tyr Lys Ala Gln Phe Val Arg Trp Leu Phe
    1025                1030                1035

Ser Ile Arg Pro Ile Phe Pro Arg Phe Ile Ser Glu Phe Tyr Thr
    1040                1045                1050

Ser Thr Tyr Phe Tyr Ile Thr Glu Ser Val Leu Ala Ile Phe Gln
    1055                1060                1065

Asn Ser Arg Thr Ile Arg Lys Val Phe Ser Lys Arg Phe Pro Lys
    1070                1075                1080

Glu Val Tyr Leu Thr Ile Val Lys Gly Glu Gln Met Ser Ile Asp
    1085                1090                1095

Ser Leu Leu Thr Thr Lys Arg Gly Ile Val Arg Glu Ala Ile Trp
    1100                1105                1110

Lys Cys Ser Ala Thr Lys Ala Asp Glu Met Arg Lys Leu Ser Trp
    1115                1120                1125

Gly Arg Asp Met Val Gly Ile Thr Thr Pro His Pro Ala Glu Phe
    1130                1135                1140

Thr Gln Glu Leu Leu Cys Ser Asp Gly Cys Ser Glu Pro His Ile
    1145                1150                1155

Val Ala Lys Lys Val Ile Tyr Ser Asp Arg Lys Leu Trp Thr Lys
    1160                1165                1170

Gly Lys Met Met Pro Tyr Leu Gly Thr Lys Thr Lys Glu Ser Thr
    1175                1180                1185

Ser Ile Leu Gln Pro Trp Glu Lys Arg Leu Glu Ile Pro Leu Leu
    1190                1195                1200

Arg Lys Ala Cys Asp Leu Arg Lys Ala Ile Arg Trp Phe Val Glu
    1205                1210                1215

Asp Asn Ser Asn Leu Ala Lys Ser Ile Tyr Lys Asn Leu Glu Ser
    1220                1225                1230

Met Thr Gly Ile Asp Leu Arg Glu Glu Leu Arg Asn Tyr Lys Arg
    1235                1240                1245

Thr Gly Ser Ser Lys His Arg Leu Arg Asn Ser Arg Val Ser Asn
    1250                1255                1260

Glu Gly Asn Pro Ala Ile Gly Tyr Asn Asn Leu Thr Tyr Val Thr
    1265                1270                1275

Val Thr Thr Asp Ser Leu Gly Asn Ile Asn Ser Glu Asn Tyr Asp
    1280                1285                1290

Phe Met Tyr Gln Ser Ile Leu Cys Trp Cys Gly Val Leu Ser Ser
    1295                1300                1305

Leu Ala Thr Asn Arg Tyr Arg Asp His Glu Thr Thr His Phe His
    1310                1315                1320

Leu Lys Cys Asn Asp Cys Phe Arg Leu Val Lys Glu Glu Ile Leu
    1325                1330                1335
```

```
Glu Ala Pro Ser Val Tyr Pro Phe Pro Asn Val Arg Ser Ser Val
1340                1345                1350

Arg Arg Met Leu Thr Gln Asp Ile Lys Leu Lys Tyr Leu Pro Arg
1355                1360                1365

Ile Ser Ala Pro Asp Glu Asn Thr Trp Asp Thr Leu Asp Val Asp
1370                1375                1380

Gln Lys Ser Trp His Ile Gly Arg Ala Gln Gly Phe Leu Trp Gly
1385                1390                1395

Leu Asn Val Phe Thr Lys Thr Thr Lys Glu Val Glu Gly Asp Ile
1400                1405                1410

Phe Pro Thr Ser Ile Thr Lys Lys Val Glu Pro Glu Asn Tyr Met
1415                1420                1425

Asp Gly Leu His Arg Gly Phe Cys Leu Gly Ala Thr Leu Ser Pro
1430                1435                1440

Met Tyr Thr Arg Tyr Gly Ser Leu Ser Arg Met Ala Arg Arg Lys
1445                1450                1455

Phe Glu Gly Ala Tyr Trp Glu Ile Val Asp Glu Ala Met Lys Thr
1460                1465                1470

Asn Leu Pro Asn Met Ile Asp His Lys Asn Phe Lys Pro Phe Leu
1475                1480                1485

Arg Arg Thr Gly Gly Asp Leu Ile Lys Ser Tyr Pro Ala Arg Lys
1490                1495                1500

Glu Glu Leu Val Leu Val Leu Lys Lys Trp Phe Leu His Lys Met
1505                1510                1515

Val Ser Glu Arg Lys Asn Asn Ser Ile Trp Glu Ser Lys Arg Val
1520                1525                1530

Ile Ala Phe Ala Asp Met Asp Thr Glu Phe Val Leu Cys Leu Phe
1535                1540                1545

Arg Leu Ala Glu Ser Ile Leu Asn Cys Tyr Gln Asn Glu Ala Leu
1550                1555                1560

Ser Ala Gly Gln Ala Arg Val Leu Gly Asn Ala Lys Glu Thr Ile
1565                1570                1575

Asp Leu Ile Ser Lys Tyr Asn Asn Ser Asn Ile Asn Ala Asp Glu
1580                1585                1590

Ile Glu Arg Leu Gln Gln Ile Leu Met Ala Ser Asp Leu Lys Asp
1595                1600                1605

His Glu Val Val Asp Ser Gln Ala Arg His Ala Ala Ser Asp Leu
1610                1615                1620

Pro Glu Leu Ala Lys Ser Glu Asn Tyr Asn Glu Val Ile Lys Tyr
1625                1630                1635

Val Glu Phe Arg Gly Tyr Gly Gly Lys Thr Ile Arg Leu Glu Tyr
1640                1645                1650

Gln Pro Ser Asp Leu Ile Asp Trp Lys Gly Gly Met Val Gln Asp
1655                1660                1665

Leu Gln Val Pro Arg Leu Lys Asn Pro Leu Ile Ser Gly Val Arg
1670                1675                1680

Val Val Gln Tyr Ser Thr Gly Ala His Tyr Lys Tyr Lys Asp Ile
1685                1690                1695

Glu Arg Glu Phe Gln Ile Ala Gly Asp Gly Ile Phe Ala Gly Asp
1700                1705                1710

Gly Ser Gly Gly Met Gly Ala Asn His Leu Arg Leu His Lys Ser
1715                1720                1725
```

```
Ala Arg Val Ile Phe Asn Ser Lys Leu Glu Leu Glu Gly Glu Ser
    1730                1735                1740

Leu Lys Gly Leu Ala Pro Ala Gly Pro Gly Ala Tyr Thr Val Ser
    1745                1750                1755

Gly Glu Asp Val Val Glu Arg Cys Val Asn Tyr Thr Thr Cys Trp
    1760                1765                1770

Glu Glu Ala Ser Asp Leu Ser Asp Glu Lys Thr Trp Lys Asn Phe
    1775                1780                1785

Phe Arg Leu Ile Lys Glu Tyr Ser Leu Asp Ile Glu Val Phe Cys
    1790                1795                1800

Cys Asp Ala Glu Val Gln Asp Pro Tyr Ile Thr Asn Lys Ile Glu
    1805                1810                1815

Ser Asn Ile Leu Lys Tyr Ile Ser Leu Ile Leu Asn Lys Arg Thr
    1820                1825                1830

Gly Thr Leu Ile Tyr Lys Thr Tyr Phe Asn Arg Leu Leu Asp Pro
    1835                1840                1845

Asn Thr Ile Thr His Phe Leu Gly Met Phe Phe His Arg Cys Tyr
    1850                1855                1860

Gly Phe Leu Pro Thr Thr Gln Gly Ser Phe Thr Ser Glu Ile Tyr
    1865                1870                1875

Ile Val Cys Gln Tyr Pro Lys Thr Leu Asp Ser Thr Ser Lys Thr
    1880                1885                1890

Glu Leu Thr Tyr Thr Ser Leu Phe Asn Ile Tyr Gln Asn Ile Arg
    1895                1900                1905

Val Met Glu Thr Tyr Gln Asn Glu Phe Asp Arg Ala Cys Ser Leu
    1910                1915                1920

Leu Phe Ser Asp Met Thr Glu Gly Leu Ile Asp Lys Thr Pro Phe
    1925                1930                1935

Leu Asp Pro Glu Glu Leu Ala Ile Phe Leu Thr Thr Val Gly Leu
    1940                1945                1950

Asp Thr Gly Trp Ala Leu Leu Ile Ala Glu Gln Leu Gln Ile Ser
    1955                1960                1965

Cys Ser Asn Lys Leu His Pro Ile Ile Ile Leu Trp Ile Leu Gly
    1970                1975                1980

Phe Ile Ile Ser Arg His Leu Val Ser Ile Thr Ser Trp Phe Arg
    1985                1990                1995

Arg Gly Thr Lys Phe Pro Pro Ser Ile Gln Leu Gln Lys Met Leu
    2000                2005                2010

Ala Ala Leu Phe Gly Ile Trp Tyr Gly Val Ser Tyr Ile Met Asn
    2015                2020                2025

Asp Ala Glu Ser Tyr Ser Arg Ile Ser Val Leu Tyr Asn Gln Glu
    2030                2035                2040

Ile Tyr Phe Ser Leu Gly Leu Thr Asn Met Val Tyr Arg Lys Lys
    2045                2050                2055

Asp Asp Met Glu Leu Gly Gln Phe Ser Thr Trp Lys Ile Gly Pro
    2060                2065                2070

Gly Asp Asn Ser Lys Leu Ile Asp Ile Gly Pro Lys Ala Gly Ile
    2075                2080                2085

Thr Gln Thr Met Ile Arg Ala Ile Val Val Leu Tyr Lys Gly Glu
    2090                2095                2100

His Ile Thr Ser Ile Val Thr Lys Glu Asp Lys Val Glu Gly Asp
    2105                2110                2115

Arg Ile Leu Ser Leu Phe Gly Lys Gly Leu Asn Leu Lys Thr Leu
```

```
                2120            2125            2130

Met Glu Arg Thr Gly Ile Asn Tyr Leu Gln Ile Gly Glu Arg Asn
        2135            2140            2145

Pro Gln Glu Ile Pro Tyr Thr Leu Glu Glu Val Leu Glu Glu
    2150            2155            2160

Val Val Glu Glu Asn Thr Gly Glu Phe Asp Gln Ser
    2165            2170            2175

<210> SEQ ID NO 19
<211> LENGTH: 519
<212> TYPE: PRT
<213> ORGANISM: Chimeric Isf-VSV G

<400> SEQUENCE: 19

Met Thr Ser Val Leu Phe Met Val Gly Val Leu Gly Ala Phe Gly
1               5                   10                  15

Ser Thr His Cys Ser Ile Gln Ile Val Phe Pro Ser Glu Thr Lys Leu
                20                  25                  30

Val Trp Lys Pro Val Leu Lys Gly Thr Arg Tyr Cys Pro Gln Ser Ala
            35                  40                  45

Glu Leu Asn Leu Glu Pro Asp Leu Lys Thr Met Ala Phe Asp Ser Lys
    50                  55                  60

Val Pro Ile Gly Ile Thr Pro Ser Asn Ser Asp Gly Tyr Leu Cys His
65                  70                  75                  80

Ala Ala Lys Trp Val Thr Thr Cys Asp Phe Arg Trp Tyr Gly Pro Lys
                85                  90                  95

Tyr Ile Thr His Ser Val His Ser Leu Arg Pro Thr Val Ser Asp Cys
                100                 105                 110

Lys Ala Ala Val Glu Ala Tyr Asn Ala Gly Thr Leu Met Tyr Pro Gly
            115                 120                 125

Phe Pro Pro Glu Ser Cys Gly Tyr Ala Ser Ile Thr Asp Ser Glu Phe
    130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
                165                 170                 175

Phe Cys Glu Thr Val His Asn Ala Thr Met Trp Ile Pro Lys Asp Leu
                180                 185                 190

Lys Thr His Asp Val Cys Ser Gln Asp Phe Gln Thr Ile Arg Val Ser
            195                 200                 205

Val Met Tyr Pro Gln Thr Lys Pro Thr Lys Gly Ala Asp Leu Thr Leu
    210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
                260                 265                 270

Phe Pro Asp Cys Leu Val Gly Ser Val Val Lys Ser Thr Leu Leu Ser
            275                 280                 285

Glu Gly Val Gln Thr Ala Leu Trp Glu Thr Arg Leu Leu Asp Tyr
    290                 295                 300

Ser Leu Cys Gln Asn Thr Trp Glu Lys Ile Asp Arg Lys Glu Pro Leu
305                 310                 315                 320
```

```
Ser Ala Val Asp Leu Ser Tyr Leu Ala Pro Arg Ser Pro Gly Lys Gly
                325                 330                 335

Met Ala Tyr Ile Val Ala Asn Gly Ser Leu Met Ser Ala Pro Ala Arg
            340                 345                 350

Tyr Ile Arg Val Trp Ile Asp Ser Pro Ile Leu Lys Glu Ile Lys Gly
        355                 360                 365

Lys Lys Glu Ser Ala Ser Gly Ile Asp Thr Val Leu Trp Glu Gln Trp
    370                 375                 380

Leu Pro Phe Asn Gly Met Glu Leu Gly Pro Asn Gly Leu Ile Lys Thr
385                 390                 395                 400

Lys Ser Gly Tyr Lys Phe Pro Leu Tyr Leu Leu Gly Met Gly Ile Val
                405                 410                 415

Asp Gln Asp Leu Gln Glu Leu Ser Ser Val Asn Pro Val Asp His Pro
            420                 425                 430

His Val Pro Ile Ala Gln Ala Phe Val Ser Glu Gly Glu Glu Val Phe
        435                 440                 445

Phe Gly Asp Thr Gly Val Ser Lys Asn Pro Ile Glu Leu Ile Ser Gly
    450                 455                 460

Trp Phe Ser Ser Trp Lys Ser Ser Ile Ala Ser Phe Phe Phe Thr Ile
465                 470                 475                 480

Gly Leu Ile Ile Gly Leu Phe Leu Val Leu Arg Val Gly Ile Tyr Leu
                485                 490                 495

Cys Ile Lys Leu Lys His Thr Lys Lys Arg Gln Ile Tyr Thr Asp Ile
            500                 505                 510

Glu Met Asn Arg Leu Gly Thr
        515

<210> SEQ ID NO 20
<211> LENGTH: 1662
<212> TYPE: DNA
<213> ORGANISM: Maraba G-Protein

<400> SEQUENCE: 20
atgaaaaaaa ctaacagggt tcaaacactc ttgatcgagg tattgagact ttttctcttt      60
tgtttcttgg ccttaggagc ccactccaaa tttactatag tattccctca tcatcaaaaa     120
gggaattgga agaatgtgcc ttccacatat cattattgcc cttctagttc tgaccagaat     180
tggcataatg atttgactgg agttagtctt catgtgaaaa ttcccaaaag tcacaaagct     240
atacaagcag atggctggat gtgccacgct gctaaatggg tgactacttg tgacttcaga     300
tggtacggac ccaaatacat cacgcattcc atacactcta tgtcacccac cctagaacag     360
tgcaagacca gtattgagca gacaaagcaa ggagtttgga ttaatccagg ctttcccccct    420 caaagctgcg gatatgctac agtgacggat gcagaggtgg ttgttgtaca agcaacacct     480
catcatgtgt tggttgatga gtacacagga gaatggattg actcacaatt ggtggggggc     540
aaatgttcca aggaggtttg tcaaacggtt cacaactcga ccgtgtggca tgctgattac     600
aagattacag ggctgtgcga gtcaaatctg gcatcagtgg atatcacctt cttctctgag     660
gatggtcaaa agacgtcttt gggaaaaccg aacactggat tcaggagtaa ttactttgct     720
tacgaaagtg gagagaaggc atgccgtatg cagtactgca cacaatgggg gatccgacta     780
ccttctggag tatggtttga attagtggac aaagatctct tccaggcggc aaaattgcct     840
gaatgtccta gaggatccag tatctcagct ccttctcaga cttctgtgga tgttagtttg     900
atacaagacg tagagaggat cttagattac tctctatgcc aggagacgtg gagtaagata     960

```
cgagccaagc ttcctgtatc tccagtagat ctgagttatc tcgccccaaa aaatccaggg     1020
agcggaccgg ccttcactat cattaatggc actttgaaat atttcgaaac aagatacatc     1080
agagttgaca taagtaatcc catcatccct cacatggtgg gaacaatgag tggaaccacg     1140
actgagcgtg aattgtggaa tgattggtat ccatatgaag acgtagagat tggtccaaat     1200
ggggtgttga aaactcccac tggtttcaag tttccgctgt acatgattgg gcacggaatg     1260
ttggattccg atctccacaa atcctcccag gctcaagtct tcgaacatcc acacgcaaag     1320
gacgctgcat cacagcttcc tgatgatgag actttatttt ttggtgacac aggactatca     1380
aaaaacccag tagagttagt agaaggctgg ttcagtagct ggaagagcac attggcatcg     1440
ttctttctga ttataggctt gggggttgca ttaatcttca tcattcgaat tattgttgcg     1500
attcgatcac gaattctgga tccgatacgt aacgctctgc agctgcgggt tgcattaatc     1560
ttcatcattc gaattattgt tgcgattcgc tataaataca aggggaggaa gacccaaaaa     1620
atttacaatg atgtcgagat gagtcgattg ggaaataaat aa                        1662
```

<210> SEQ ID NO 21
<211> LENGTH: 518
<212> TYPE: PRT
<213> ORGANISM: Muir Spring virus G-Protein
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (386)..(386)
<223> OTHER INFORMATION: Xaa can be any naturally occurring amino acid
<220> FEATURE:
<221> NAME/KEY: misc_feature
<222> LOCATION: (389)..(390)
<223> OTHER INFORMATION: Xaa can be any naturally occurring amino acid

<400> SEQUENCE: 21

```
Met Lys Tyr Pro Val Leu Leu Tyr Gln Asn Gln Ile Leu Leu Lys
1               5                   10                  15

Trp Asn Thr Cys Leu Leu Met Ser Trp Asn Ser Gln Lys His His Glu
            20                  25                  30

Leu Ala Pro Val Gln Gly Tyr Leu Cys Ser Gly Leu Arg Tyr Lys Val
        35                  40                  45

Ile Cys Ser Glu Gly Phe Phe Gly Gln Lys Thr Ile Thr Lys Lys Ile
    50                  55                  60

Glu Asn Leu Glu Pro Asp Gln Asn Lys Cys Val Gln Asp Leu Glu Lys
65                  70                  75                  80

Phe Ile Asn Asp Asp Tyr Leu Leu Pro Tyr Phe Pro Ser Glu Asp Cys
                85                  90                  95

Asn Trp Met Lys Glu Thr Pro Val His Gln Asp Phe Ile Val Tyr Gln
            100                 105                 110

Lys His Gln Val Lys Tyr Asp Pro Tyr His Asn Gly Phe Tyr Asp Ala
        115                 120                 125

Leu Phe Lys Lys Asp Phe Cys Gln Glu Lys Ile Cys Glu Thr Glu His
    130                 135                 140

Asp Gln Thr Ile Trp Ile Thr Asn Gln Glu Leu Lys Gln Glu Cys Thr
145                 150                 155                 160

Phe Asn Tyr Pro Val Lys Lys His Val Phe Tyr Lys Arg Asp Tyr Ser
                165                 170                 175

Lys Met Ile Ile Asp Tyr Glu Ile Asn Gln Trp Thr Ser Val Glu Asp
            180                 185                 190
```

Gly Cys Leu Ile Arg Tyr Cys Gly Gln Glu Gly Ile Arg Leu Ser Asn
            195                 200                 205

Gly Met Phe Phe Val Gly Lys Phe Tyr Lys Leu Ile Ser Asn Leu Pro
    210                 215                 220

Ile Cys Pro Glu Gly Thr Lys Ile Ser Tyr Lys Pro Ile Lys Ala Gln
225                 230                 235                 240

Leu Asp Glu Ile Glu Asn Glu Ile Ile Leu Asn Gln Glu Arg Leu Leu
                245                 250                 255

Cys Leu Asp Ser Ile Arg Gln Met Thr Ala Ser Lys Lys Leu Ser Phe
            260                 265                 270

Tyr Ser Leu Ser Phe Leu Glu Pro Lys Ser Met Ser Arg His Lys Val
        275                 280                 285

Tyr Arg Ile His Asn Asn Thr Leu Glu Tyr Thr Glu Thr Glu Trp Glu
    290                 295                 300

Pro Ile Val Ala Phe Asn Phe Asn Gly Lys Asn Gln Ile Gly Val Asn
305                 310                 315                 320

Lys Glu Gly Lys Glu Val Tyr Trp Asn Glu Trp Val Pro Ser Gly Lys
                325                 330                 335

Asp Gly Leu Leu Ser Gly Phe Asn Gly Val Tyr Lys Lys Val Asn Ser
            340                 345                 350

Ser Lys Ile Ser Ile Ser Arg Leu Glu Thr Ile Lys Glu Asp Tyr Glu
        355                 360                 365

Arg Glu Met Met Ile Asp His Glu Leu Val Thr Val Glu His Pro Xaa
    370                 375                 380

Ile Xaa His Leu Xaa Xaa Glu Asn Ile Thr Gly Ser Arg Val Glu Ile
385                 390                 395                 400

Val Asn Thr Glu His Ser Asp Val Ser Gly Trp Phe Ser Ser Val Leu
                405                 410                 415

Lys Ser Phe Trp Gly Lys Leu Met Met Thr Val Val Ser Ile Ile Ile
            420                 425                 430

Ile Ile Ile Ile Gly Leu Leu Ile Ile Asn Cys Gly Pro Ile Ile Cys
        435                 440                 445

Lys Thr Cys Ile Ser Ser Tyr Lys Lys Lys Ser Arg Arg Asp Arg
    450                 455                 460

Phe Arg Ala Asp Arg Glu Thr Glu Thr Gly Leu Arg Arg Gln His Arg
465                 470                 475                 480

Val Val Phe His Asn Asn Glu Thr Asp Asp Glu Arg Ala Ile Glu Met
                485                 490                 495

Thr Gly His His Phe Gly Lys His Val Arg Ser Glu Leu Arg Pro Arg
            500                 505                 510

Arg His Pro Gly Ser Gly
        515

<210> SEQ ID NO 22
<211> LENGTH: 2248
<212> TYPE: DNA
<213> ORGANISM: Muir Spring virus G-Protein

<400> SEQUENCE: 22
gcggcggggg ctggccatca ctttggcaag cacgtgagat ctgattcgcg gccgcgtcga     60
cgcccctgaa actcctgatc ctatcctcct ccaaggagat aaaacttatc tcttttagt    120 cccttcagag agcaaaaatt ggaaacccgc agatcttaat gaagtatcct gtcctcctct    180
tatatcaaaa ccagatactg ctgaaatgga atacatgtct actgatgtca tggaactcgc    240

```
aaaaacatca tgaactcgcg cctgtgcaag ggtatttatg ttctggctta agatataaag      300
ttatttgttc tgaaggattc tttggacaaa aacaataac taagaaaatt gaaaatcttg      360
aacctgatca gaacaaatgt gttcaagatt tagaaaagtt tattaatgac gattatttgc      420
taccctattt cccatcagaa gattgtaatt ggatgaaaga acaccagtt catcaagatt       480 tcatagttta ccaaaaacat caggttaaat atgatccata ccacaatggc ttttacgatg      540
ctctgttcaa gaaagatttt tgtcaagaga aatatgtga cacagagcat gatcagacaa      600
tatggataac taaccaagaa ttaaaacaag aatgcacttt taattatccg gttaaaaaac     660
atgtattcta aagagagat tatagcaaaa tgatcatcga ttatgaaatc aaccaatgga      720
cttcagttga ggatggatgt ttgataagat attgtggtca ggaaggaatt agattatcta     780
atgggatgtt ctttgtagga aaattttaca aattaatatc gaatctgcca atttgtccag     840
aaggaaccaa gatcagctac aagcccatta agcacaatt agatgaaata gaaaatgaaa      900 taatttaaa tcaagaaaga cttttatgtt tagattctat acgacaaatg actgcttcta     960
aaaaattatc tttttattca ttatccttct tggagcctaa atccatgagt agacataagg    1020
tctatagaat tcacaataat actttagaat acactgaaac tgaatgggaa cctatagtgg    1080
cttttaattt taatggaaag aatcaaatcg gagtaaataa agaagggaag gaagtttatt     1140
ggaatgaatg ggtgcccagt ggaaaagatg gattgctctc aggattcaat ggagtttata    1200
agaaagttaa ttcttccaaa atttcaatat caagattaga aaccattaaa gaagattatg    1260
aaagagaaat gatgatagat catgaattgg ttacagttga gcatcctama attgkccatc    1320
ttaawasaga aaacatmaca ggttctagag tggagatagt taatactgaa cattcagacg     1380
tcagtggttg gttctcatct gtttttaaga gttttttgggg aaagttgatg atgactgttg    1440
tcagtataat aataattatc atcataggcc tattgattat caattgtggt ccaattatct    1500
gtaaaacttg cattagcagc tataaaaaga aaaagagtag aagagataga tttagagcag    1560
atagagaaac tgaaactgga ctgcgtcgac aacatagagt ggtatttcat aataatgaaa    1620
cagatgatga aagagcaata gagatgactg ccatcacttt tggcaagcac gtgagatctg    1680
aattgcggcc gcgtcgacat cctggctcag gatgaacgct ggctgtgtgc ctaatacatg    1740
catgtcgagc gaggtctttt tgaacctagc ggcgaatggg tgagtaacac gtgcttaatc    1800 tacccttttag attggaatac ccaatggaaa cattggctaa tgccggatac gcatggaatc    1860
gcatgattcc gttgtgaaag gagcctttaa agctccgcta gaggatgagg gtgcggaaca    1920
ttagttagtt ggtagggtaa tggcctacca agactatgat gtttagccgg gtcgagagac    1980
tgaacggcca cattgggact gagatacggc ccaaactcct acgggaggca gcagtaggga   2040
atattccaca atgagcgaaa gcttgatgga gcgacacagc gtgcacgatg aaggtcttcg    2100
gattgtaaag tgctgttata gggaaagaac acctggttga ggaaatgctt ccaggctgac    2160
ggtaccctgt cagaaagcga tggctaacta tgtgccagca gccgcggtaa tacataggtc    2220
gcaagcgtta tccggaatta ttgggcgt                                       2248

<210> SEQ ID NO 23
<211> LENGTH: 1948
<212> TYPE: DNA
<213> ORGANISM: VSV g protein

<400> SEQUENCE: 23
acgcgttttc gccaccatgc c

```
gcagaggaac tccctgacgc atcaaatgca acgcatgacg ctgagcgagc ccacgagtga    120
gctgcccacc cagaggcaaa ttgaagcgct aatgcgctac gcctggaatg aggcacatgt    180
acaacctccg gtgacaccta ctaacatctt gatcatgtta ttattattgt tacagcgggt    240
acaaaatggg gcagctgcgg cttttttgggc gtacattcct gatccgccaa tgattcaatc    300
cttaggatgg gatagagaaa tagtacccgt atatgttaat gatacgagcc ttttaggagg    360
aaaatcagat attcacattt cccctcagca agcaaatatc tcttttatg gccttaccac    420 tcaatatccc atgtgctttt cttatcaatc gcagcatcct cattgtatac aggtatcagc    480
tgacatatca tatcctcgag tgactatctc aggcattgat gaaaaaactg ggaaaaaatc    540
atacgggaac ggatctggac ccctcgacat tccgttttgt gacaagcatt taagcattgg    600
cataggcata gacactcctt ggactttatg tcgagcccgg gtcgcgtcag tatataacat    660
caataatgcc aatgccacct ttttatggga ttgggcaccct ggaggaacac ctgattttcc    720
tgaatatcga ggacagcatc cgcctatttt ctctgtgaat accgctccaa tataccaaac    780
ggaactatgg aaacttttgg ctgcttttgg tcatggcaat agtttatatt tacagcccaa    840
tatcagtgga agcaaaatatg gtgatgtagg agttacagga ttttatatc ctcgagcttg    900 cgtgccgtat ccattcatgt tgatacaagg ccatatggaa ataacactgt cattaaatat    960
ttatcatttg aattgttcta attgcatact gactaattgt atcaggggag tagccaaagg   1020
agaacaggtt ataatagtaa acagcctgc ctttgtaatg ctgcccgttg aaatagctga   1080
agcctggtat gatgaaactg ctttagaatt attcaacgc attaatacgg ctcttagccg   1140
ccctaagaga ggcctgagcc tgattattct gggtatagta tctttaatca ccctcatagc   1200
tacagctgtt acggcttccg tatctttagc acagtctatt caagctgcgc acacggtaga   1260
ctccttatca tataatgtta ctaaagtgat ggggacccaa gaagatattg ataaaaaaat   1320
agaagatagg ctatcagctc tatatgatgt agtcagagtc ttaggagagc aagttcagag   1380
cattaatttt cgcatgaaaa tccaatgtca tgctaactat aaatggattt gtgttacaaa   1440
aaaaccatac aacacttctg attttccatg ggacaaagtg aagaaacatt gcaaggaat   1500 ttggttcaat actaatctat cgttagacct tttacaactg cataatgaga ttcttgatat   1560
tgaaaattcg ccgaaggcta cactaaatat agccgatact gttgataatt tcttgcaaaa   1620
tttattctct aatttcccta gtctccattc gctgtggaaa accctgattg gtgtaggaat   1680
acttgtgttt attataattg tcgtaatcct tatatttcct tgcctcgtac gtagtagttg   1740
gaagagctct attgcctctt ttttctttac cataggggtta atcattggac tattcttggt   1800
tctccgagtt ggtatttatc tttgcattaa attaaagcac accaagaaaa gacagattta   1860
tacagacata gagatgaacc gacttggaac gtaactcaaa tcctcgaggc taggtatgaa   1920
aaaaactaac agatatcacg gctagcgg                                      1948

<210> SEQ ID NO 24
<211> LENGTH: 2031
<212> TYPE: DNA
<213> ORGANISM: EBOLA G PROTEIN

<400> SEQUENCE: 24
atgggcgtta caggaatatt gcagttacct cgtgatcgat tcaagaggac atcattcttt     60
ctttgggtaa ttatcctttt ccaaagaaca ttttccatcc cacttggagt catccacaat    120
agcacattac aggttagtga tgtcgacaaa ctagtttgtc gtgacaaact gtcatccaca    180
aatcaattga gatcagttgg actgaatctc gaagggaatg gagtggcaac tgacgtgcca    240
```

```
tctgcaacta aaagatgggg cttcaggtcc ggtgtccac caaaggtggt caattatgaa      300
gctggtgaat gggctgaaaa ctgctacaat cttgaaatca aaaaacctga cgggagtgag      360
tgtctaccag cagcgccaga cgggattcgg ggcttccccc ggtgccggta tgtgcacaaa      420
gtatcaggaa cgggaccgtg tgccggagac tttgccttcc ataaagaggg tgctttcttc      480
ctgtatgatc gacttgcttc cacagttatc taccgaggaa cgactttcgc tgaaggtgtc      540
gttgcatttc tgatactgcc ccaagctaag aaggacttct tcagctcaca ccccttgaga      600
gagccggtca atgcaacgga ggacccgtct agtggctact attctaccac aattagatat      660
caggctaccg gttttggaac caatgagaca gagtacttgt tcgaggttga caatttgacc      720
tacgtccaac ttgaatcaag attcacacca cagtttctgc tccagctgaa tgagacaata      780
tatacaagtg ggaaaaggag caataccacg ggaaaaactaa tttggaaggt caaccccgaa      840
attgatacaa caatcgggga gtgggccttc tgggaaacta aaaaaaacct cactagaaaa      900
attcgcagtg aagagttgtc tttcacagtt gtatcaaacg gagccaaaaa catcagtggt      960
cagagtccgg cgcgaacttc ttccgaccca gggaccaaca caacaactga agaccacaaa     1020
atcatggctt cagaaaattc ctctgcaatg gttcaagtgc acagtcaagg aagggaagct     1080
gcagtgtcgc atctaacaac ccttgccaca atctccacga gtccccaatc cctcacaacc     1140
aaaccaggtc cggacaacag cacccataat acaccgtgt ataaacttga catctctgag     1200
gcaactcaag ttgaacaaca tcaccgcaga acagacaacg acagcacagc ctccgacact     1260
ccctctgcca cgaccgcagc cggaccccca aaagcagaga acaccaacac gagcaagagc     1320
actgacttcc tggaccccgc caccacaaca gtccccaaa accacagcga accgctggc     1380 aacaacaaca ctcatcacca agataccgga gaagagagtg ccagcagcgg gaagctaggc     1440
ttaattacca atactattgc tggagtcgca ggactgatca caggcgggag aagaactcga     1500
agagaagcaa ttgtcaatgc tcaacccaaa tgcaacccta atttacatta ctggactact     1560
caggatgaag gtgctgcaat cggactggcc tggataccat atttcgggcc agcagccgag     1620
ggaatttaca tagaggggct aatgcacaat caagatggtt taatctgtgg gttgagacag     1680
ctggccaacg agacgactca agctcttcaa ctgttcctga gagccacaac tgagctacgc     1740 acctttcaa tcctcaaccg taaggcaatt gatttcttgc tgcagcgatg gggcggcaca     1800
tgccacattc tgggaccgga ctgctgtatc gaaccacatg attggaccaa gaacataaca     1860
gacaaaattg atcagattat tcatgatttt gttgataaaa cccttccgga ccagggggac     1920
aatgacaatt ggtggacagg atggagacaa tggataccgg caggtattgg agttacaggc     1980
gttataattg cagttatcgc tttattctgt atatgcaaat ttgtctttta g             2031
```

<210> SEQ ID NO 25
<211> LENGTH: 39
<212> TYPE: DNA
<213> ORGANISM: Artificial
<220> FEATURE:
<223> OTHER INFORMATION: Synthetic primer

<400> SEQUENCE: 25
ctcgagggta tgaaaaaaac taacagatat cacggctag                             39

<210> SEQ ID NO 26
<211> LENGTH: 523
<212> TYPE: PRT
<213> ORGANISM: Isfahan G protein

```
<400> SEQUENCE: 26

Met Thr Ser Val Leu Phe Met Val Gly Val Leu Leu Gly Ala Phe Gly
1               5                   10                  15

Ser Thr His Cys Ser Ile Gln Ile Val Phe Pro Ser Glu Thr Lys Leu
            20                  25                  30

Val Trp Lys Pro Val Leu Lys Gly Thr Arg Tyr Cys Pro Gln Ser Ala
        35                  40                  45

Glu Leu Asn Leu Glu Pro Asp Leu Lys Thr Met Ala Phe Asp Ser Lys
    50                  55                  60

Val Pro Ile Gly Ile Thr Pro Ser Asn Ser Asp Gly Tyr Leu Cys His
65                  70                  75                  80

Ala Ala Lys Trp Val Thr Thr Cys Asp Phe Arg Trp Tyr Gly Pro Lys
                85                  90                  95

Tyr Ile Thr His Ser Val His Ser Leu Arg Pro Thr Val Ser Asp Cys
            100                 105                 110

Lys Ala Ala Val Glu Ala Tyr Asn Ala Gly Thr Leu Met Tyr Pro Gly
        115                 120                 125

Phe Pro Pro Glu Ser Cys Gly Tyr Ala Ser Ile Thr Asp Ser Glu Phe
    130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
                165                 170                 175

Phe Cys Glu Thr Val His Asn Ala Thr Met Trp Ile Pro Lys Asp Leu
            180                 185                 190

Lys Thr His Asp Val Cys Ser Gln Asp Phe Gln Thr Ile Arg Val Ser
        195                 200                 205

Val Met Tyr Pro Gln Thr Lys Pro Thr Lys Gly Ala Asp Leu Thr Leu
210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
            260                 265                 270

Phe Pro Asp Cys Leu Val Gly Ser Val Val Lys Ser Thr Leu Leu Ser
        275                 280                 285

Glu Gly Val Gln Thr Ala Leu Trp Glu Thr Asp Arg Leu Leu Asp Tyr
    290                 295                 300

Ser Leu Cys Gln Asn Thr Trp Glu Lys Ile Asp Arg Lys Glu Pro Leu
305                 310                 315                 320

Ser Ala Val Asp Leu Ser Tyr Leu Ala Pro Arg Ser Pro Gly Lys Gly
                325                 330                 335

Met Ala Tyr Ile Val Ala Asn Gly Ser Leu Met Ser Ala Pro Ala Arg
            340                 345                 350

Tyr Ile Arg Val Trp Ile Asp Ser Pro Ile Leu Lys Glu Ile Lys Gly
        355                 360                 365

Lys Lys Glu Ser Ala Ser Gly Ile Asp Thr Val Leu Trp Glu Gln Trp
    370                 375                 380

Leu Pro Phe Asn Gly Met Glu Leu Gly Pro Asn Gly Leu Ile Lys Thr
385                 390                 395                 400

Lys Ser Gly Tyr Lys Phe Pro Leu Tyr Leu Leu Gly Met Gly Ile Val
                405                 410                 415
```

```
Asp Gln Asp Leu Gln Glu Leu Ser Ser Val Asn Pro Val Asp His Pro
            420                 425                 430

His Val Pro Ile Ala Gln Ala Phe Val Ser Glu Gly Glu Val Phe
            435                 440                 445

Phe Gly Asp Thr Gly Val Ser Lys Asn Pro Ile Glu Leu Ile Ser Gly
450                 455                 460

Trp Phe Ser Asp Trp Lys Glu Thr Ala Ala Ala Leu Gly Phe Ala Ala
465                 470                 475                 480

Ile Ser Val Ile Leu Ile Ile Gly Leu Met Arg Leu Pro Leu Leu
            485                 490                 495

Cys Arg Arg Lys Gln Lys Lys Val Ile Tyr Lys Asp Val Glu Leu
            500                 505                 510

Asn Ser Phe Asp Pro Arg Gln Ala Phe His Arg
            515                 520

<210> SEQ ID NO 27
<211> LENGTH: 530
<212> TYPE: PRT
<213> ORGANISM: Chandipura G protein

<400> SEQUENCE: 27

Met Thr Ser Ser Val Thr Ile Ser Val Val Leu Leu Ile Ser Phe Ile
1               5                   10                  15

Thr Pro Ser Tyr Ser Ser Leu Ser Ile Ala Phe Pro Glu Asn Thr Lys
                20                  25                  30

Leu Asp Trp Lys Pro Val Thr Lys Asn Thr Arg Tyr Cys Pro Met Gly
            35                  40                  45

Gly Glu Trp Phe Leu Glu Pro Gly Leu Gln Glu Glu Ser Phe Leu Ser
        50                  55                  60

Ser Thr Pro Ile Gly Ala Thr Pro Ser Lys Ser Asp Gly Phe Leu Cys
65                  70                  75                  80

His Ala Ala Lys Trp Val Thr Thr Cys Asp Phe Arg Trp Tyr Gly Pro
                85                  90                  95

Lys Tyr Ile Thr His Ser Ile His Asn Ile Lys Pro Thr Arg Ser Asp
            100                 105                 110

Cys Asp Thr Ala Leu Ala Ser Tyr Lys Ser Gly Thr Leu Val Ser Pro
        115                 120                 125

Gly Phe Pro Pro Glu Ser Cys Gly Tyr Ala Ser Val Thr Asp Ser Glu
    130                 135                 140

Phe Leu Val Ile Met Ile Thr Pro His His Val Gly Val Asp Asp Tyr
145                 150                 155                 160

Arg Gly His Trp Val Asp Pro Leu Phe Val Gly Gly Glu Cys Asp Gln
                165                 170                 175

Ser Tyr Cys Asp Thr Ile His Asn Ser Ser Val Trp Ile Pro Ala Asp
            180                 185                 190

Gln Thr Lys Lys Asn Ile Cys Gly Gln Ser Phe Thr Pro Leu Thr Val
        195                 200                 205

Thr Val Ala Tyr Val Lys Thr Lys Glu Ile Ala Ala Gly Ala Ile Val
    210                 215                 220

Phe Lys Ser Lys Tyr His Ser His Met Glu Gly Ala Arg Thr Cys Arg
225                 230                 235                 240

Leu Ser Tyr Cys Gly Arg Asn Gly Ile Lys Phe Pro Asn Gly Glu Trp
                245                 250                 255

Val Ser Leu Asp Val Lys Thr Lys Ile Gln Glu Lys Pro Leu Leu Pro
```

-continued

```
                260                 265                 270
Leu Phe Lys Glu Cys Pro Ala Gly Thr Glu Val Arg Ser Thr Leu Gln
            275                 280                 285

Ser Asp Gly Ala Gln Val Leu Thr Ser Glu Ile Gln Arg Ile Leu Asp
        290                 295                 300

Tyr Ser Leu Cys Gln Asn Thr Trp Asp Lys Val Glu Arg Lys Glu Pro
305                 310                 315                 320

Leu Ser Pro Leu Asp Leu Ser Tyr Leu Ala Ser Lys Ser Pro Gly Lys
                325                 330                 335

Gly Leu Ala Tyr Thr Val Ile Asn Gly Thr Leu Ser Phe Ala His Thr
            340                 345                 350

Arg Tyr Val Arg Met Trp Ile Asp Gly Pro Val Leu Lys Glu Met Lys
        355                 360                 365

Gly Lys Arg Glu Ser Pro Ser Gly Ile Ser Ser Asp Ile Trp Thr Gln
    370                 375                 380

Trp Phe Lys Tyr Gly Asp Met Glu Ile Gly Pro Asn Gly Leu Leu Lys
385                 390                 395                 400

Thr Ala Gly Gly Tyr Lys Phe Pro Trp His Leu Ile Gly Met Gly Ile
                405                 410                 415

Val Asp Asn Glu Leu His Glu Leu Ser Glu Ala Asn Pro Leu Asp His
            420                 425                 430

Pro Gln Leu Pro His Ala Gln Ser Ile Ala Asp Asp Ser Glu Glu Ile
        435                 440                 445

Phe Phe Gly Asp Thr Gly Val Ser Lys Asn Pro Val Glu Leu Val Thr
    450                 455                 460

Gly Trp Phe Thr Ser Trp Lys Glu Ser Leu Ala Ala Gly Val Val Leu
465                 470                 475                 480

Ile Leu Val Val Val Leu Ile Tyr Gly Val Leu Arg Cys Phe Pro Val
                485                 490                 495

Leu Cys Thr Thr Cys Arg Lys Pro Lys Trp Lys Lys Gly Val Glu Arg
            500                 505                 510

Ser Asp Ser Phe Glu Met Arg Ile Phe Lys Pro Asn Asn Met Arg Ala
        515                 520                 525

Arg Val
    530

<210> SEQ ID NO 28
<211> LENGTH: 611
<212> TYPE: PRT
<213> ORGANISM: Jaagsietke sheep retrovirus virus G protein

<400> SEQUENCE: 28

Met Pro Lys Arg Arg Ala Gly Phe Arg Lys Gly Trp Tyr Ala Arg Gln
1               5                   10                  15

Arg Asn Ser Leu Thr His Gln Met Gln Arg Met Thr Leu Ser Glu Pro
            20                  25                  30

Thr Ser Glu Leu Pro Thr Gln Arg Gln Ile Glu Ala Leu Met Arg Tyr
        35                  40                  45

Ala Trp Asn Glu Ala His Val Gln Pro Pro Val Thr Pro Thr Asn Ile
    50                  55                  60

Leu Ile Met Leu Leu Leu Leu Gln Arg Ile Gln Asn Gly Ala Ala
65                  70                  75                  80

Ala Thr Phe Trp Ala Tyr Ile Pro Asp Pro Pro Met Leu Gln Ser Leu
                85                  90                  95
```

-continued

Gly Trp Asp Lys Glu Thr Val Pro Val Tyr Val Asn Asp Thr Ser Leu
            100                 105                 110
Leu Gly Gly Lys Ser Asp Ile His Ile Ser Pro Gln Gln Ala Asn Ile
        115                 120                 125
Ser Phe Tyr Gly Leu Thr Thr Gln Tyr Pro Met Cys Phe Ser Tyr Gln
    130                 135                 140
Ser Gln His Pro His Cys Ile Gln Val Ser Ala Asp Ile Ser Tyr Pro
145                 150                 155                 160
Arg Val Thr Ile Ser Gly Ile Asp Glu Lys Thr Gly Met Arg Ser Tyr
                165                 170                 175
Arg Asp Gly Thr Gly Pro Leu Asp Ile Pro Phe Cys Asp Lys His Leu
            180                 185                 190
Ser Ile Gly Ile Gly Ile Asp Thr Pro Trp Thr Leu Cys Arg Ala Arg
        195                 200                 205
Ile Ala Ser Val Tyr Asn Ile Asn Asn Ala Asn Thr Thr Leu Leu Trp
    210                 215                 220
Asp Trp Ala Pro Gly Gly Thr Pro Asp Phe Pro Glu Tyr Arg Gly Gln
225                 230                 235                 240
His Pro Pro Ile Ser Ser Val Asn Thr Ala Pro Ile Tyr Gln Thr Glu
                245                 250                 255
Leu Trp Lys Leu Leu Ala Ala Phe Gly His Gly Asn Ser Leu Tyr Leu
            260                 265                 270
Gln Pro Asn Ile Ser Gly Ser Lys Tyr Gly Asp Val Gly Val Thr Gly
        275                 280                 285
Phe Leu Tyr Pro Arg Ala Cys Val Pro Tyr Pro Phe Met Val Ile Gln
    290                 295                 300
Gly His Met Glu Ile Thr Pro Ser Leu Asn Ile Tyr Tyr Leu Asn Cys
305                 310                 315                 320
Ser Asn Cys Ile Leu Thr Asn Cys Ile Arg Gly Val Ala Lys Gly Glu
                325                 330                 335
Gln Val Ile Ile Val Lys Gln Pro Ala Phe Val Met Leu Pro Val Glu
            340                 345                 350
Ile Thr Glu Glu Trp Tyr Asp Glu Thr Ala Leu Glu Leu Leu Gln Arg
        355                 360                 365
Ile Asn Thr Ala Leu Ser Arg Pro Lys Arg Gly Leu Ser Leu Ile Ile
    370                 375                 380
Leu Gly Ile Val Ser Leu Ile Thr Leu Ile Ala Thr Ala Val Thr Ala
385                 390                 395                 400
Ser Val Ser Leu Ala Gln Ser Ile Gln Val Ala His Thr Val Asp Ser
                405                 410                 415
Leu Ser Ser Asn Val Thr Lys Val Met Gly Thr Gln Glu Asn Ile Asp
            420                 425                 430
Lys Lys Ile Glu Asp Arg Leu Pro Ala Leu Tyr Asp Val Val Arg Val
        435                 440                 445
Leu Gly Glu Gln Val Gln Ser Ile Asn Phe Arg Met Lys Ile Gln Cys
    450                 455                 460
His Ala Asn Tyr Lys Trp Ile Cys Val Thr Lys Lys Pro Tyr Asn Thr
465                 470                 475                 480
Ser Asp Phe Pro Trp Asp Lys Val Lys Lys His Leu Gln Gly Ile Trp
                485                 490                 495
Phe Asn Thr Thr Val Ser Leu Asp Leu Leu Gln Leu His Asn Glu Ile
            500                 505                 510
Leu Asp Ile Glu Asn Ser Pro Lys Ala Thr Leu Asn Ile Ala Asp Thr

```
                515                 520                 525
Val Asp Asn Phe Leu Gln Asn Leu Phe Ser Asn Phe Pro Ser Leu His
    530                 535                 540

Ser Leu Trp Arg Ser Ile Ile Ala Met Gly Ala Val Leu Thr Phe Val
545                 550                 555                 560

Leu Ile Ile Ile Cys Leu Ala Pro Cys Leu Ile Arg Ser Ile Val Lys
                565                 570                 575

Glu Phe Leu His Met Arg Val Leu Ile His Lys Asn Met Leu Gln His
            580                 585                 590

Gln His Leu Met Glu Leu Leu Asn Asn Lys Glu Arg Gly Ala Ala Gly
        595                 600                 605

Asp Asp Pro
    610

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 29

Asn Pro Met Gly Xaa Leu
1               5
```